US012615962B2

(12) United States Patent
Li et al.

(10) Patent No.: US 12,615,962 B2
(45) Date of Patent: Apr. 28, 2026

(54) ORGANIC MATERIAL COMPOSITION AND APPLICATIONS THEREOF

(71) Applicant: Ningbo Lumilan Advanced Materials Co., Ltd., Ningbo City (CN)

(72) Inventors: Xiangzhi Li, Ningbo City (CN); Ye Cai, Ningbo City (CN); Ting-Wei Wei, Ningbo City (CN); Zhi-Kuan Chen, Ningbo City (CN)

(73) Assignee: NINGBO LUMILAN ADVANCED MATERIALS CO., LTD., Ningbo City (CN)

( * ) Notice: Subject to any disclaimer, the term of this patent is extended or adjusted under 35 U.S.C. 154(b) by 890 days.

(21) Appl. No.: 17/949,776

(22) Filed: Sep. 21, 2022

(65) Prior Publication Data

US 2023/0134923 A1 May 4, 2023

(30) Foreign Application Priority Data

Sep. 26, 2021 (CN) .......................... 202111128530.0

(51) Int. Cl.

| | |
|---|---|
| ***H10K 85/60*** | (2023.01) |
| ***C07D 403/04*** | (2006.01) |
| ***C07D 403/10*** | (2006.01) |
| ***C07D 403/14*** | (2006.01) |
| ***C07D 405/14*** | (2006.01) |
| ***C07D 487/04*** | (2006.01) |
| ***C07D 495/04*** | (2006.01) |
| ***H10K 50/11*** | (2023.01) |
| ***H10K 101/10*** | (2023.01) |

(52) U.S. Cl.

CPC ......... *H10K 85/654* (2023.02); *C07D 403/04* (2013.01); *C07D 403/10* (2013.01); *C07D 403/14* (2013.01); *C07D 405/14* (2013.01); *C07D 487/04* (2013.01); *C07D 495/04* (2013.01); *H10K 85/6572* (2023.02); *H10K 85/6574* (2023.02); *H10K 50/11* (2023.02); *H10K 2101/10* (2023.02)

(58) Field of Classification Search

None

See application file for complete search history.

(56) References Cited

U.S. PATENT DOCUMENTS

2022/0123230 A1* 4/2022 Kang .................. C07D 403/04

* cited by examiner

*Primary Examiner* — Vu A Nguyen

(74) *Attorney, Agent, or Firm* — MUNCY, GEISSLER, OLDS & LOWE, P.C.

(57) ABSTRACT

The present invention provides an organic material composition and applications thereof. By the combination of the compounds comprised in the organic material composition, the organic material composition makes the element have a lower driving voltage, a higher current efficiency and a longer service life.

12 Claims, 1 Drawing Sheet

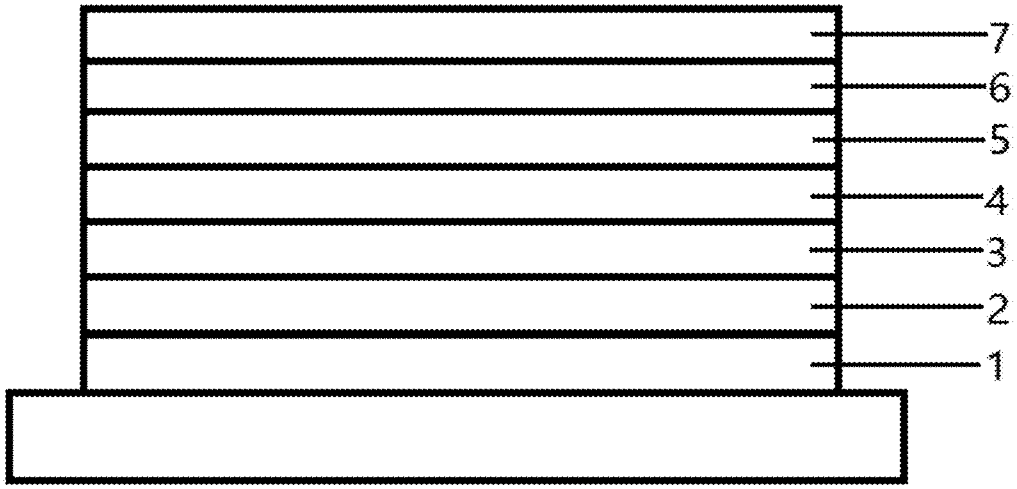
7
6
5
4
3
2
1

ORGANIC MATERIAL COMPOSITION AND APPLICATIONS THEREOF

CROSS-REFERENCE TO RELATED APPLICATION

Pursuant to 35 U.S.C. § 119(a), this application claims the benefit of the priority to Chinese Patent Application No. 202111128530.0, filed on Sep. 26, 2021. The content of the prior application is incorporated herein by its entirety.

BACKGROUND OF THE INVENTION

1. Field of the Invention

The present invention belongs to the field of organic electroluminescence, which relates to an organic material composition and applications thereof.

2. Description of the Prior Arts

Nowadays, the growth of the demand for flat panel displays has drawn the attention to organic light-emitting diodes (OLEDs). An OLED device may comprise organic layers such as a hole injection layer, a hole transport layer, a hole auxiliary layer, an emitting auxiliary layer, an electron blocking layer, an emitting layer (comprising a host material and a dopant material), an electron buffer layer, a hole blocking layer, an electron transport layer, an electron injection layer, and the like. The materials used in the organic layers can be categorized by their functions into a hole injection material, a hole transport material, a hole auxiliary material, an emitting auxiliary material, an electron blocking material, an emitting material, an electron buffer material, a hole blocking material, an electron transport material, an electron injection material, and the like. In an OLED device, a voltage is applied to inject holes of the anode and electrons of the cathode into the emitting layer, and the recombination of the holes and electrons produces high energy excitons. The organic light-emitting compounds turn into the excited state by energy, and light is emitted when the organic light-emitting compounds at the excited state return to their base state.

The most important key factor to decide the light-emitting efficiency of an OLED device is the light-emitting material. A light-emitting material not only needs higher quantum efficiency, higher electron mobility and hole mobility, but also needs to be uniform and stable. Thus, in the field of the present invention, it is important to further develop a light-emitting material.

SUMMARY OF THE INVENTION

To overcome the shortcomings of the existing technology, the objective of the present invention is to provide an organic material composition and applications thereof.

To achieve the above objective, the present invention uses the following technical approaches:

In one aspect, the present invention provides an organic material composition comprising at least one compound having a structure represented by Formula 1 and at least one compound having a structure represented by Formula 2, Formula 1

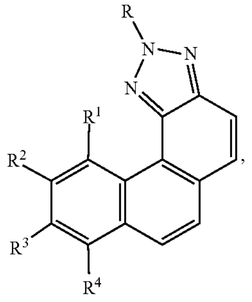

wherein, R is selected from hydrogen, deuterium, halogen, a cyano group, a substituted or unsubstituted C1-C30 alkyl group, a substituted or unsubstituted C3-C30 cycloalkyl group, a substituted or unsubstituted C6-C30 aryl group, and a substituted or unsubstituted C3-C30 heteroaryl group;

$R^1$ is-$L^1Ar^1$; $R^2$ is-$L^2Ar^2$; $R^3$ is-$L^3Ar^3$; $R^4$ is-$L^4Ar^4$;

$L^1$ to $L^4$ are each independently selected from a bond, a substituted or unsubstituted C6-C30 arylene group, and a substituted or unsubstituted C3-C30 heteroarylene group; and $Ar^1$ to $Ar^4$ are each independently selected from hydrogen, deuterium, halogen, a cyano group, and a substituted or unsubstituted C3-C60 heteroaryl group;

Formula 2

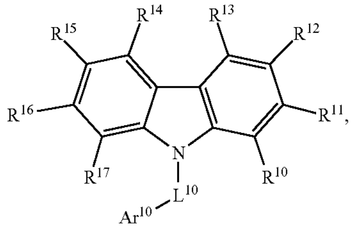

$Ar^{10}$ is selected from a substituted or unsubstituted C6-C60 aryl group, and a substituted or unsubstituted C3-C60 heteroaryl group; and $L^{10}$ is selected from a bond, a substituted or unsubstituted C6-C30 arylene group, and a substituted or unsubstituted C3-C30 heteroarylene group;

$R^{10}$ to $R^{17}$ are each independently selected from hydrogen, deuterium, halogen, a cyano group, a substituted or unsubstituted C1-C30 alkyl group, a C1-C30 alkyl group in which one or more methylene groups are independently substituted by —O— and/or —S— in a manner that O atom and/or S atom are not adjacent to each other, a substituted or unsubstituted C2-C30 alkenyl group, a C2-C30 alkenyl group in which one or more methylene groups are independently substituted by —O— and/or —S— in a manner that O atom and/or S atom are not adjacent to each other, a substituted or unsubstituted C7-C30 arylalkyl group, a substituted or unsubstituted C6-C30 aryl group, a substituted or unsubstituted C3-C30 heteroaryl group, a substituted or unsubstituted C4-C30 heteroarylalkyl group, a substituted or unsubstituted C3-C30 cycloalkyl group, a substituted or unsubstituted C3-C30 heterocycloalkyl group, a substituted or unsubstituted C3-C30 cycloalkenyl group, a substituted or unsubstituted C1-C30 alkoxy group, and a substituted or unsubstituted C6-C30 aryloxy group;

$R^{10}$ to $R^{17}$ are present individually without forming a ring, or any adjacent two to four of $R^{10}$ to $R^{17}$ joined to form a ring A, and the ring A is a substituted or unsubstituted C6-C30 aromatic ring, or a substituted or unsubstituted C3-C30 heteroaromatic ring.

Preferably, in Formula 1, at least one of $Ar^1$ to $Ar^4$ is a group represented by Formula a:

Formula a

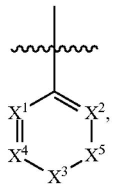

$X^1$ is selected from N and $CR^{X1}$; $X^2$ is selected from N and $CR^{X2}$; $X^3$ is selected from N and $CR^{X3}$; $X^4$ is selected from N and $CR^{X4}$; $X^5$ is selected from N and $CR^{X5}$;

$R^{X1}$ to $R^{X5}$ are each independently selected from hydrogen, deuterium, a cyano group, a substituted or unsubstituted C1-C30 alkyl group, a substituted or unsubstituted C3-C30 cycloalkyl group, a substituted or unsubstituted C6-C30 aryl group, and a substituted or unsubstituted C3-C30 heteroaryl group; $R^{X1}$ to $R^{X5}$ are present individually without forming a ring, or any adjacent two of $R^{X1}$ to $R^{X5}$ joined to form a ring B, and the ring B is a benzene ring.

Preferably, $X^{r}$ is N; $X^2$ is N; $X^3$ is $CR^{X3}$; $X^4$ is $CR^{X4}$; $X^5$ is $CR^{X5}$.

Preferably, $X^{r}$ is N; $X^3$ is N; $X^2$ is $CR^{X2}$; $X^4$ is $CR^{X4}$; $X^5$ is $CR^{X5}$.

Preferably, $X^{r}$ is N; $X^2$ is N; $X^3$ is N; $X^4$ is $CR^{X4}$; $X^5$ is $CR^{X5}$.

Preferably, the Formula a is selected from,

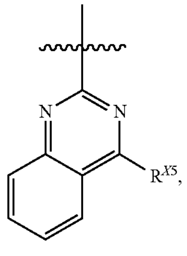

and $R^{X5}$ is the same as described above.

Preferably, the Formula a is selected from,

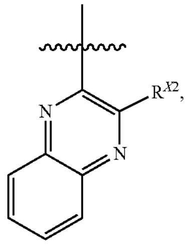

and $R^{X2}$ is the same as described above.

Preferably, in Formula 1, $R^{X1}$ to $R^{X5}$ are each independently selected from hydrogen, deuterium, and a group selected from a phenyl group, a biphenylyl group, a terphenylyl group, a naphthyl group, a phenanthryl group, an anthryl group, a phenylnaphthyl group, a naphthylphenyl group, a pyridyl group, a bipyridyl group, a dibenzofuryl group, a dibenzothiophenyl group, a carbazolyl group, a carbazolylphenyl group, a phenylcarbazolyl group, a dimethylfluorenyl group, a diphenylfluorenyl group, a spirobifluorenyl group, a dibenzofurylphenyl group, a dibenzothiophenylphenyl group, a dimethylfluorenylphenyl group, a benzocarbazolyl group, a benzonaphthofuryl group, and a benzonaphthothiophenyl group, each of which is substituted or unsubstituted.

Preferably, in Formula 1, at least one of $R^1$, $R^2$, $R^3$ and $R^4$ is hydrogen.

Preferably, at least two of $R^1$, $R^2$, $R^3$ and $R^4$ are hydrogen.

Preferably, at least three of $R^1$, $R^2$, $R^3$ and $R^4$ are hydrogen.

Preferably, $R^2$ is-$L^2Ar^2$; and $R^1$, $R^3$, and $R^4$ are all hydrogen.

Preferably, $R^3$ is-$L^3Ar^3$; and $R^1$, $R^2$, and $R^4$ are all hydrogen.

Preferably, R is selected from a phenyl group and a biphenylyl group, each of which is substituted or unsubstituted.

Preferably, $L^1$ to $L^4$ are each independently selected from a bond, and a group selected from a phenylene group, a naphthylene group, a biphenylene group, and a terphenylene group, each of which is substituted or unsubstituted.

Preferably, the compound having a structure represented by Formula 1 is selected from the following compounds:

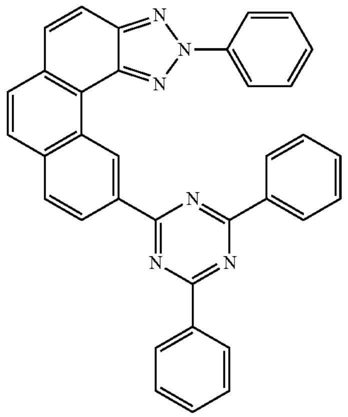

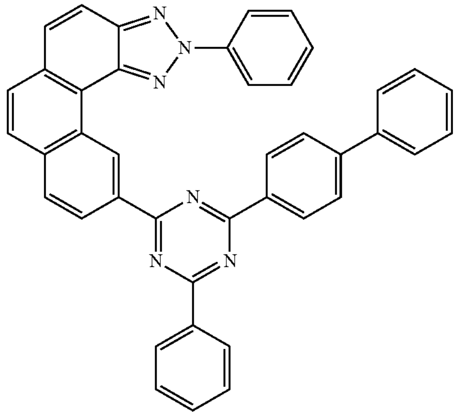

-continued
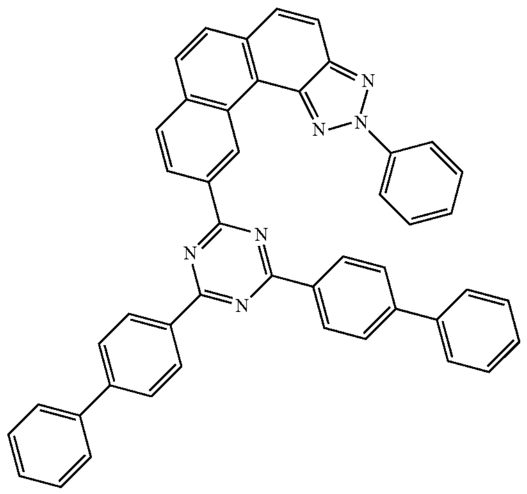
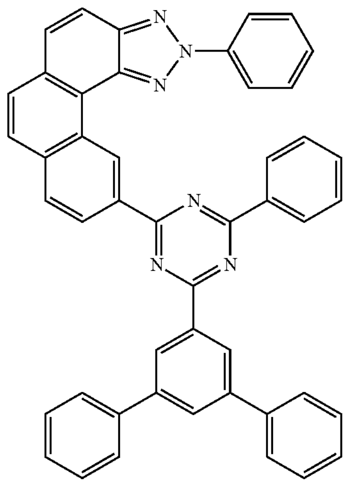
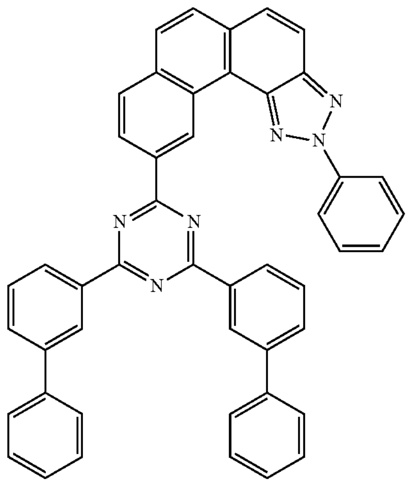
-continued
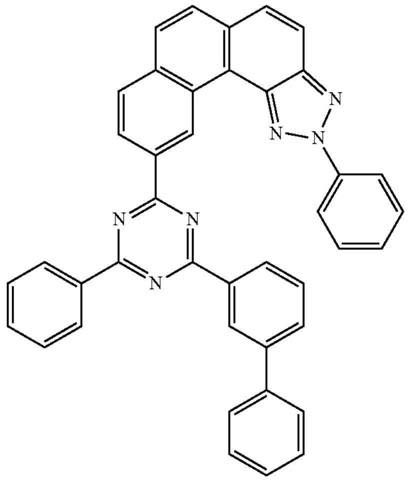
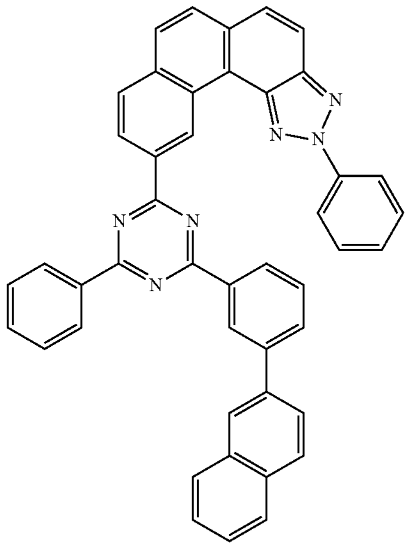
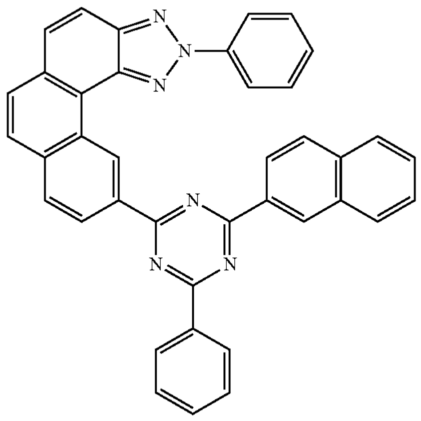

-continued
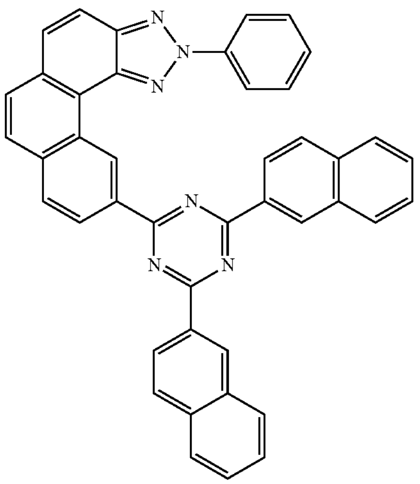
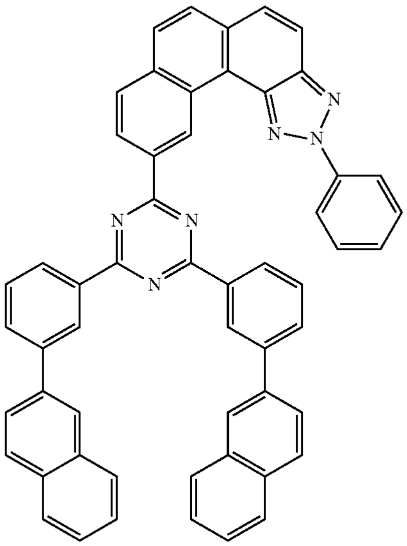
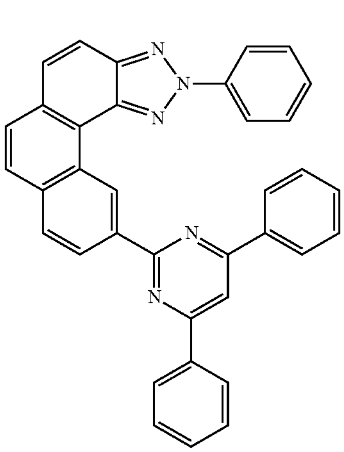
-continued
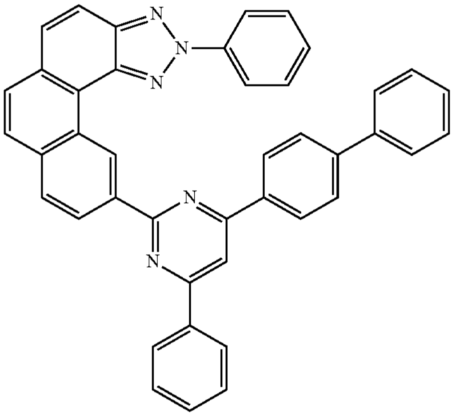
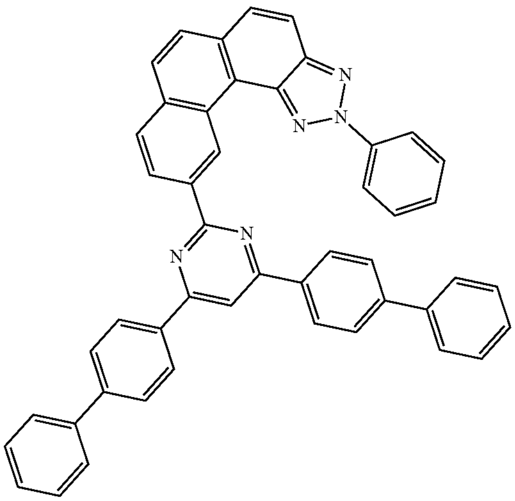
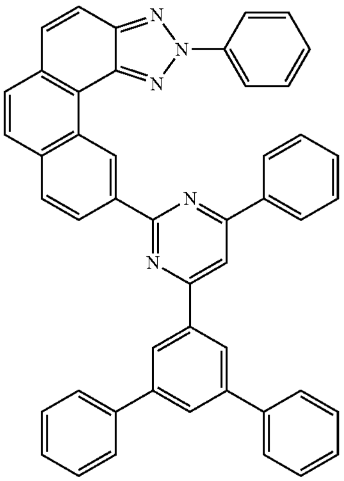

-continued
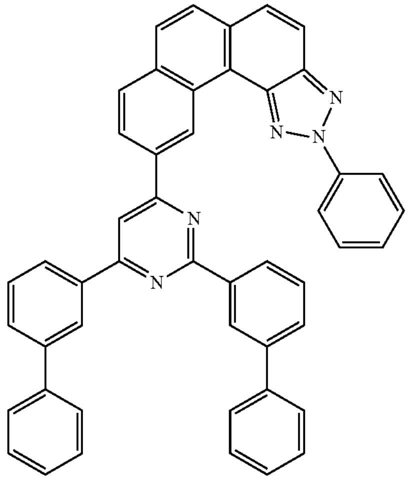
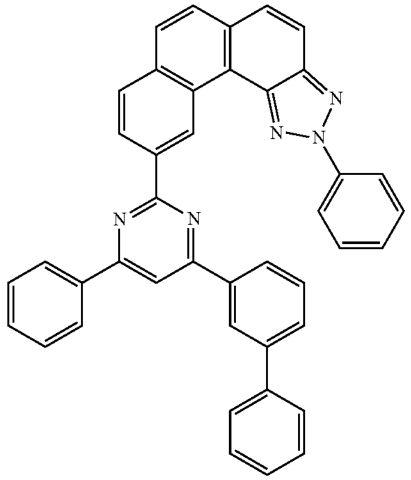
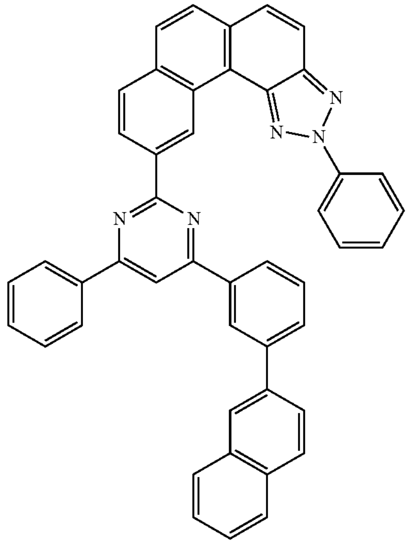
-continued
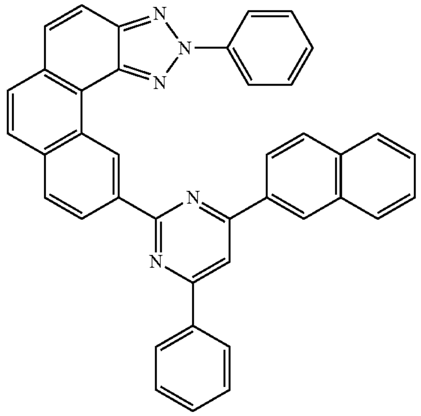
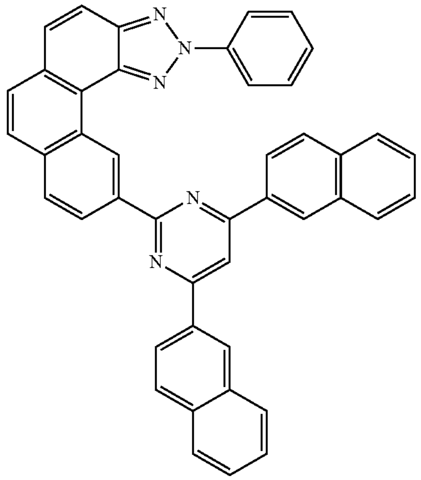
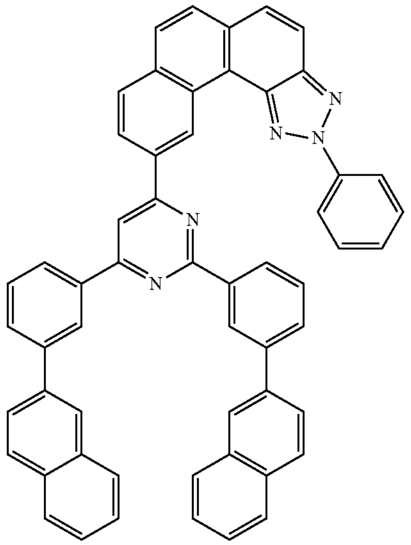

-continued
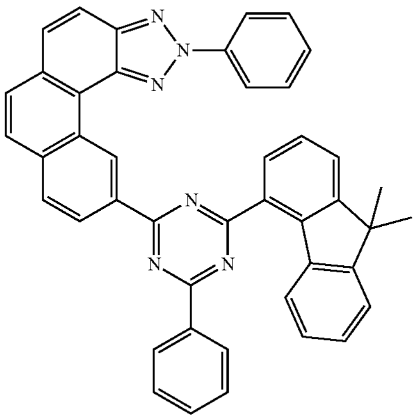
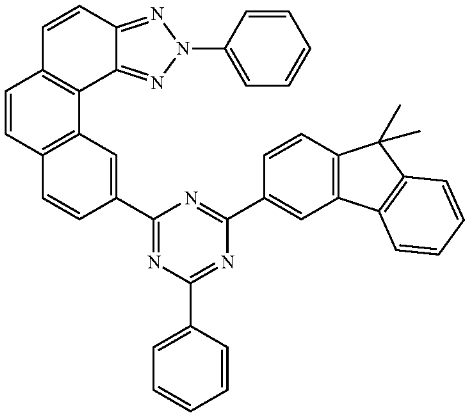
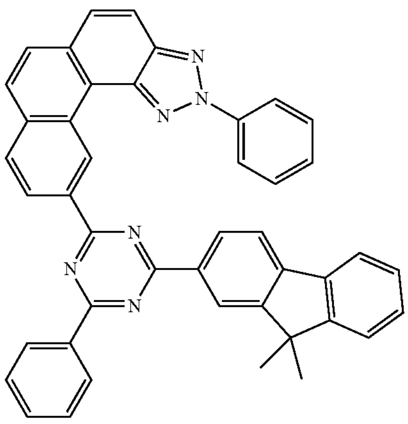
-continued
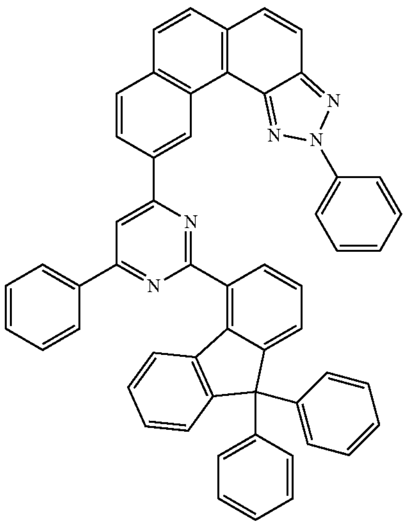
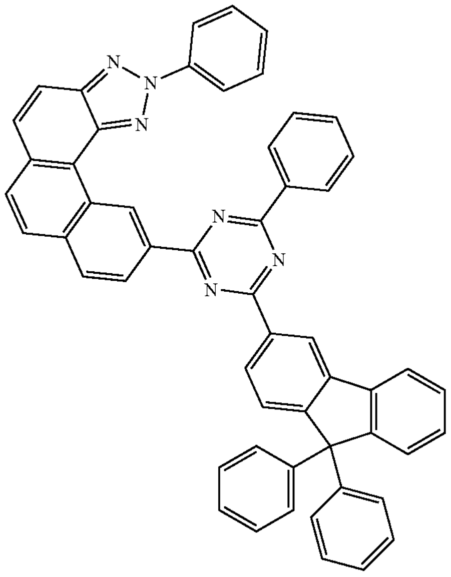
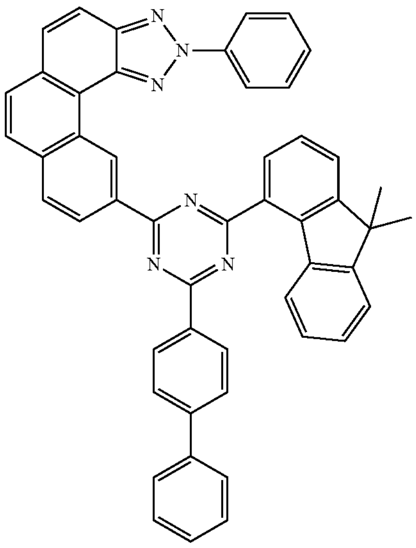

-continued
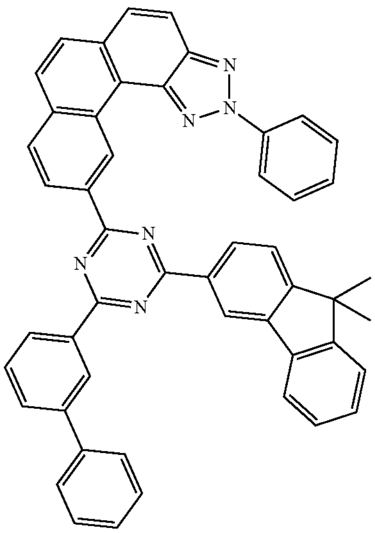
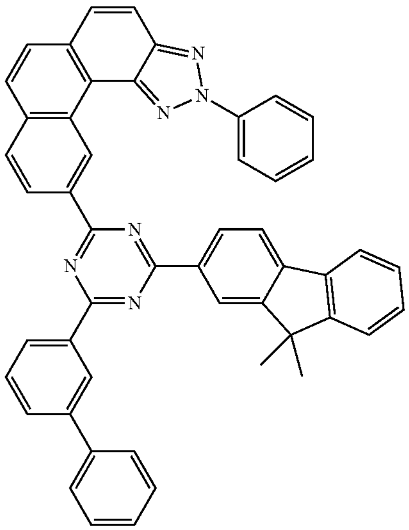
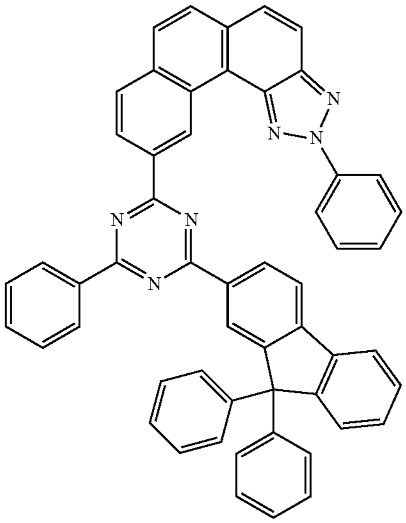
-continued
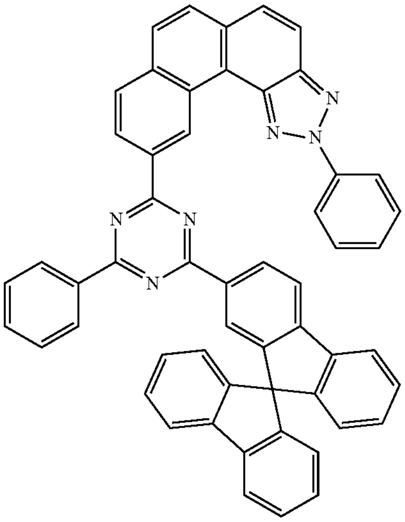
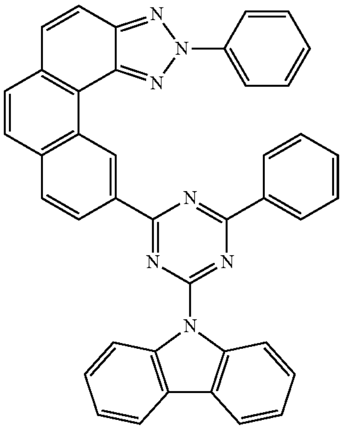
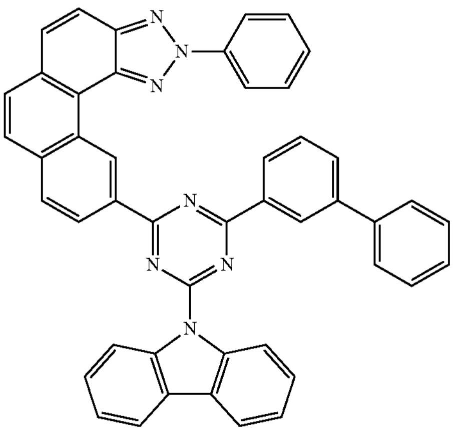

-continued
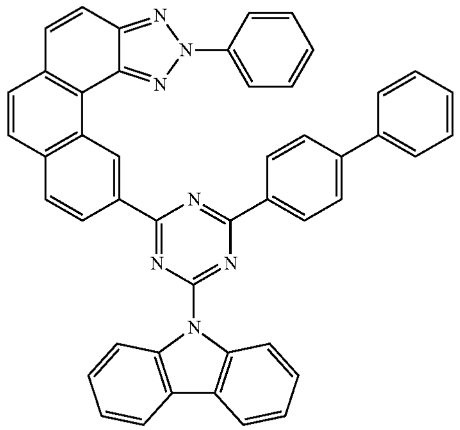
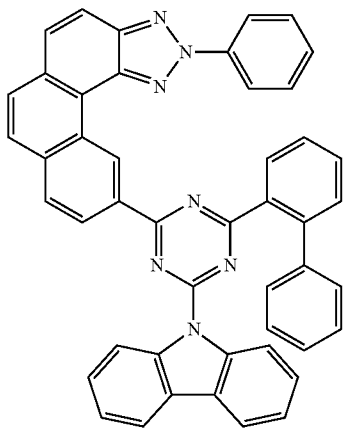
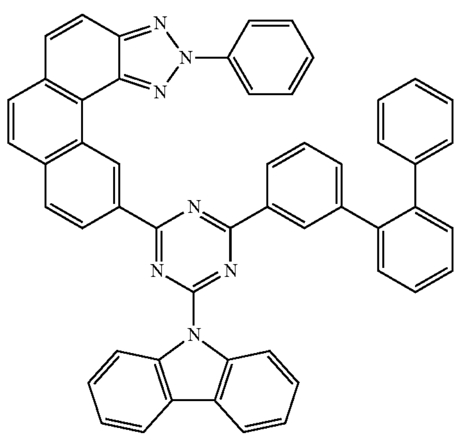
-continued
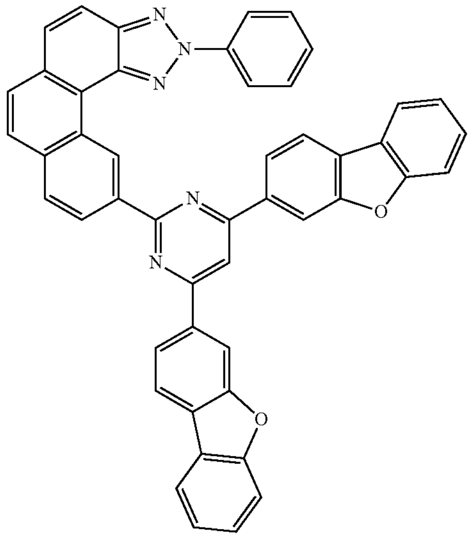
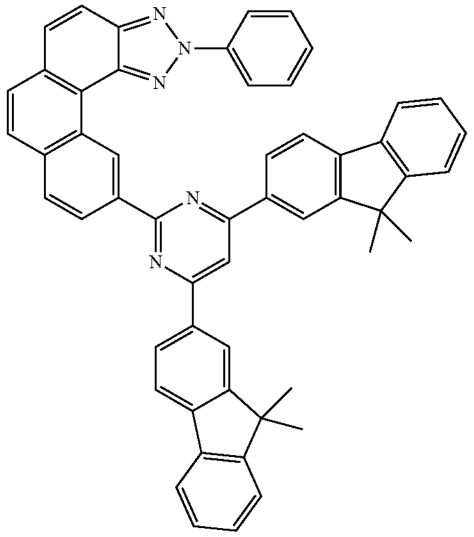
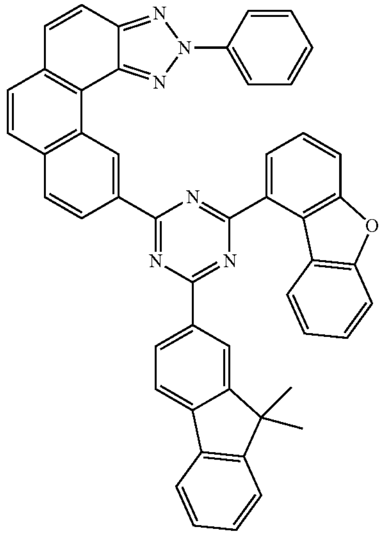

-continued
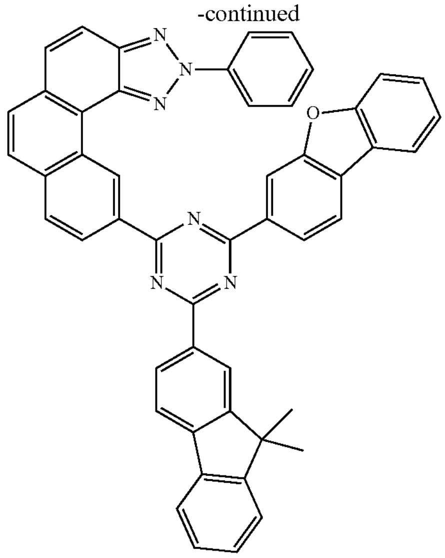
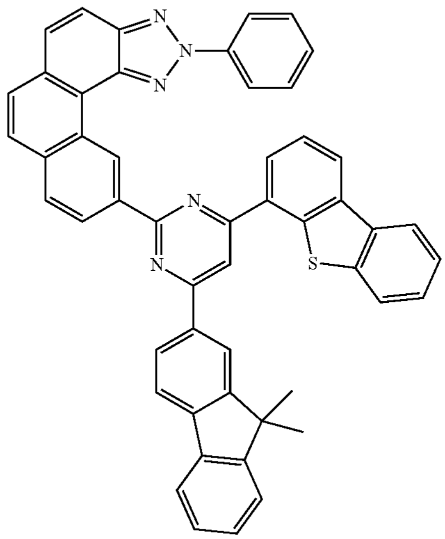
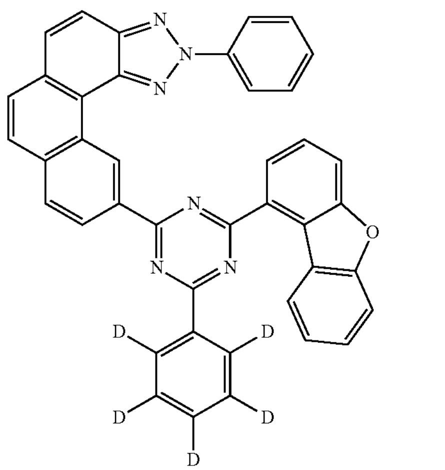
-continued
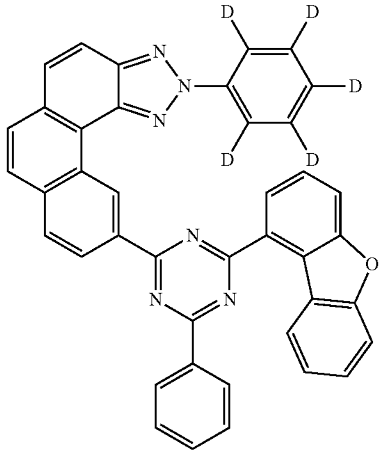
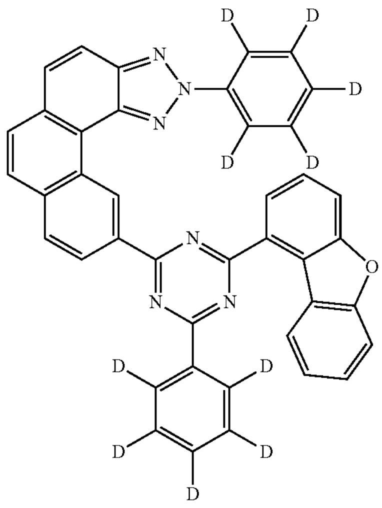
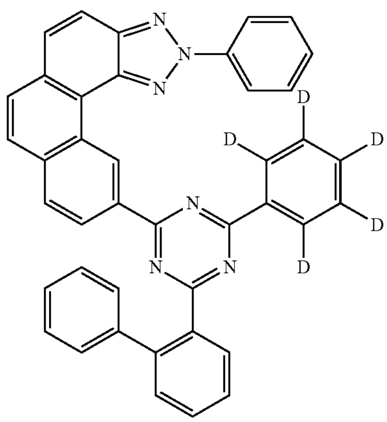

-continued
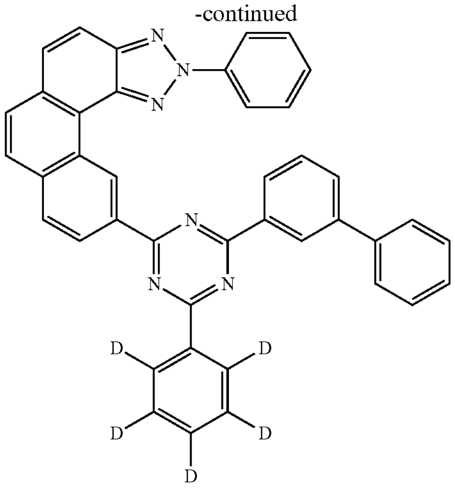
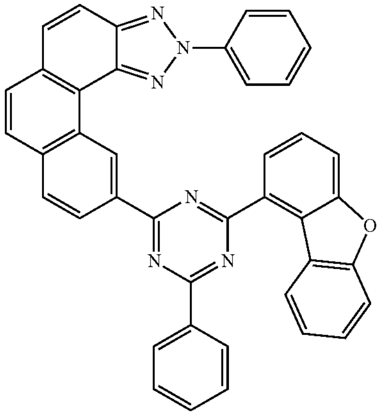
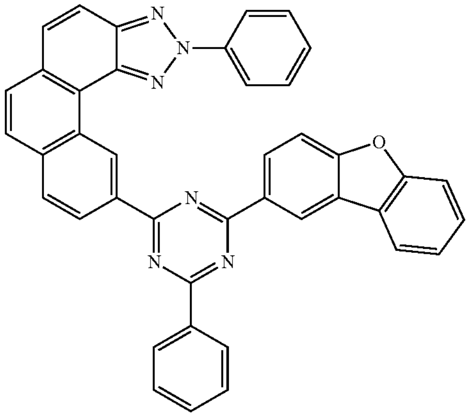
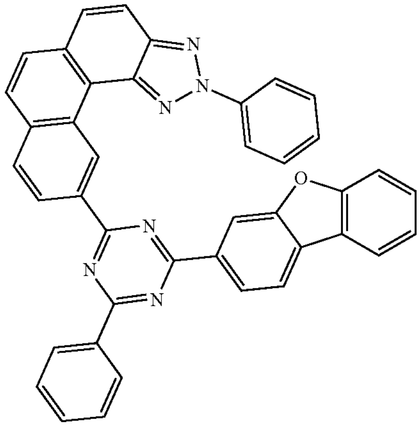
-continued
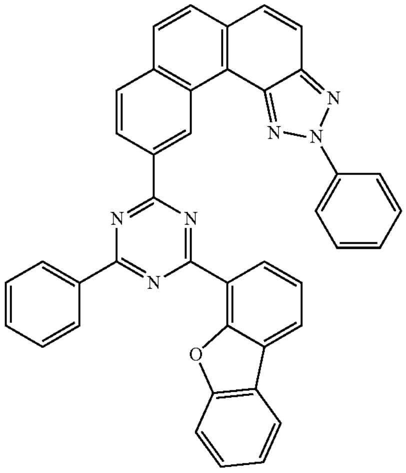
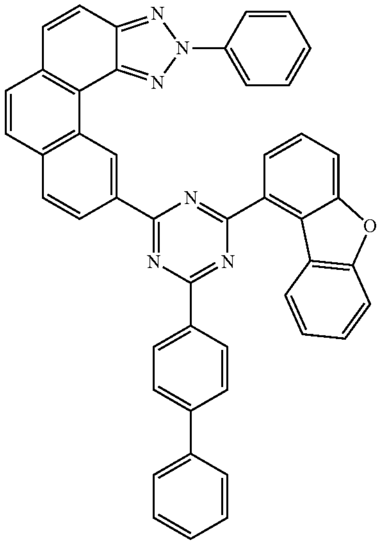
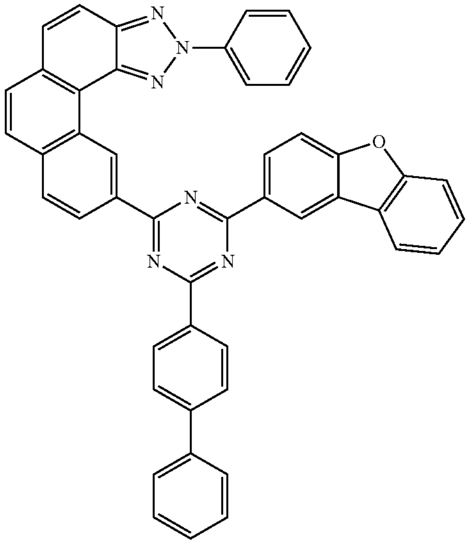

-continued
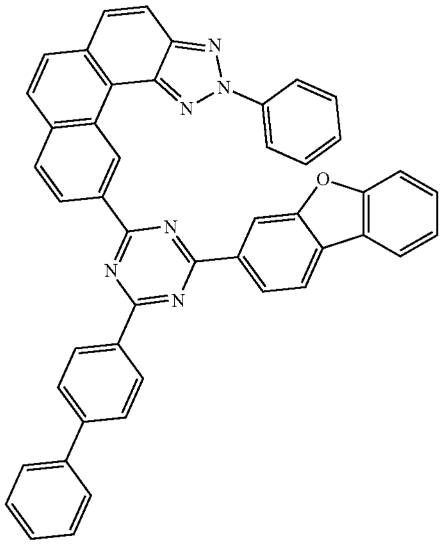
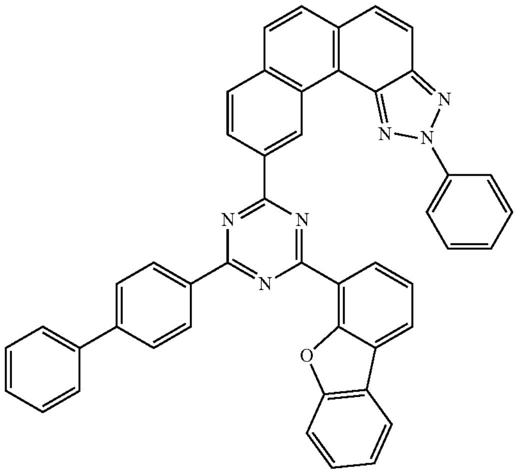
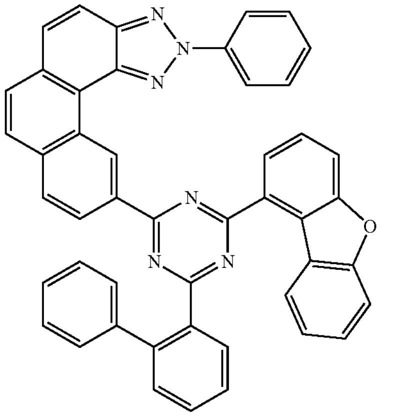
-continued
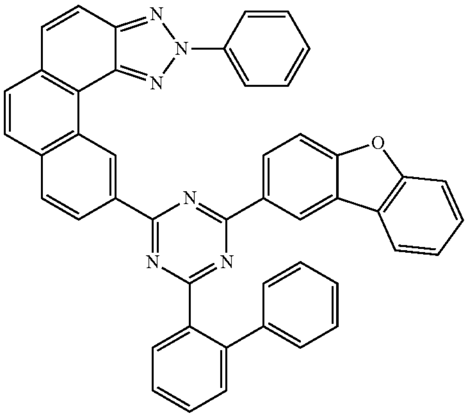
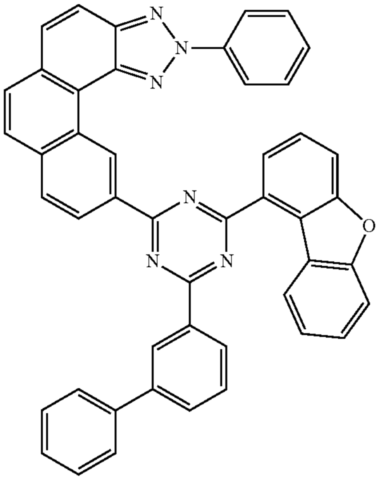
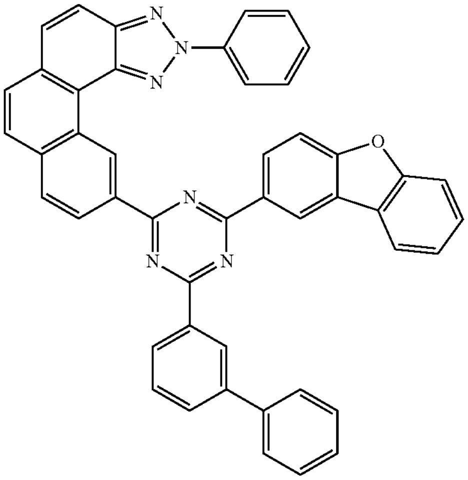

-continued
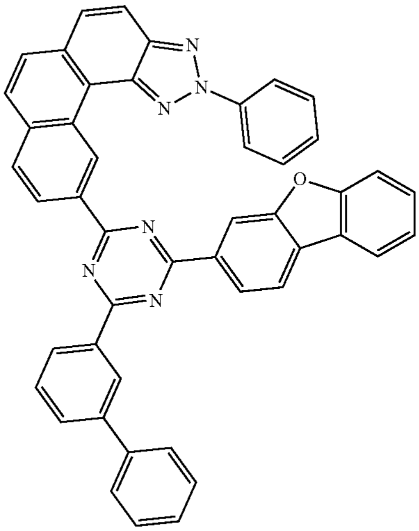 [SMILES: c1ccc(-c2cccc(-c3nc(-c4ccc5c(c4)oc4ccccc45)nc(-c4ccc5ccc6ccc7nn(-c8ccccc8)nc7c6c5c4)n3)c2)cc1]
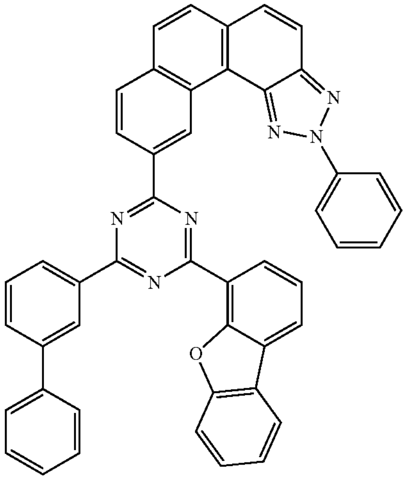
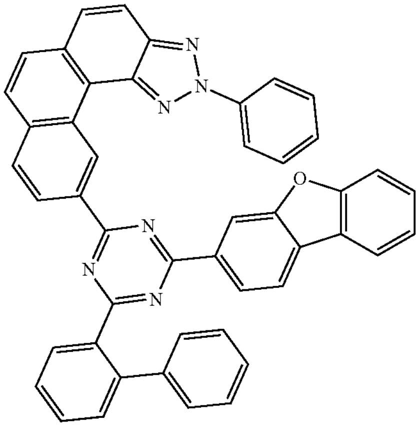
-continued
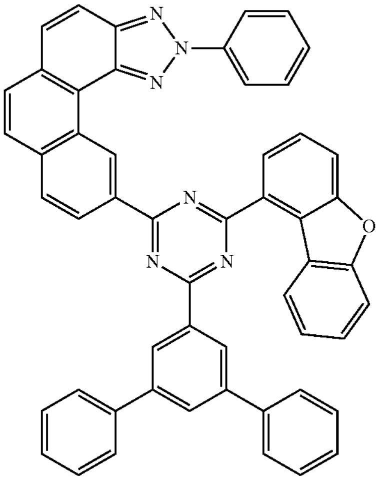
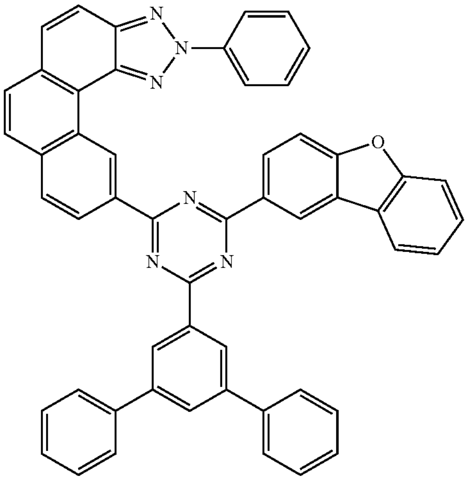
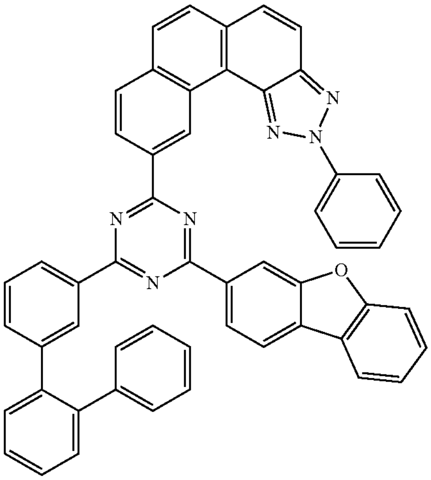

-continued
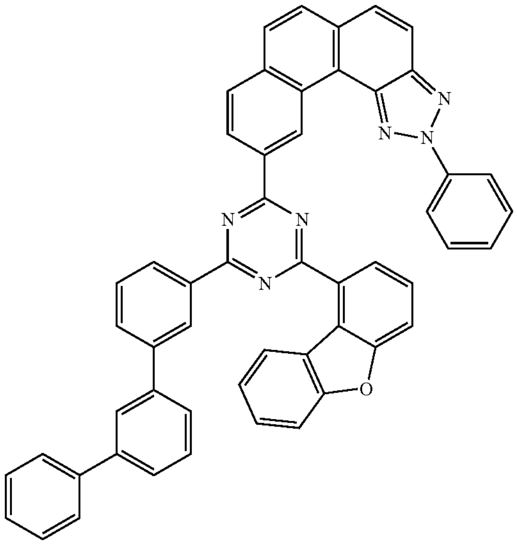
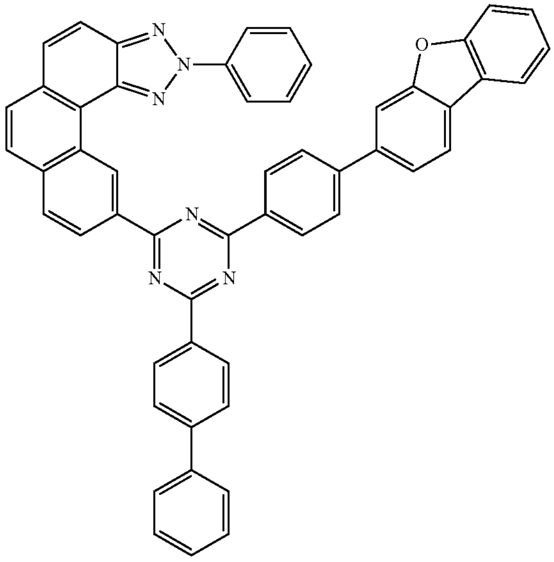
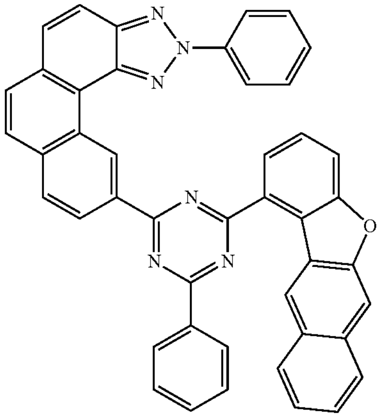
-continued
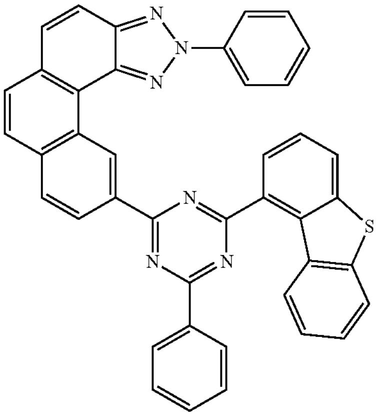
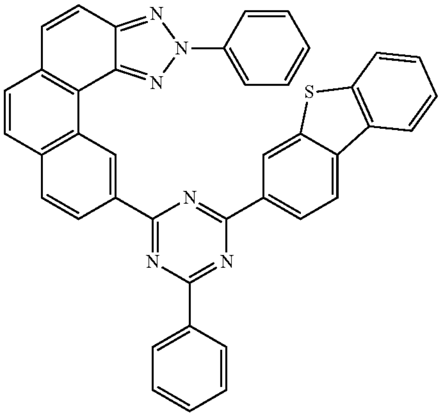
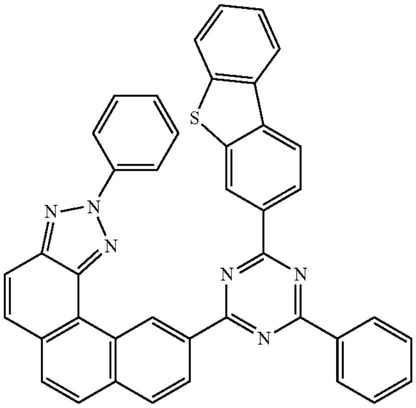
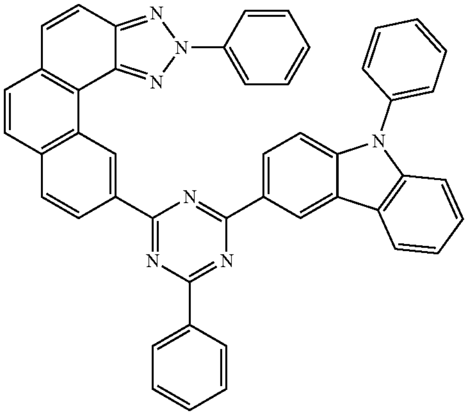

-continued
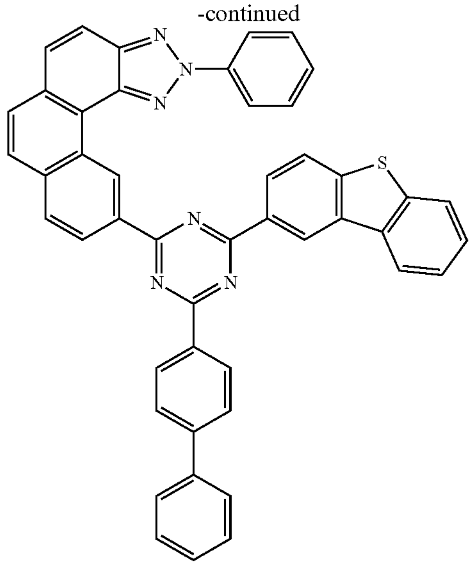
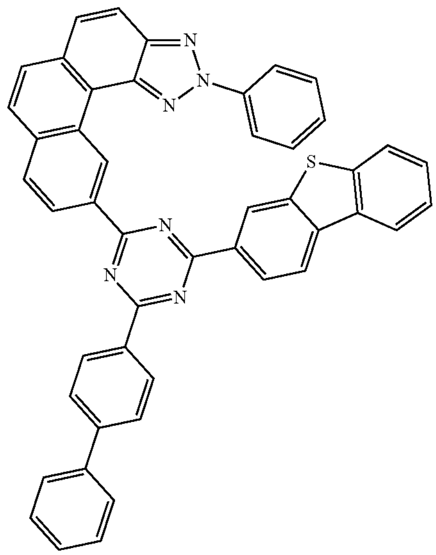 [SMILES: c1ccc(-c2ccc(-c3nc(-c4ccc5c(c4)sc4ccccc45)nc(-c4ccc5ccc6ccc7nn(-c8ccccc8)nc7c6c5c4)n3)cc2)cc1]
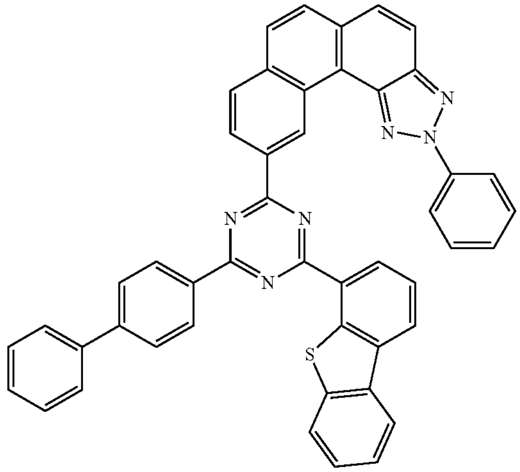
-continued
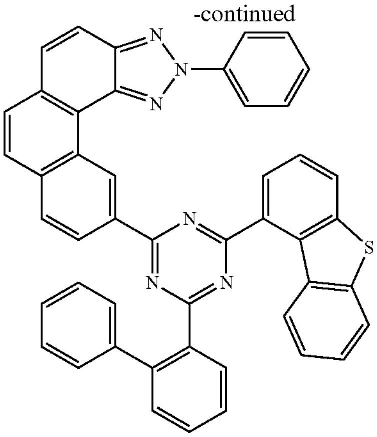
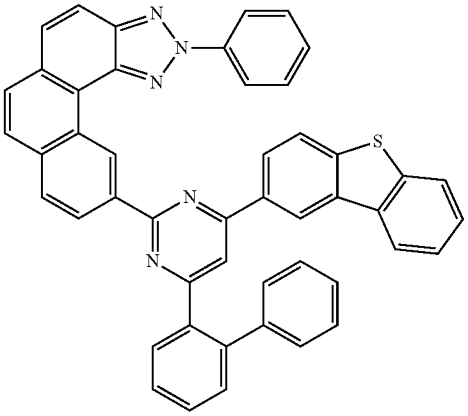
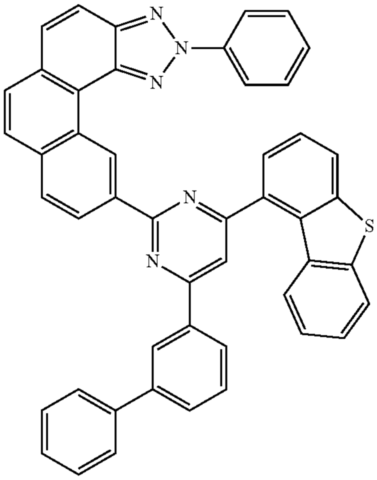

-continued
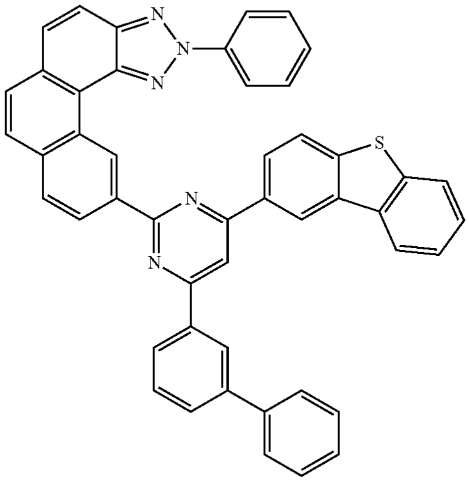
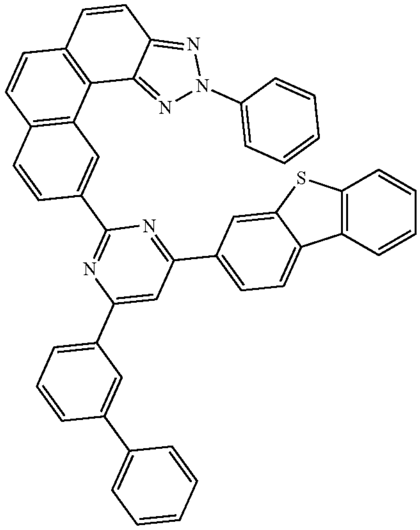
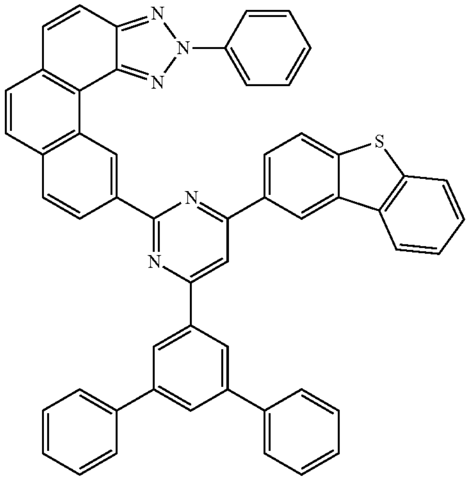
-continued
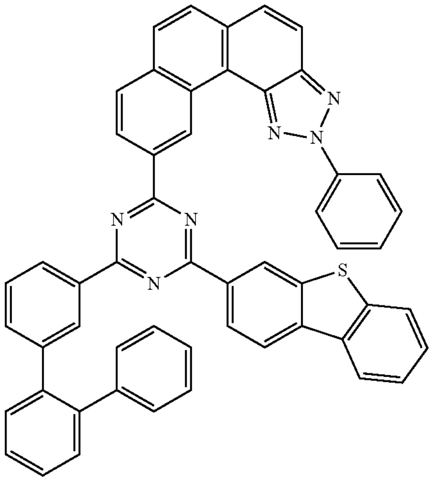
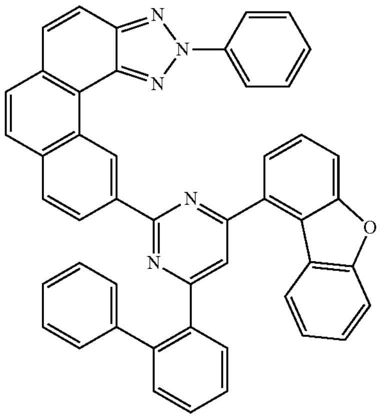
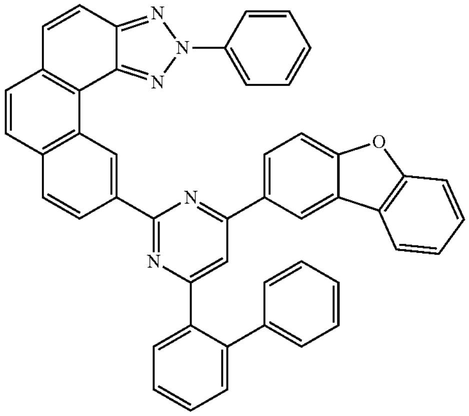

-continued
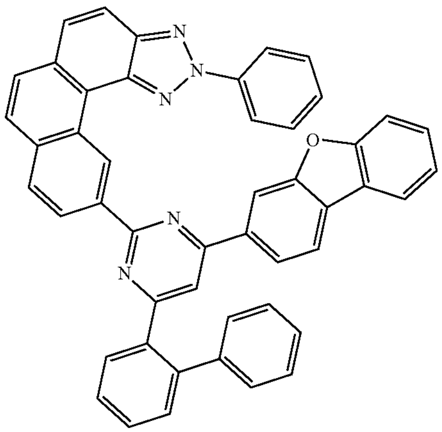
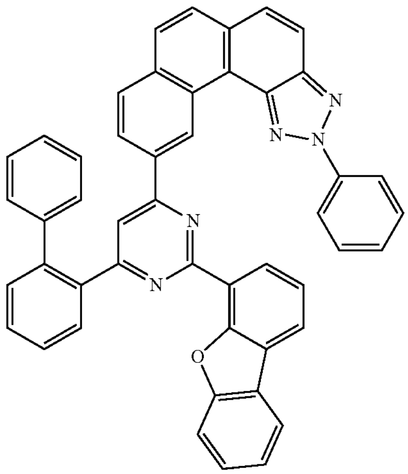
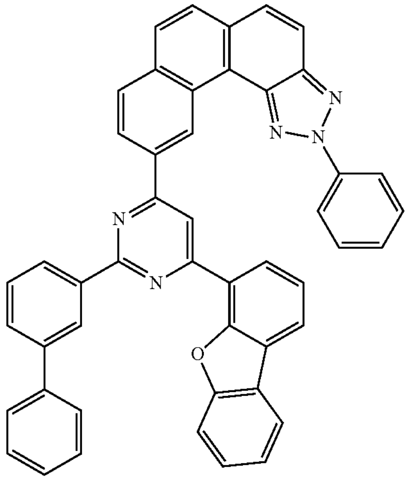
-continued
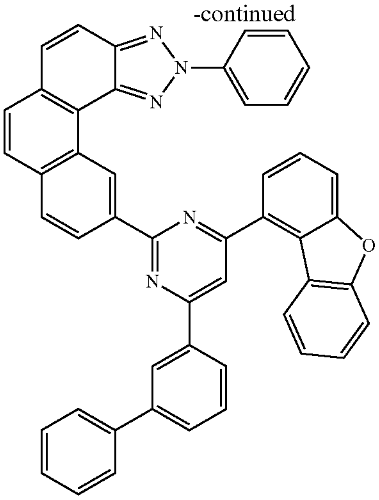
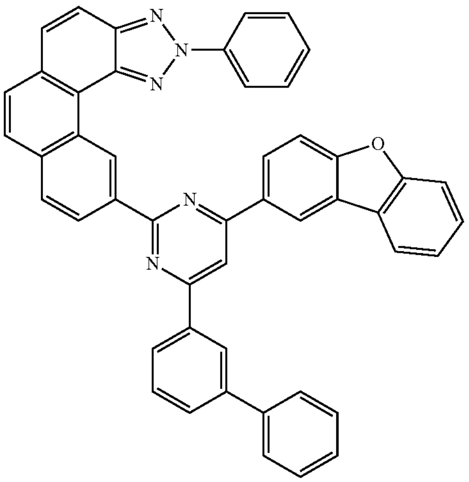
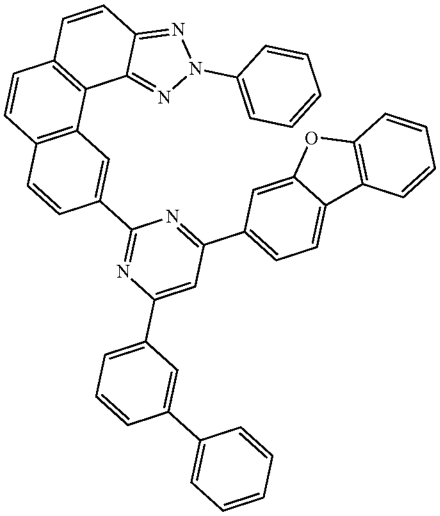

-continued
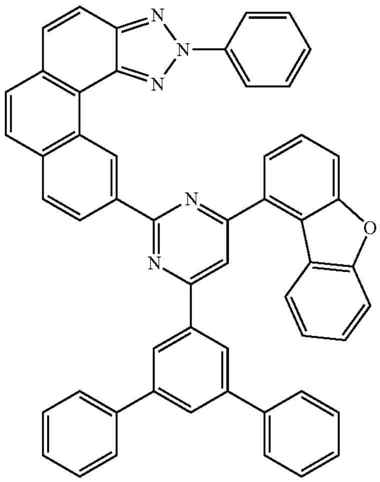
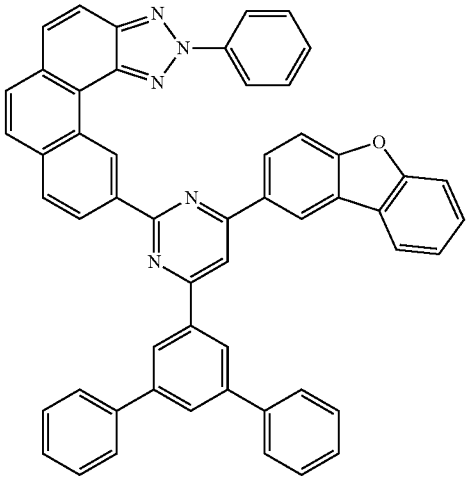
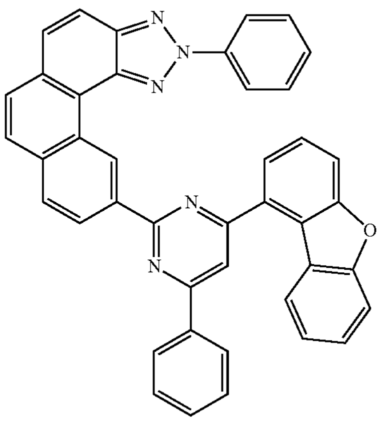
-continued
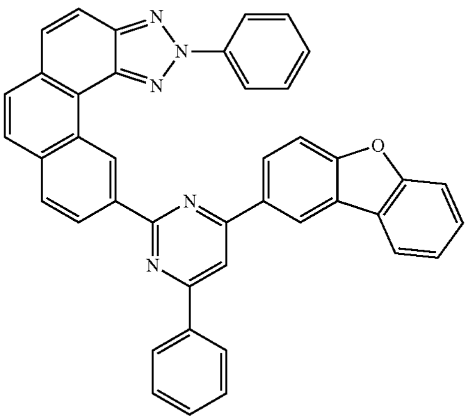
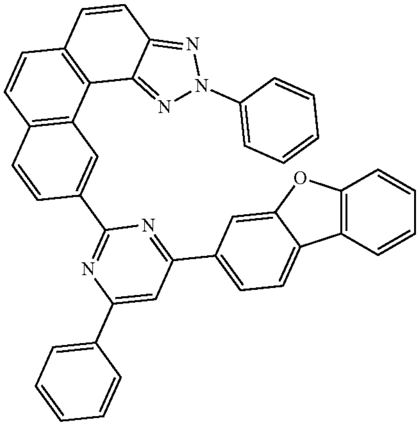
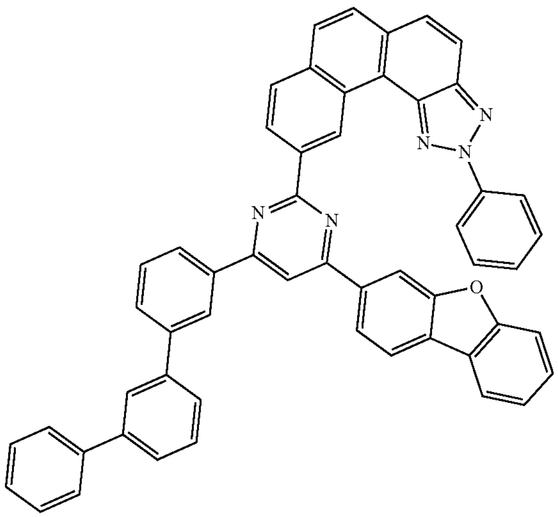

-continued
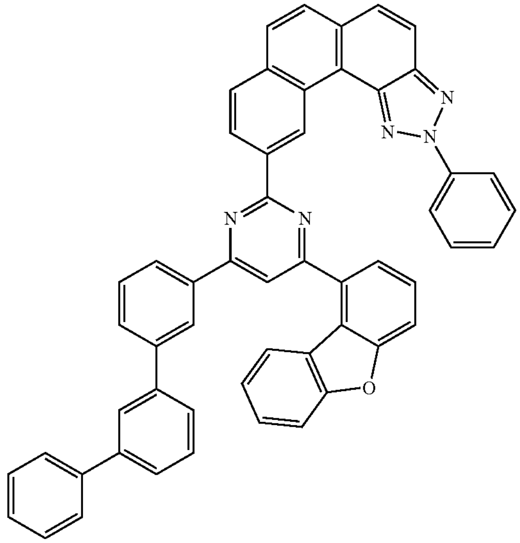
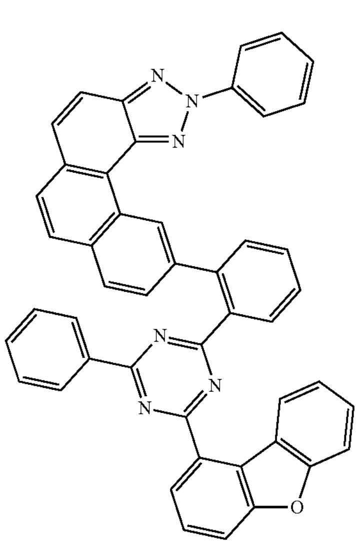
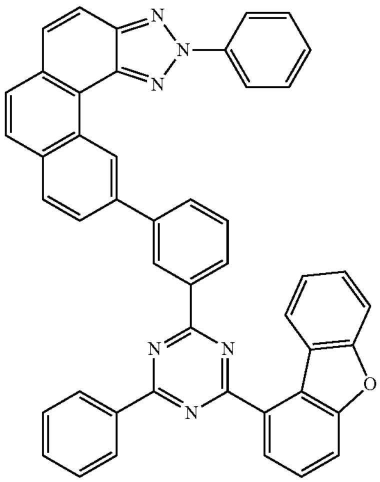
-continued
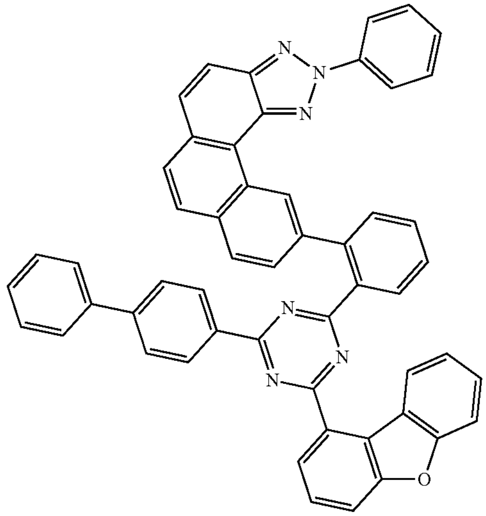
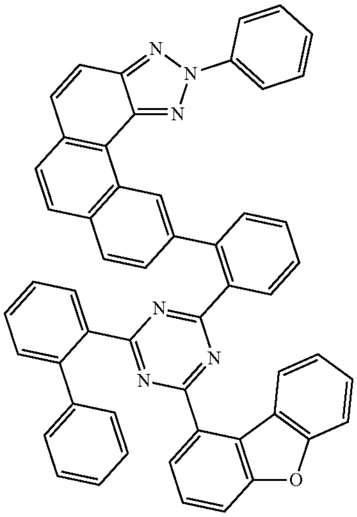
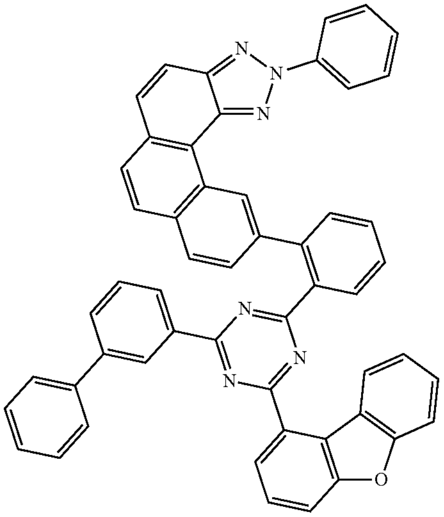

-continued
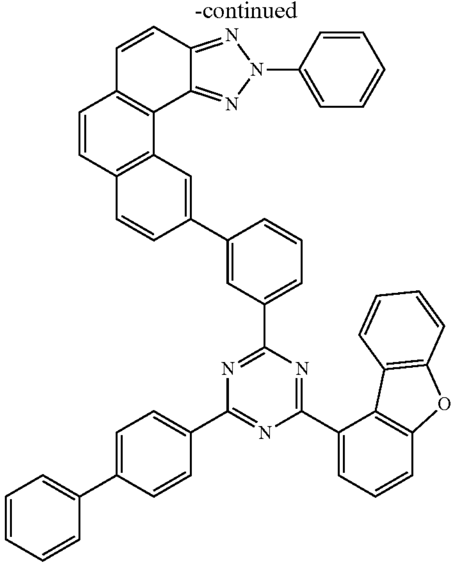
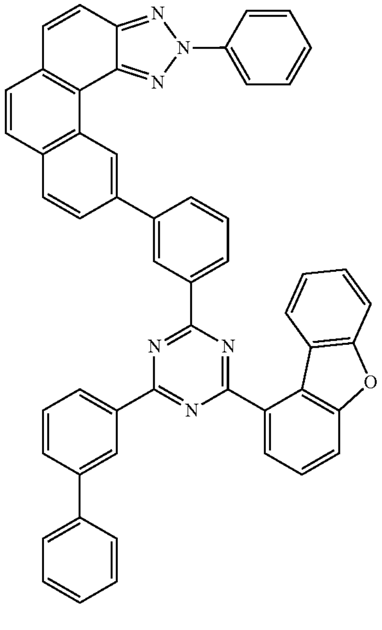
-continued
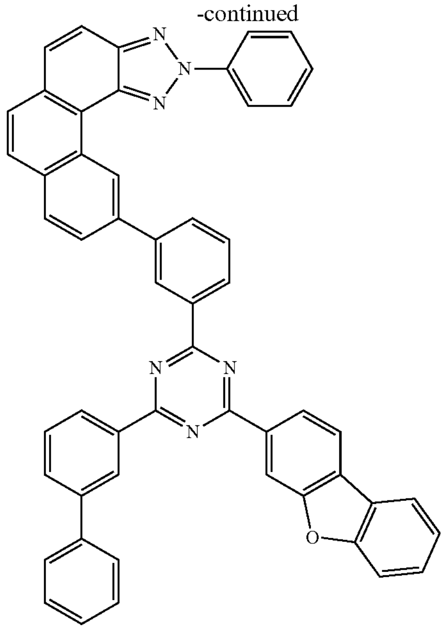
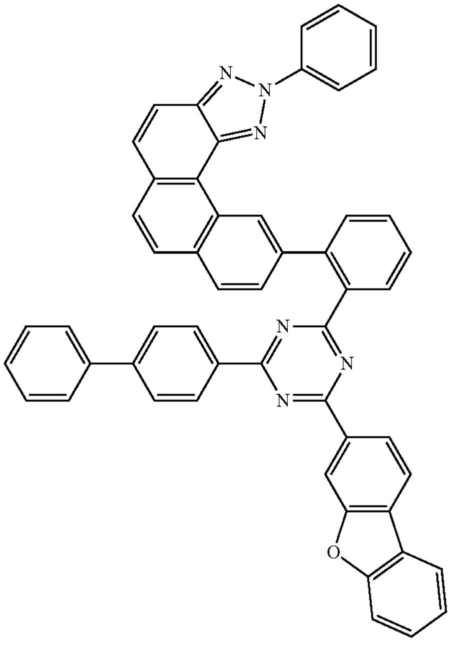

-continued
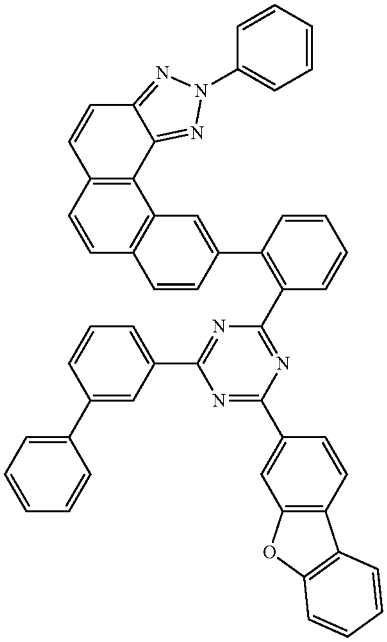
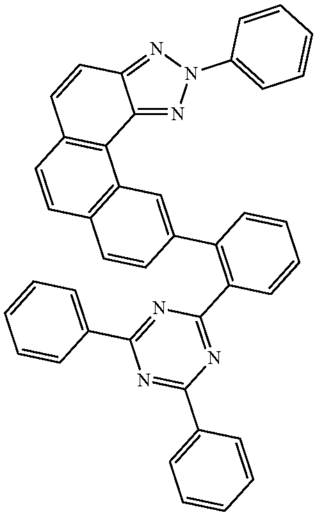
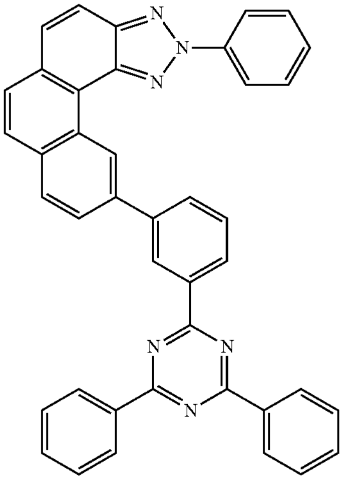
-continued
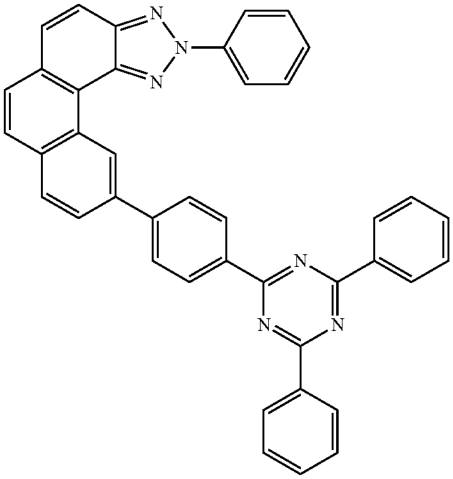
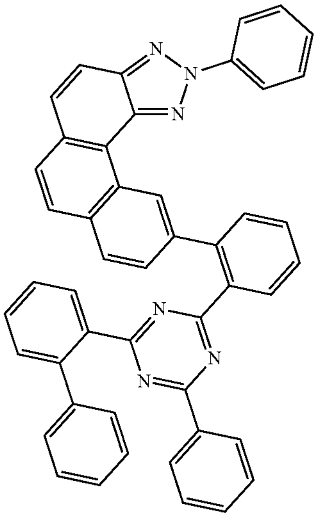
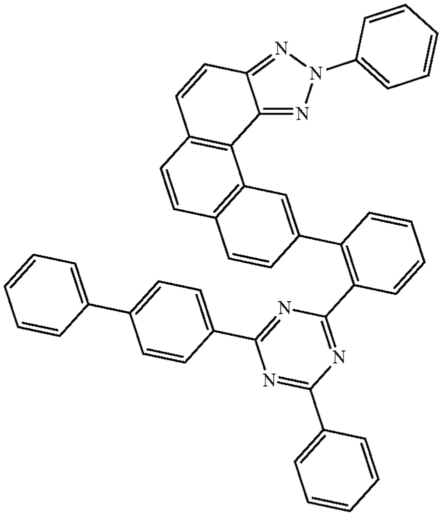 [SMILES: c1ccc(-c2ccc(-c3nc(-c4ccccc4)nc(-c4ccccc4-c4ccc5ccc6ccc7nn(-c8ccccc8)nc7c6c5c4)n3)cc2)cc1]

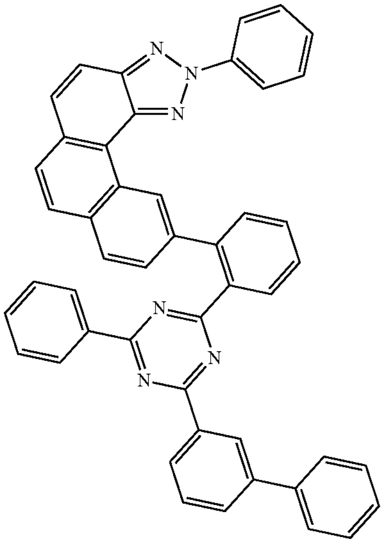
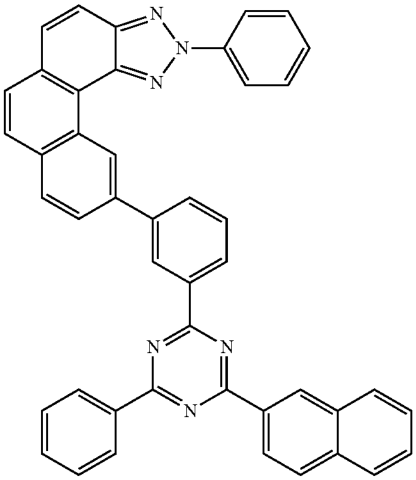
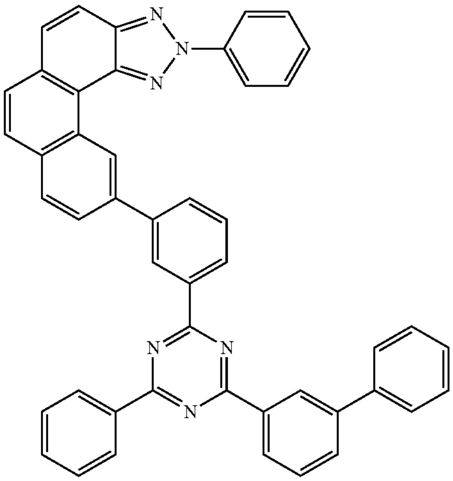
-continued
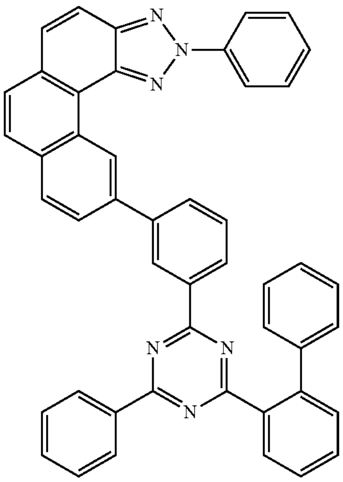
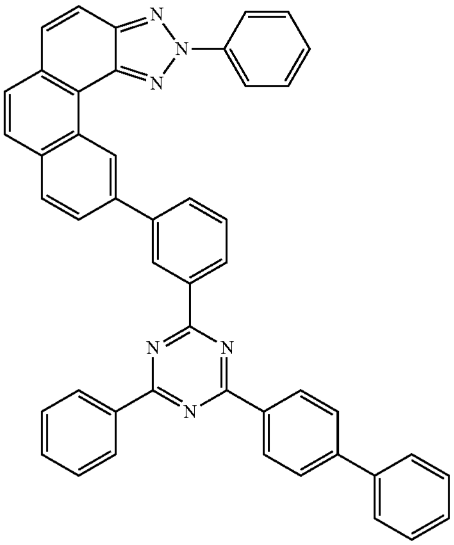
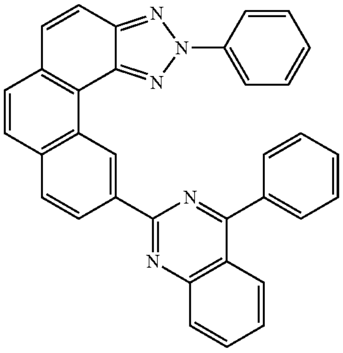

-continued
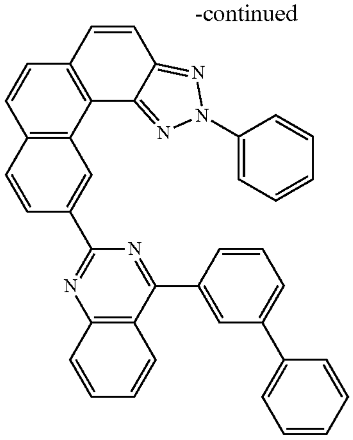
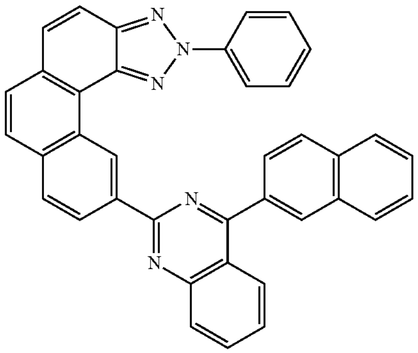
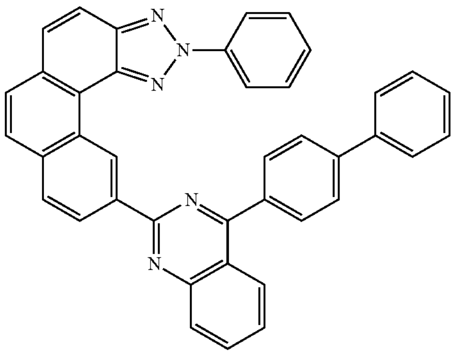
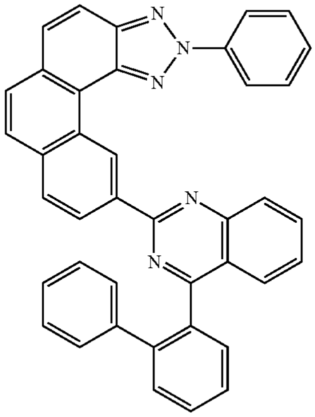
-continued
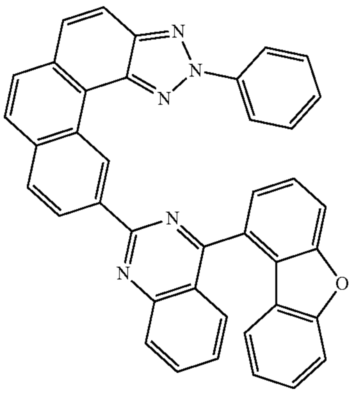
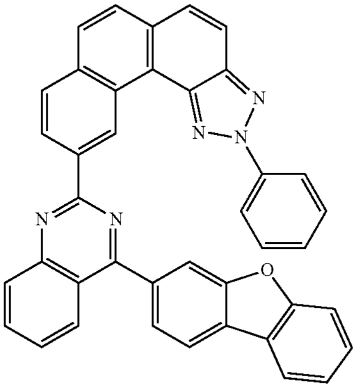
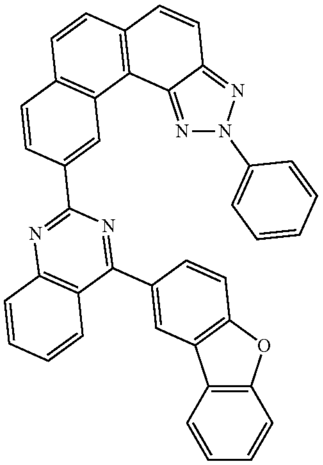
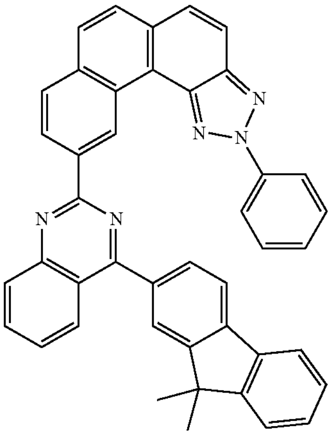

-continued
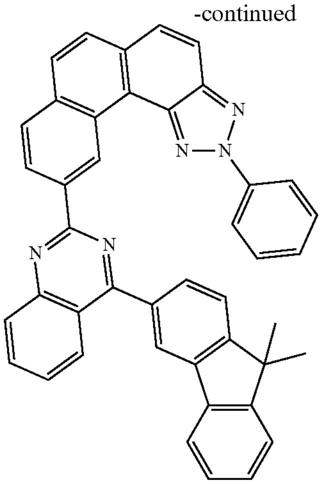
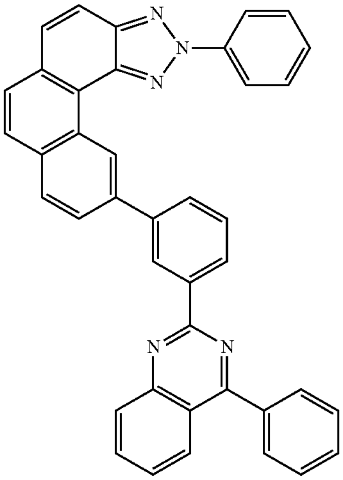
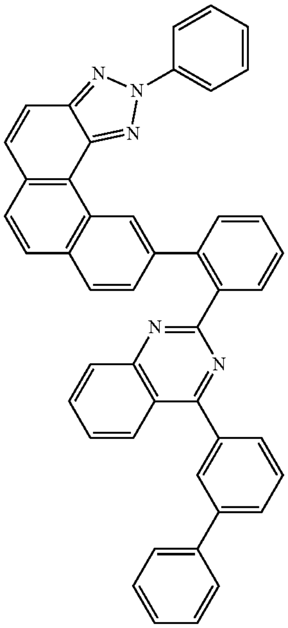
-continued
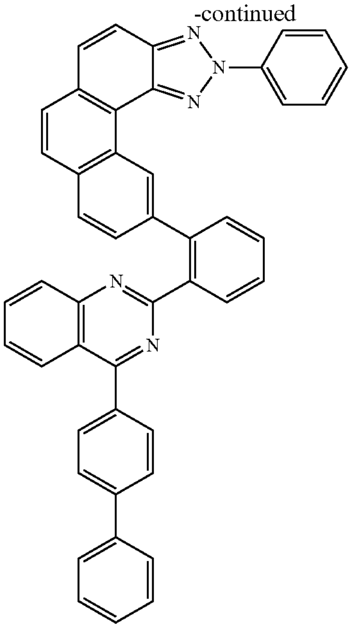
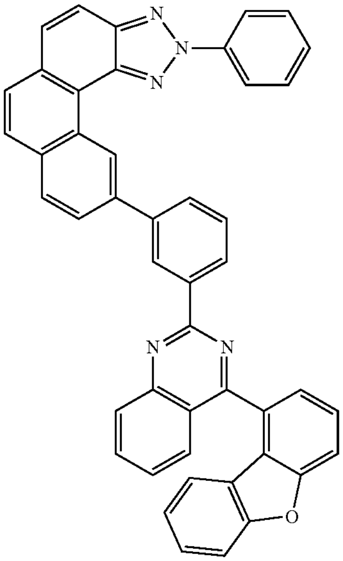
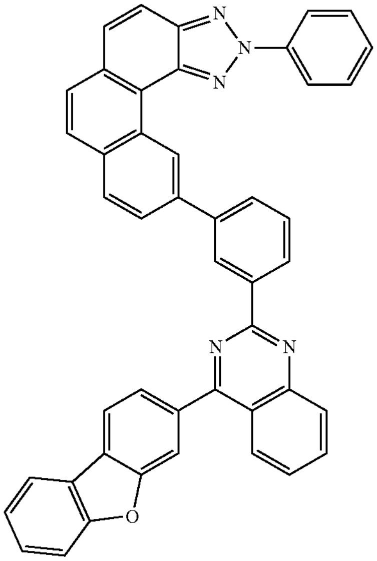

-continued
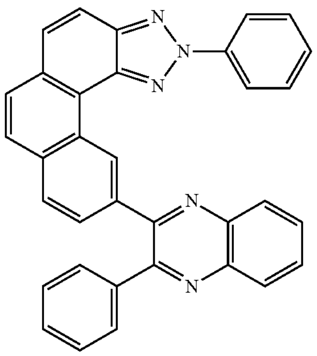
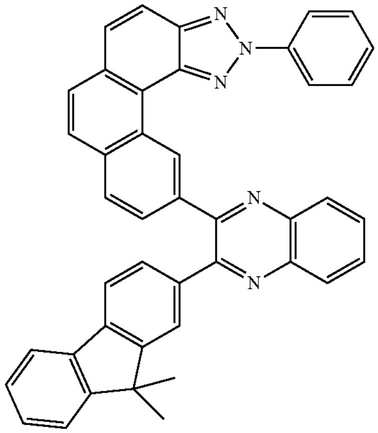
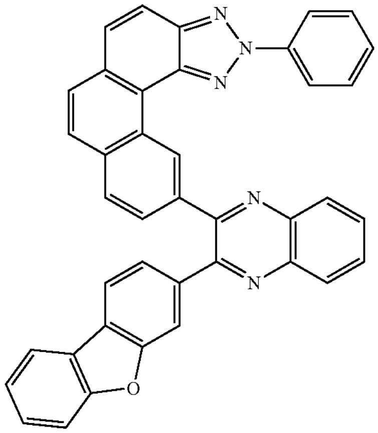
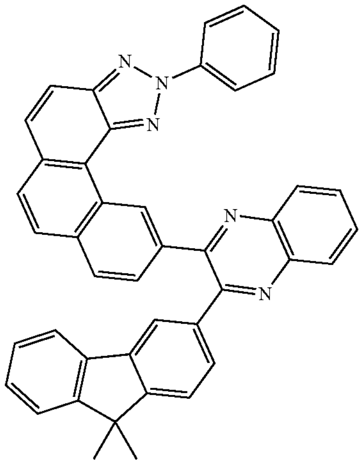
-continued
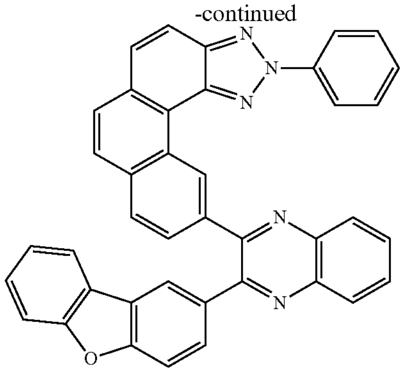
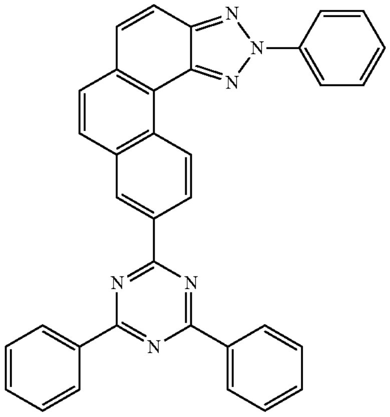
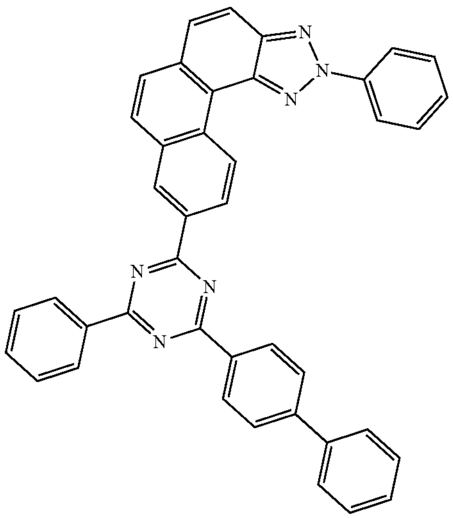

-continued
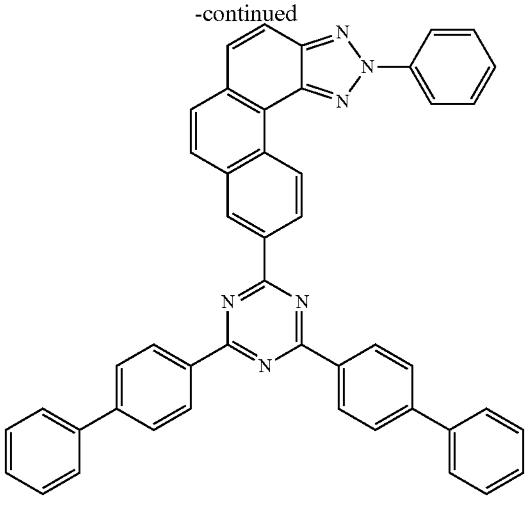
-continued
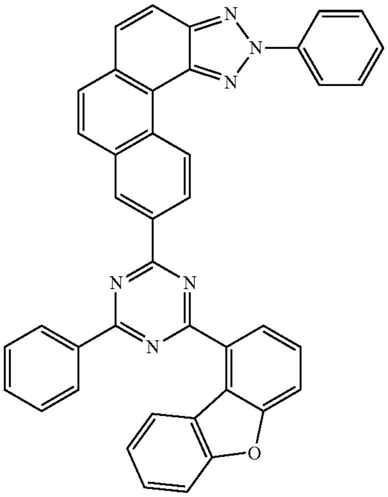
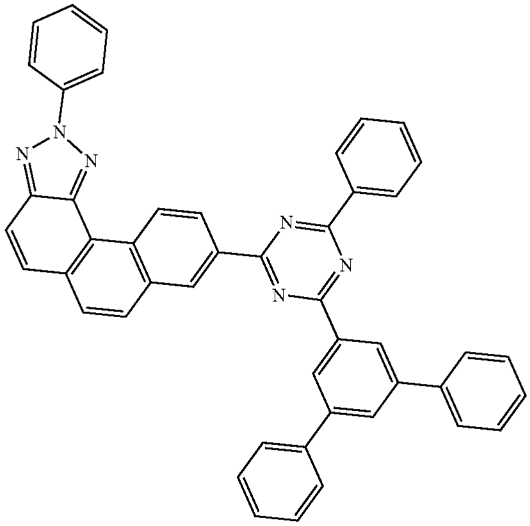
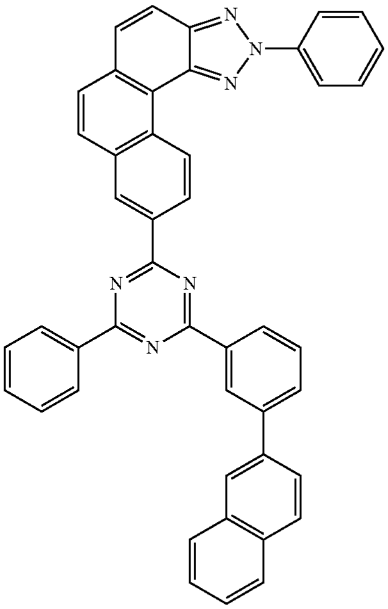
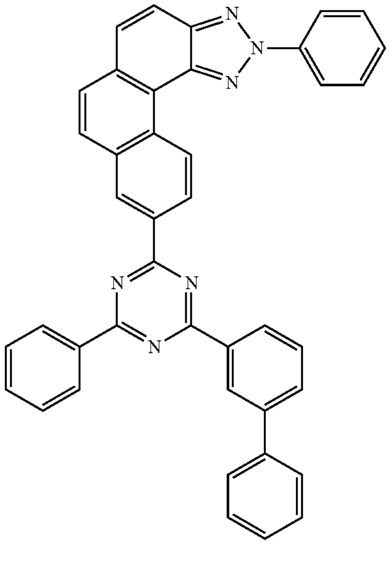
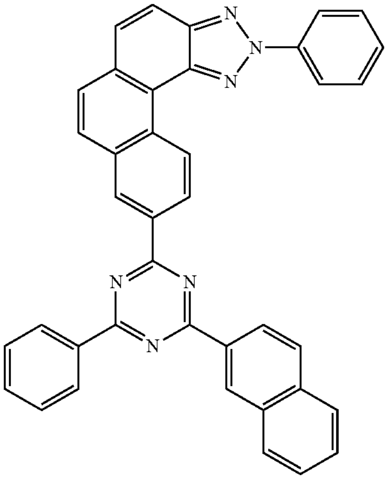

-continued
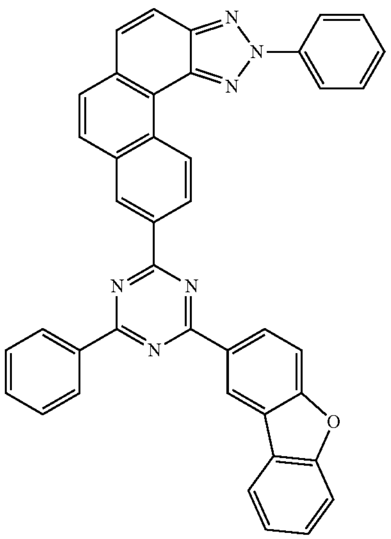
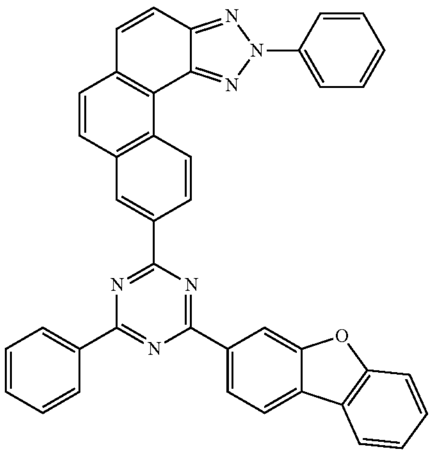
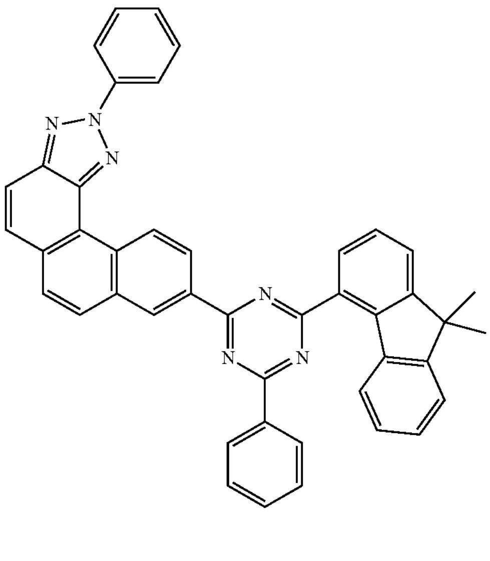
-continued
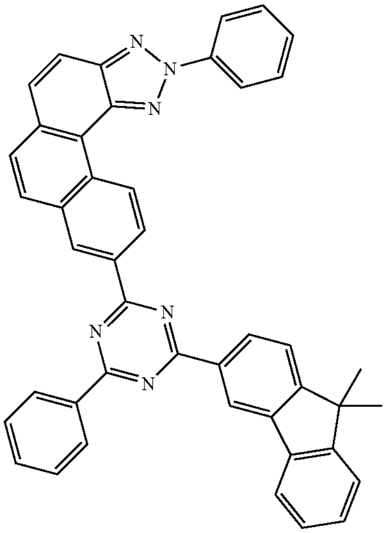
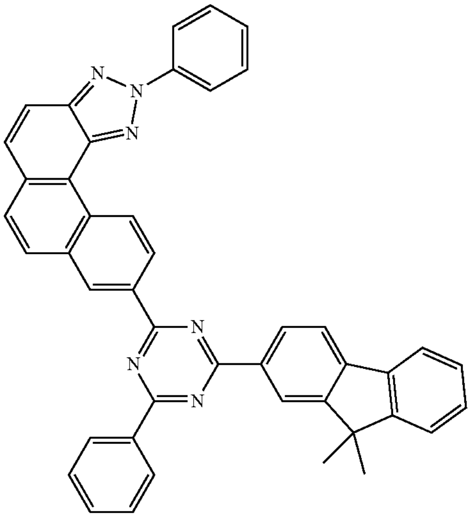
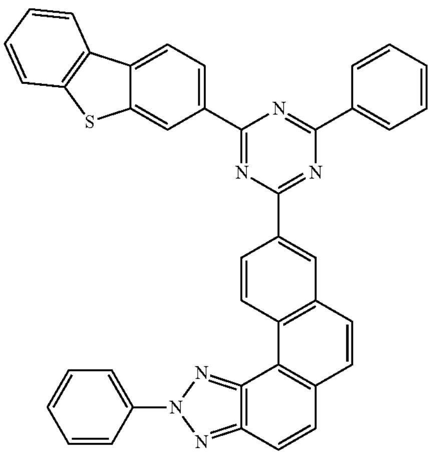

-continued
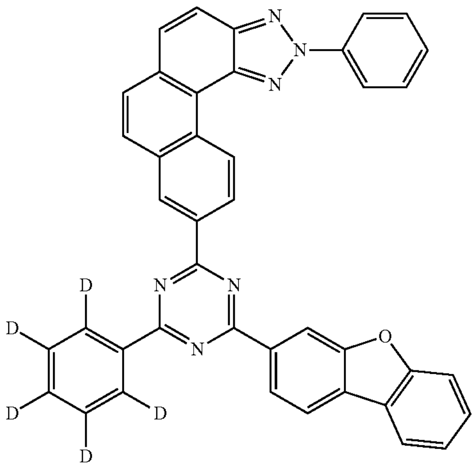
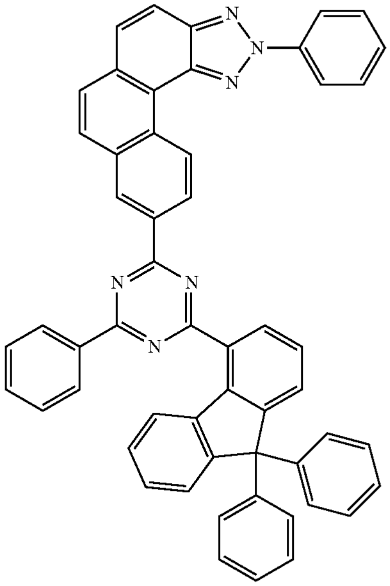
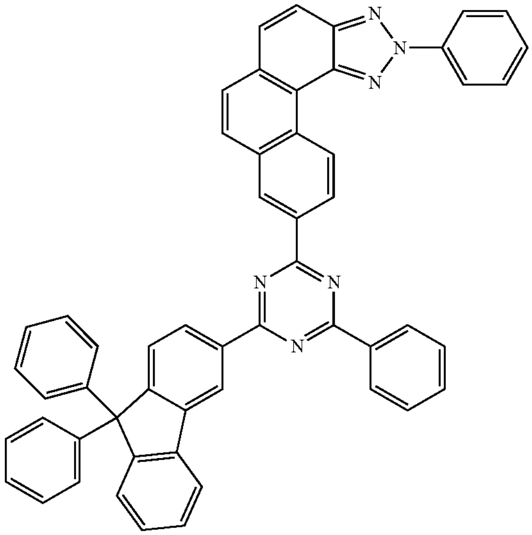
-continued
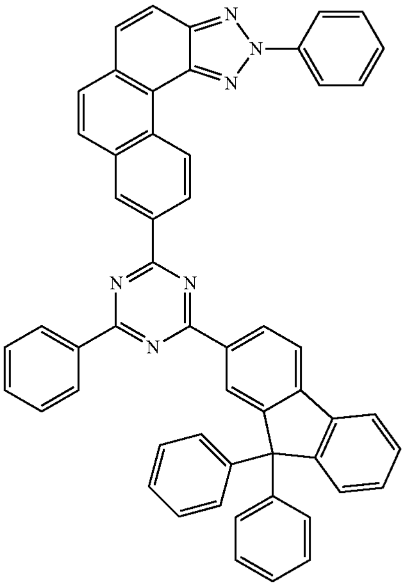
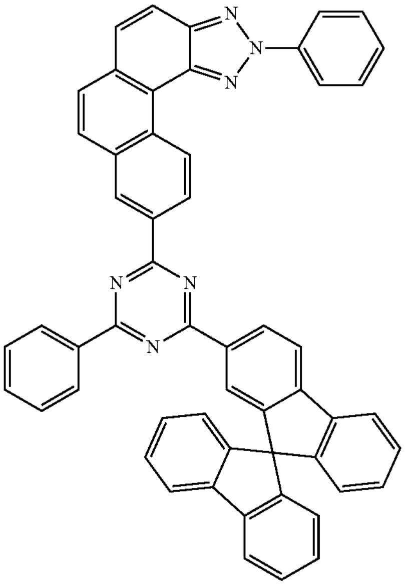

-continued
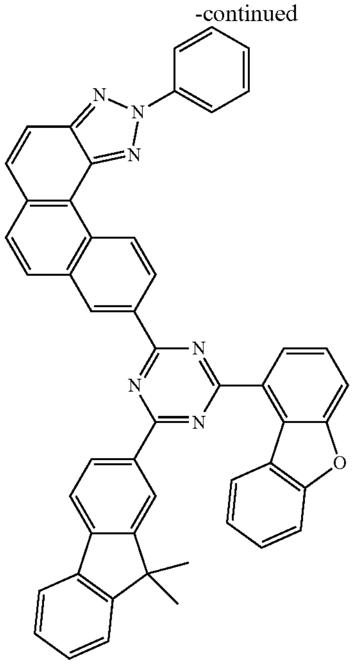
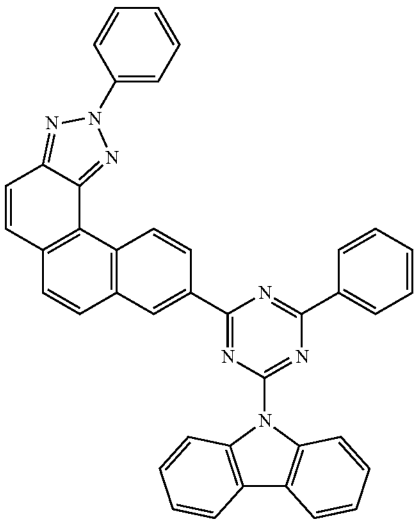
-continued
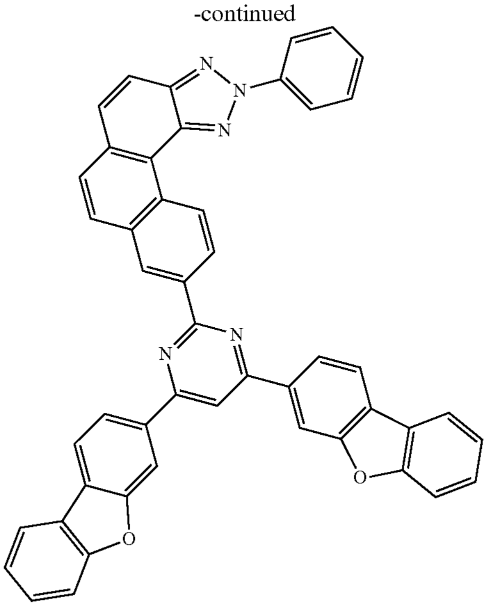
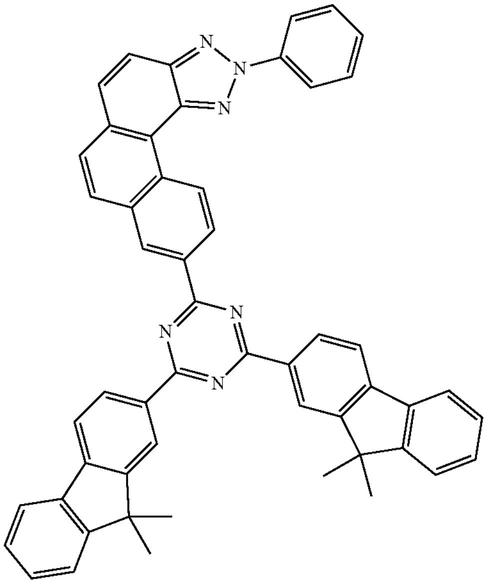
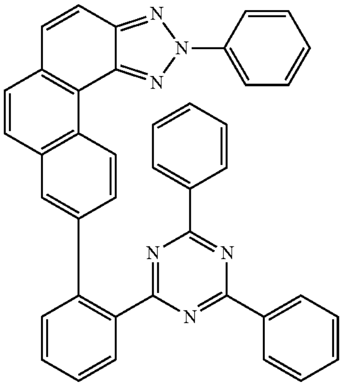

-continued
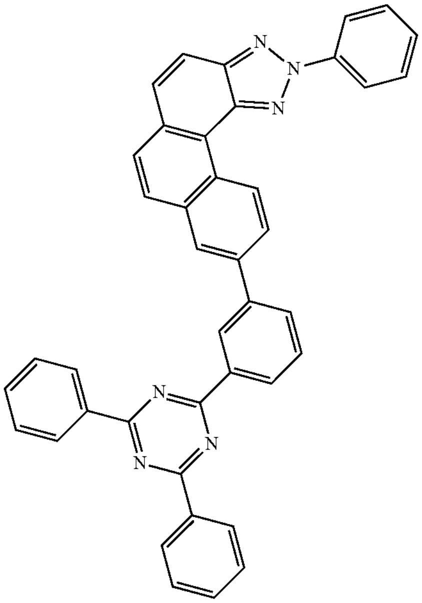
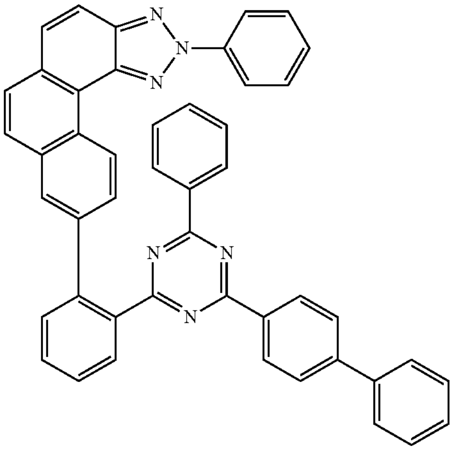
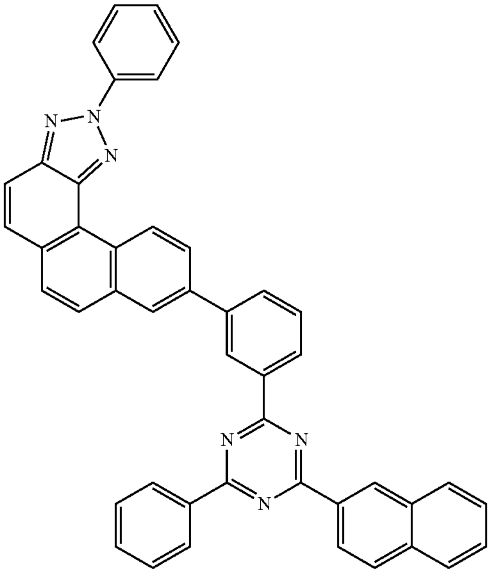
-continued
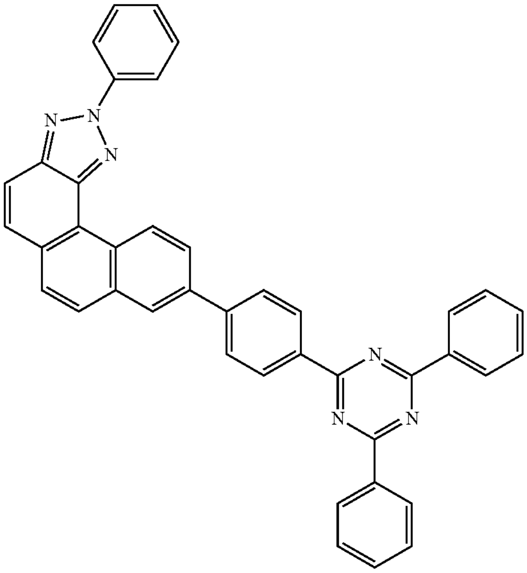
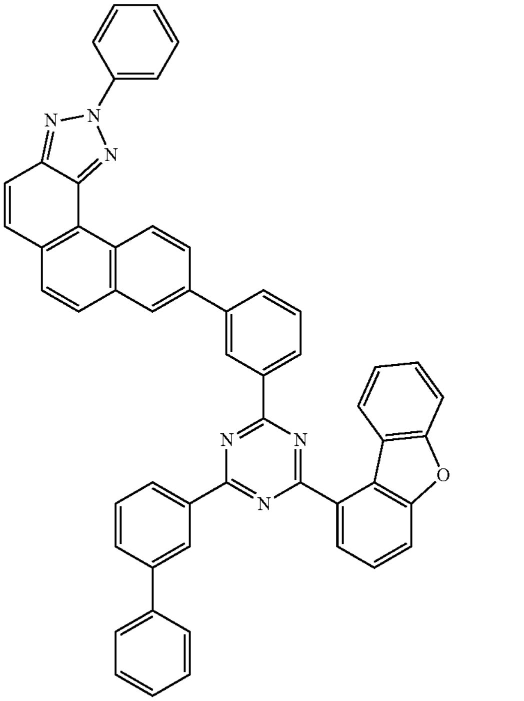

-continued
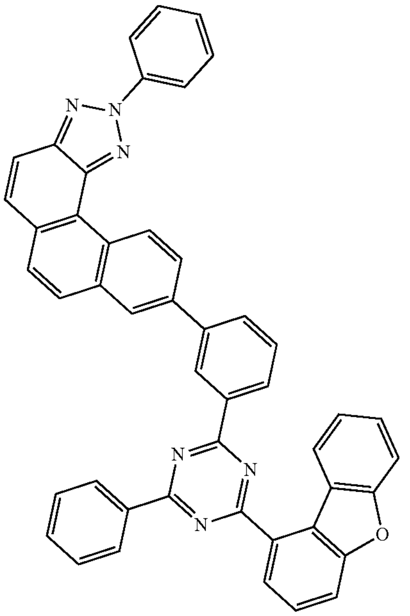
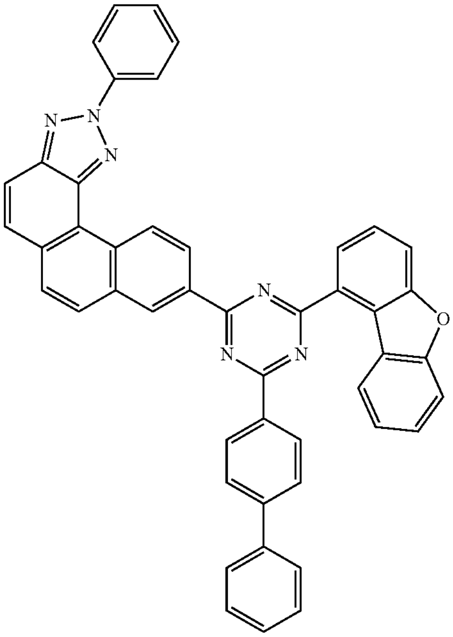
-continued
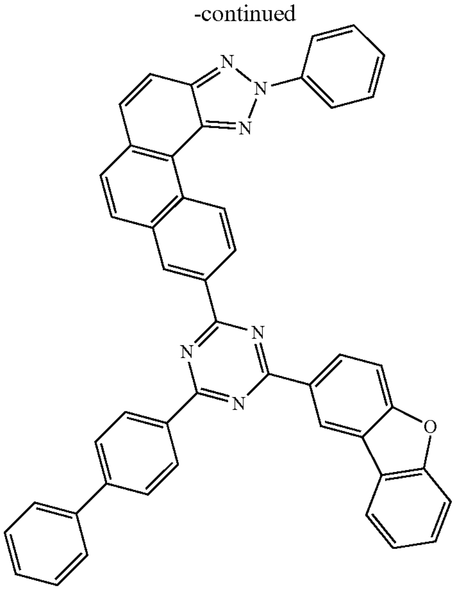
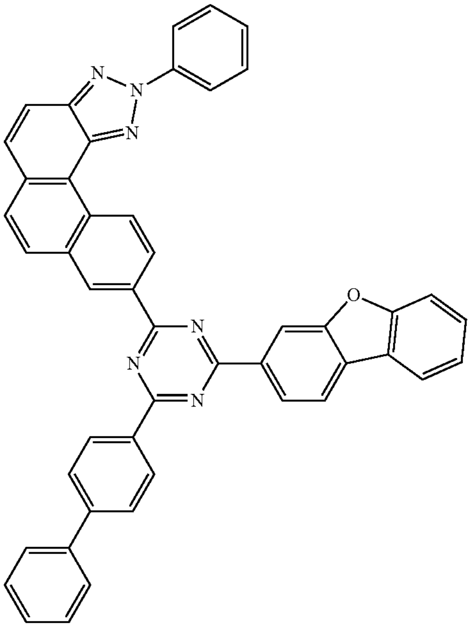
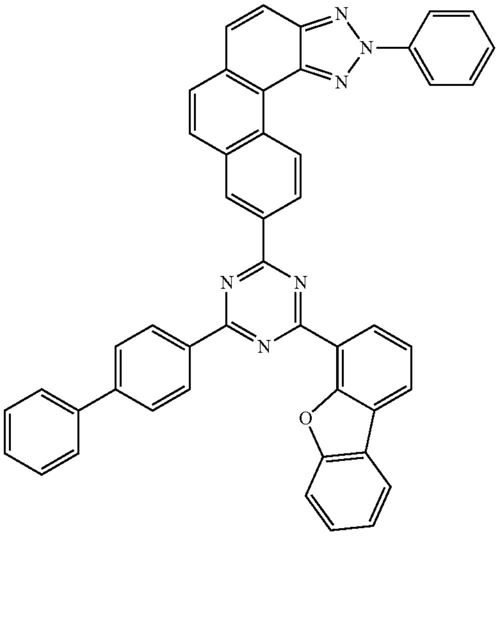

-continued
-continued
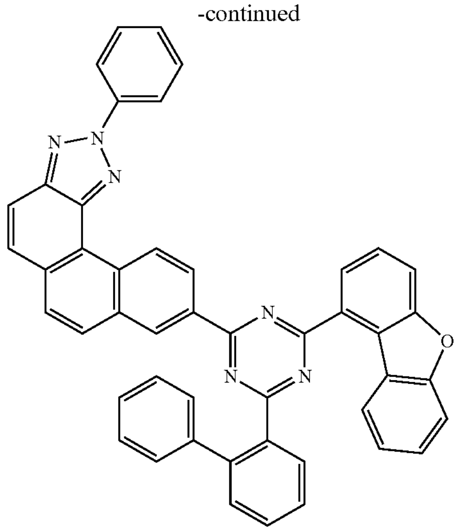
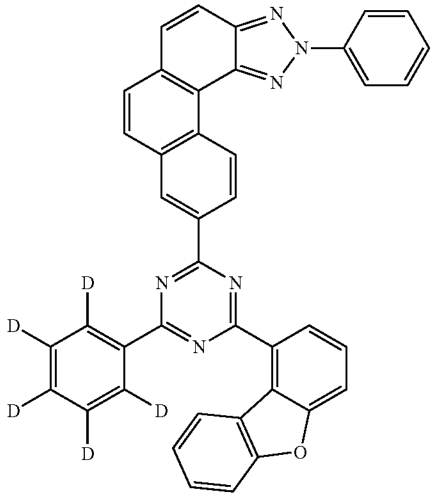
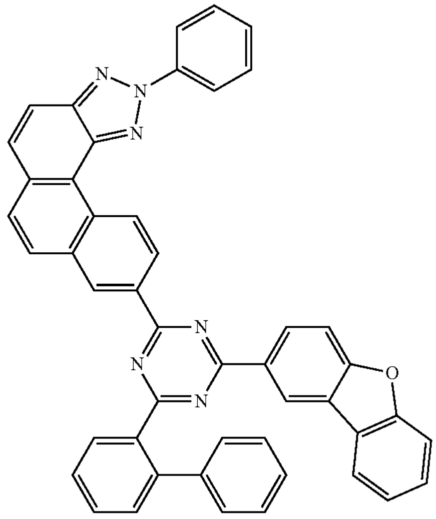
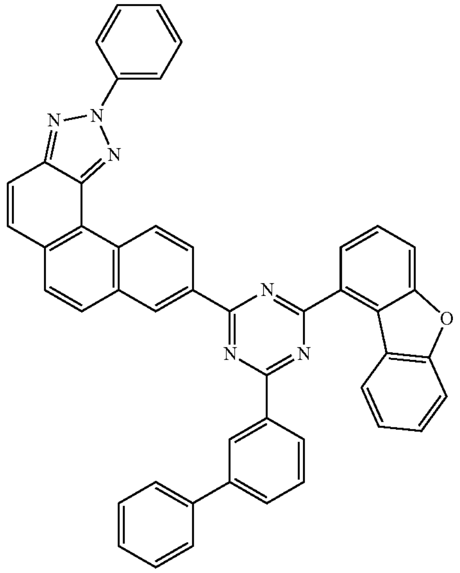
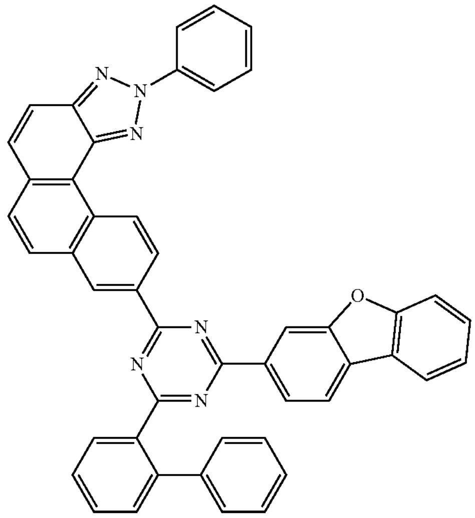
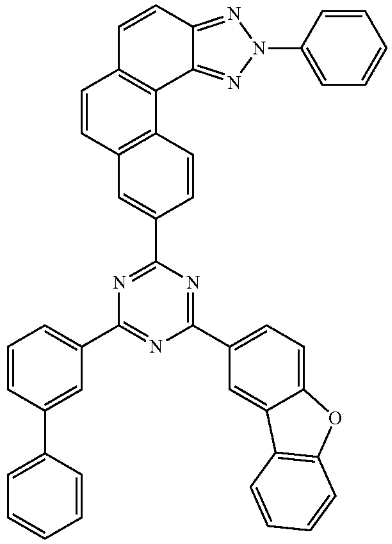

-continued
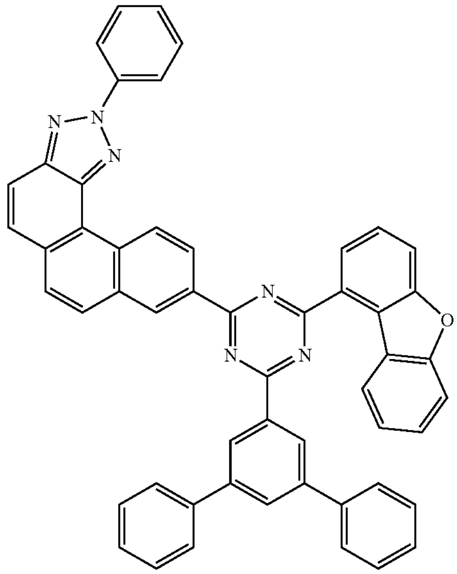
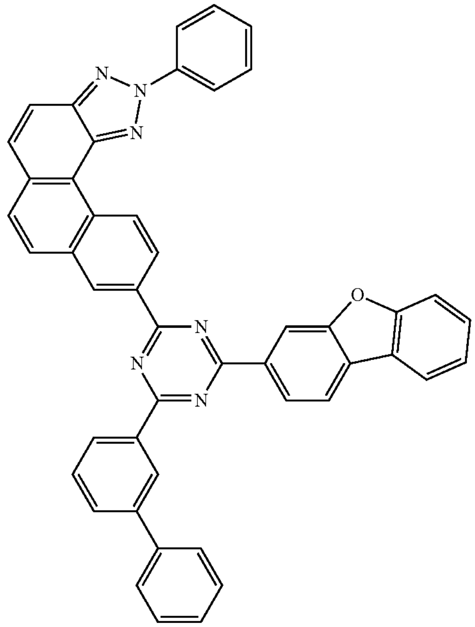
-continued
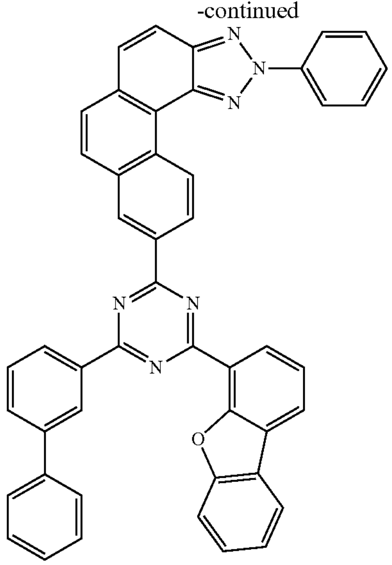
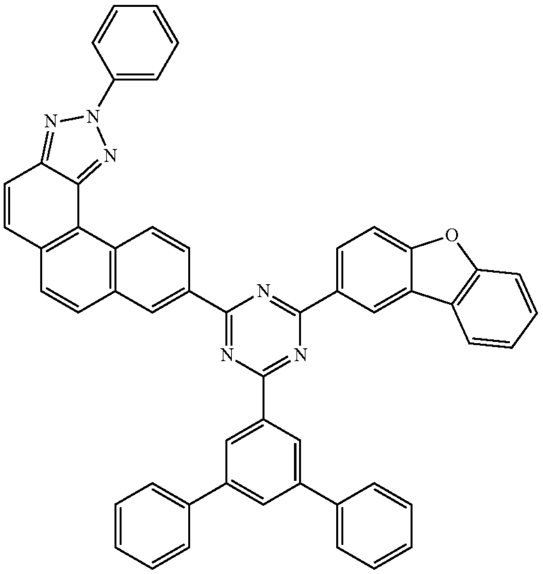
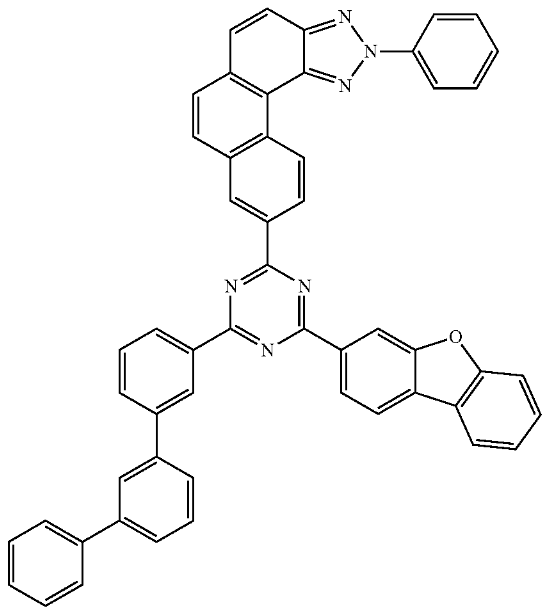

-continued
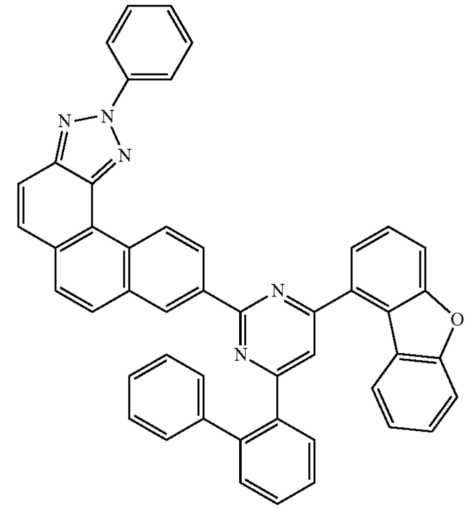
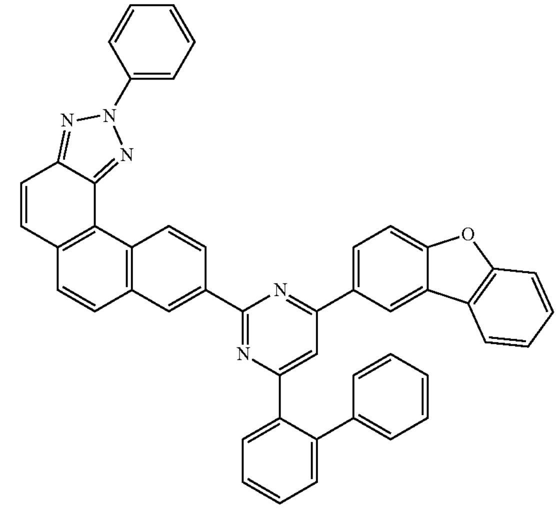
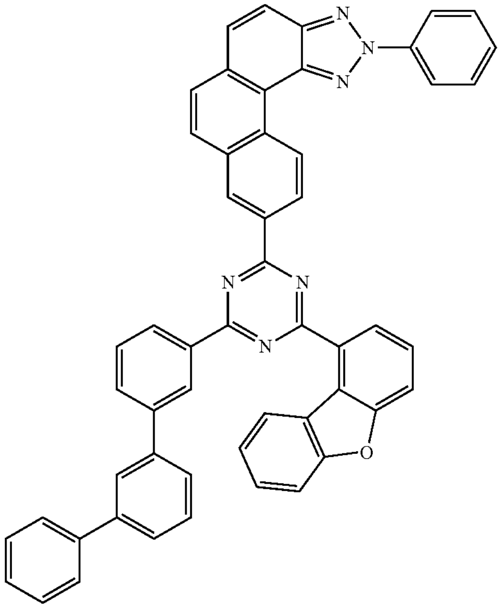
-continued
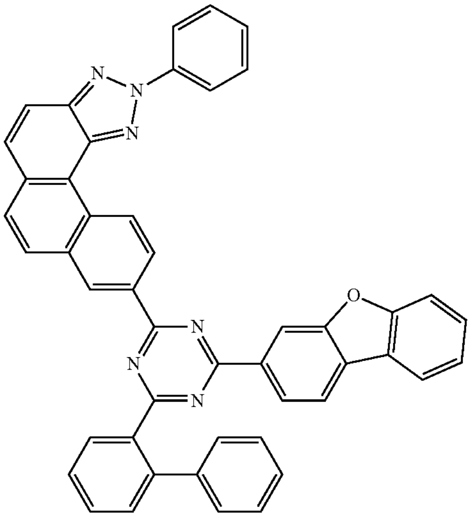
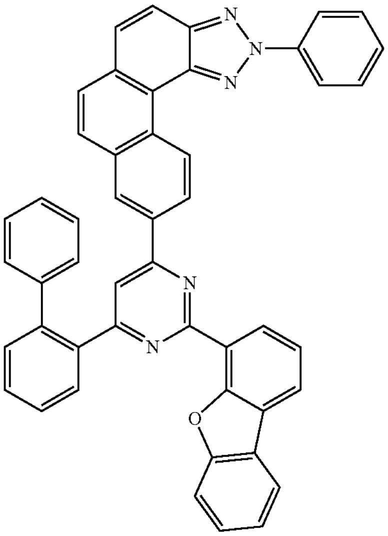
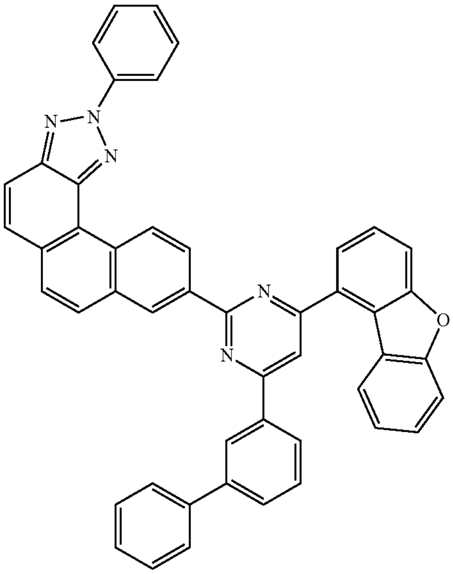

-continued
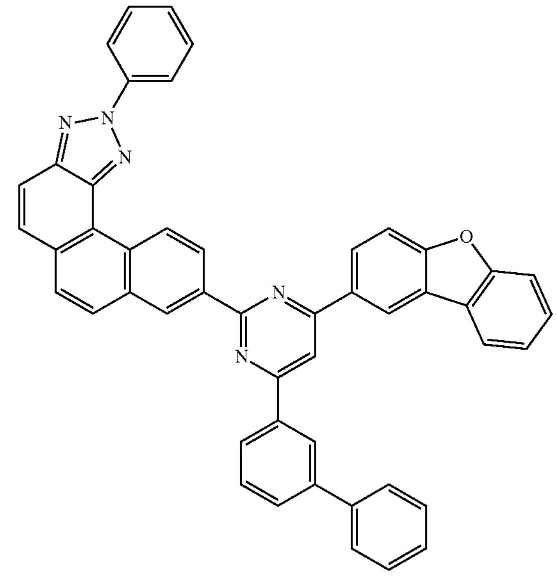
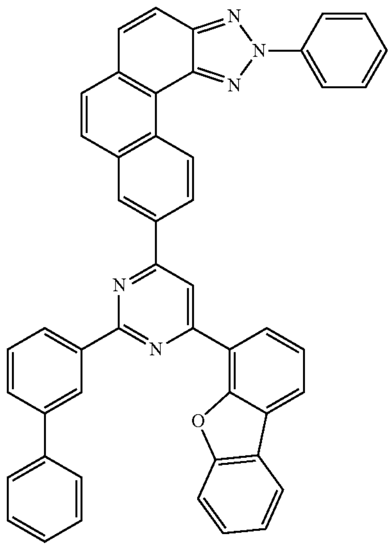
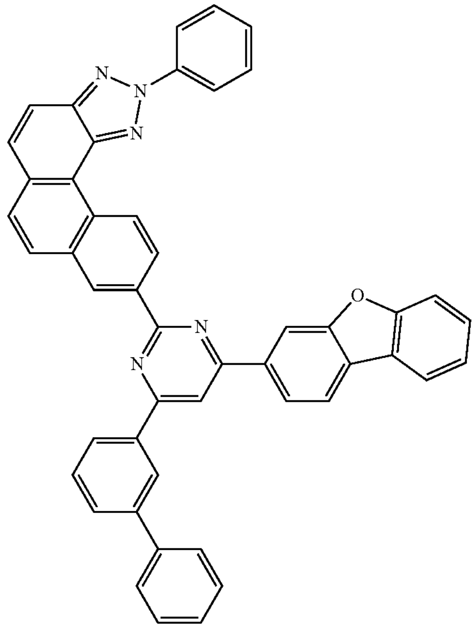
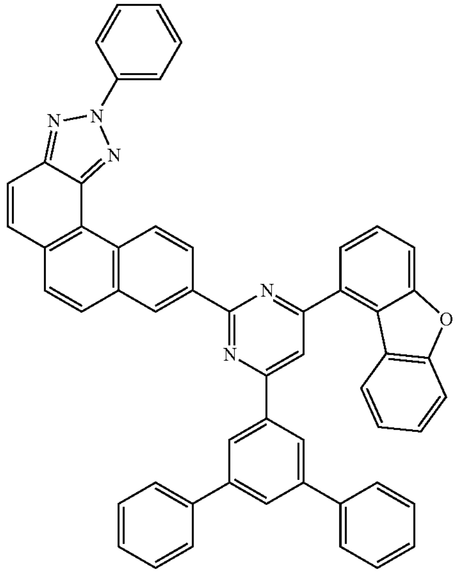
-continued

-continued
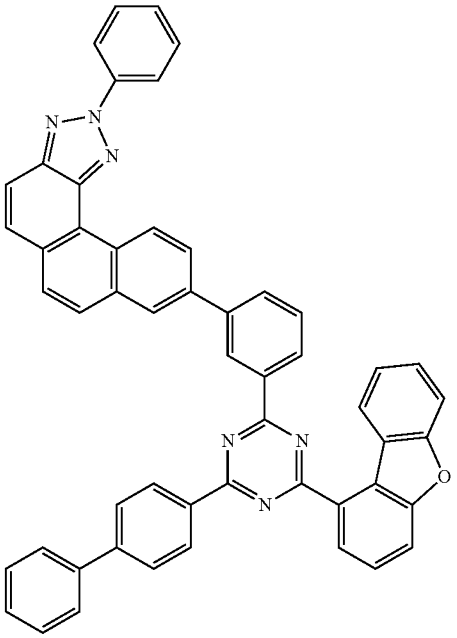
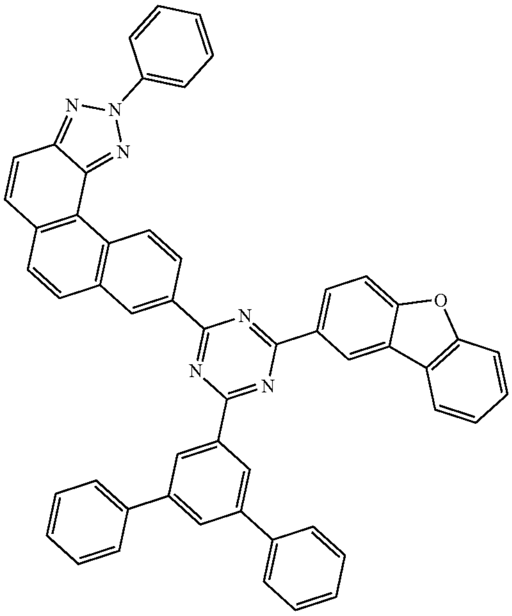
-continued
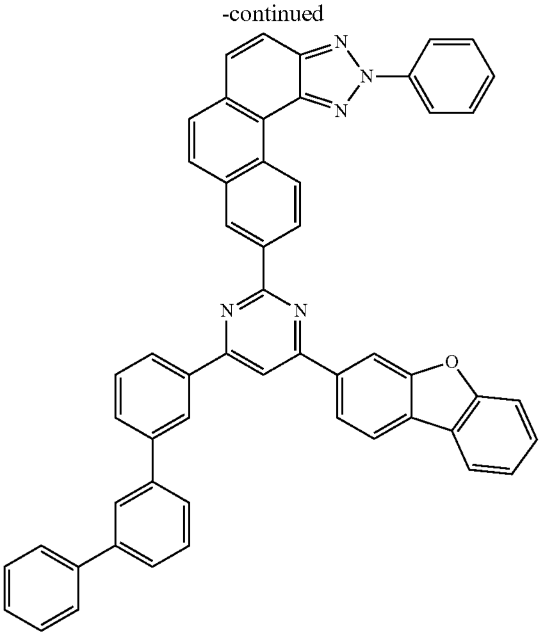
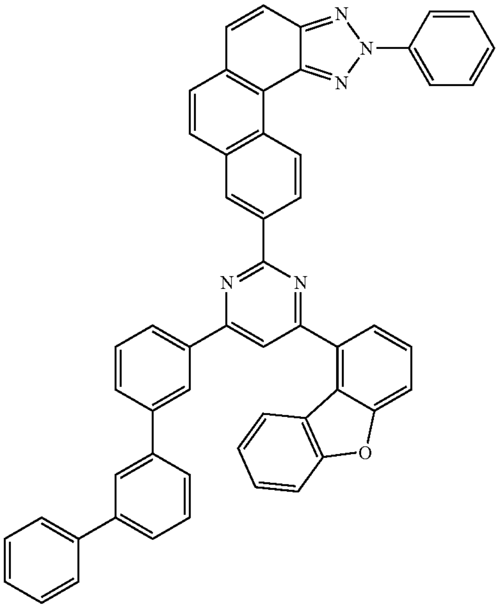
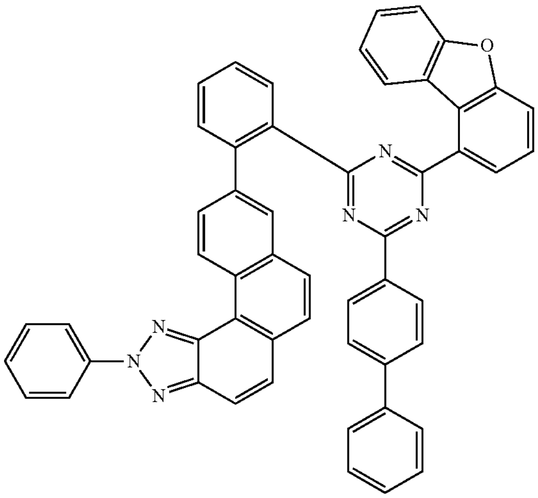

-continued
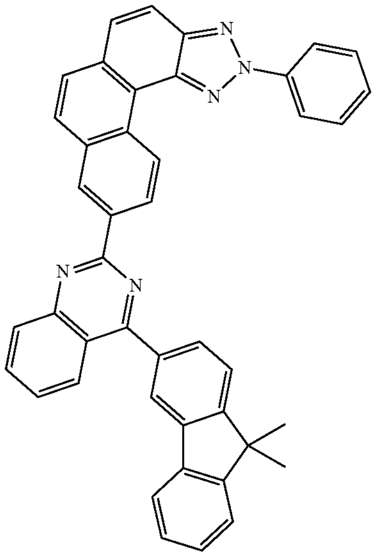
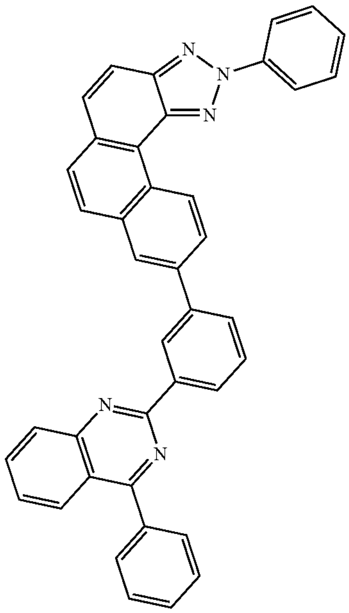
-continued
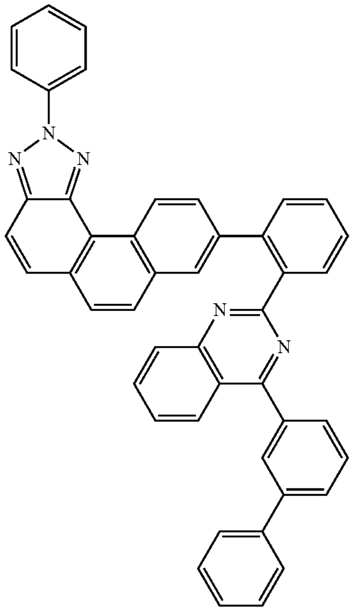
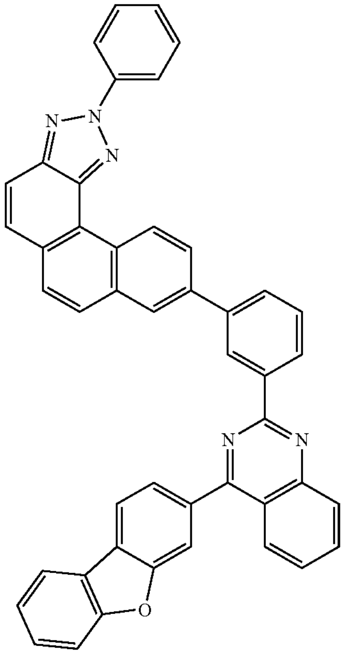

-continued
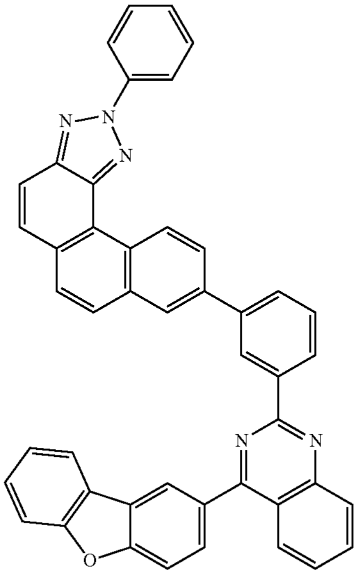
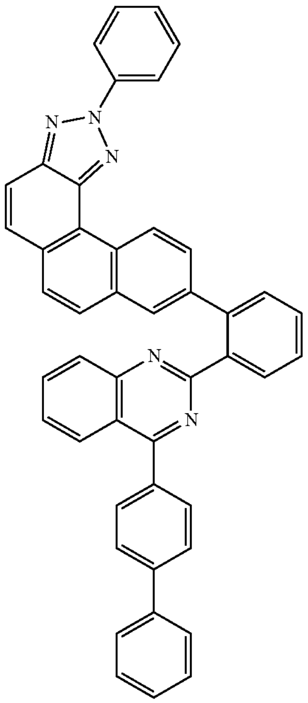
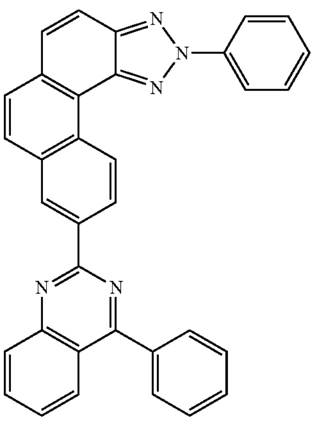
-continued
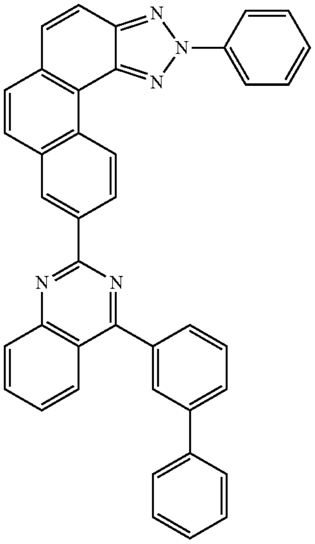
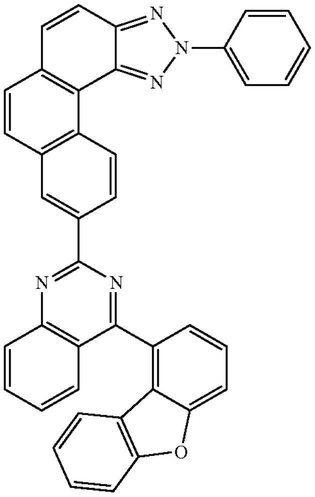
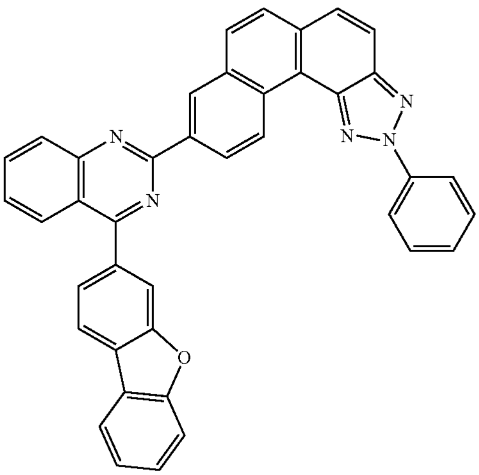

-continued

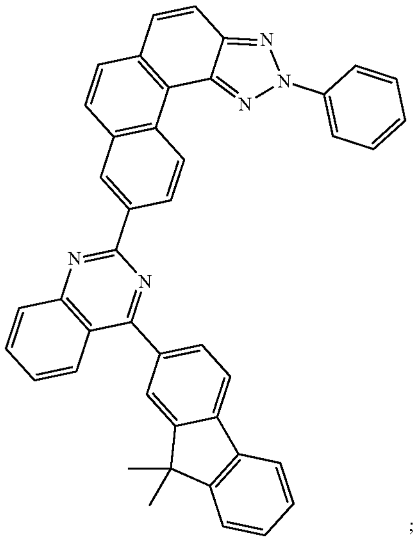

;

Preferably, in Formula 2, the ring A is a substituted or unsubstituted benzene ring.

Preferably, the compound having a structure represented by Formula 2 is a compound having any of the structures represented as below:

2-21

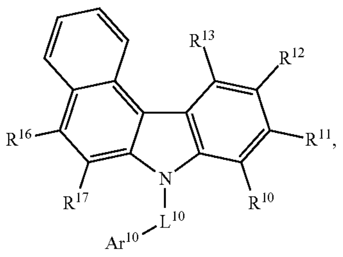

2-22

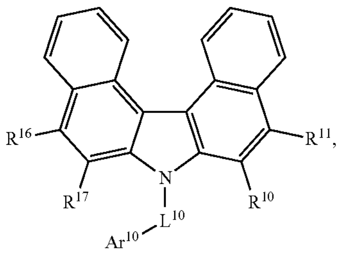

2-23

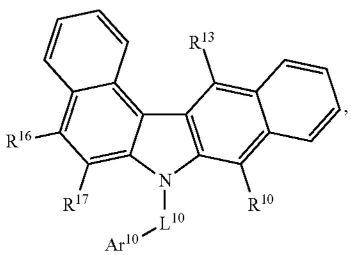

-continued 2-24

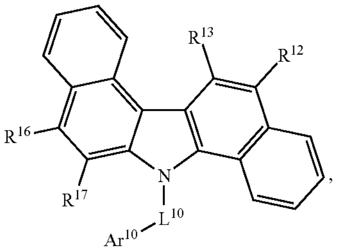

2-25

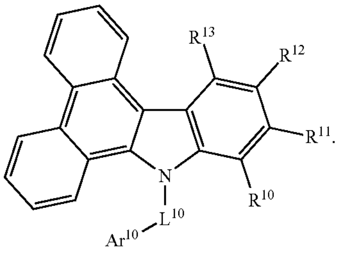

Preferably, the ring A is an indene ring, an indole ring, a benzofuran ring, a naphthofuran ring, a benzothiophene ring, a naphthothiophene ring, a benzoindole ring, or a naphthoindole ring, each of which is substituted or unsubstituted.

Preferably, any adjacent two of $R^{10}$ to $R^{17}$ are fused with

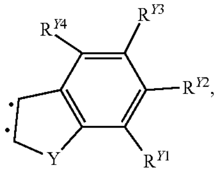

wherein the bonds at the positions marked with black dots are fusion bonds;

Y is selected from O, S, $CR^{Y5}R^{Y6}$ and $NR^{Y}$, in which $R^{Y}$ is-$L^{Y7}R^{Y7}$;

$R^{Y1}$, $R^{Y2}$, $R^{Y3}$ and $R^{Y4}$ are each independently selected from hydrogen, deuterium, halogen, a cyano group, a substituted or unsubstituted C1-C30 alkyl group, a C1-C30 alkyl group in which one or more methylene groups are independently substituted by —O— and/or —S— in a manner that O atom and/or S atom are not adjacent to each other, a substituted or unsubstituted C7-C30 arylalkyl group, a substituted or unsubstituted C6-C30 aryl group, a substituted or unsubstituted C3-C30 heteroaryl group, a substituted or unsubstituted C4-C30 heteroarylalkyl group, a substituted or unsubstituted C3-C30 cycloalkyl group, a substituted or unsubstituted C3-C30 heterocycloalkyl group, a substituted or unsubstituted C3-C30 cycloalkenyl group, a substituted or unsubstituted C1-C30 alkoxy group, and a substituted or unsubstituted C6-C30 aryloxy group;

$R^{Y1}$, $R^{Y2}$, $R^{Y3}$ and $R^{Y4}$ are present individually without forming a ring, or any adjacent two of $R^{Y1}$, $R^{Y2}$, $R^{Y3}$ and $R^{Y4}$ joined to form a benzene ring or a naphthalene ring;

$R^{Y5}$, $R^{Y6}$ are each independently selected from a substituted or unsubstituted C1-C30 alkyl group, and a substituted or unsubstituted C6-C30 aryl group;

$R^{Y7}$ is selected from a substituted or unsubstituted C1-C30 alkyl group, a substituted or unsubstituted C7-C30 arylalkyl group, a substituted or unsubstituted C6-C30 aryl group, a substituted or unsubstituted C3-C30 heteroaryl group, a substituted or unsubstituted C4-C30 heteroarylalkyl group, a substituted or unsubstituted C3-C30 cycloalkyl group, a substituted or unsubstituted C3-C30 heterocycloalkyl group, and a substituted or unsubstituted C6-C30 aryloxy group;

$L^{17}$ is selected from a bond, a substituted or unsubstituted C6-C30 arylene group, and a substituted or unsubstituted C3-C30 heteroarylene group.

Preferably, the compound having a structure represented by Formula 2 is a compound having any of the structures represented as below:

2-31

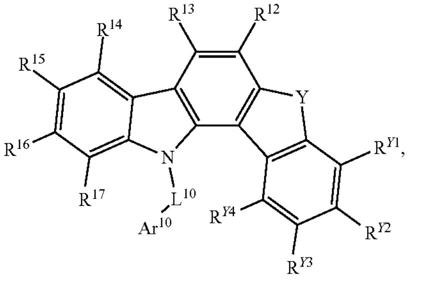

2-32

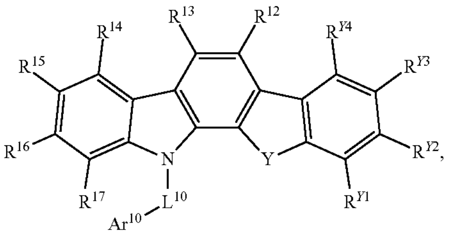

2-33

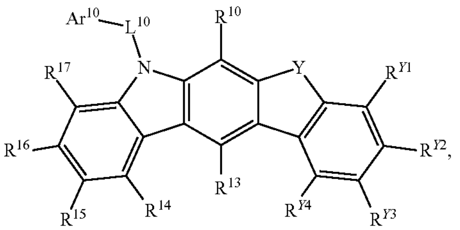

2-34

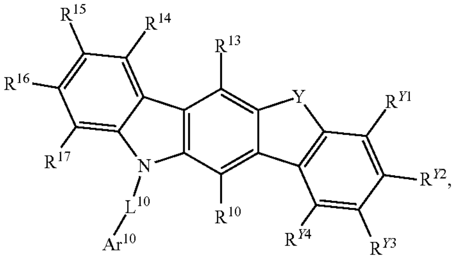

-continued 2-35

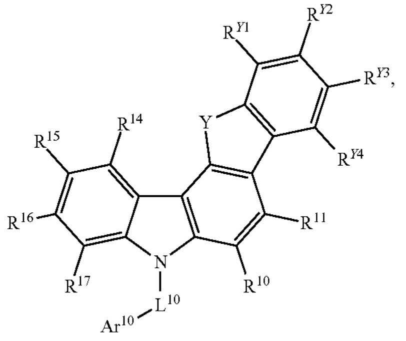

2-36

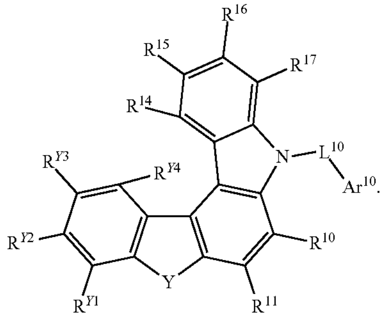

Preferably, $Ar^{10}$ and $R^{Y7}$ are each independently selected from a phenyl group, a biphenylyl group, a terphenylyl group, a triphenylenylene group, a naphthyl group, a phenylnaphthyl group, a naphthylphenyl group, an anthryl group, a phenanthryl group, a benzophenanthryl group, a pyridyl group, a dibenzofuryl group, a dibenzothiophenyl group, a carbazolyl group, a phenylcarbazolyl group, a pyridylcarbazolyl group, a naphthylcarbazolyl group, a biphenylylcarbazolyl group, a dibenzofurylphenyl group, a dibenzothiophenylphenyl group, a dimethylfluorenyl group, a diphenylfluorenyl group, a spiro-bifluorenyl group, a benzonaphthofuryl group, a benzonaphthothiophenyl group, a benzocarbazolyl group and a dibenzocarbazolyl group, each of which is substituted or unsubstituted.

Preferably, $R^{10}$ to $R^{17}$ and $R^{Y1}$ to $R^{Y4}$ are each independently selected from hydrogen, deuterium, a phenyl group, a biphenylyl group, a terphenylyl group, a naphthyl group, a phenylnaphthyl group, a naphthylphenyl group, an anthryl group, a phenanthryl group, a benzophenanthryl group, a pyridyl group, a dibenzofuryl group, a dibenzothiophenyl group, a dibenzofurylphenyl group, a dibenzothiophenylphenyl group, a dimethylfluorenyl group, a diphenylfluorenyl group, a spiro-bifluorenyl group, a benzonaphthofuryl group, and a benzonaphthothiophenyl group; $R^{10}$ to $R^{17}$ and $R^{Y1}$ to $R^{Y4}$ are present individually without forming a ring, or any adjacent two of $R^{10}$ to $R^{17}$ and $R^{Y1}$ to $R^{Y4}$ joined to form a benzene ring or a naphthalene ring.

Preferably, $R^{Y5}$ and $R^{Y6}$ are each independently selected from a methyl group and a phenyl group; or, $R^{Y5}$ and $R^{Y6}$ joined to form a fluorene ring group.

Preferably, $L^{10}$ and $L^{Y7}$ are each independently selected from a bond, a phenylene group, a biphenylene group, and a naphthylene group.

Preferably,
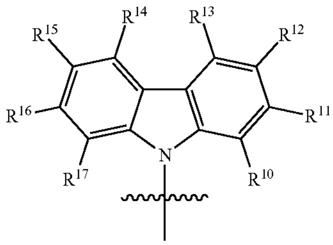
is selected from a group shown as below:
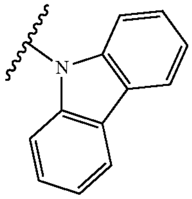
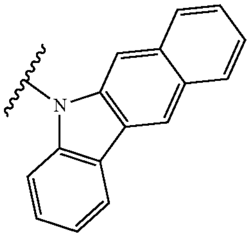
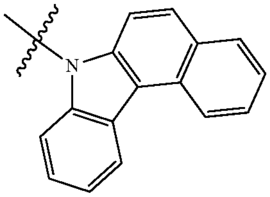
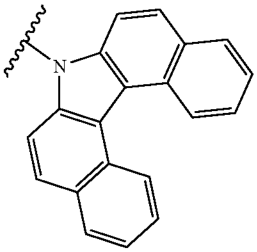
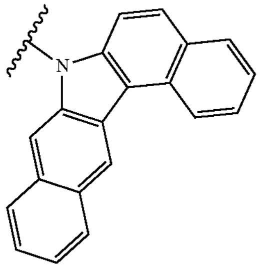
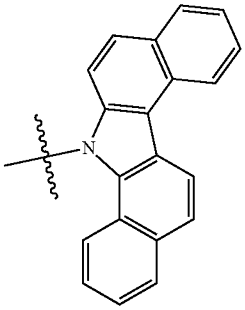
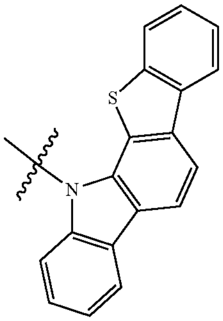
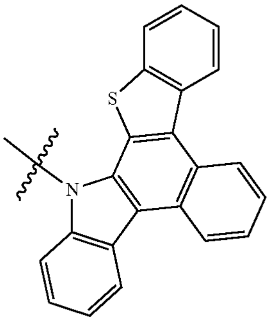
-continued
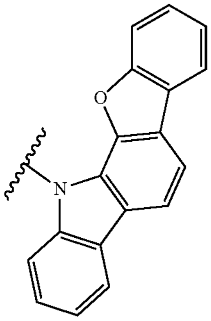
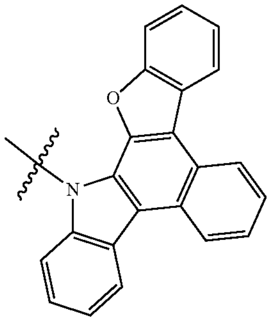
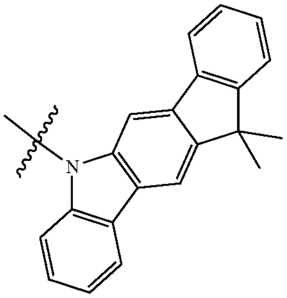
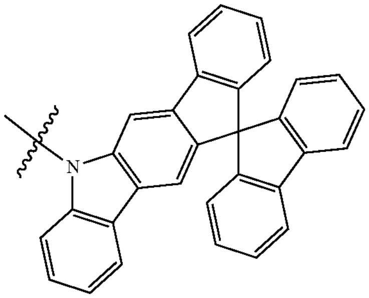
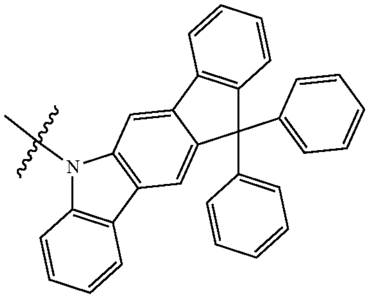
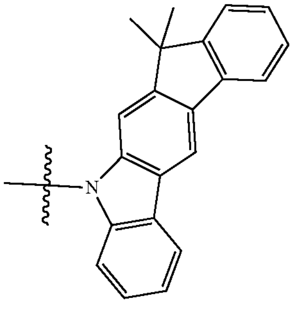

-continued
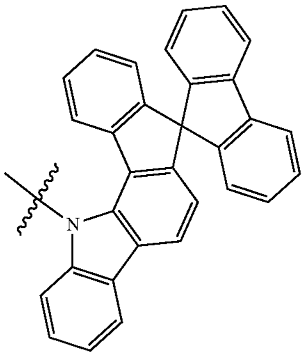
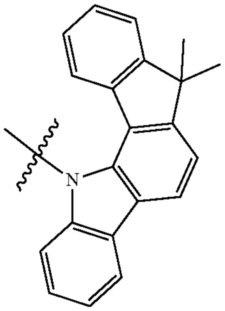
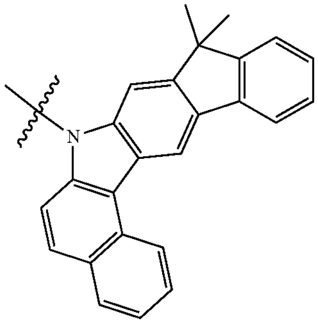
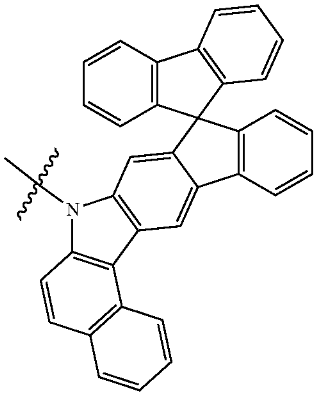
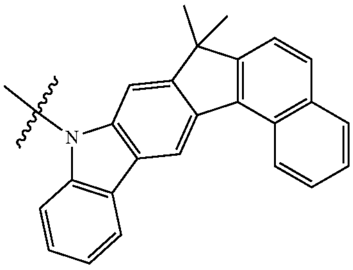
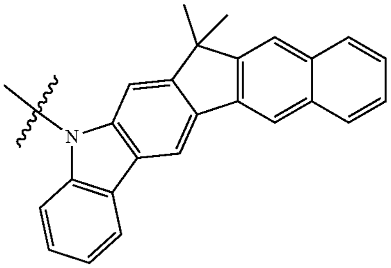
-continued
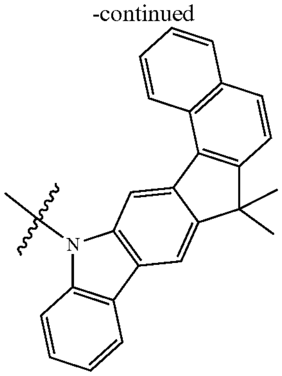
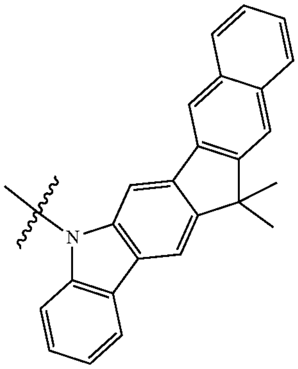
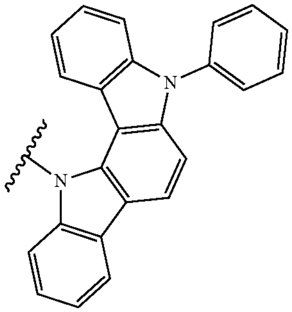
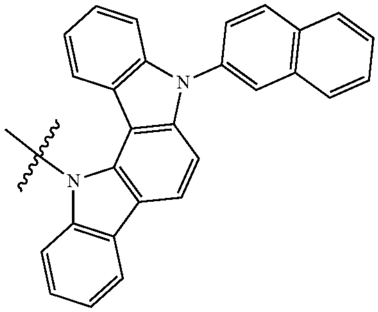
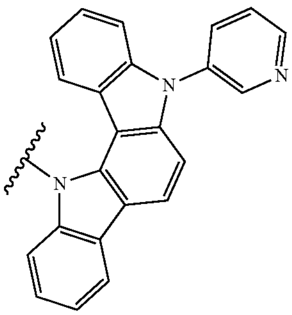

-continued
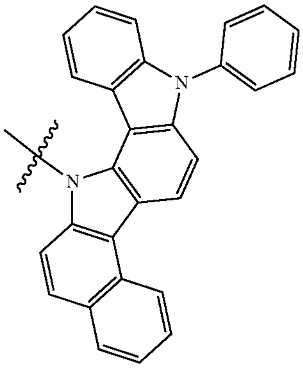
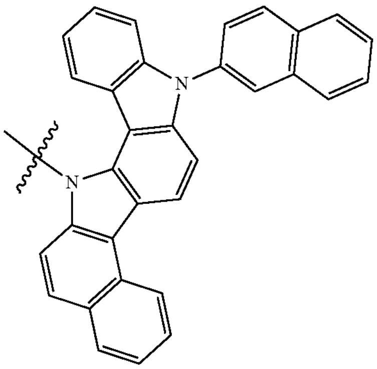
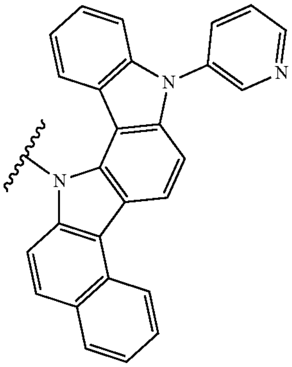
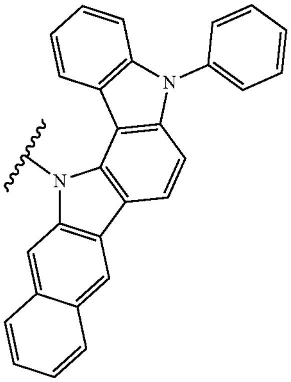
-continued
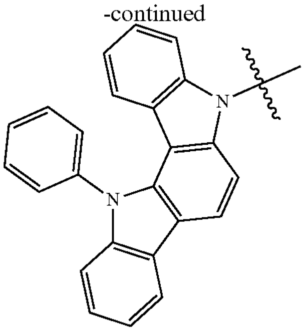
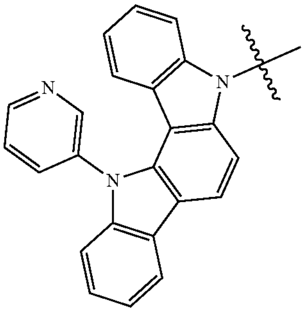
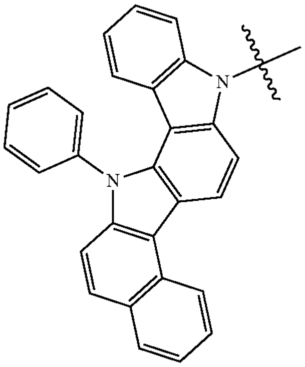
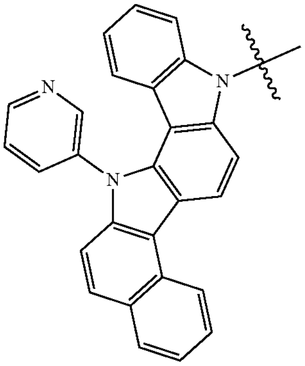
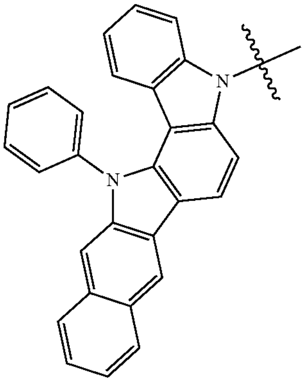

-continued
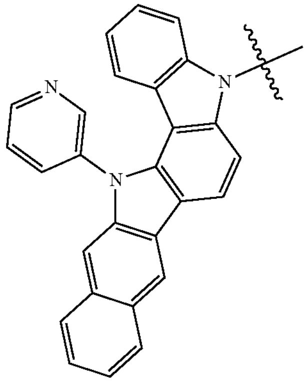
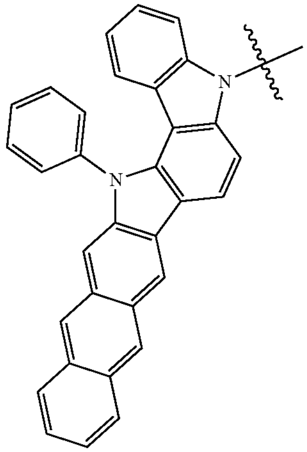
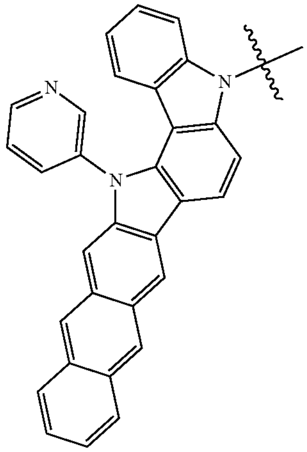
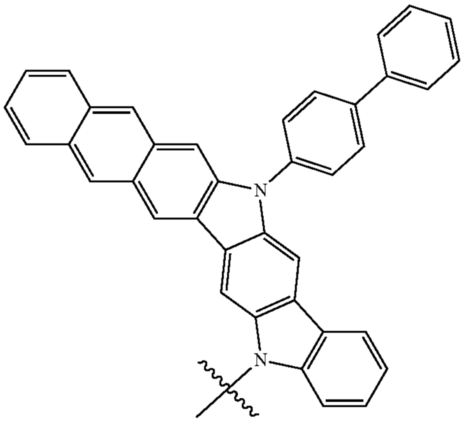
-continued
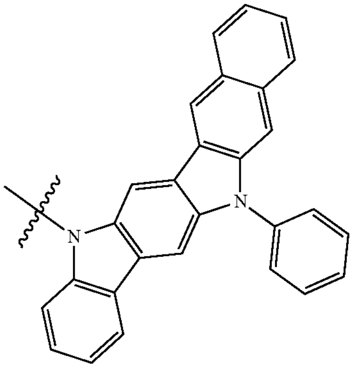
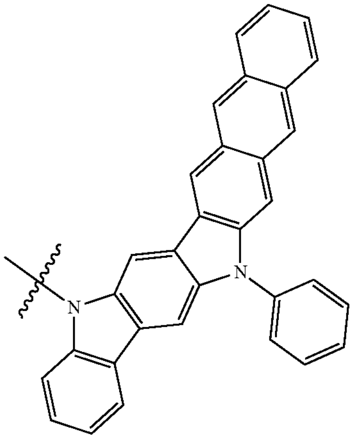
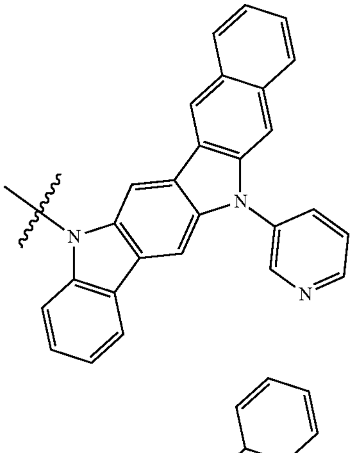
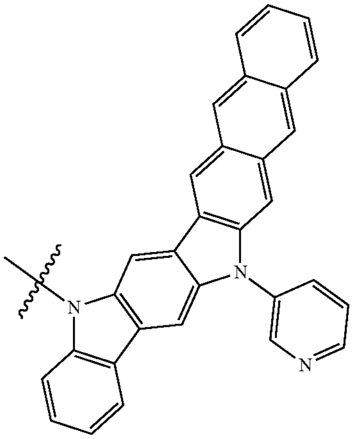

-continued
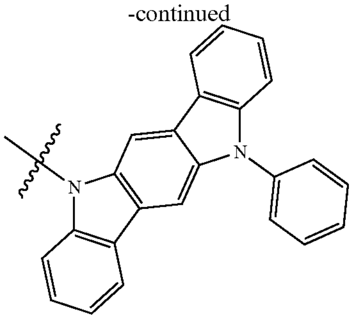
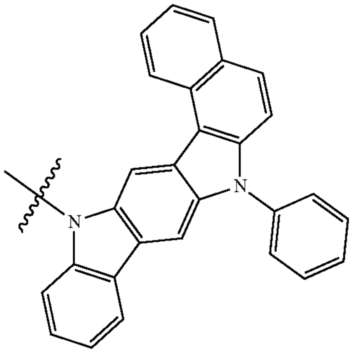
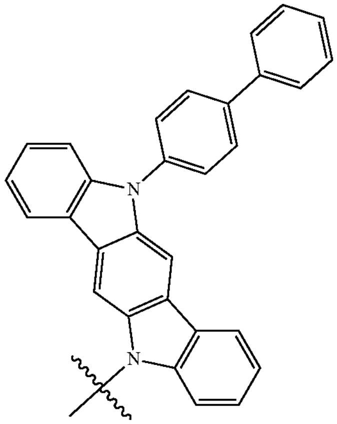
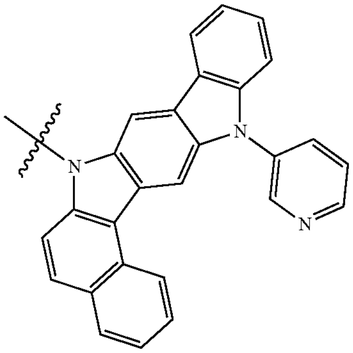
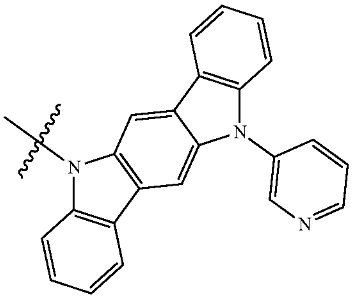
-continued
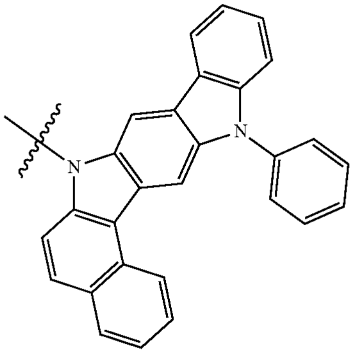
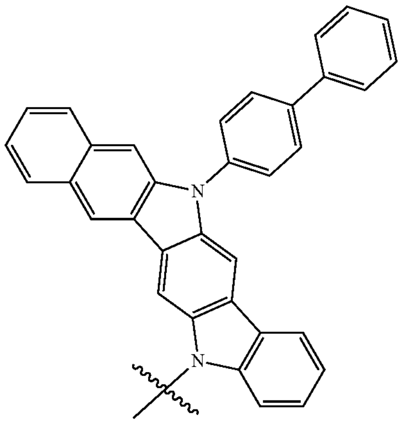
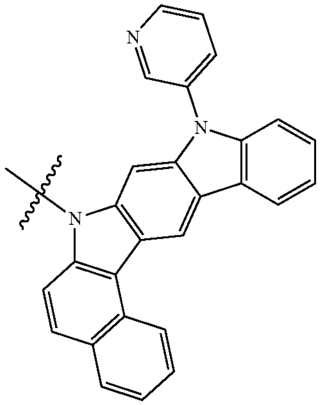
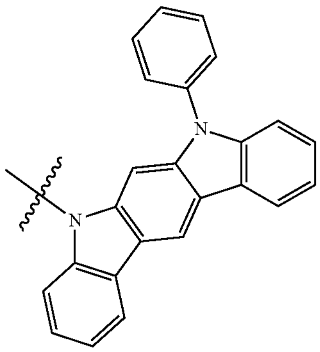

-continued
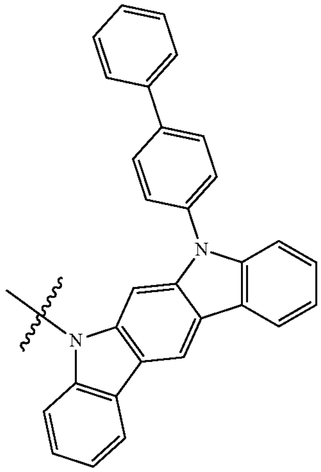
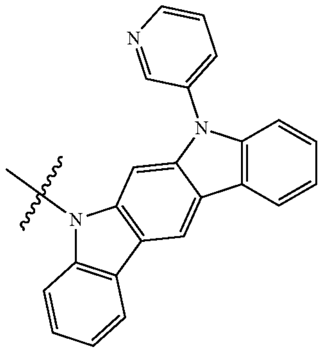
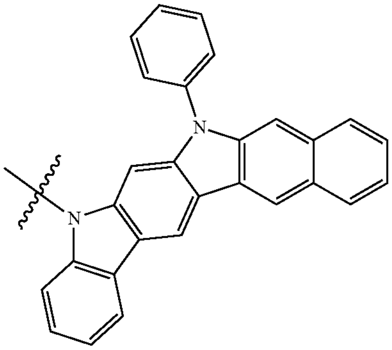
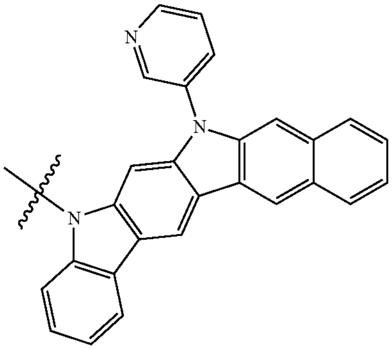
-continued
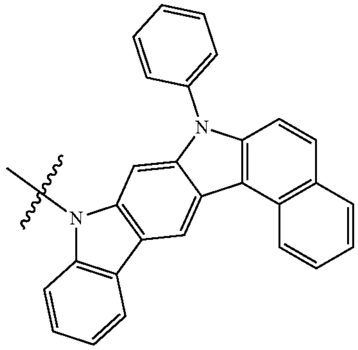
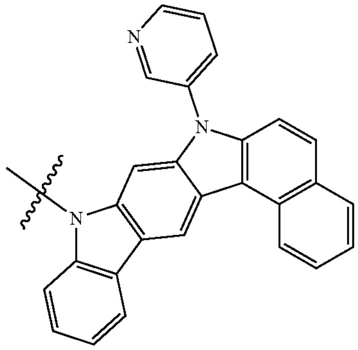
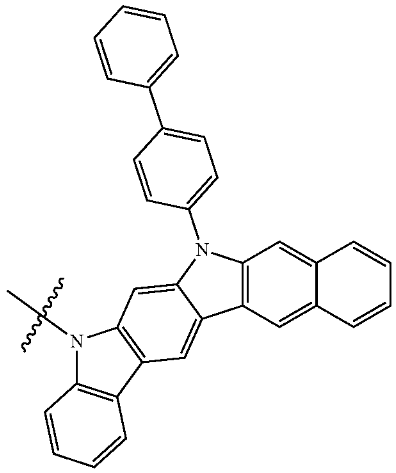
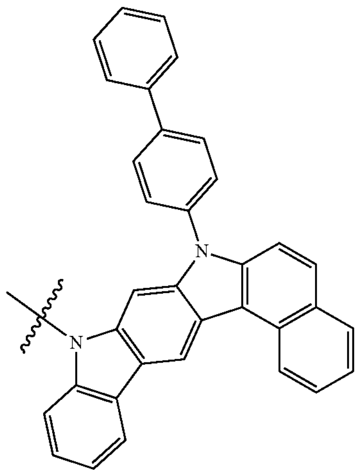

-continued
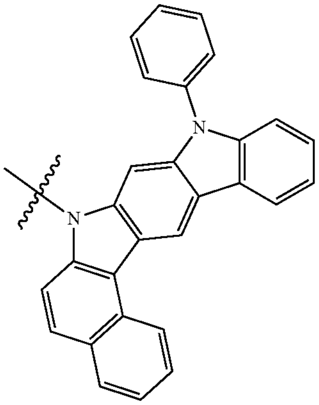
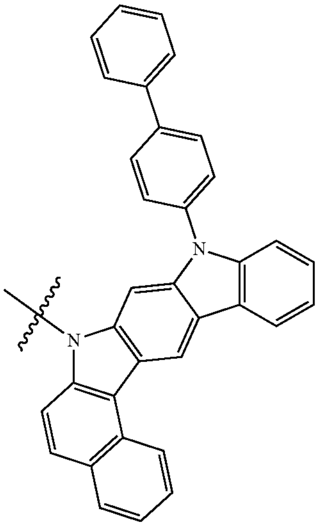
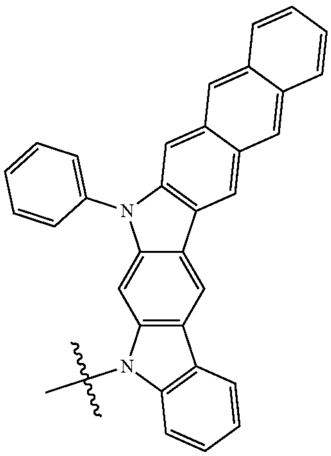
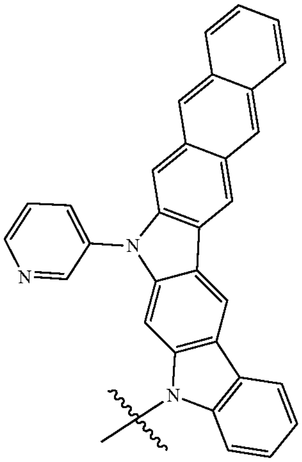
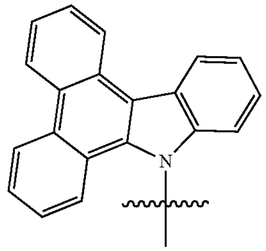
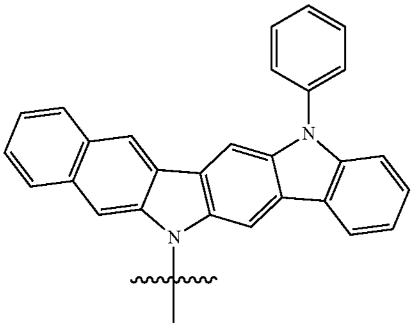
-continued
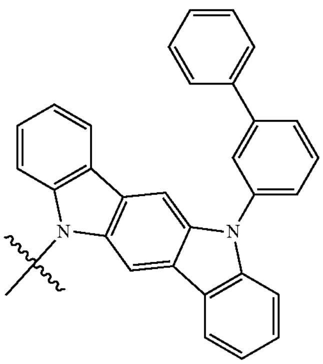

-continued

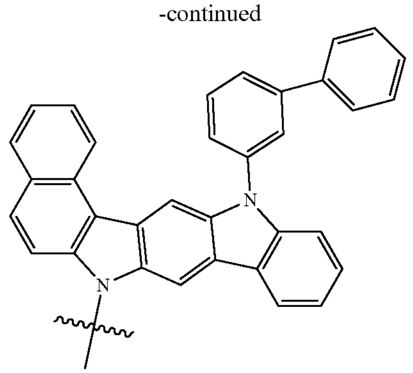

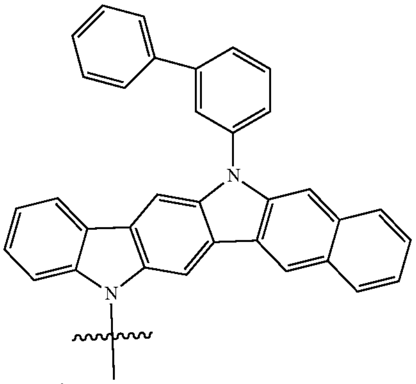

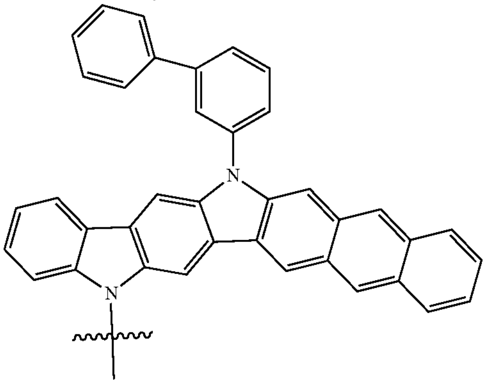

, each of which is substituted or unsubstituted; wherein the wavy line represents the connection position of the group.

In the present invention, preferably, the aforementioned substituents are each independently selected from deuterium, halogen, a cyano group, a nitro group, an unsubstituted or R'-substituted C1-C4 straight or branched alkyl group, an unsubstituted or R'-substituted C6-C20 aryl group, an unsubstituted or R'-substituted C3-C20 heteroaryl group, and an unsubstituted or R'-substituted C6-C20 arylamino group; R' is selected from deuterium, halogen, a cyano group and a nitro group.

Preferably, the aryl group is selected from a phenyl group, a biphenylyl group, a terphenylyl group, a naphthyl group, an anthryl group, a phenanthryl group, a benzophenanthryl group, a naphthylphenyl group, a dimethylfluorenyl group, a diphenylfluorenyl group and a spiro-bifluorenyl group.

Preferably, the heteroaryl group is selected from a pyridyl group, a dibenzofuryl group, a dibenzothiophenyl group, a carbazolyl group, a phenylcarbazolyl group, a pyridylcarbazolyl group, a naphthylcarbazolyl group, a biphenylylcarbazolyl group, a dibenzofurylphenyl group, a dibenzothiophenylphenyl group, a benzonaphthofuryl group, a benzonaphthothiophenyl group, a benzocarbazolyl group and a dibenzocarbazolyl group.

Preferably, the alkyl group is selected from a methyl group, an ethyl group, a propyl group, a tert-butyl group, a cyclohexyl group and adamantyl.

Preferably, the compound having a structure represented by Formula 2 is selected from the compounds shown as below:

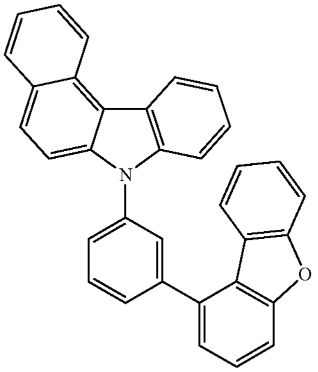

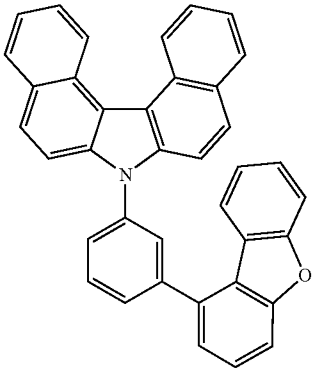

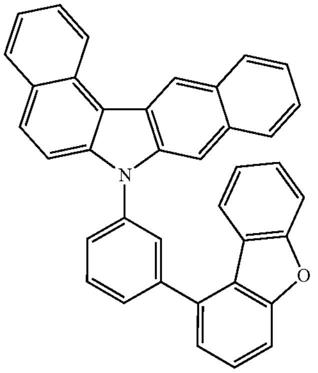

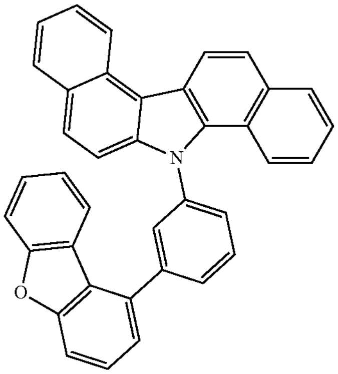

-continued
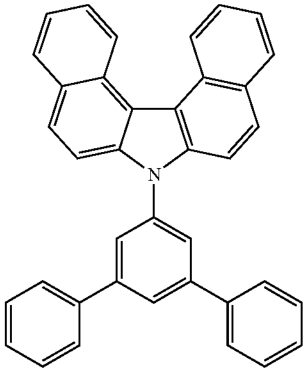
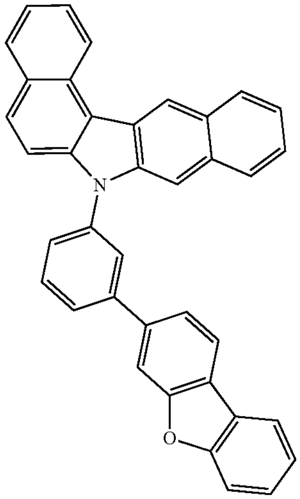
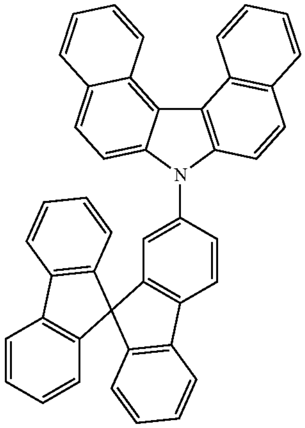
-continued
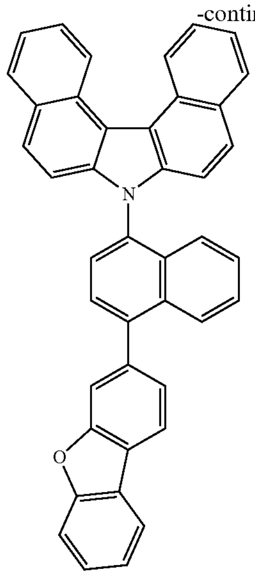
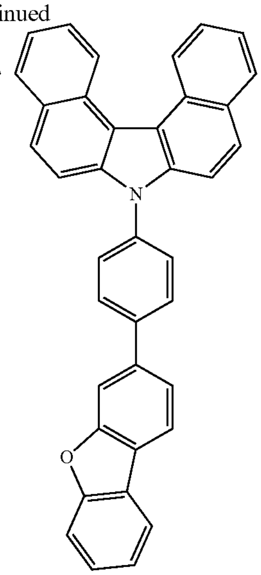
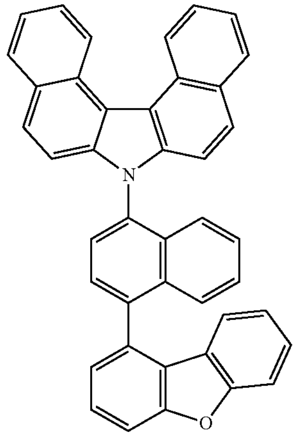
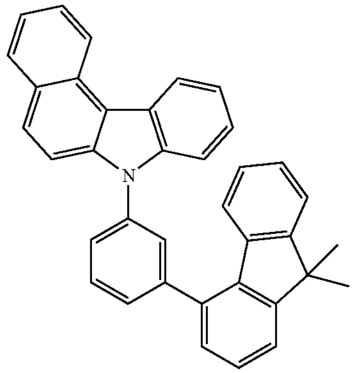
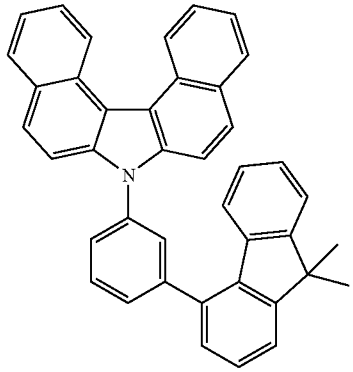

-continued
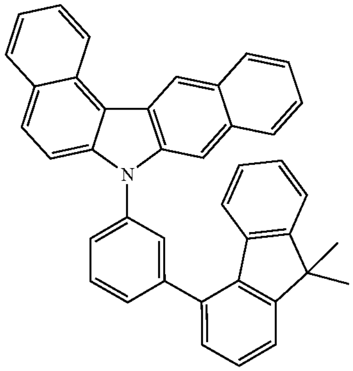
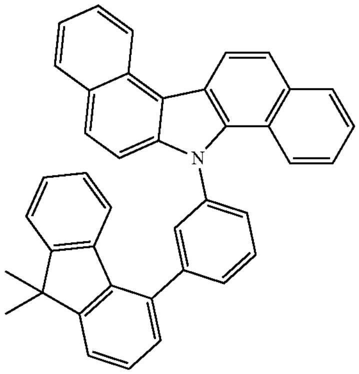
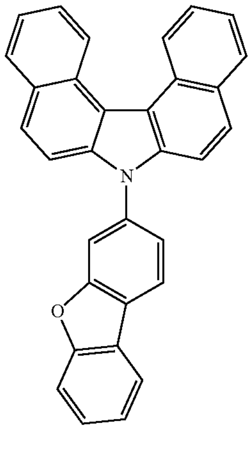
-continued
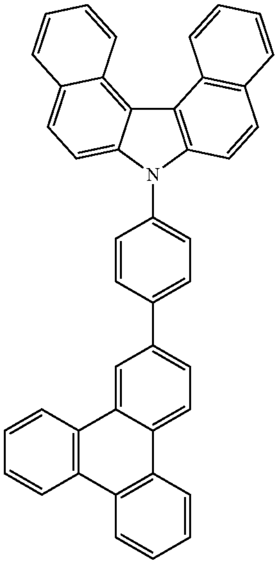
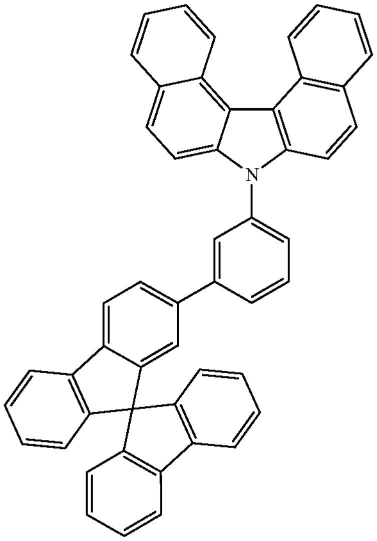
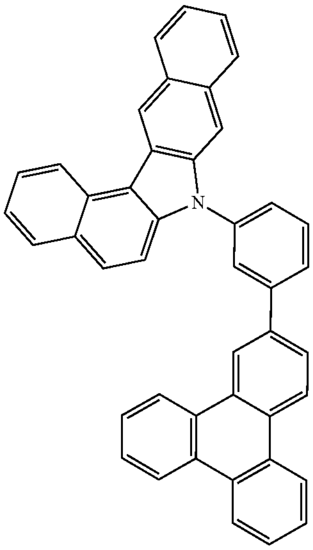

-continued
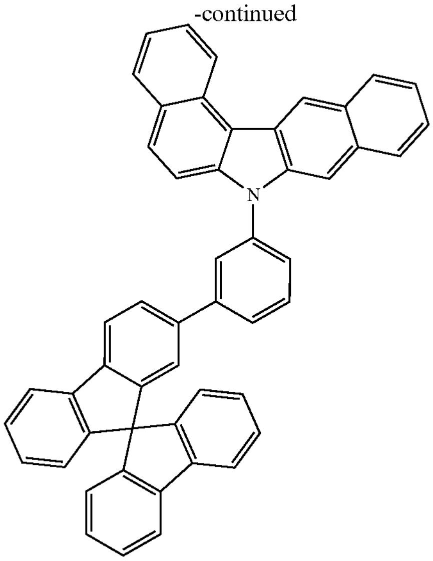
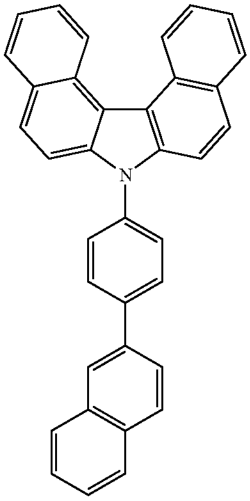
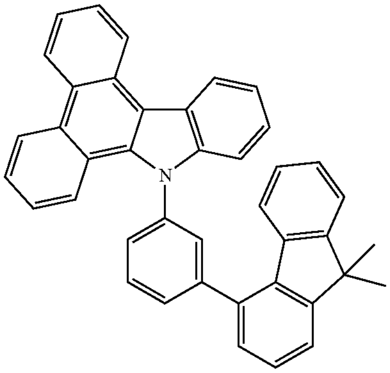
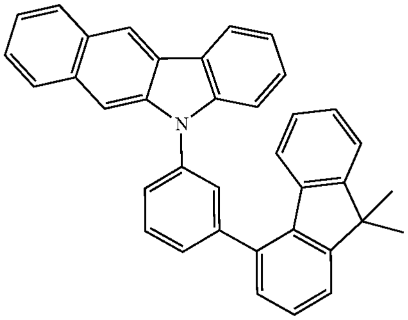
-continued
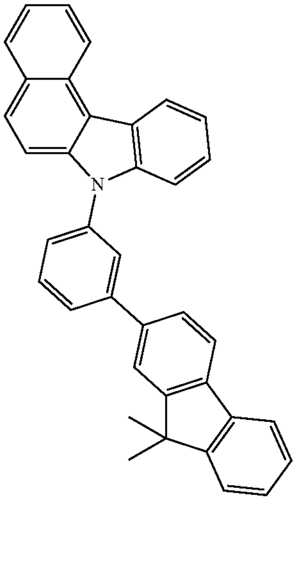
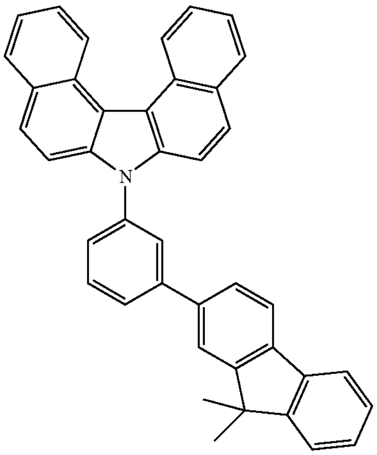
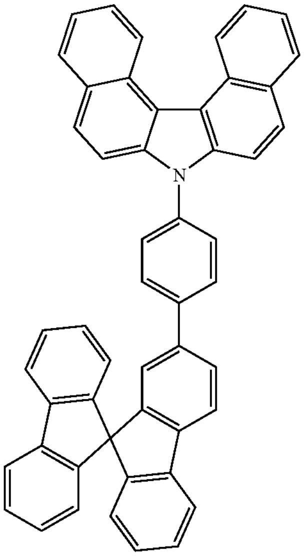

-continued
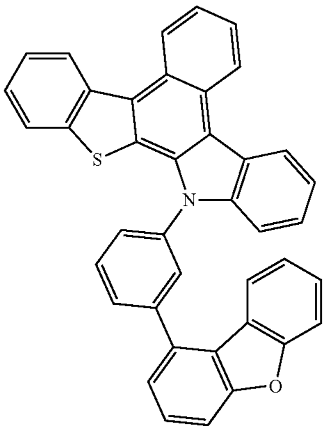
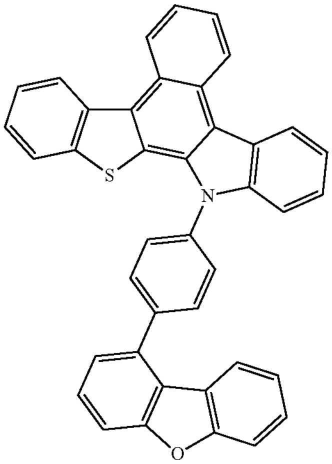
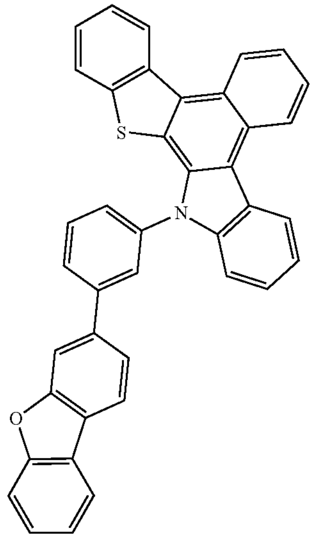
-continued
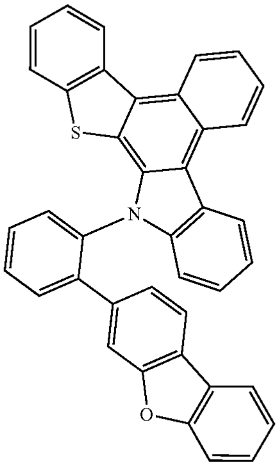
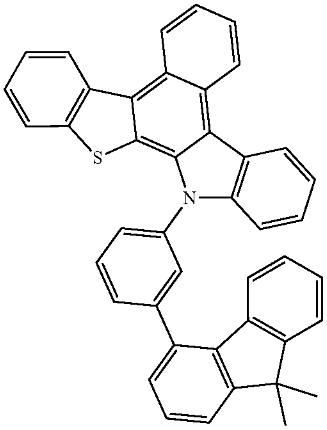
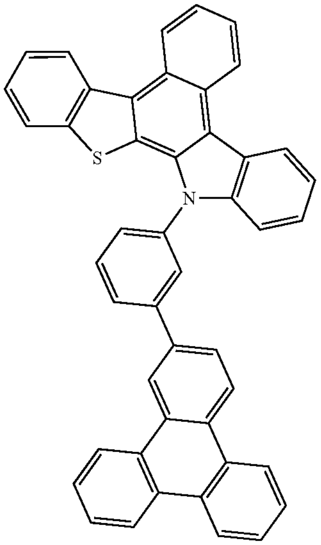

-continued
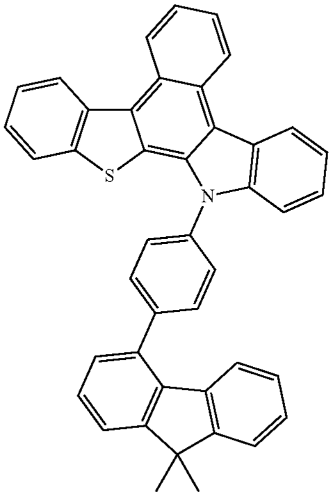
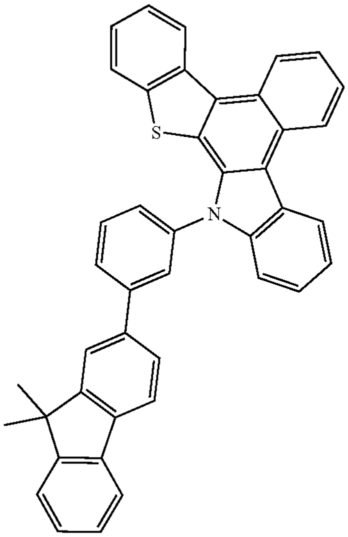
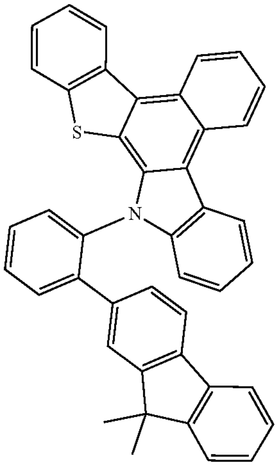
-continued
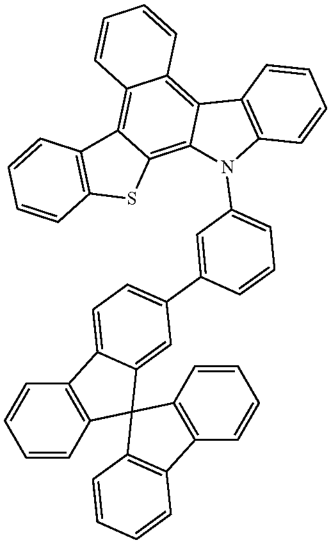
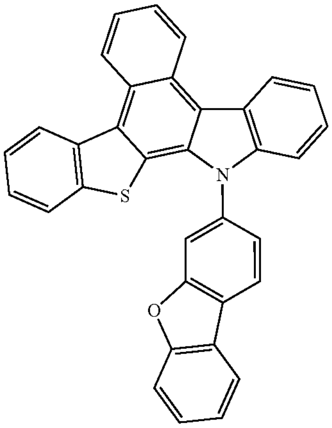
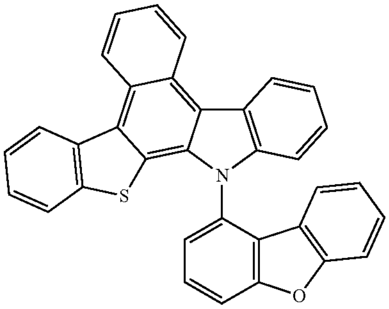
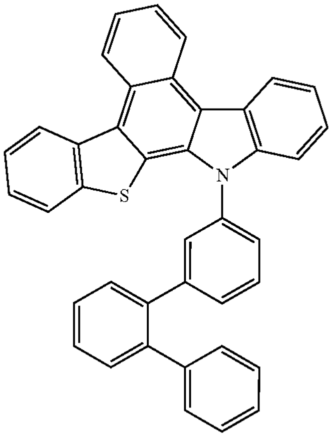

-continued
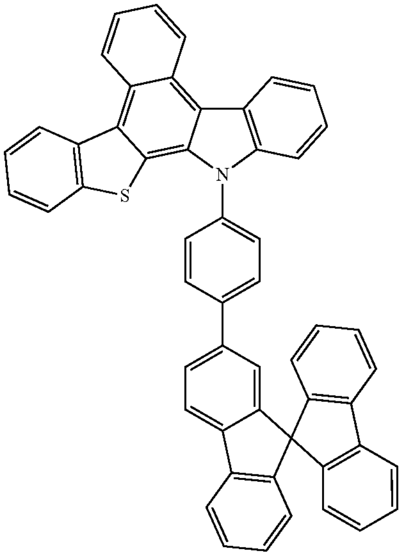
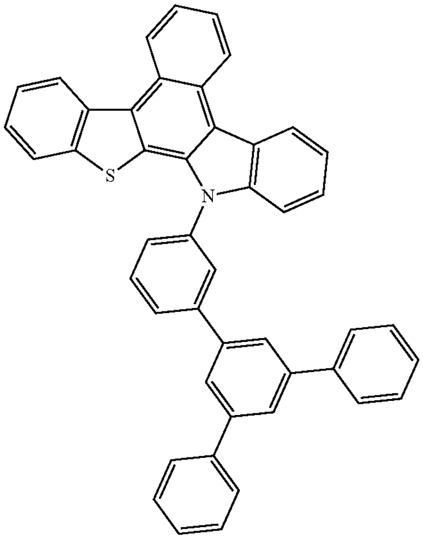
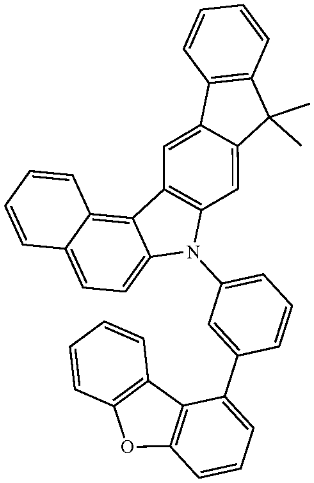
-continued
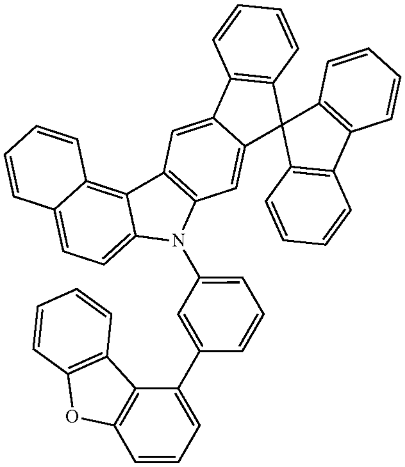
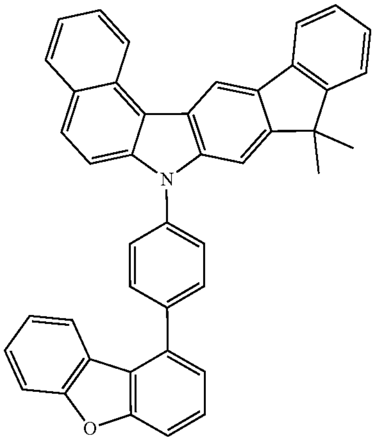
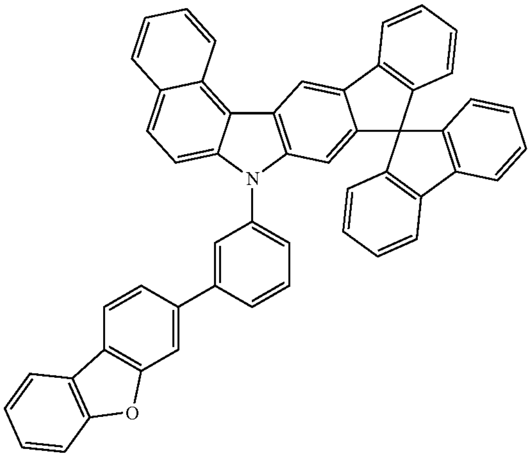

-continued
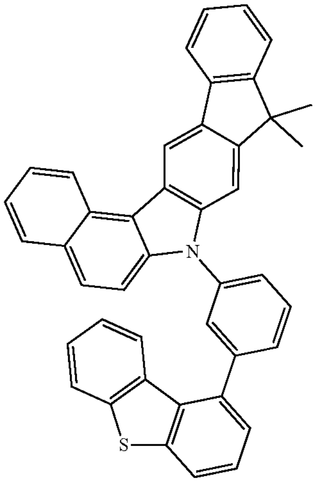
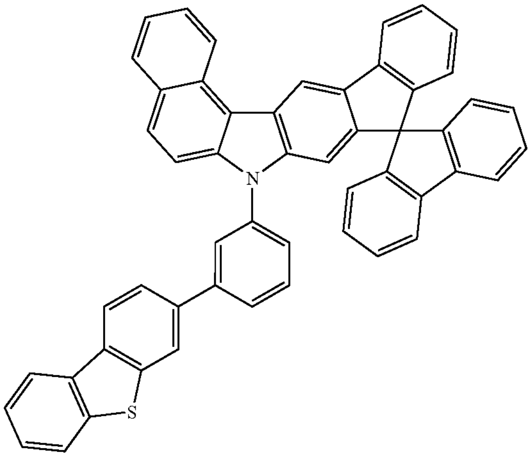
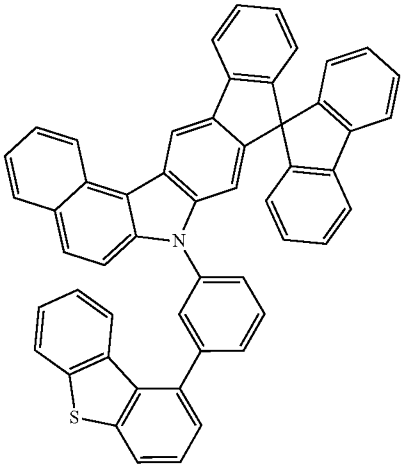
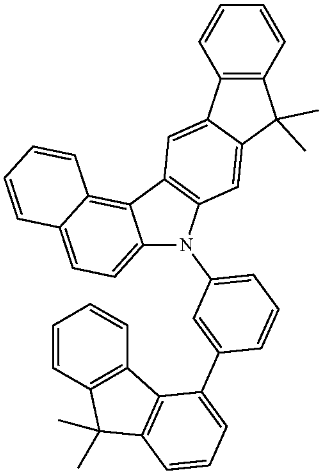
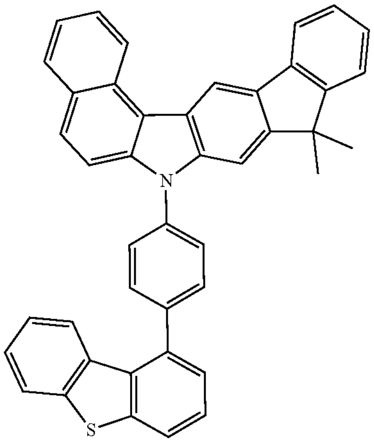
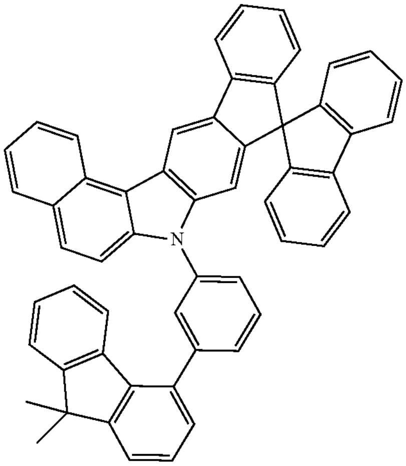
-continued -continued
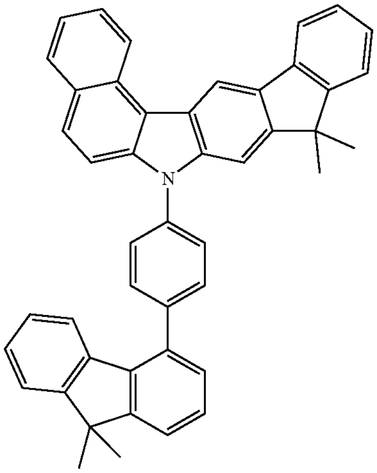
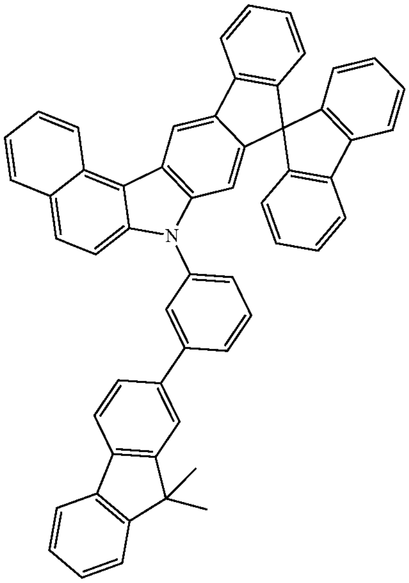
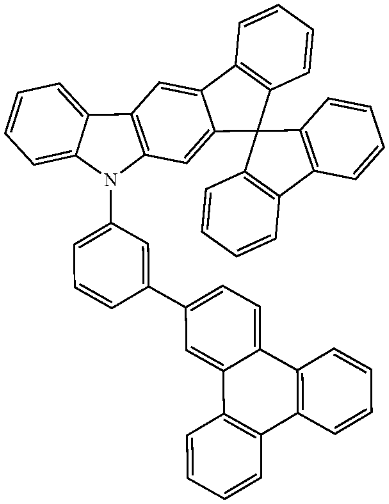
-continued
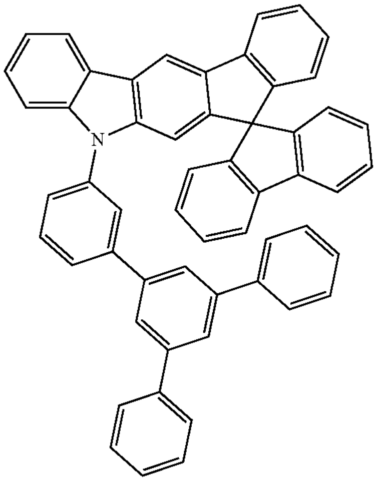
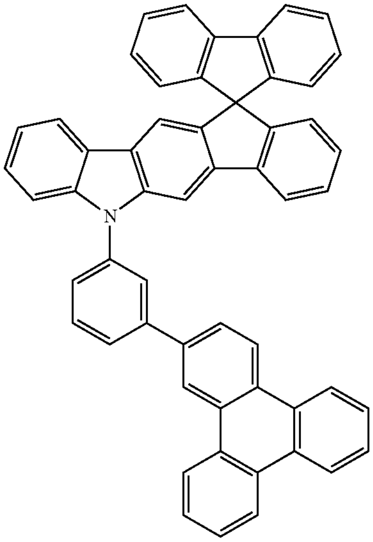
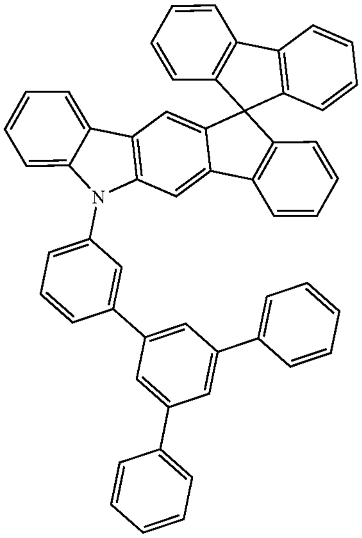

-continued
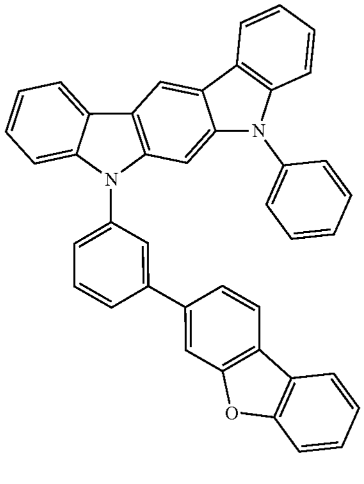
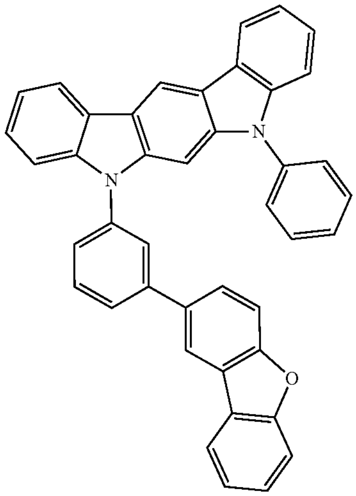
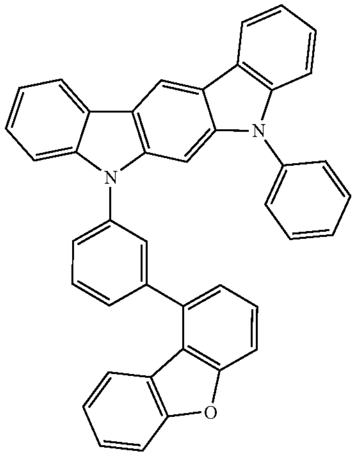
-continued
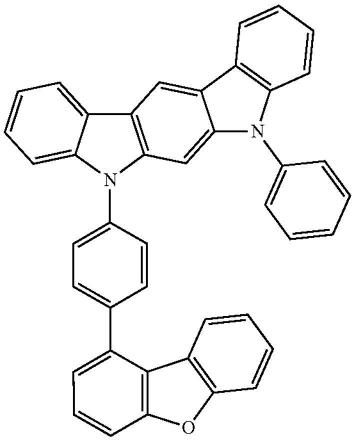
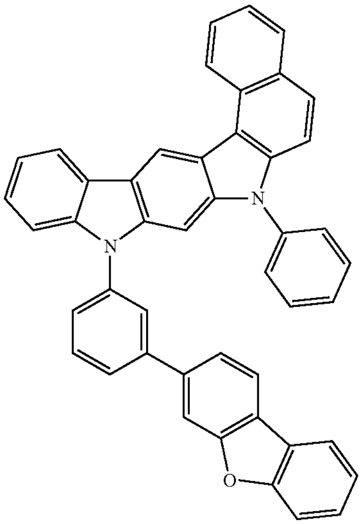
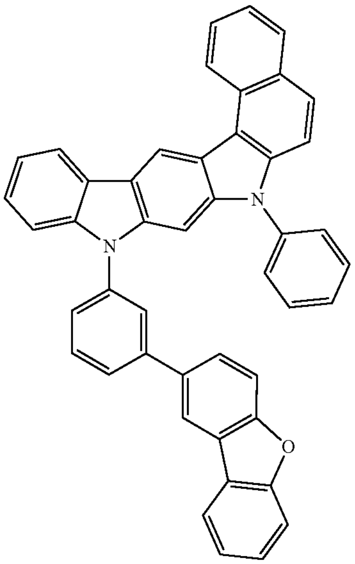

-continued
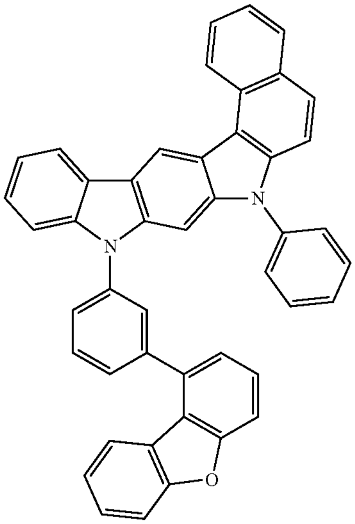
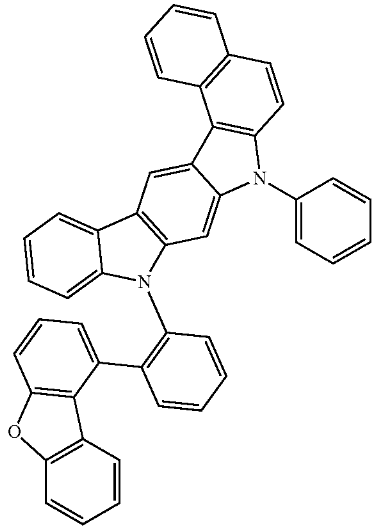
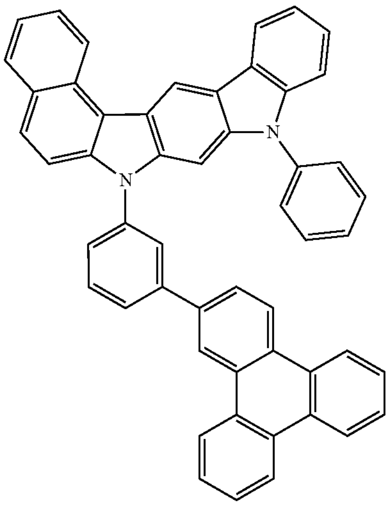
-continued
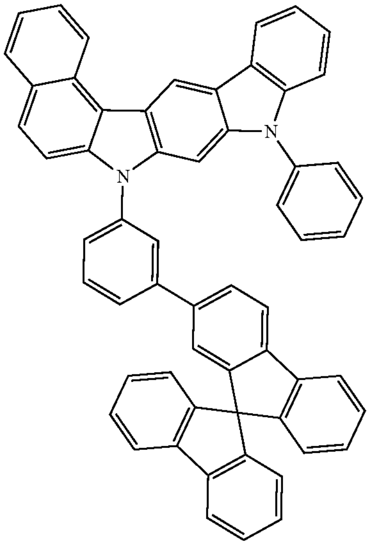
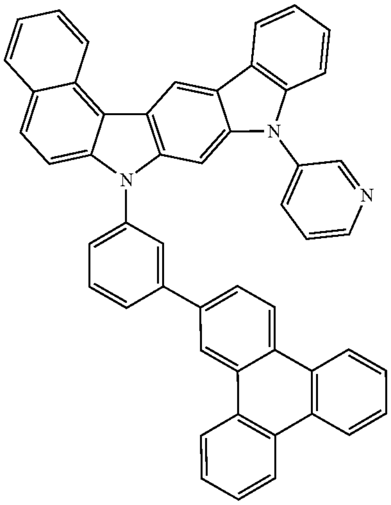
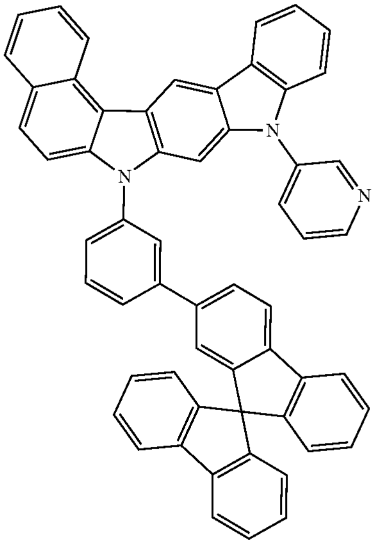

-continued
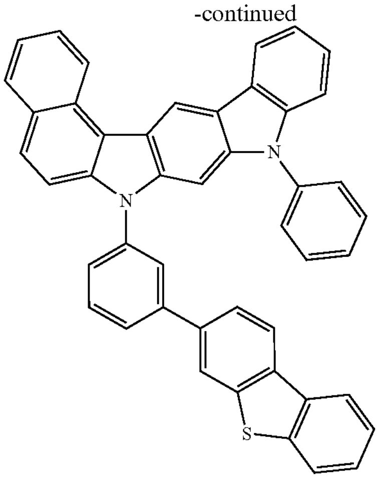
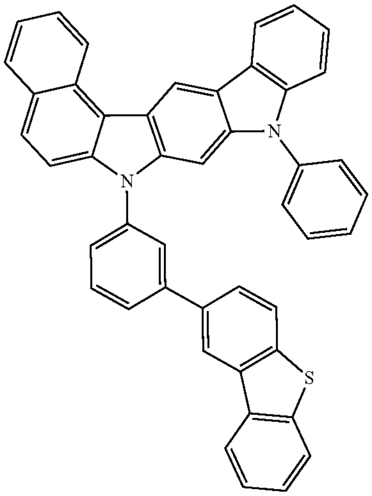
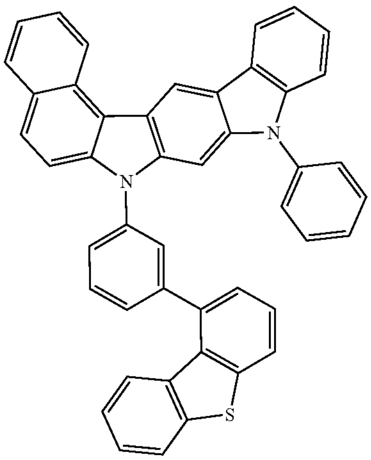
-continued
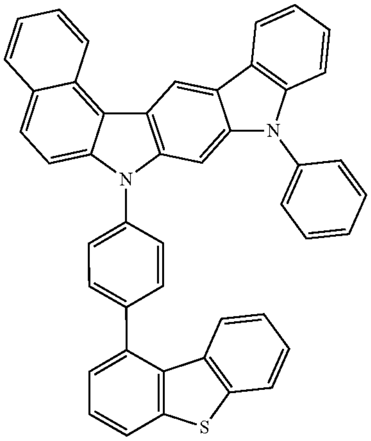
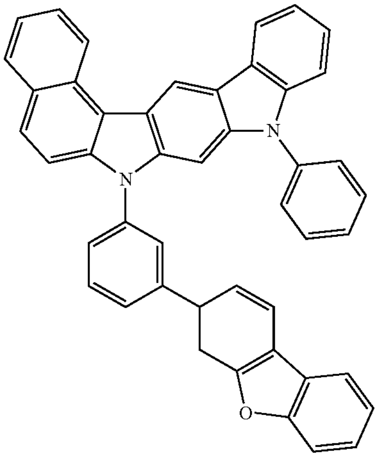
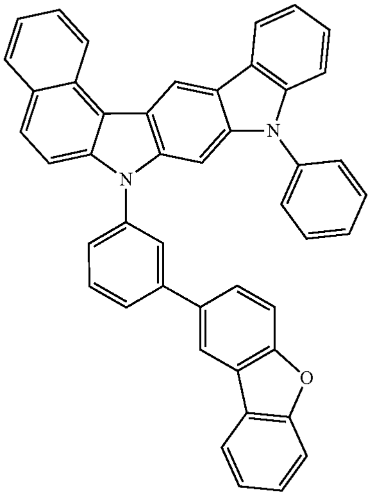

-continued
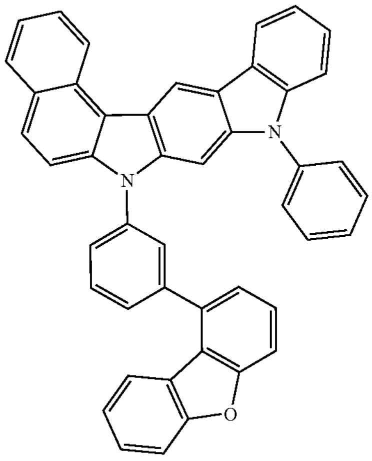
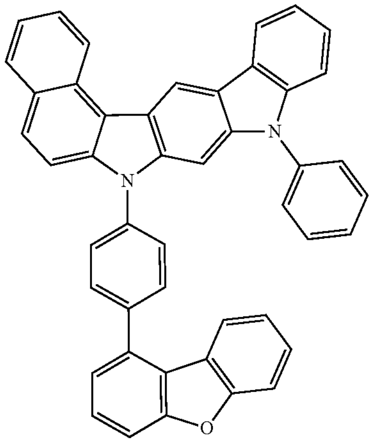
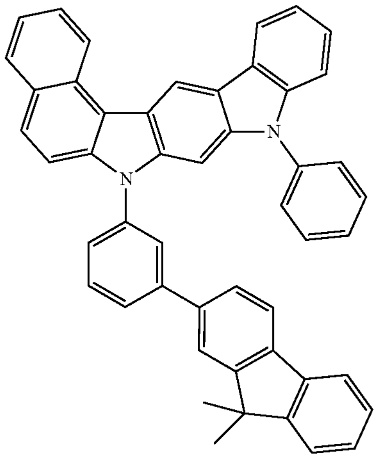
-continued
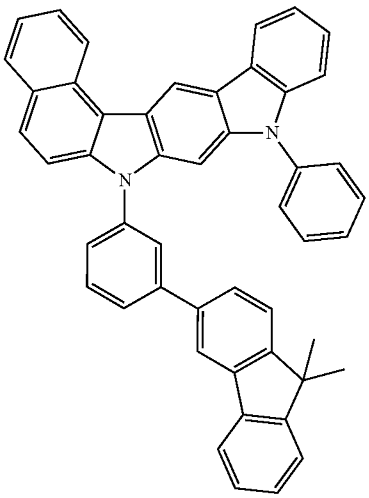
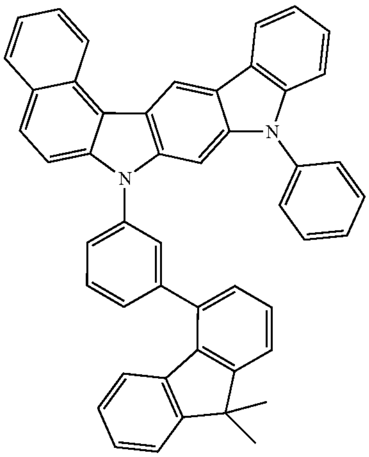
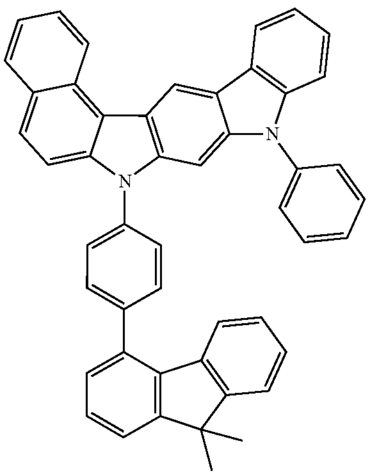

-continued
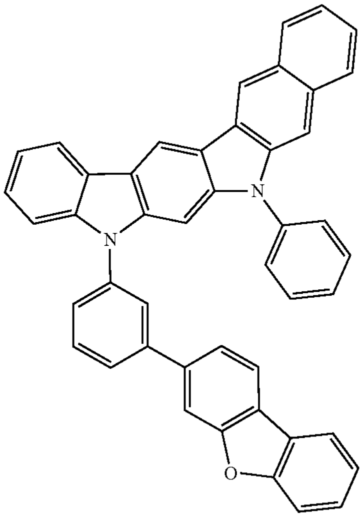
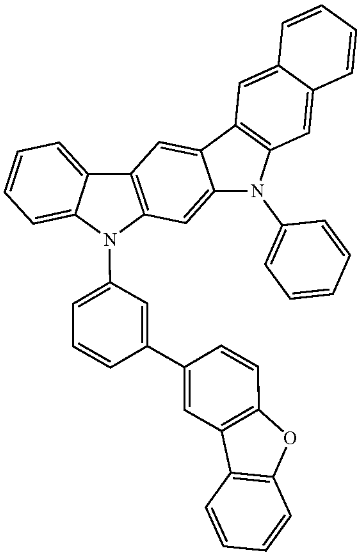
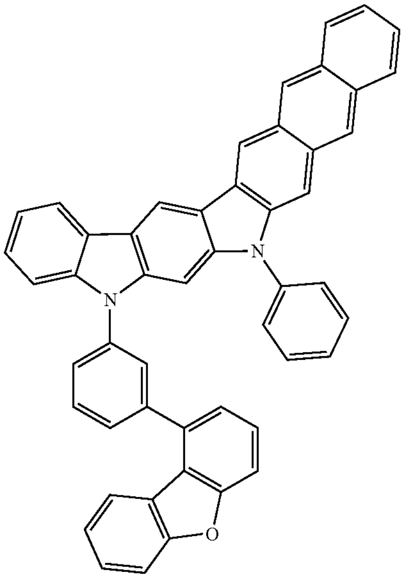
-continued
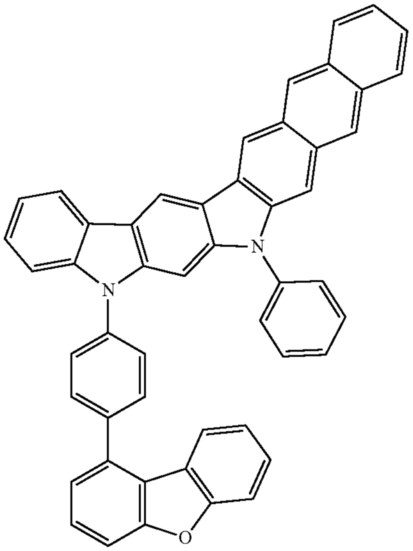
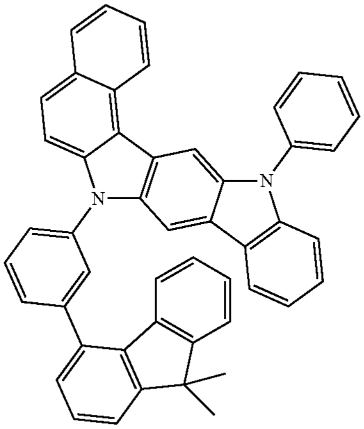
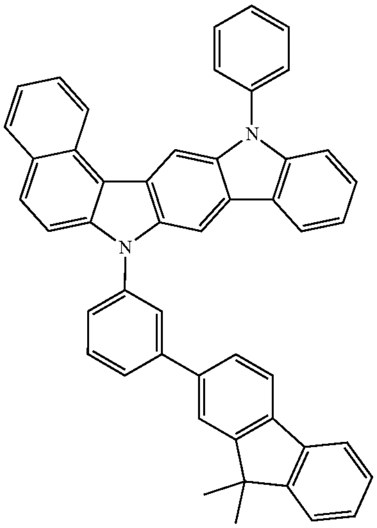

-continued
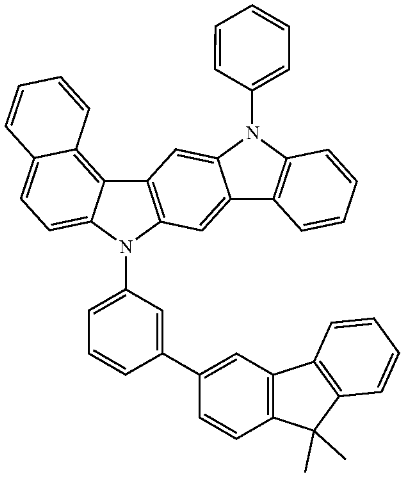
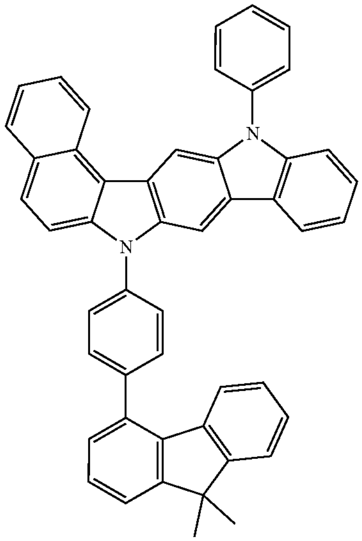
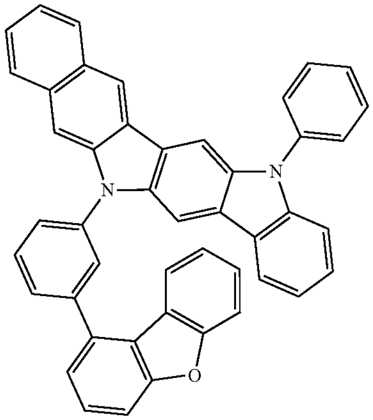
-continued
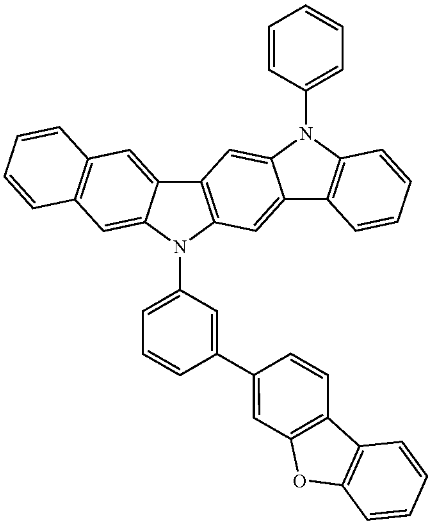
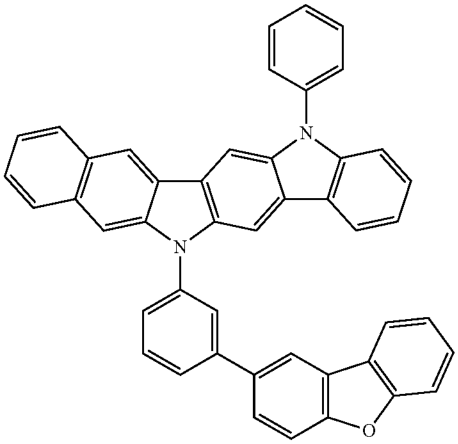
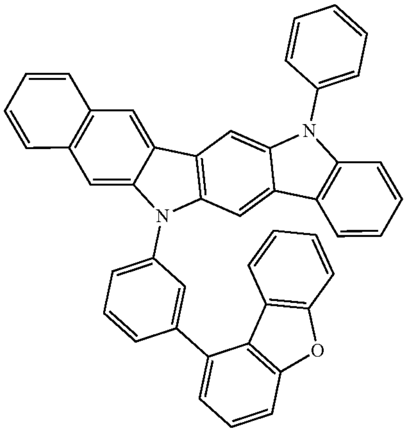

-continued
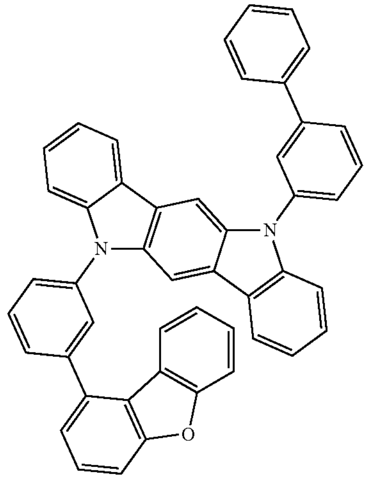
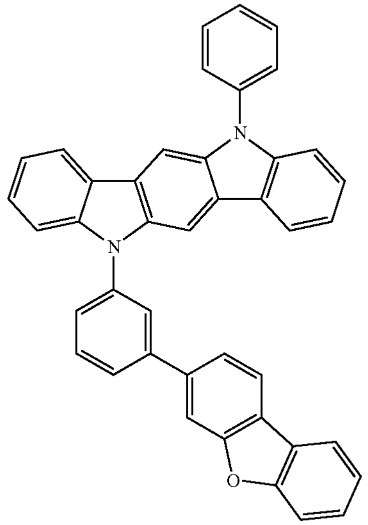
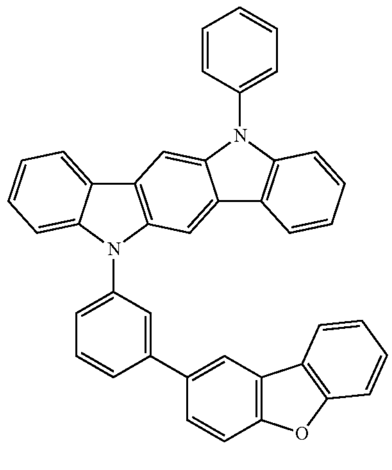
-continued
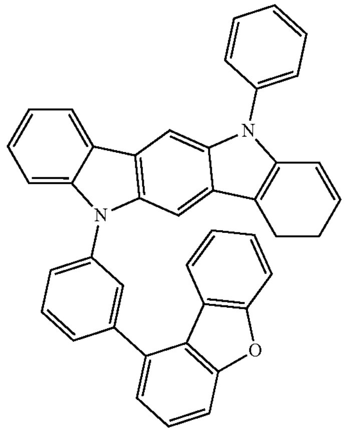
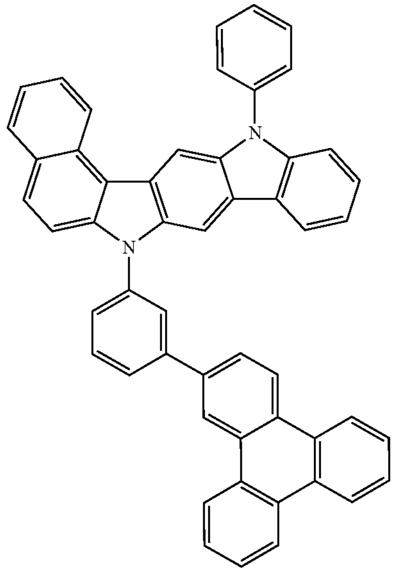
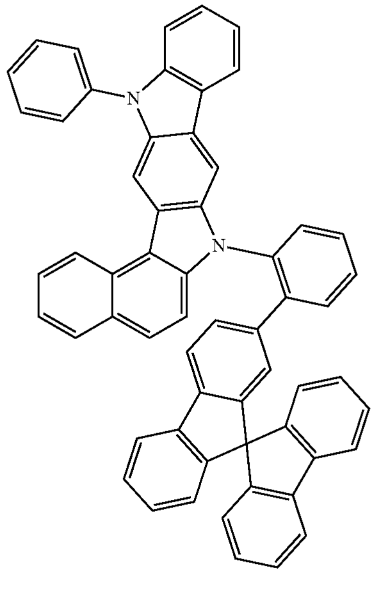

-continued
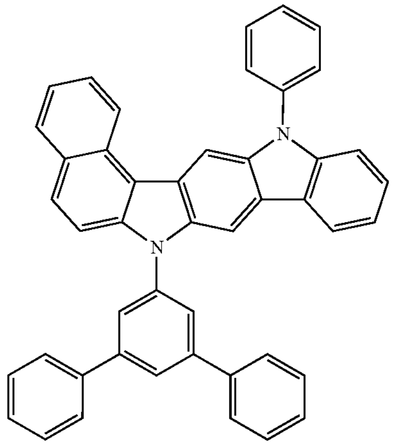
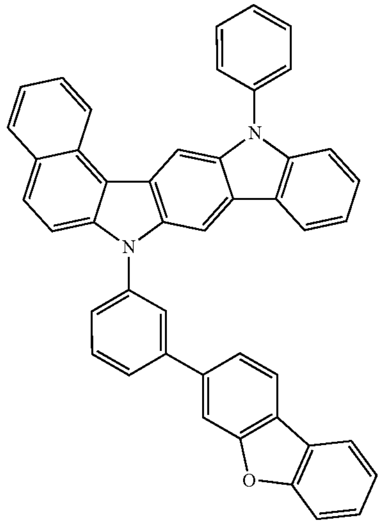
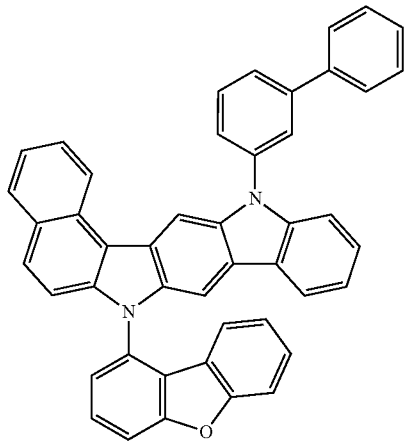
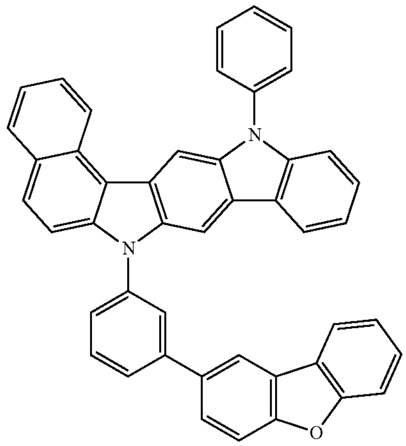
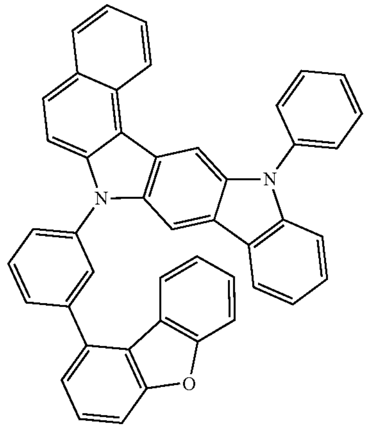
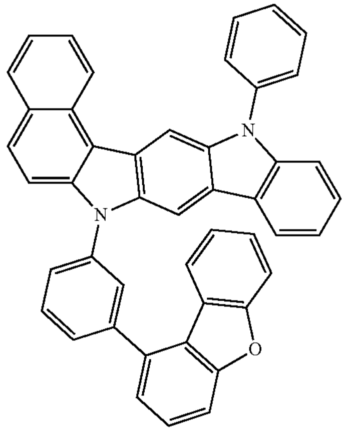
-continued -continued
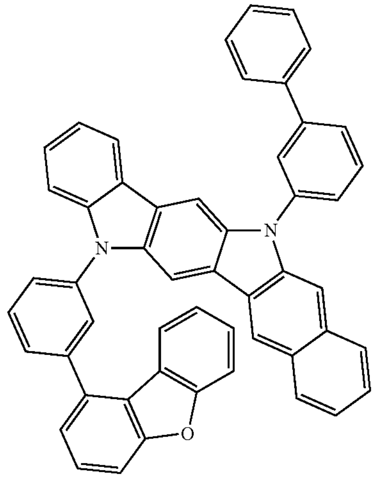
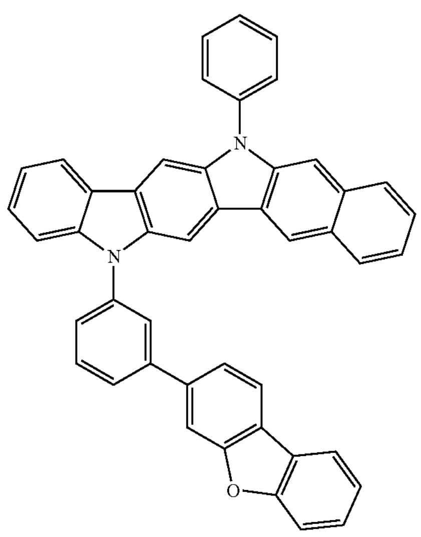
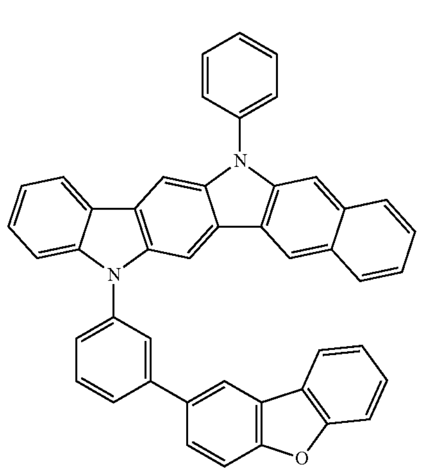
-continued
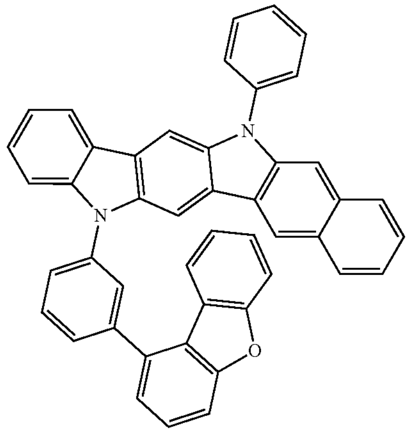
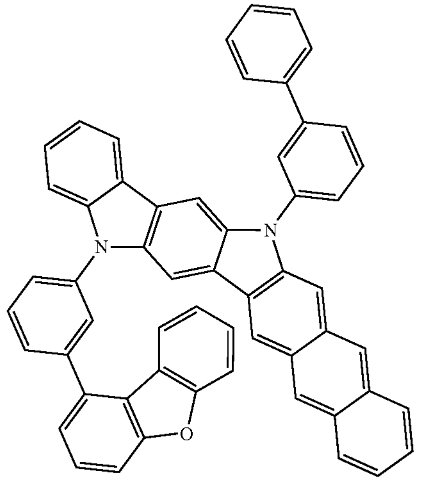
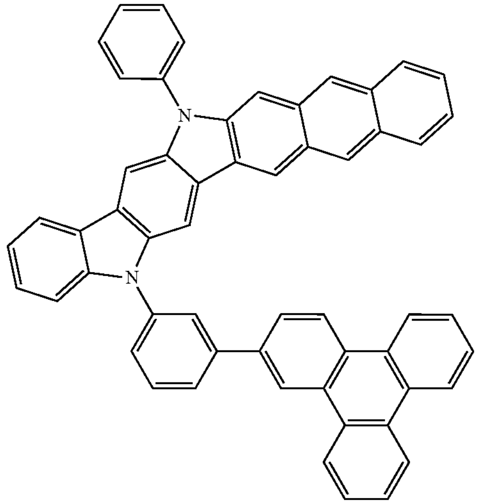

-continued
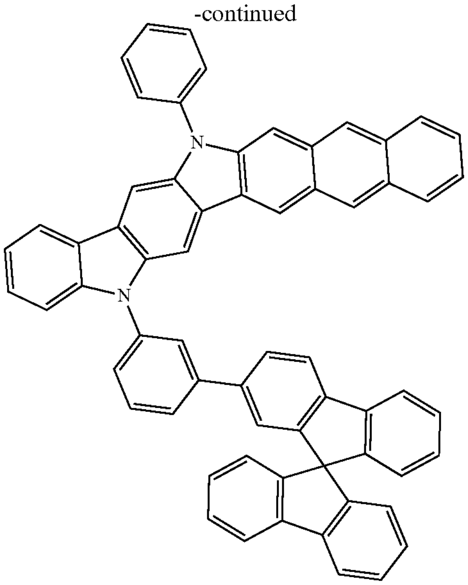
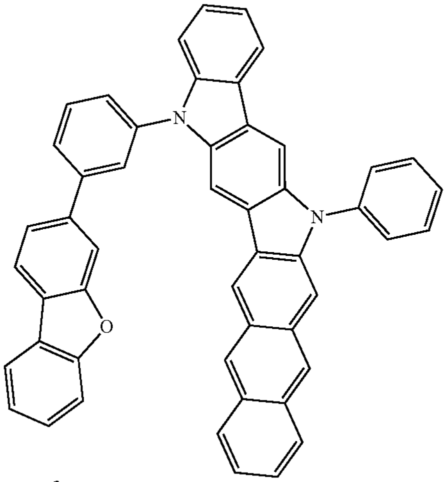
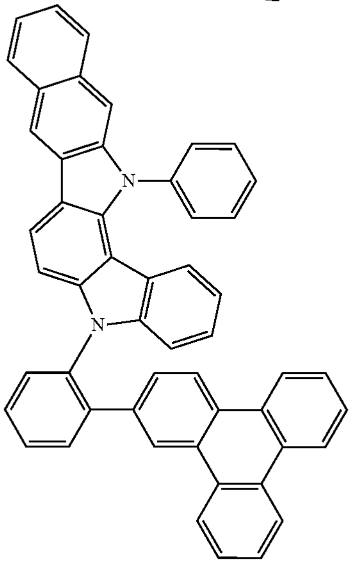
-continued
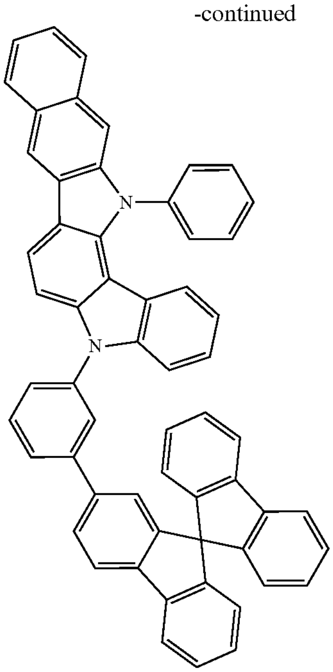
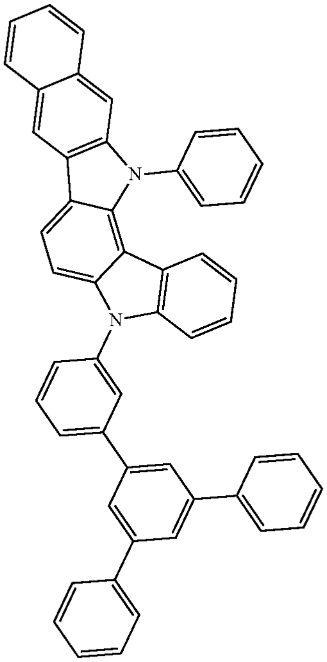

-continued
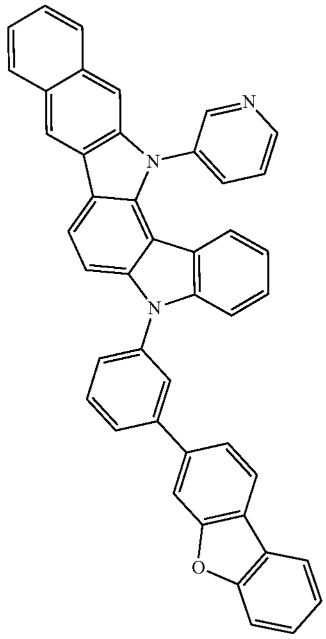
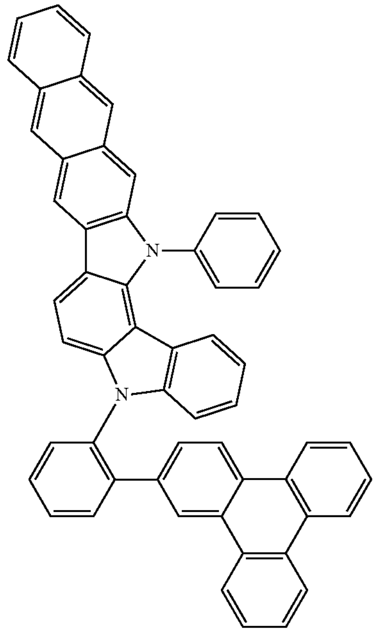
-continued
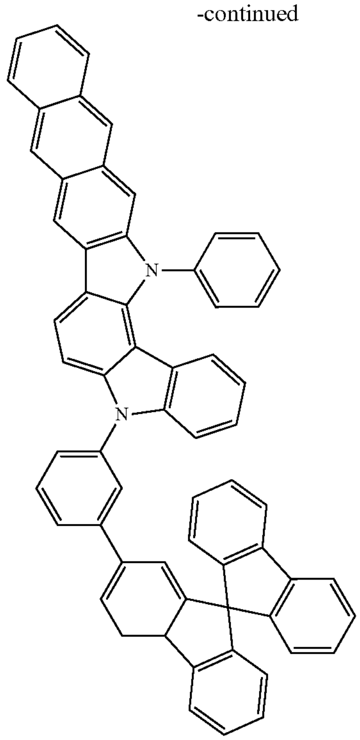
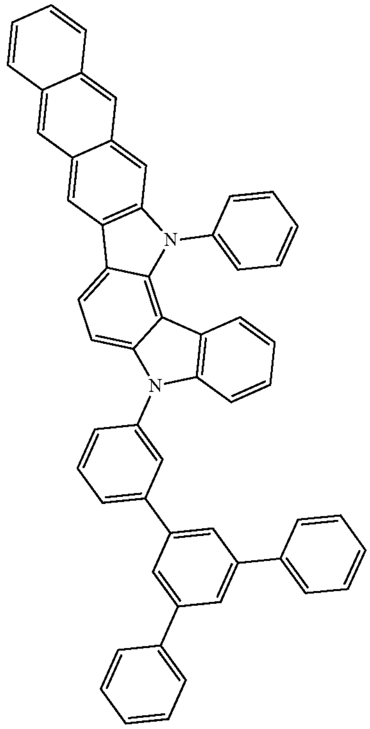

133
-continued
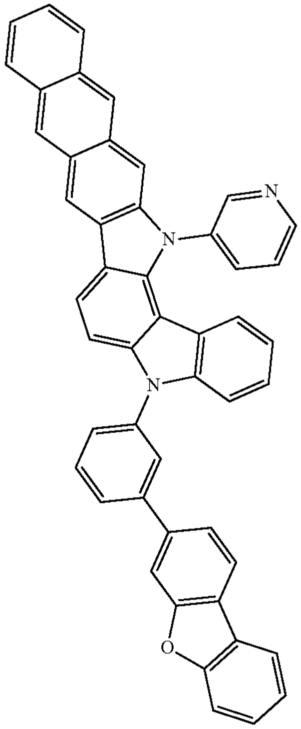
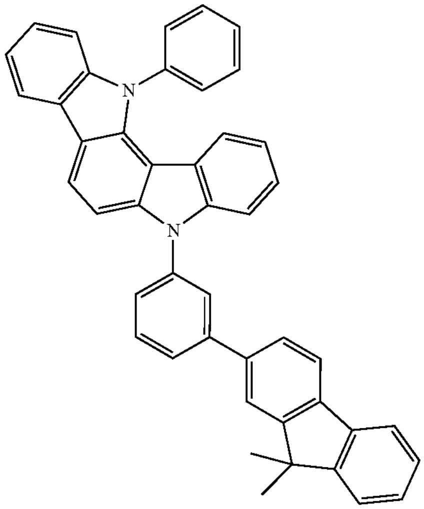
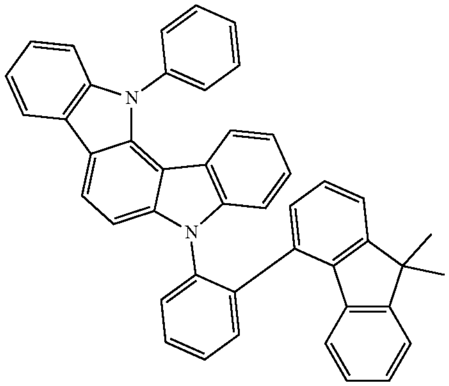
134
-continued
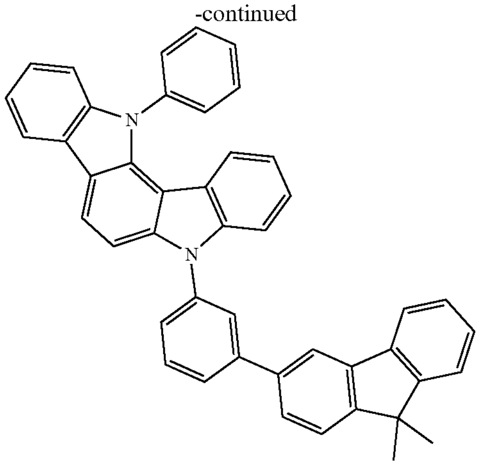
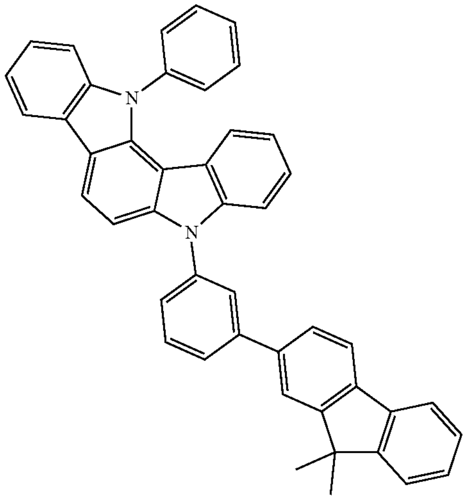
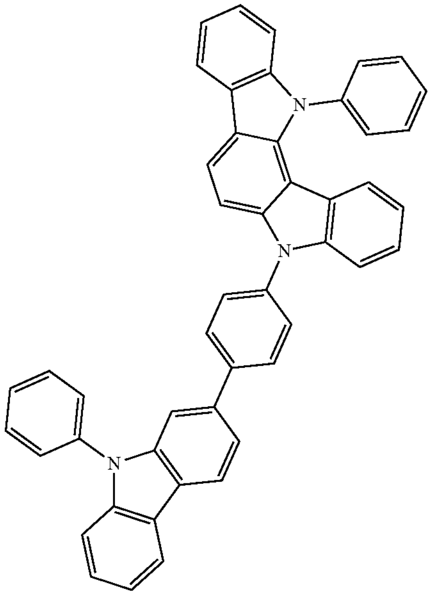

-continued
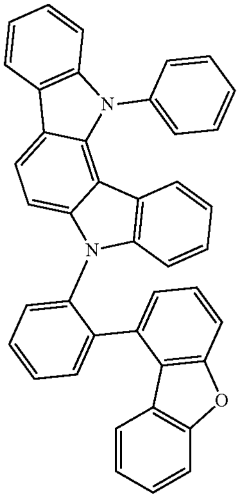
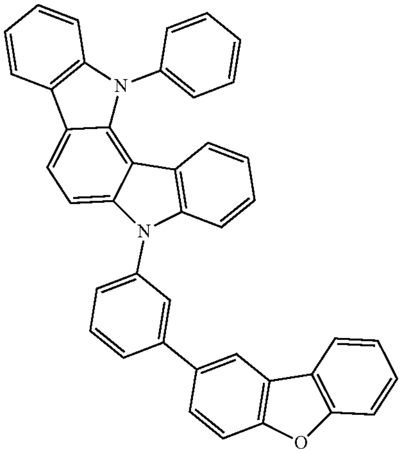
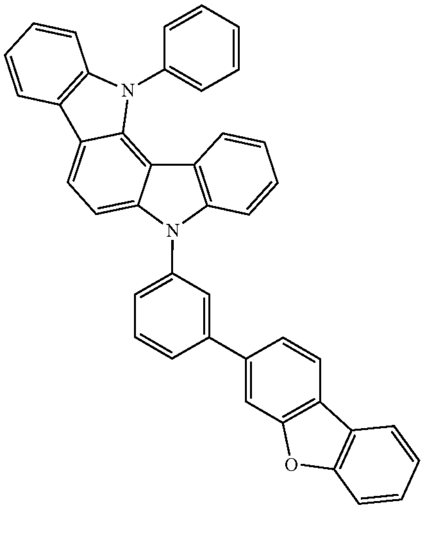
-continued
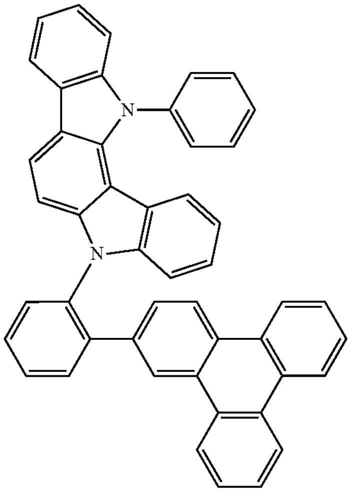
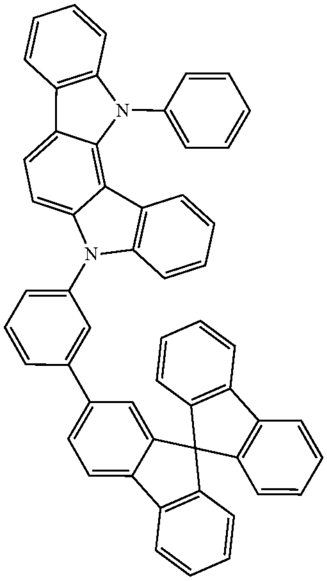
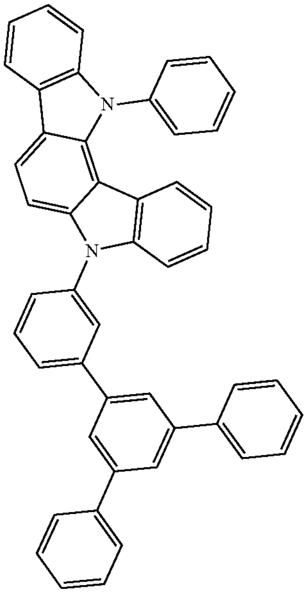

-continued
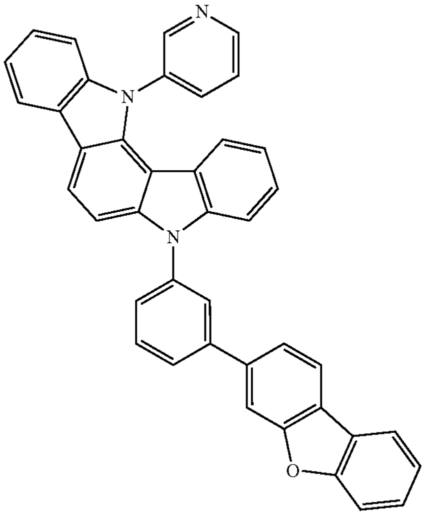
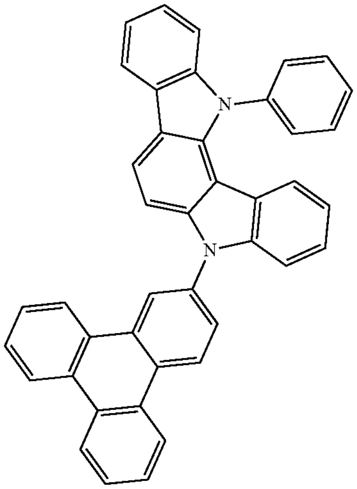
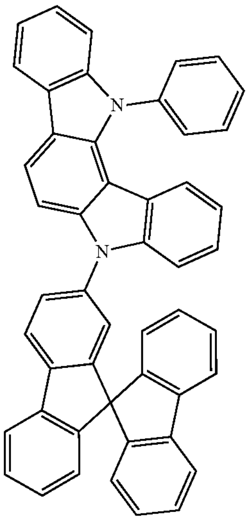
-continued
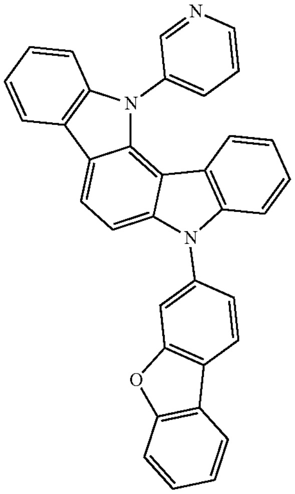
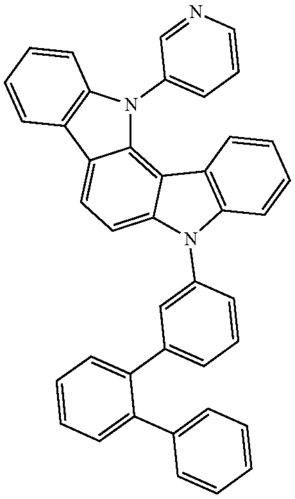
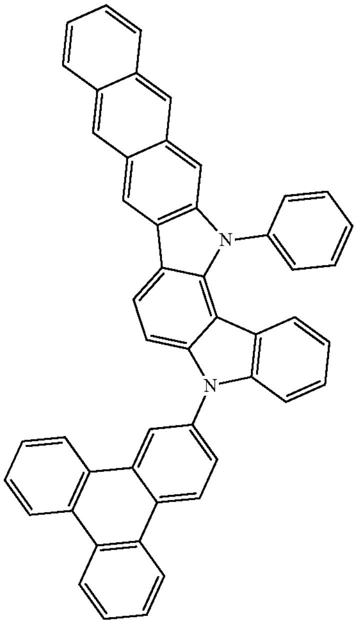

-continued

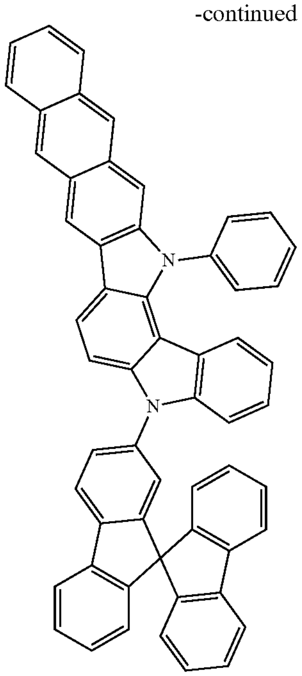

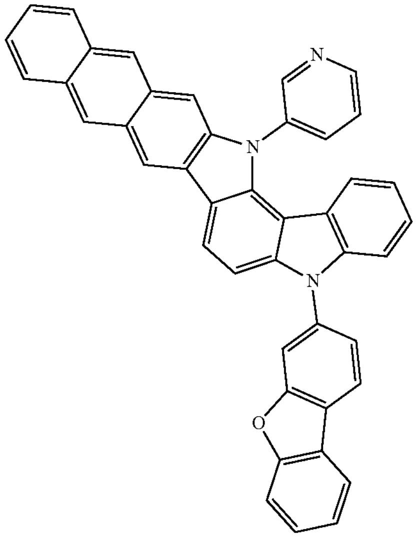

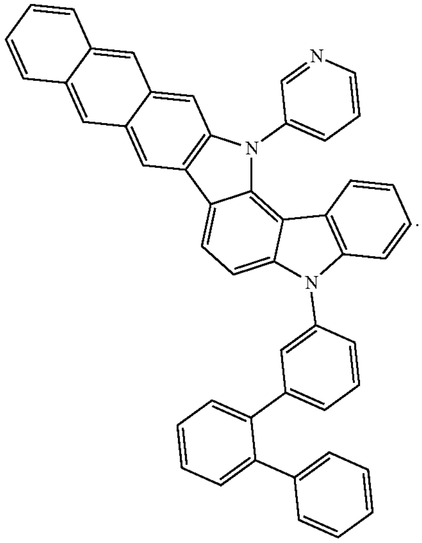

Preferably, the compound having a structure represented by Formula 1 and the compound having a structure represented by Formula 2 have a weight ratio of 1:9 to 9:1, such as 1:9, 2:8, 3:7, 4:6, 5:5, 6:4, 7:3, 8:2, 9:1, or the like; preferably 2:8 to 8:2; more preferably 3:7 to 7:3; even more preferably 4:6 to 6:4.

As used in the present invention, the term "organic electroluminescence material" indicates a material that can be used in an organic electroluminescence element, and may comprise at least one compound. The organic electroluminescence material may be comprised in any of the layers which constitute the organic electroluminescence element, if necessary. For example, the organic electroluminescence material may be a hole injection material, a hole transport material, an electron blocking material, an emitting auxiliary material, an emitting layer material (comprising a host material and a dopant material), an electron buffer material, a hole blocking material, an electron transport material, an electron injection material or the like.

As used in the present invention, the term "halogen" may comprise fluorine, chlorine, bromine or iodine.

As used in the present invention, the term "C1-C30 alkyl group" indicates a monovalent substituent derived from a straight or branched saturated hydrocarbon having 1 to 30 carbon atoms, for example, it comprises, but is not limited to, a methyl group, an ethyl group, a propyl group, an isobutyl group, a sec-butyl group, a tert-butyl group, a pentyl group, an isopentyl group, or a hexyl.

As used in the present invention, the term "C3-C30 cycloalkyl group" indicates a group derived from a monocyclic hydrocarbon or a multicyclic hydrocarbon having 1 to 30 carbon atoms on the main chain, and the cycloalkyl group may comprise cyclopropyl, cyclobutyl, adamantyl group, or the like.

In the present invention, the aryl group and arylene group comprise a monocyclic, a multicyclic or a fused cyclic aryl group, in which the rings may be interrupted by a short non-aromatic unit, and they may comprise a spiro-structure. The aryl group and arylene group of the present invention comprise, but are not limited to, a phenyl group, a biphenylyl group, a terphenylyl group, a naphthyl group, a phenanthryl group, an anthryl group, a fluorenyl group, a spiro-bifluorenyl group, or the like.

In the present invention, the heteroaryl group and heteroarylene group comprise a monocyclic, a multicyclic or a fused cyclic heteroaryl group in which the rings may be interrupted by a short non-aromatic unit, and the hetero atom comprises nitrogen, oxygen or sulfur. The heteroaryl group and heteroarylene group of the present invention comprise, but are not limited to, a furyl group, a thiophenyl group, a pyrrolyl group, an imidazolyl group, a pyrazolyl group, a thiazolyl group, a thiadiazolyl group, an isothiazolyl group, an isoxazolyl group, an oxazolyl group, an oxadizolyl group, a triazinyl group, a tetrazinyl group, a triazolyl group, a tetrazolyl group, a furazanyl group, a pyridyl group, a pyrazinyl group, a pyrimidinyl group, a pyridazinyl group, a benzofuryl group, a benzothiophenyl group, an isobenzofuryl group, a dibenzofuryl group, a dibenzothiophenyl group, a benzimidazolyl group, a benzothiazolyl group, a benzisothiazolyl group, a benzisoxazolyl group, a benzoxazolyl group, an isoindolyl group, an indolyl group, an indazolyl group, a benzothiadiazolyl group, a quinolyl group, an isoquinolyl group, a cinnolinyl group, a quinazolinyl group, a quinoxalinyl group, a carbazolyl group, a phenoxazinyl group, a phenothiazinyl group, a phenanthridinyl group, a 1,3-benzodioxolyl group, a dihydroacridinyl group, or derivatives thereof.

Preferably, the aryl group is selected from a phenyl group, a biphenylyl group, a terphenylyl group, a naphthyl group, an anthryl group, a phenanthryl group, a 9,9'-dimethylfluorenyl group, a 9,9'-diphenylfluorenyl group and a spirobifluorenyl group.

Preferably, the heteroaryl group is selected from a dibenzofuryl group, a dibenzothiophenyl group, a carbazolyl group, a triazinyl group, a pyridyl group, a pyrimidinyl group, an imidazolyl group, an oxazolyl group, a thiazolyl group, a benzimidazolyl group, a benzoxazolyl group, a benzothiazolyl, a naphthimidazolyl group, a naphthoxazolyl group, a naphthothiazolyl group, a phenanthrimidazolyl group, a phenanthroxazolyl group, a phenanthrothiazolyl group, a quinoxalinyl group, a quinazolinyl group, an indolocarbazolyl group, an indolofluorenyl group, a benzothienopyrazinyl group, a benzothienopyrimidinyl group, a benzofuropyrazinyl group, a benzofuropyrimidinyl group, an indolopyrazinyl group, an indolopyrimidinyl group, an indenopyrazinyl group, an indenopyrimidinyl group, a spiro[fluorene-9,1'-indene]-pyrazinyl group, a spiro[fluorene-9,1'-indene]-pyrimidinyl group, benzofurocarbazolyl and benzothienocarbazolyl.

As used in the present invention, the term "C6-C30 aryloxy group" indicates a monovalent substituent represented by ZO—, wherein Z represents an aryl group having 6 to 30 carbon atoms. Examples of such aryloxy group comprise, but are not limited to, a phenoxy group, a naphthyloxy group, a diphenoxy group, or the like.

As used in the present invention, the term "C1-C30 alkoxy group" indicates a monovalent substituent represented by Z'O—, wherein Z' represents an alkyl group having 1 to 30 carbon atoms.

As used in the present invention, the term "substituted" indicates a hydrogen atom comprised in a compound is replaced by another substituent. The position of substitution is not specifically limited, provided that the hydrogen at the position can be replaced by the substituent. When two or more substituents are simultaneously present, the two or more substituents can be the same or different.

As used in the present invention, unless otherwise specified, the hydrogen atom comprises protium, deuterium or tritium.

In the present invention, "adjacent two groups joined to form a ring" indicates that 2 substituents at adjacent positions on the same ring or adjacent rings can be joined to form a ring by chemical bonding. The specific way to form a ring in the present invention is not limited (for example, joined via a single bond, joined via a benzene ring, joined via a naphthalene ring, fused via

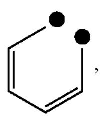
, fused via

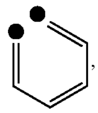
, fused via

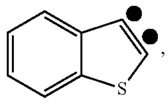
, fused via

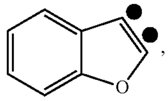
, fused

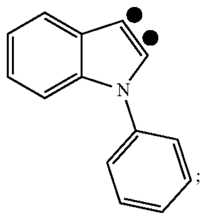 [SMILES: c1ccc(-n2ccc3ccccc32)cc1]
;

via wherein the •• represents fusion positions). In the same description present hereinafter, it has the same meaning.

In the present invention, when the range of carbon atom number is limited in the definition of a functional group, the functional group may have a carbon atom number of any integer in the limited range. For example, a C6-C60 aryl group represents an aryl group that may give a carbon number of any one integer comprised in the range of 6 to 60, such as 6, 8, 10, 15, 20, 30, 35, 40, 45, 50, 55 or 60, etc.

In the present invention, the organic compounds substituted at each of the described positions are prepared by a synthesis route shown as below:

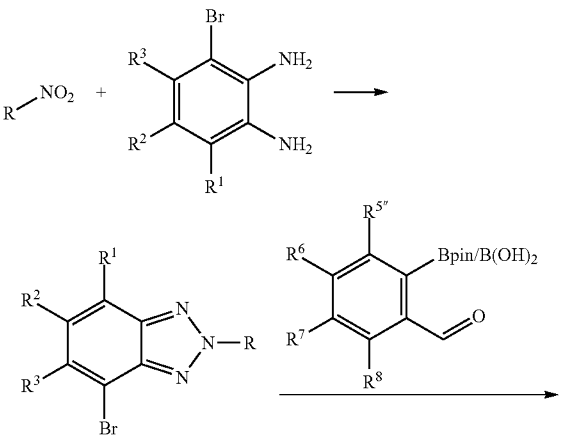

-continued
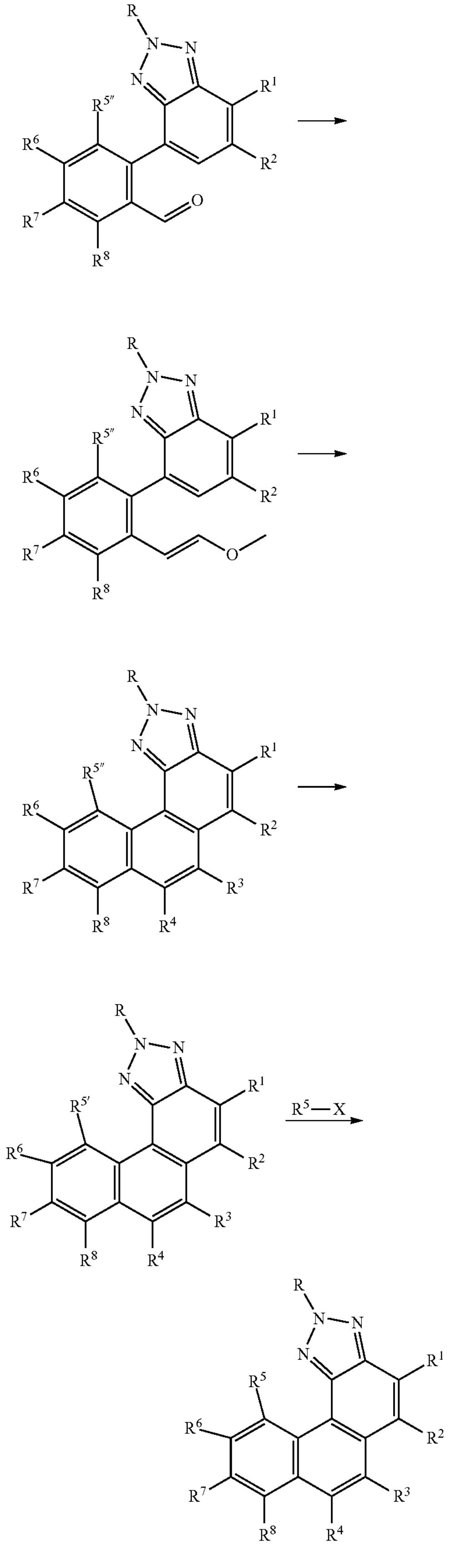
$R^{5''}$ is chlorine; $R^{5''}$ is
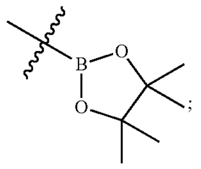 [SMILES: *B1OC(C)(C)C(C)(C)O1]
X is halogen, preferably chlorine or bromine.
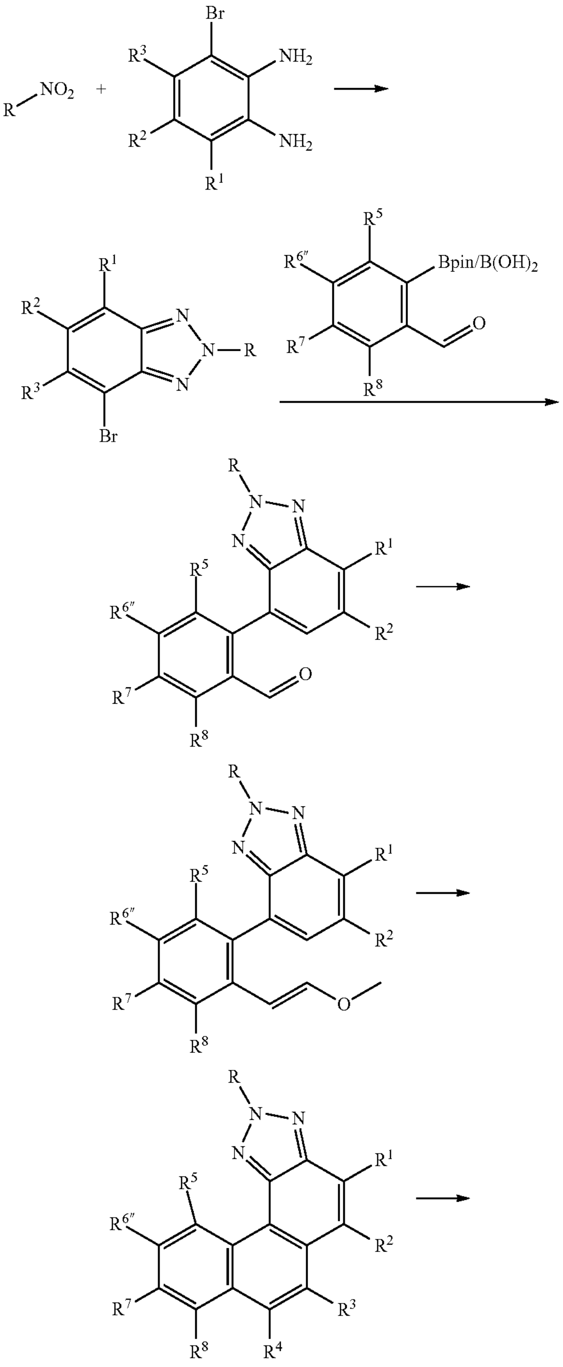

-continued
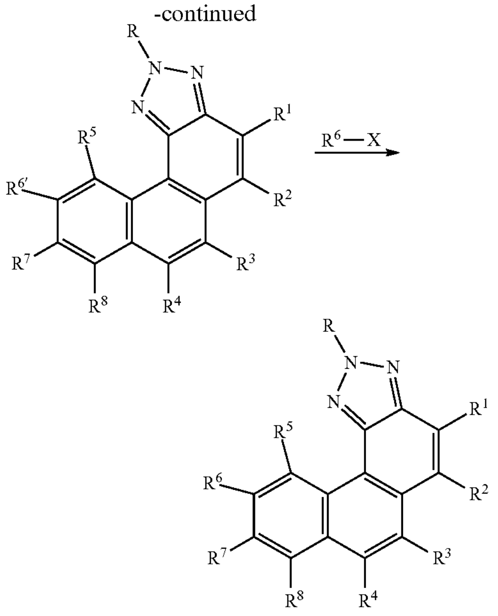
$R^{6''}$ is chlorine; $R^{6'}$ is
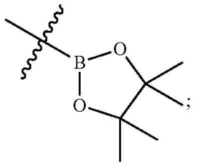 [SMILES: *B1OC(C)(C)C(C)(C)O1]
X is halogen, preferably chlorine or bromine.
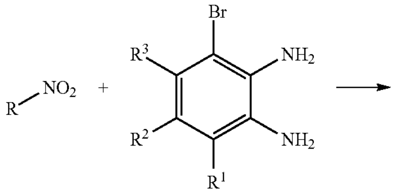
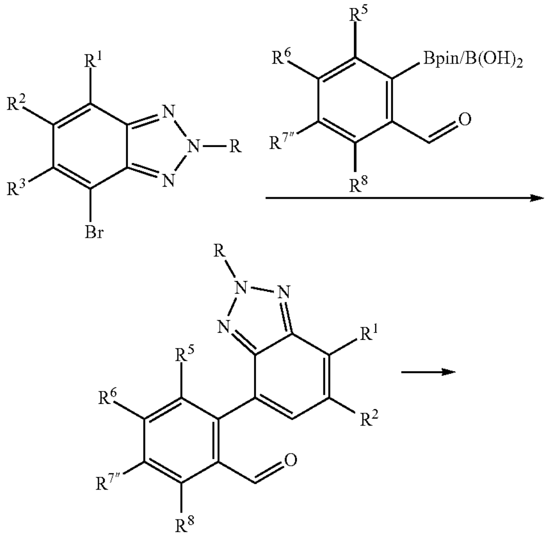
-continued
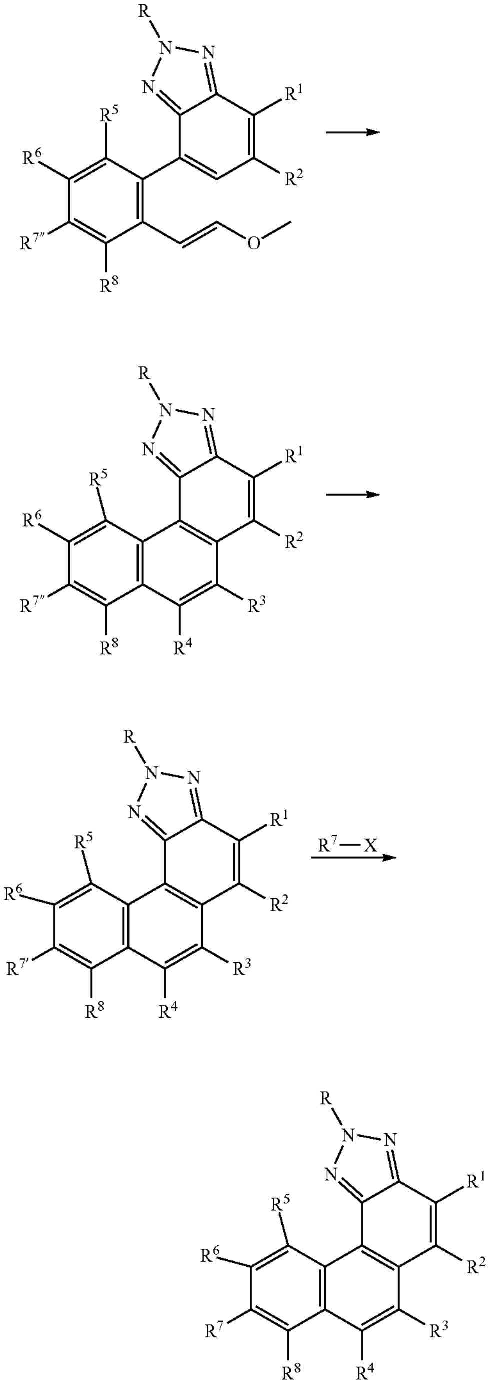
$R^{7''}$ is chlorine; $R^{7'}$ is
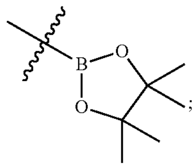 [SMILES: *B1OC(C)(C)C(C)(C)O1]
X is halogen, preferably chlorine or bromine.

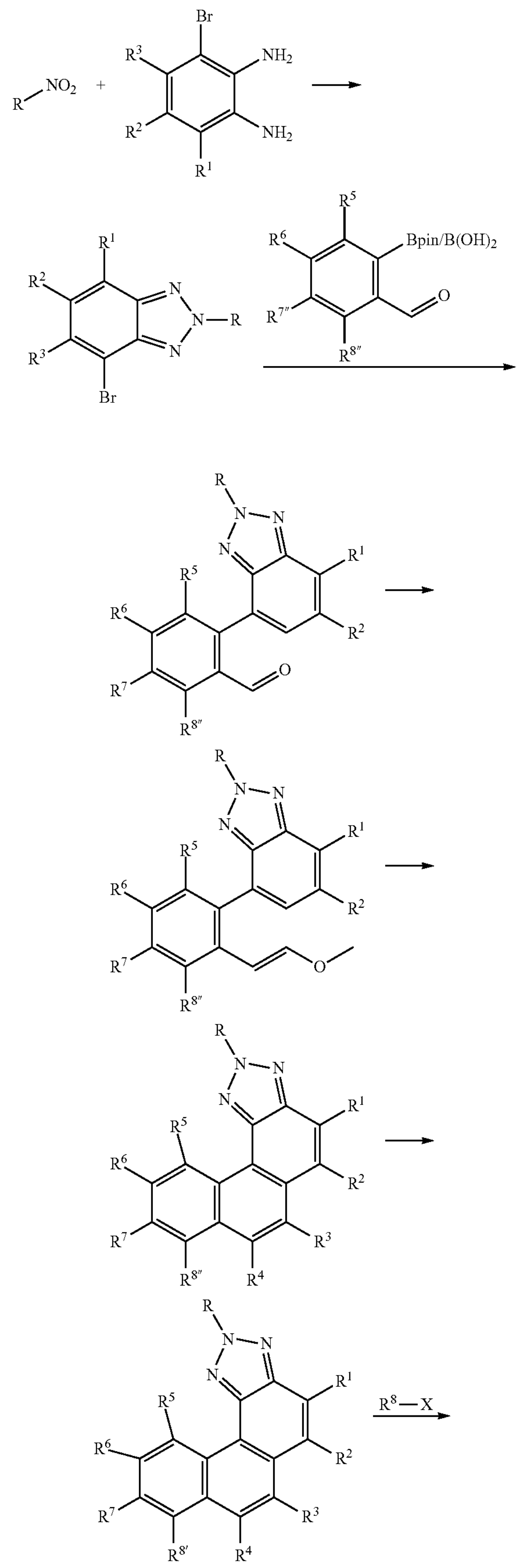

-continued

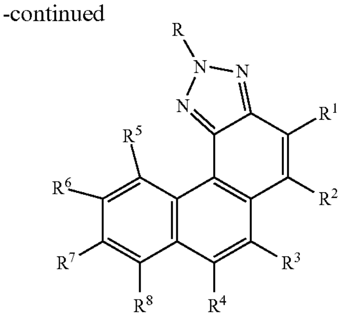

$R^{8''}$ is chlorine; $R^{8'}$ is

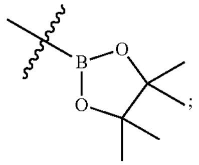 [SMILES: *B1OC(C)(C)C(C)(C)O1]

X is halogen, preferably chlorine or bromine.

In another aspect, the present invention provides an organic electroluminescence material, and the organic electroluminescence material comprises the above-mentioned organic material composition.

In another aspect, the present invention provides an application of the above-mentioned organic material composition or the above-mentioned organic electroluminescence material in preparation of an optical element.

Preferably, the optical element comprises any one of an organic electroluminescence element, an organic field-effect transistor, an organic thin film transistor, an organic light-emitting transistor, an organic integrated circuit, an organic solar cell, an organic field quenching element, a light-emitting electrochemical cell, an organic laser diode, and an organic photoreceptor.

In another aspect, the present invention provides an organic electroluminescence element, wherein the organic electroluminescence element comprises an anode, a cathode, and an organic layer disposed between the anode and the cathode, and the organic layer comprises the above-mentioned organic material composition or the above-mentioned organic electroluminescence material.

Preferably, the organic layers comprise a hole injection layer, a hole transport layer, an emitting layer, an electron transport layer and an electron injection layer, which are sequentially layered from a side of the anode to a side of the cathode.

Preferably, the emitting layer is made of a material comprising a host material and a guest material, wherein the host material comprises the above-mentioned organic material composition or the above-mentioned organic electroluminescence material.

Preferably, the guest material comprises a phosphorescence dopant, and the phosphorescence dopant comprises a coordination complex of a transition metal.

In another aspect, the present invention provides an organic electroluminescence device, wherein the organic electroluminescence device comprises the above-mentioned organic electroluminescence element.

Compared to the existing technology, the present invention has the following advantages:

By the combination of at least one compound having a structure represented by Formula 1 and at least one compound having a structure represented by Formula 2, the above-mentioned organic material composition can promote the electron transport properties of the host material, further increase the combination rate of electrons and holes, thereby enhancing the light-emitting efficiency of an organic light-emitting diode and prolonging its service life.

BRIEF DESCRIPTION OF THE DRAWINGS

The FIGURE is a schematic diagram of the structure of the organic electroluminescence element provided by the application example of the present invention, wherein 1 is an anode, 2 is a hole injection layer, 3 is a hole transport layer, 4 is an emitting layer, 5 is an electron transport layer, 6 is an electron injection layer, and 7 is a cathode.

DETAILED DESCRIPTION OF THE PREFERRED EMBODIMENTS

Specific embodiments are further illustrated by the following examples to demonstrate the technical approaches of the present invention. Those skilled in the art should understand that the illustrative examples are helpful to understand the present invention; however, they should not be construed as being limiting to the scope of the present invention.

Preparation Example of Compound of Formula 1

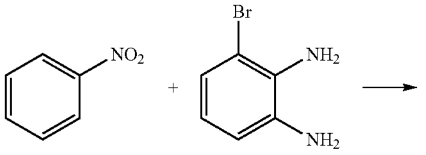

1A

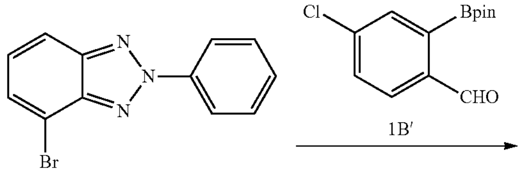

1B'

1B

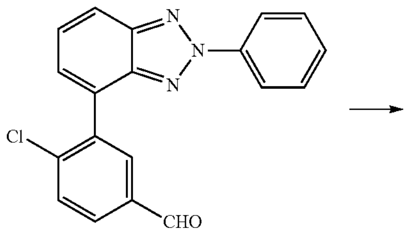

1C

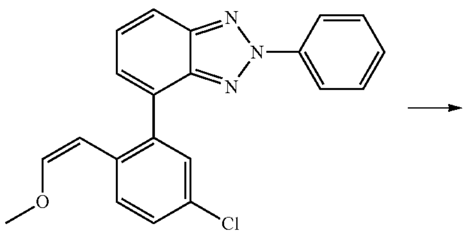

1D

-continued

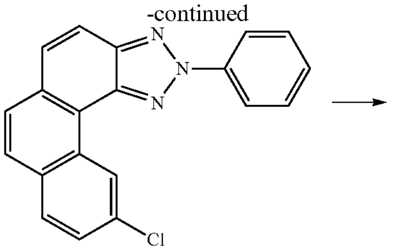

1E

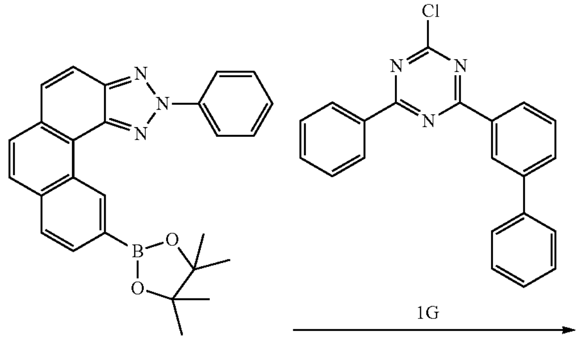

1G

1F

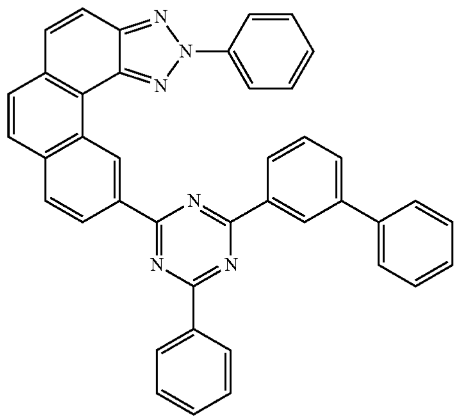

1

Synthesis of 1B: In a three-necked bottle of 25 milliliters (mL), 1A (10 millimoles (mmol)), nitrobenzene (10 mmol), potassium hydroxide (22 mmol), copper(I) thiocyanate (1 mmol) and anhydrous tetrahydrofuran (10 mL) were added, nitrogen gas was purged for three times, and heated to 90° C. under nitrogen gas protection to react for 48 hours (h). After the reaction ended, the reaction mixture was quenched by water, the reaction system was extracted by ethyl acetate, and the organic solvent was removed by rotary evaporation to give a crude product. The crude product was purified by column chromatography (ethyl acetate: n-hexane=1:50 (volume ratio)), to obtain 1B (1.34 g, 49% yield).

Synthesis of 1B': In a three-necked bottle of 50 mL, 2-bromo-4-chlorobenzaldehyde (10 mmol), bis(pinacolato) diboron (12 mmol), potassium acetate (100 mmol), [1,1'-bis (diphenylphosphino)ferrocene]palladium(II) dichloride (0.2 mmol) and 1,4-dioxane (25 mL) were added, nitrogen gas was purged, and heated to 100° C. under nitrogen gas protection for reaction. After the reaction ended, the reaction mixture was quenched by water, extracted by methylene dichloride to give a crude product. The crude product was purified by column chromatography (methylene dichloride: n-hexane=1:50 (volume ratio)), to obtain 1B' (1.7 g, 64% yield).

Synthesis of 1C: In a three-necked bottle of 50 mL, 1B (10 mmol), 1B' (10 mmol), sodium bicarbonate (20 mmol), tetrakis(triphenylphosphine)palladium (0.2 mmol), tetrahydrofuran (20 mL) and water (10 mL) were added, nitrogen gas was purged, and heated to 60° C. under nitrogen gas protection to react overnight. After the reaction ended, the reaction mixture was quenched by water, extracted by methylene dichloride, and the organic solvent was removed by rotary evaporation to give a crude product. The crude product was purified by column chromatography (ethyl acetate: n-hexane=1:50 (volume ratio)), to obtain 1C (3.06 g, 92% yield).

Synthesis of 1D: In a three-necked bottle of 50 mL, 1C (10 mmol), (methoxymethyl)triphenylphosphonium chloride (20 mmol), tetrahydrofuran (10 mL) were added, and the temperature was reduced to 0° C. Potassium tert-butoxide (2 mmol) was resolved in 5 mL tetrahydrofuran. The three-necked bottle was purged with nitrogen gas. Under nitrogen gas protection, the potassium tert-butoxide solution was added dropwise at 0° C. to obtain a mixture. After the addition, the mixture was stirred to react for half an hour. After the reaction ended, the reaction mixture was quenched by water, extracted by methylene dichloride, and the organic solvent was removed by rotary evaporation to give a crude product. The crude product was purified by column chromatography (ethyl acetate: n-hexane=1:50 (volume ratio)), to obtain 1D (1.8 g, 50% yield).

Synthesis of 1E: In a three-necked bottle of 25 mL, 1D (1 mmol) and hexafluoroisopropanol (5 mL) were added, the temperature was reduced to 0° C., and nitrogen gas was purged. Under nitrogen gas protection, trifluoromethanesulfonic acid (1 mL) was added dropwise to obtain a mixture, and the mixture was stirred to react for half an hour to give a crude product. The crude product was purified by column chromatography (ethyl acetate: n-hexane=1:50 (volume ratio)), to obtain 1E (0.24 g, 73% yield).

Synthesis of 1F: In a three-necked bottle of 50 mL, 1E (10 mmol), bis(pinacolato)diboron (12 mmol), sodium acetate (20 mmol), tris(dibenzylideneacetone)dipalladium(0) (0.5 mmol) and 2-dicyclohexylphosphino-2',6'-dimethoxybiphenyl (1.5 mmol) were added, then 1,4-dioxane (20 mL) was added, nitrogen gas was purged for three times, and heated to 100° C. under nitrogen gas protection for reaction. After the reaction ended, the reaction mixture was quenched by water, extracted by methylene dichloride, and the organic solvent was removed by rotary evaporation to give a crude product. The crude product was purified by column chromatography (ethyl acetate: n-hexane=1:50 (volume ratio)), to obtain 1F (3.24 g, 77% yield).

Synthesis of 1: In a three-necked bottle of 100 mL, a stir bar was put at the bottom and a refluxing tube was connected on the top. The bottle was dried and purged with nitrogen gas, and 1F (10 mmol), 1G (10 mmol CAS1689576-03-1), sodium bicarbonate (23 mmol), tetrakis(triphenylphosphine) palladium (0.5 mmol), bis(di-tert-butyl(4-dimethylaminophenyl)phosphine) dichloropalladium(II) (0.5 mmol), toluene (25 mL), ethanol (7 mL) and water (7 mL) were separately added, nitrogen gas was purged for three times, and heated to 80° C. to react for 8 h. After the reaction ended, the reaction mixture was extracted by ethyl acetate, and the resulting extract was dried by magnesium sulfate, filtered, and dried by rotary evaporation to give a crude product. The crude product was purified by column chromatography (ethyl acetate: n-hexane=1:10 (volume ratio)), to obtain compound 1 (4.13 g, 69% yield).

Anal. Calcd. $C_{41}H_{26}N_6$: C, 81.71; H, 4.35; N, 13.94. Found: C, 81.78; H, 4.33; N, 13.89. HRMS (ESI) m/z[M+H]$^+$: Calcd.: 602.22. Found: 603.40.

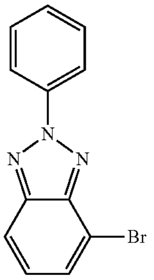

1B

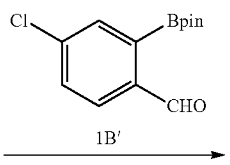

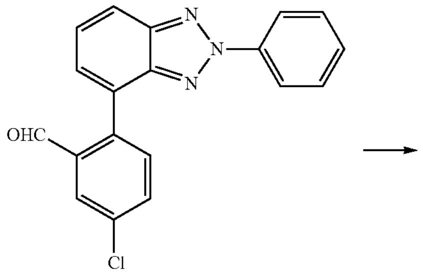

8C

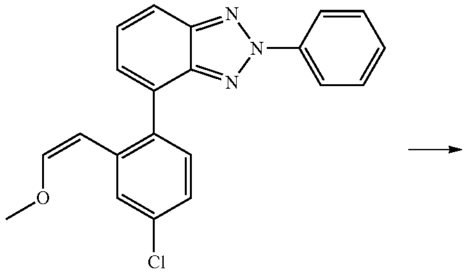

8D

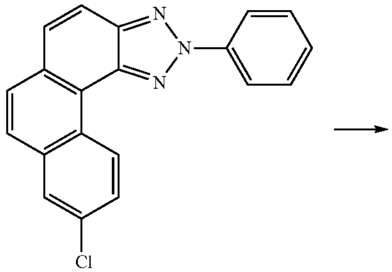

8E

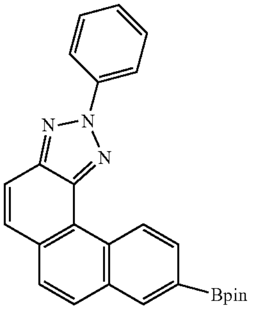

8F

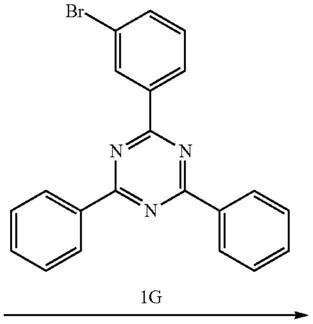

-continued

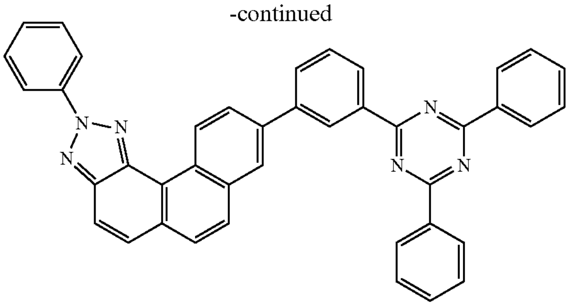

8

Synthesis of 1B": Similar to the synthesis of 1B', with the difference that 2-bromo-5-chlorobenzaldehyde is used to replace 2-bromo-4-chlorobenzaldehyde, to obtain 1B" (1.60 g, 60% yield).

Synthesis of 8C: Similar to the synthesis of 1C, with the difference that 4-fluoro-2-formylbenzeneboronic acid pinacol ester is used to replace 5-fluoro-2-formylbenzeneboronic acid pinacol ester, to obtain 8C (2.13 g, 64% yield).

Synthesis of 8D: Similar to the synthesis of 1D, with the difference that 8C is used to replace 1C, to obtain 8D (3.21 g, 89% yield).

Synthesis of 8E: Similar to the synthesis of 1E, with the difference that 8D is used to replace 1D, to obtain 8E (0.16 g, 48% yield).

Synthesis of 8F: Similar to the synthesis of 1F, with the difference that 8E is used to replace 1E, to obtain 8F (4.00 g, 95% yield).

Synthesis of compound 8: Similar to the synthesis of compound 1, with the difference that 8F is used to replace 1F, and 8G is used to replace 1G, to obtain compound 8 (4.70 g, 78% yield).

Anal. Calcd. $C_{41}H_{26}N_6$: C, 81.71; H, 4.35; N, 13.94. Found: C, 81.73; H, 4.37; N, 13.90. HRMS (ESI) m/z ($M^+$): Calcd.: 602.22. Found: 603.29.

The corresponding products shown in Table 1 were prepared by the above-mentioned preparation method using the Material 1 and Material 2 as raw materials. The structure and characteristic data of the products are shown in Table 2.

TABLE 1

| Material 1 | Material 2 | Product | Yield (%) |
|---|---|---|---|
| 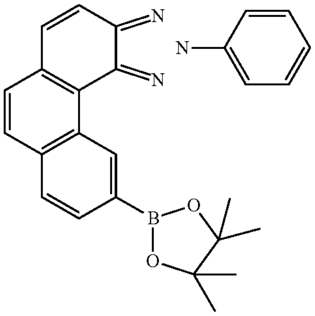 1F | 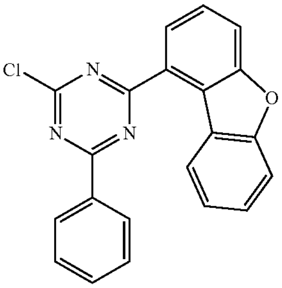 [SMILES: Clc1nc(-c2ccccc2)nc(-c2cccc3oc4ccccc4c23)n1] 2G CAS2142681-84-1 | 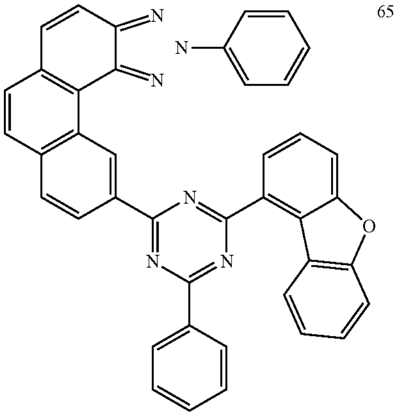 2 | 65 |
| 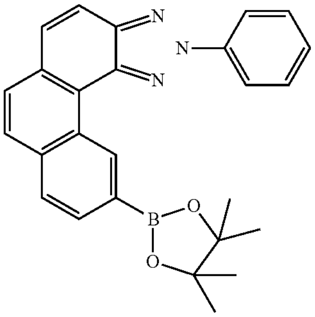 1F | 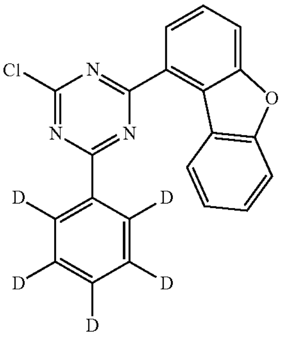 [SMILES: [2H]c1c([2H])c([2H])c(-c2nc(Cl)nc(-c3cccc4oc5ccccc5c34)n2)c([2H])c1[2H]] 3G CAS2391956-00-4 | 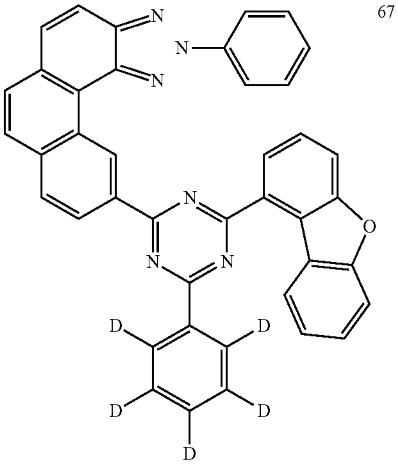 3 | 67 |

TABLE 1-continued
| Material 1 | Material 2 | Product | Yield (%) |
|---|---|---|---|
| 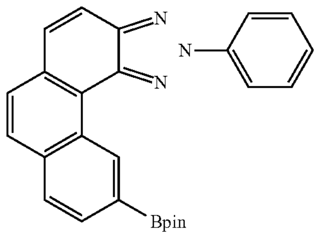 | 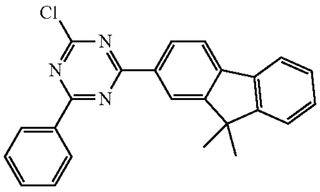 [SMILES: CC1(C)c2ccccc2-c2ccc(-c3nc(Cl)nc(-c4ccccc4)n3)cc21] CAS1618106-98-1 | 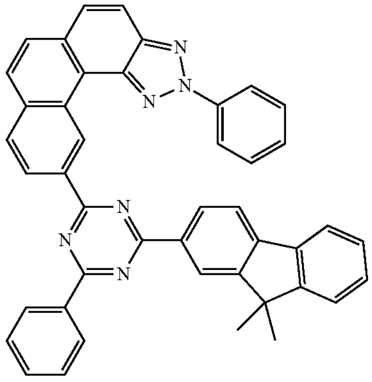 [SMILES: CC1(C)c2ccccc2-c2ccc(-c3nc(-c4ccccc4)nc(-c4ccc5ccc6ccc7nn(-c8ccccc8)nc7c6c5c4)n3)cc21] 4 | 74 |
| 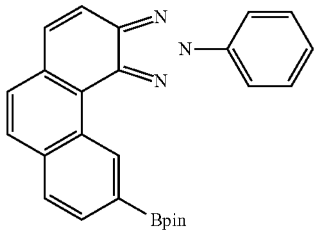 | 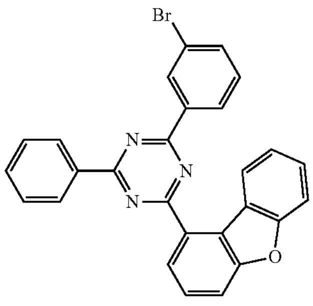 [SMILES: Brc1cccc(-c2nc(-c3ccccc3)nc(-c3cccc4oc5ccccc5c34)n2)c1] CAS2102445-28-1 | 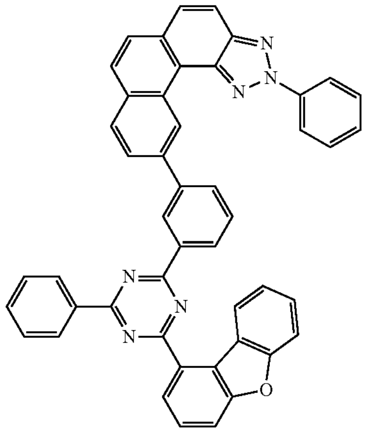 [SMILES: c1ccc(-c2nc(-c3cccc(-c4ccc5ccc6ccc7nn(-c8ccccc8)nc7c6c5c4)c3)nc(-c3cccc4oc5ccccc5c34)n2)cc1] 5 | 65 |
| 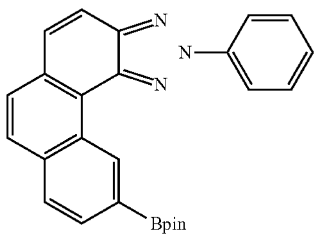 | 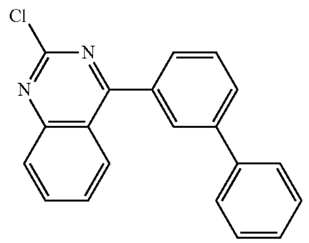 [SMILES: Clc1nc(-c2cccc(-c3ccccc3)c2)c2ccccc2n1] CAS1413365-66-8 | 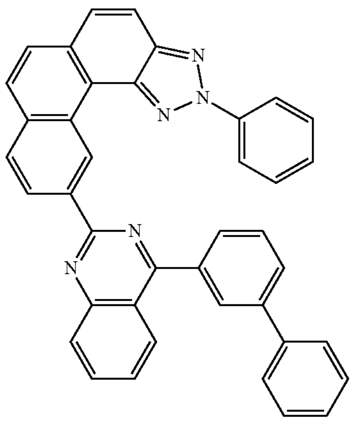 [SMILES: c1ccc(-c2cccc(-c3nc(-c4ccc5ccc6ccc7nn(-c8ccccc8)nc7c6c5c4)nc4ccccc34)c2)cc1] 6 | 68 |

TABLE 1-continued
| Material 1 | Material 2 | Product | Yield (%) |
|---|---|---|---|
| 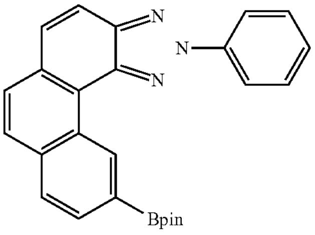 | 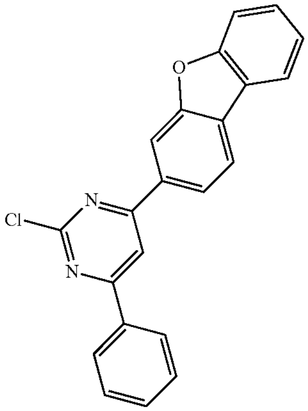 [SMILES: Clc1nc(-c2ccccc2)cc(-c2ccc3c(c2)oc2ccccc23)n1] CAS2286234-09-9 | 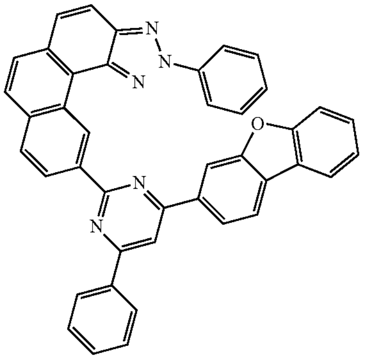 [SMILES: N=C1/C(=N\Nc2ccccc2)C=Cc2ccc3ccc(-c4nc(-c5ccccc5)cc(-c5ccc6c(c5)oc5ccccc56)n4)cc3c21] 7 | 68 |
| 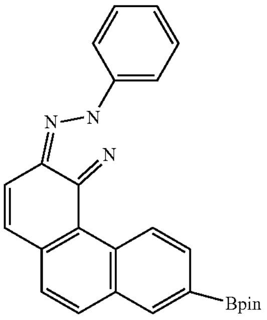 | 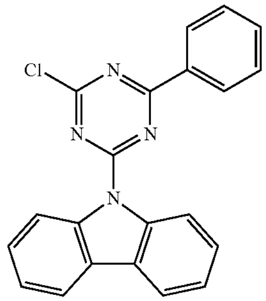 [SMILES: Clc1nc(-c2ccccc2)nc(-n2c3ccccc3c3ccccc32)n1] CAS1268244-56-9 | 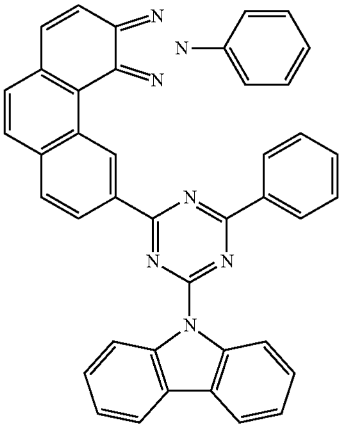 9 | 61 |
TABLE 2
| | Elemental analysis | | HRMS (ESI) m/z [M + H]$^+$ | |
|---|---|---|---|---|
| Compound | Calcd. | Found | Calcd. | Found |
| 2 | C, 79.85; H, 3.92; N, 13.63; | C, 79.92; H, 3.91; N, 13.59; | 616.20 | 617.26 |
| 3 | C, 79.21; H, 4.70; N, 13.52; | C, 79.24; H, 4.71; N, 13.48; | 621.23 | 622.26 |
| 4 | C, 82.22; H, 4.70; N, 13.08; | C, 82.16; H, 4.72; N, 13.12; | 642.25 | 643.25 |
| 5 | C, 81.49; H, 4.07; N, 12.13; | C, 81.53; H, 4.08; N, 12.08; | 692.23 | 693.20 |
| 6 | C, 83.46; H, 4.38; N, 12.17; | C, 83.39; H, 4.40; N, 12.21; | 575.21 | 576.24 |
| 7 | C, 81.93; H, 4.09; N, 11.37; | C, 81.89; H, 4.11; N, 11.40; | 615.21 | 616.17 |
| 9 | C, 79.98; H, 4.09; N, 15.92; | C, 80.04; H, 4.08; N, 15.88; | 615.22 | 616.16 |
Preparation Example of Compound of Formula 2
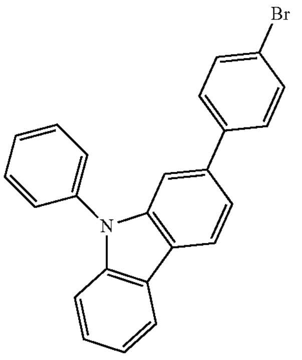
1'-A
+

-continued

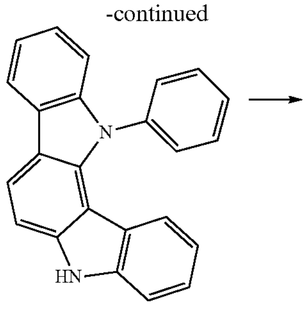

1'-B

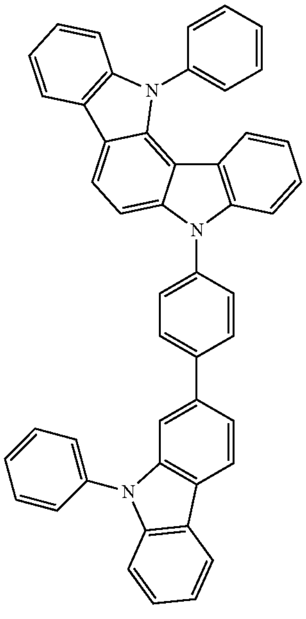

1'

Synthesis of compound 1': In a three-necked bottle of 25 mL, nitrogen gas was purged, 1'-A (1 mmol), 1'-B (1 mmol), sodium tert-butoxide (2 mmol), tris(dibenzylideneacetone) dipalladium(0) (0.02 mmol), 50% tri-tert-butylphosphine solution (0.1 mmol) and toluene 8 mL was added, and stirred under reflux to react. After the reaction ended, the reaction mixture was cooled to room temperature, and the organic layer was extracted by ethyl acetate and $H_2O$, and the extracted organic layer was dried by $MgSO_4$, filtered, and the filtrate was concentrated under vacuum to give a crude product. The crude product was purified by column chromatography (ethyl acetate: n-hexane=1:50 (volume ratio)), to obtain compound 1' (0.40 g, 62% yield).

Anal. Calcd. $C_{48}H_{11}N_3$: C, 88.72; H, 4.81; N, 6.47; Found: C, 88.76; H, 4.79; N, 6.45; HRMS (ESI) m/z[M+H]+: Calcd.: 649.25; Found: 650.33.

The corresponding products shown in Table 3 were prepared by the above-mentioned preparation method using the Material 1 and Material 2 as raw materials. The structure and characteristic data of the products are shown in Table 4.

TABLE 3

| Material 1 | Material 2 | Product | Yield % |
|---|---|---|---|
| 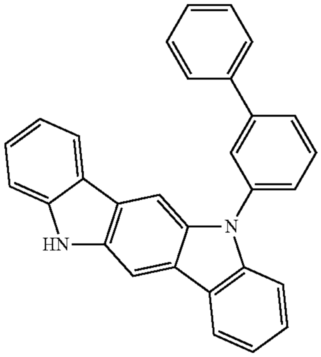 [SMILES: c1ccc(-c2cccc(-n3c4ccccc4c4cc5[nH]c6ccccc6c5cc43)c2)cc1] CAS 2417389-54-7 | 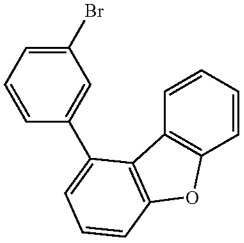 [SMILES: Brc1cccc(-c2cccc3oc4ccccc4c23)c1] CAS2229864-78-0 | 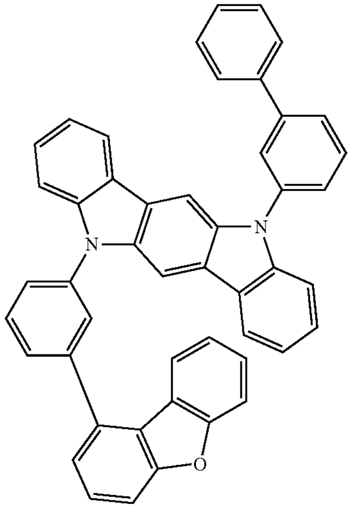 [SMILES: c1ccc(-c2cccc(-n3c4ccccc4c4cc5c(cc43)c3ccccc3n5-c3cccc(-c4cccc5oc6ccccc6c45)c3)c2)cc1] 2' | 65 |

TABLE 3-continued
| Material 1 | Material 2 | Product | Yield % |
|---|---|---|---|
| 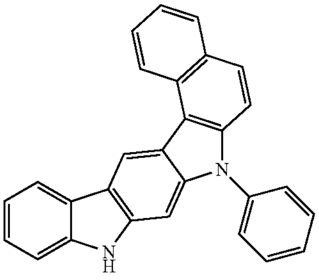 [SMILES: c1ccc(-n2c3cc4[nH]c5ccccc5c4cc3c3c4ccccc4ccc32)cc1] CAS1800022-02-9 | 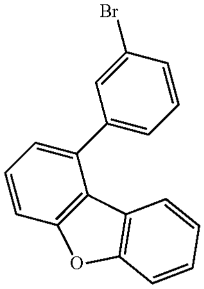 [SMILES: Brc1cccc(-c2cccc3oc4ccccc4c23)c1] CAS2229864-78-0 | 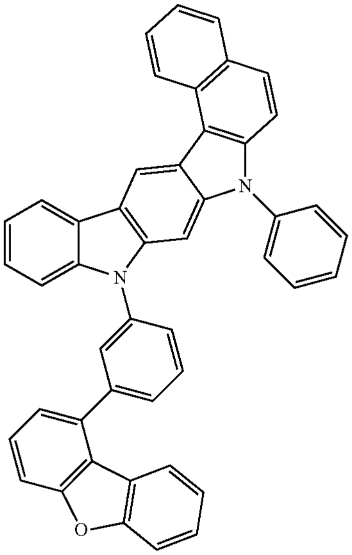 [SMILES: c1ccc(-n2c3cc4c(cc3c3c5ccccc5ccc32)c2ccccc2n4-c2cccc(-c3cccc4oc5ccccc5c34)c2)cc1] 3' | 60 |
| 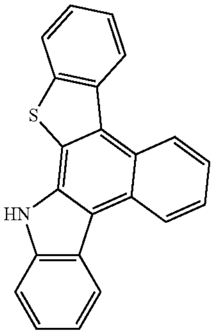 [SMILES: c1ccc2c(c1)[nH]c1c3sc4ccccc4c3c3ccccc3c21] CAS1313395-18-4 | 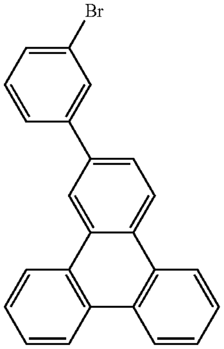 [SMILES: Brc1cccc(-c2ccc3c4ccccc4c4ccccc4c3c2)c1] CAS1313514-53-2 | 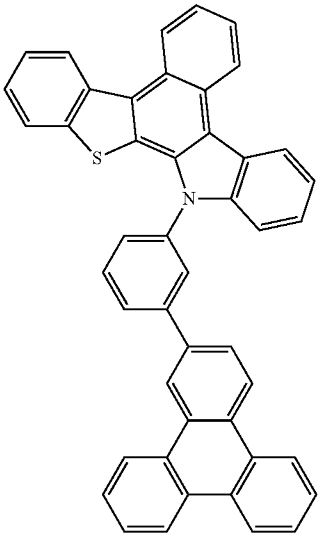 [SMILES: c1cc(-c2ccc3c4ccccc4c4ccccc4c3c2)cc(-n2c3ccccc3c3c4ccccc4c4c5ccccc5sc4c32)c1] 4' | 61 |

TABLE 3-continued

| Material 1 | Material 2 | Product | Yield % |
|---|---|---|---|
| 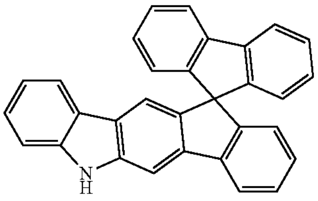 [SMILES: c1ccc2c(c1)-c1ccccc1C21c2ccccc2-c2cc3[nH]c4ccccc4c3cc21] CAS1219841-59-4 | 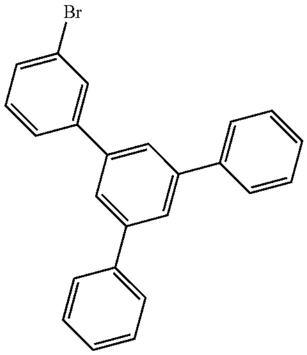 [SMILES: Brc1cccc(-c2cc(-c3ccccc3)cc(-c3ccccc3)c2)c1] CAS1233200-57-1 | 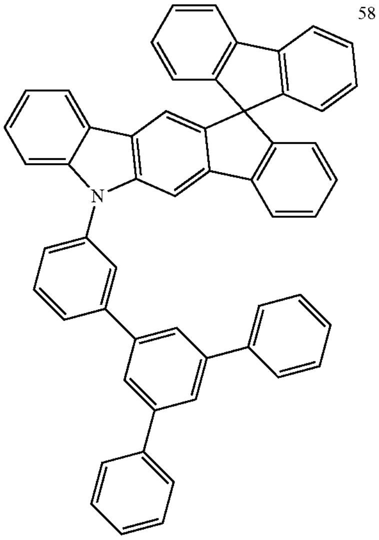 5' | 58 |

TABLE 4

| | Elemental analysis | | HRMS (ESI) m/z $[M + H]^+$ | |
|---|---|---|---|---|
| Compound | Calcd. | Found | Calcd. | Found |
| 2' | C, 88.59; H, 4.65; N, 4.30; | C, 88.56; H, 4.67; N, 4.31; | 650.24 | 651.29 |
| 3' | C, 88.44; H, 4.52; N, 4.48; | C, 88.39; H, 4.55; N, 4.50; | 624.22 | 625.29 |
| 4' | C, 88.29; H, 4.35; N, 2.24; S, 5.12; | C, 88.34; H, 4.32; N, 2.24; S, 5.10; | 625.19 | 626.16 |
| 5' | C, 93.06; H, 4.97; N, 1.97; | C, 93.03; H, 4.99; N, 1.98; | 709.28 | 710.28 |

Application Examples

An organic electroluminescence element having a structure shown in the FIGURE with the following layer structure was provided: base (indium tin oxide (ITO, as an anode 1) coated glass substrate)/hole injection layer 2 (HIL)/hole transport layer 3 (HTL)/emitting layer 4 (EML)/electron transport layer 5 (ETL)/electron injection layer 6 (EIL), and the cathode 7 at last.

The materials needed to prepare OLED are listed below, wherein the REF-1 is comparative compound 1:

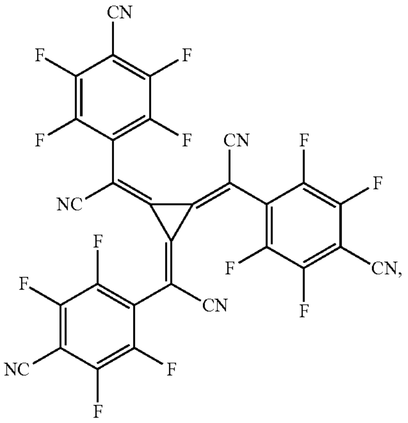
NDP-9

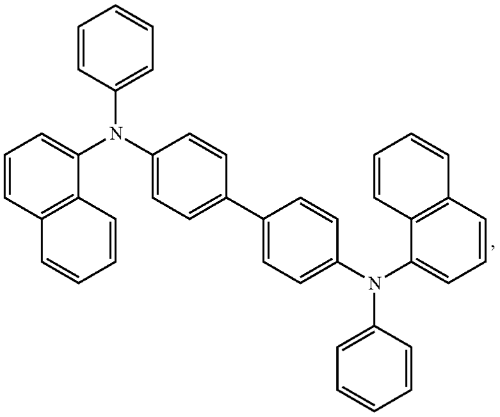
HT

-continued

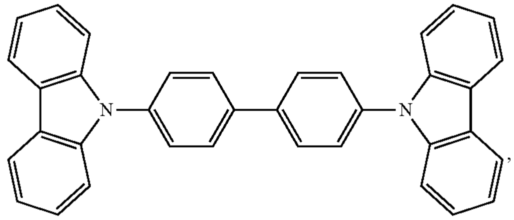
,

CBP

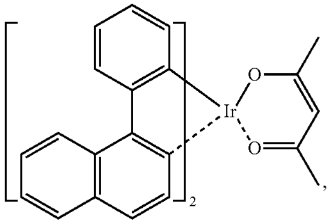
, $(piq)_2Ir(acac)$

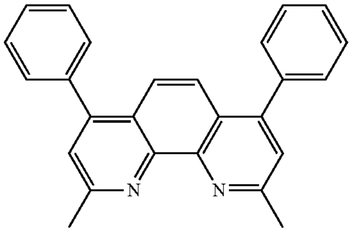

BPhen

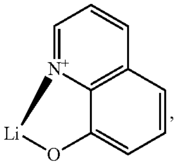
,

LiQ

-continued

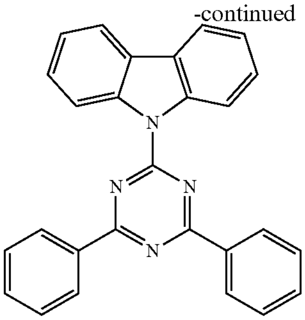
.

REF-1

The above-mentioned organic electroluminescence elements were prepared by the following steps:

(1) Cleaning the substrate: a glass substrate coated with transparent ITO layer (the anode 1) was ultrasonicated in an aqueous detergent (the content and concentration of the aqueous detergent: an ethylene glycol solvent of ≤10 percent by weight (wt %), triethanolamine of ≤1 wt %), washed in deionized water, degreased in an acetone/ethanol mixed solvent (volume ratio=1:1) by ultrasonication, baked in a clear environment until water was completely removed, and washed by ozone under ultraviolet light;

(2) Depositing organic emitting functional layers:

The glass substrate with the anode 1 was placed in a chamber, and the chamber was vacuumized until $1\times10^{-6}$ Pascal (Pa) to $2\times10^{-4}$ Pa, and a mixture of NDP-9 and HT (mass ratio of NDP-9 and HT is 3:97) was deposited on the anode 1 in vacuum to form a hole injection layer 2, in which the deposited thickness was 10 nanometers (nm).

A hole transport layer 3 was deposited on the hole injection layer 2, in which the deposited thickness was 80 nm.

An emitting layer 4 was deposited on the hole transport layer 3. Specifically, the preparation method was: the light-emitting host material (materials shown in Table 5) and a guest material were co-deposited in vacuum, in which the total deposited thickness was 30 nm.

An electron transport layer 5 was deposited on the emitting layer 4. Specifically, the preparation method was: BPhen and LiQ were co-deposited in vacuum, in which the total deposited thickness was 30 nm.

An electron injection layer 6 was deposited on the electron transport layer 5, in which the total deposited thickness was 1 nm.

A1 (as cathode 7) was deposited on the electron injection layer 6, in which the deposited thickness was 80 nm.

The materials (mat.) of each layer in the element and parameters such as thickness (thk.) of Element Examples 1 to 11 (E1 to E11) and Comparative Element Examples 1 to 3 (CE1 to CE3) are shown in Table 5.

TABLE 5

| No. | HIL mat./thk. | HTL mat./thk. | EML mat./thk. | ETL mat./thk. | EIL mat./thk. | Cathode mat./thk. |
|---|---|---|---|---|---|---|
| E1 | NDP-9:HT (mass ratio 3:97)/ 10 nm | HT/ 80 nm | compound 1:compound 3':$(piq)_2Ir(acac)$ (mass ratio 47.5:47.5:5)/ 30 nm | BPhen:LiQ (mass ratio 1:1)/ 30 nm | LiQ/ 1 nm | Al/ 80 nm |
| E2 | NDP-9:HT (mass ratio 3:97)/ 10 nm | HT/ 80 nm | compound 2:compound 3':$(piq)_2Ir(acac)$ (mass ratio 47.5:47.5:5)/ 30 nm | BPhen:LiQ (mass ratio 1:1)/ 30 nm | LiQ/ 1 nm | Al/ 80 nm |

TABLE 5-continued

| No. | HIL mat./thk. | HTL mat./thk. | EML mat./thk. | ETL mat./thk. | EIL mat./thk. | Cathode mat./thk. |
|---|---|---|---|---|---|---|
| E3 | NDP-9:HT (mass ratio 3:97)/ 10 nm | HT/ 80 nm | compound 3:compound 3':$(piq)_2Ir(acac)$ (mass ratio 47.5:47.5:5)/ 30 nm | BPhen:LiQ (mass ratio 1:1)/ 30 nm | LiQ/ 1 nm | Al/ 80 nm |
| E4 | NDP-9:HT (mass ratio 3:97)/ 10 nm | HT/ 80 nm | compound 4:compound 1':$(piq)_2Ir(acac)$ (mass ratio 47.5:47.5:5)/ 30 nm | BPhen:LiQ (mass ratio 1:1)/ 30 nm | LiQ/ 1 nm | Al/ 80 nm |
| E5 | NDP-9:HT (mass ratio 3:97)/ 10 nm | HT/ 80 nm | compound 5:compound 5':$(piq)_2Ir(acac)$ (mass ratio 47.5:47.5:5)/ 30 nm | BPhen:LiQ (mass ratio 1:1)/ 30 nm | LiQ/ 1 nm | Al/ 80 nm |
| E6 | NDP-9:HT (mass ratio 3:97)/ 10 nm | HT/ 80 nm | compound 6:compound 4':$(piq)_2Ir(acac)$ (mass ratio 47.5:47.5:5)/ 30 nm | BPhen:LiQ (mass ratio 1:1)/ 30 nm | LiQ/ 1 nm | Al/ 80 nm |
| E7 | NDP-9:HT (mass ratio 3:97)/ 10 nm | HT/ 80 nm | compound 7:compound 4':$(piq)_2Ir(acac)$ (mass ratio 47.5:47.5:5)/ 30 nm | BPhen:LiQ (mass ratio 1:1)/ 30 nm | LiQ/ 1 nm | Al/ 80 nm |
| E8 | NDP-9:HT (mass ratio 3:97)/ 10 nm | HT/ 80 nm | compound 9:compound 4':$(piq)_2Ir(acac)$ (mass ratio 47.5:47.5:5)/ 30 nm | BPhen:LiQ (mass ratio 1:1)/ 30 nm | LiQ/ 1 nm | Al/ 80 nm |
| E9 | NDP-9:HT (mass ratio 3:97)/ 10 nm | HT/ 80 nm | compound 8:compound 2':$(piq)_2Ir(acac)$ (mass ratio 47.5:47.5:5)/ 30 nm | BPhen:LiQ (mass ratio 1:1)/ 30 nm | LiQ/ 1 nm | Al/ 80 nm |
| E10 | NDP-9:HT (mass ratio 3:97)/ 10 nm | HT/ 80 nm | compound 1:compound 3':$(piq)_2Ir(acac)$ (mass ratio 57:38:5)/ 30 nm | BPhen:LiQ (mass ratio 1:1)/ 30 nm | LiQ/ 1 nm | Al/ 80 nm |
| E11 | NDP-9:HT (mass ratio 3:97)/ 10 nm | HT/ 80 nm | compound 1:compound 3':$(piq)_2Ir(acac)$ (mass ratio 2:17:5)/ 30 nm | BPhen:LiQ (mass ratio 1:1)/ 30 nm | LiQ/ 1 nm | Al/ 80 nm |
| CE1 | NDP-9:HT (mass ratio 3:97)/ 10 nm | HT/ 80 nm | compound 1:$(piq)_2Ir(acac)$ (mass ratio 95:5)/ 30 nm | BPhen:LiQ (mass ratio 1:1)/ 30 nm | LiQ/ 1 nm | Al/ 80 nm |
| CE2 | NDP-9:HT (mass ratio 3:97)/ 10 nm | HT/ 80 nm | compound 1':$(piq)_2Ir(acac)$ (mass ratio 95:5)/ 30 nm | BPhen:LiQ (mass ratio 1:1)/ 30 nm | LiQ/ 1 nm | Al/ 80 nm |
| CE3 | NDP-9:HT (mass ratio 3:97)/ 10 nm | HT/ 80 nm | REF-1:compound 1':$(piq)_2Ir(acac)$ (mass ratio 47.5:47.5:5)/ 30 nm | BPhen:LiQ (mass ratio 1:1)/ 30 nm | LiQ/ 1 nm | Al/ 80 nm |

Characteristic Tests of Elements:

Instruments: the characteristics such as current, voltage, luminance, emission spectrum and the like of the elements of the above Element Examples to 11 and Comparative Element Examples 1 to 3 were synchronously tested by PR 650 SpectraScan Colorimeter and Keithley K 2400 SourceMeter;

Conditions for testing electrooptical characteristics: a current density of 10 milliamperes/square centimeter ($mA/cm^2$) under room temperature;

Service life test: tested with a current density of 50 $mA/cm^2$ under room temperature, and the time period recorded when the luminance of the tested element was reduced to 98% of the original luminance (in hour).

The test results of the elements are shown in Table 6.

TABLE 6

| No. | Driving voltage (V) | Current efficiency (Cd/A) | Service life (h) |
|---|---|---|---|
| E1 | 3.72 | 23 | 70 |
| E2 | 3.77 | 23 | 65 |
| E3 | 3.78 | 22 | 63 |
| E4 | 3.81 | 20 | 57 |
| E5 | 3.82 | 18 | 55 |
| E6 | 3.85 | 21 | 53 |
| E7 | 3.80 | 20 | 50 |

TABLE 6-continued

| No. | Driving voltage (V) | Current efficiency (Cd/A) | Service life (h) |
|---|---|---|---|
| E8 | 3.83 | 20 | 48 |
| E9 | 3.90 | 20 | 45 |
| E10 | 3.70 | 24 | 65 |
| E11 | 3.80 | 21 | 50 |
| CE1 | 4.01 | 17 | 34 |
| CE2 | 4.63 | 12 | 20 |
| CE3 | 4.45 | 14 | 25 |

From Table 6, it is clear that every single compound used as the host material has different electron and hole transport abilities, and the organic material composition can promote the electron transport properties, further increase the combination rate of electrons and holes, thereby enhancing the light-emitting efficiency of an organic light-emitting diode and prolonging its service life. When the organic material composition is used as the material of an organic functional layer, the element has a lower driving voltage (3.90 voltages (V) or lower), a higher current efficiency (18 Candelas/Ampere (Cd/A) or more) and a longer service life (45 h or more).

The applicant claims herein that even though the organic material composition of the present invention and the applications thereof are demonstrated by the above examples, the scope of the present invention is not limited by these examples. That is to say, it does not mean that the present invention has to be carried out based on the above examples. Those skilled in the art should understand that any improvement of the present invention, equivalent replacement of materials, addition of auxiliary components, selection of specific means and the like are all within the scope of protection and disclosure of the present invention.

What is claimed is:

1. An organic material composition, wherein the organic material composition comprises at least one compound having a structure represented by Formula 1 and at least one compound having a structure represented by Formula 2:

Formula 1

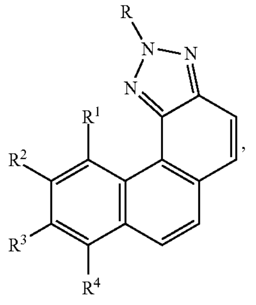

wherein, R is selected from hydrogen, deuterium, halogen, a cyano group, a substituted or unsubstituted C1-C30 alkyl group, a substituted or unsubstituted C3-C30 cycloalkyl group, a substituted or unsubstituted C6-C30 aryl group, and a substituted or unsubstituted C3-C30 heteroaryl group;

$R^1$ is $-L^1Ar^1$; $R^2$ is $—L^2Ar^2$; $R^3$ is $—L^3Ar^3$; $R^4$ is $—L^4Ar^4$;

$L^1$ to $L^4$ are each independently selected from a bond, a substituted or unsubstituted C6-C30 arylene group, and a substituted or unsubstituted C3-C30 heteroarylene group; and $Ar^1$ to $Ar^4$ are each independently selected from hydrogen, deuterium, halogen, a cyano group, and a substituted or unsubstituted C3-C60 heteroaryl group;

at least one of $Ar^1$ to $Ar^4$ is a group represented by Formula a:

Formula a

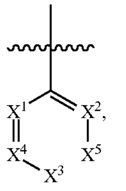

$X^1$ is selected from N and $CR^{X1}$; $X^2$ is selected from N and $CR^{X2}$; $X^3$ is selected from N and $CR^{X3}$; $X^4$ is selected from N and $CR^{X4}$; $X^5$ is selected from N and $CR^{X5}$;

$R^{X1}$ to $R^{X5}$ are each independently selected from hydrogen, deuterium, a cyano group, a substituted or unsubstituted C1-C30 alkyl group, a substituted or unsubstituted C3-C30 cycloalkyl group, a substituted or unsubstituted C6-C30 aryl group, and a substituted or unsubstituted C3-C30 heteroaryl group; $R^{X1}$-$R^{X5}$ are present individually without forming a ring, or any adjacent two of $R^{X1}$-$R^{X5}$ joined to form a ring B, and the ring B is a benzene ring;

Formula 2

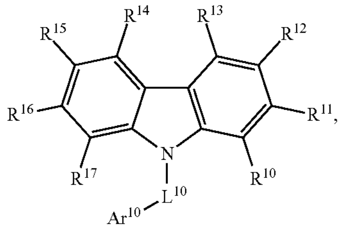

$Ar^{10}$ is selected from a substituted or unsubstituted C6-C60 aryl group, and a substituted or unsubstituted C3-C60 heteroaryl group;

$L^{10}$ is selected from a bond, a substituted or unsubstituted C6-C30 arylene group, and a substituted or unsubstituted C3-C30 heteroarylene group;

$R^{10}$ to $R^{17}$ are each independently selected from hydrogen, deuterium, halogen, a cyano group, a substituted or unsubstituted C1-C30 alkyl group, a C1-C30 alkyl group in which one or more methylene groups are independently substituted by —O— and/or —S— in a manner that O atom and/or S atom are not adjacent to each other, a substituted or unsubstituted $C_2$-$C_{30}$ alkenyl group, a C2-C30 alkenyl group in which one or more methylene groups are independently substituted by —O— and/or —S— in a manner that O atom and/or S atom are not adjacent to each other, a substituted or unsubstituted C7-C30 arylalkyl group, a substituted or unsubstituted C6-C30 aryl group, a substituted or unsubstituted C3-C30 heteroaryl group, a substituted or unsubstituted C4-C30 heteroarylalkyl group, a substituted or unsubstituted C3-C30 cycloalkyl group, a substituted or unsubstituted C3-C30 heterocycloalkyl group, a substituted or unsubstituted C3-C30 cycloalkenyl group, a substituted or unsubstituted C1-C30 alkoxy group, and a substituted or unsubstituted C6-C30 aryloxy group;

$R^{10}$ to $R^{17}$ are present individually without forming a ring, or any adjacent two to four of $R^{10}$ to $R^{17}$ joined to form a ring A, and the ring A is a substituted or unsubstituted C6-C30 aromatic ring, or a substituted or unsubstituted C3-C30 heteroaromatic ring.

2. The organic material composition according to claim 1, wherein the $R^{X1}$ to $R^{X5}$ are each independently selected from hydrogen, deuterium, and a group selected from a phenyl group, a biphenylyl group, a terphenylyl group, a naphthyl group, a phenanthryl group, an anthryl group, a phenylnaphthyl group, a naphthylphenyl group, a pyridyl group, a bipyridyl group, a dibenzofuryl group, a dibenzothiophenyl group, a carbazolyl group, a carbazolylphenyl group, a phenylcarbazolyl group, a dimethylfluorenyl group, a diphenylfluorenyl group, a spiro-bifluorenyl group, a dibenzofurylphenyl group, a dibenzothiophenylphenyl group, a dimethylfluorenylphenyl group, a benzocarbazolyl group, a benzonaphthofuryl group, and a benzonaphthothiophenyl group, each of which is substituted or unsubstituted.

3. The organic material composition according to claim 1, wherein the compound having a structure represented by Formula 1 is selected from the following compounds:

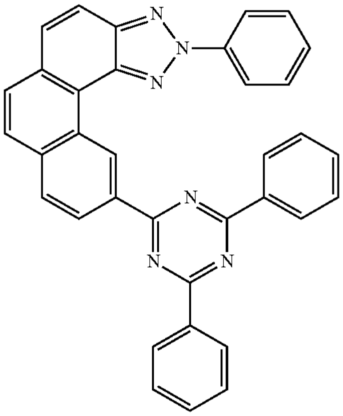

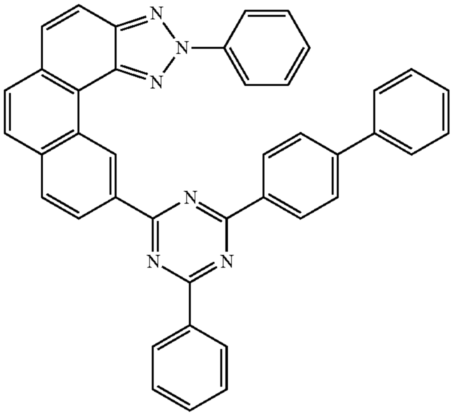

-continued

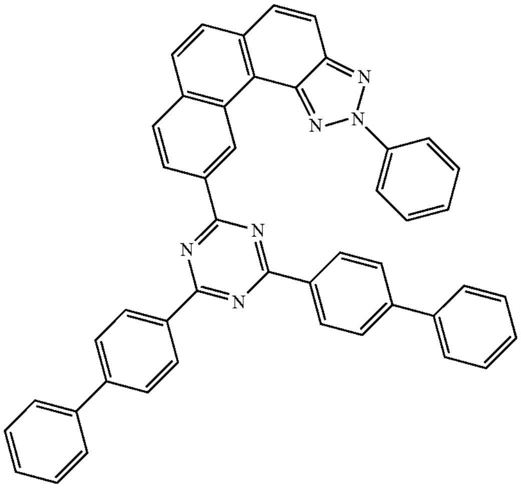

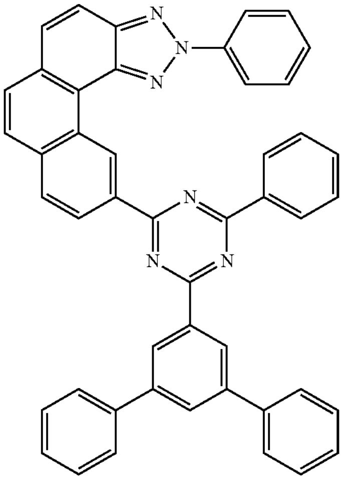

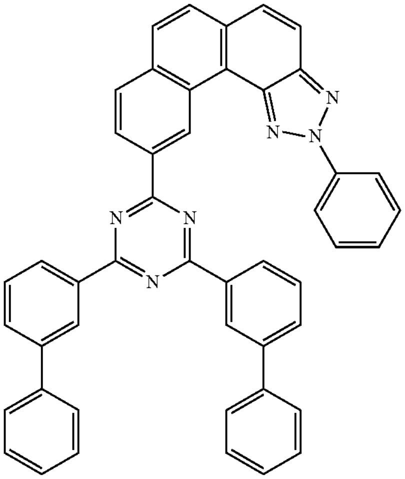

-continued
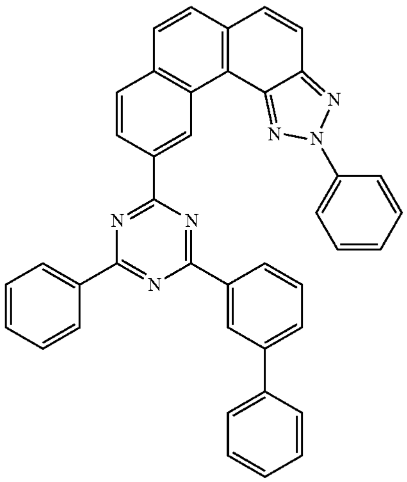
-continued
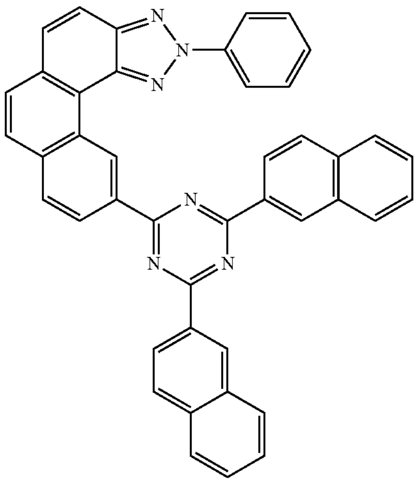
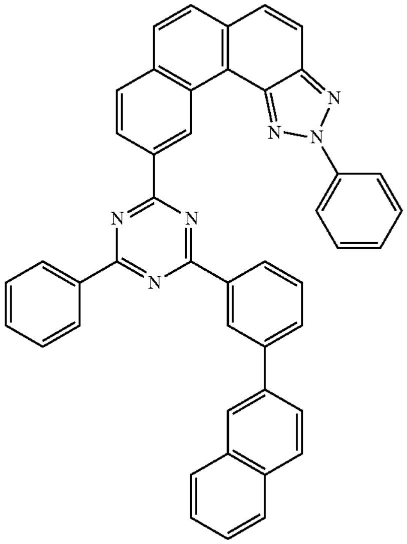
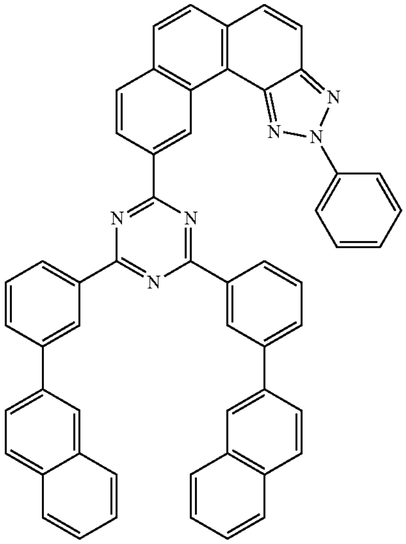
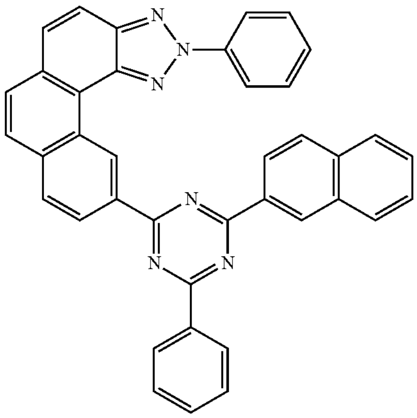
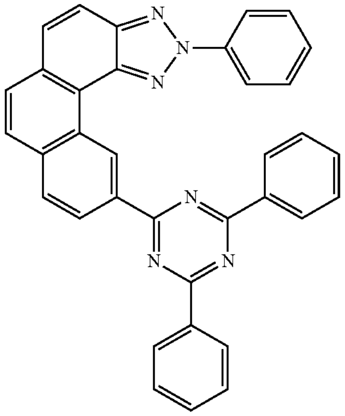

-continued
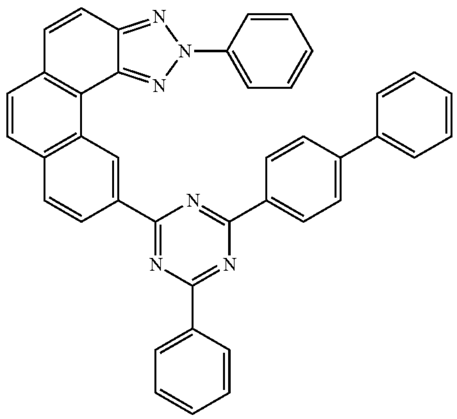
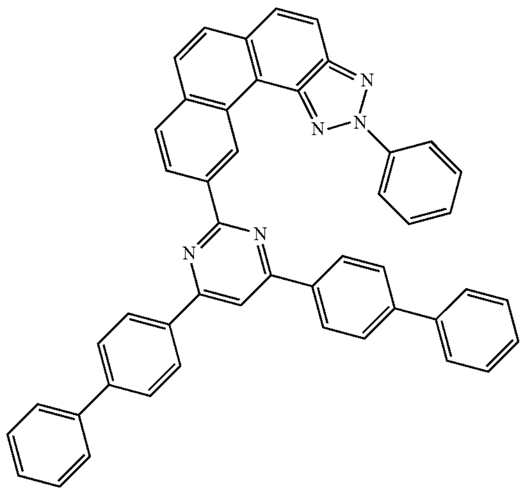
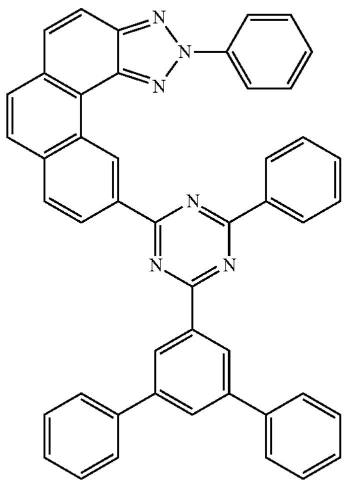
-continued
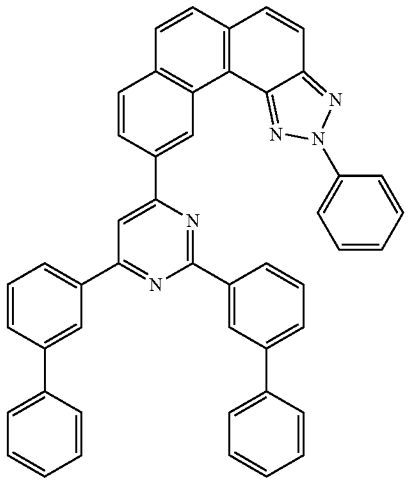
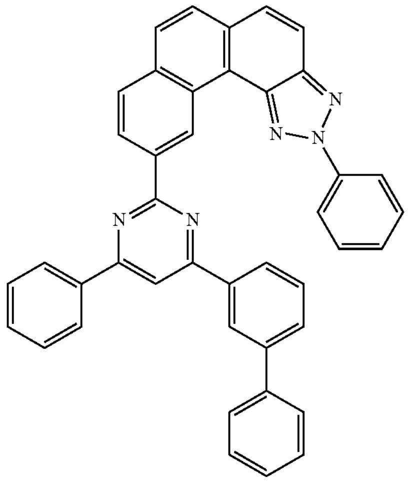
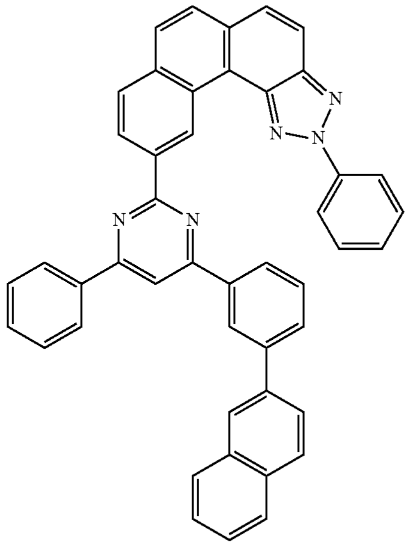

-continued
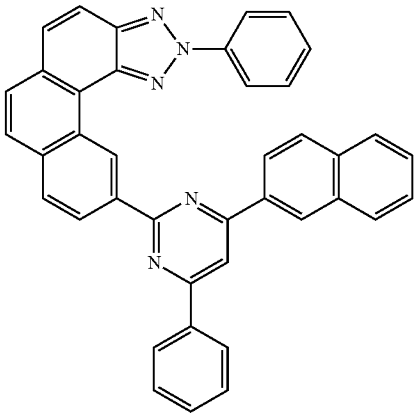
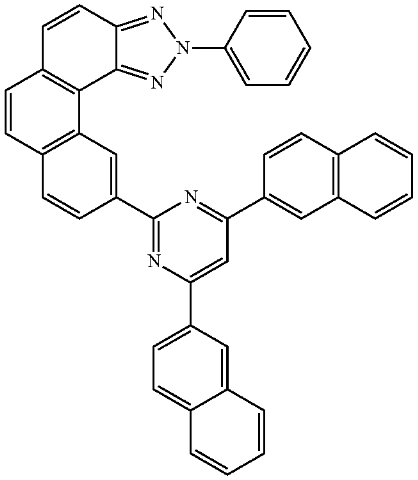
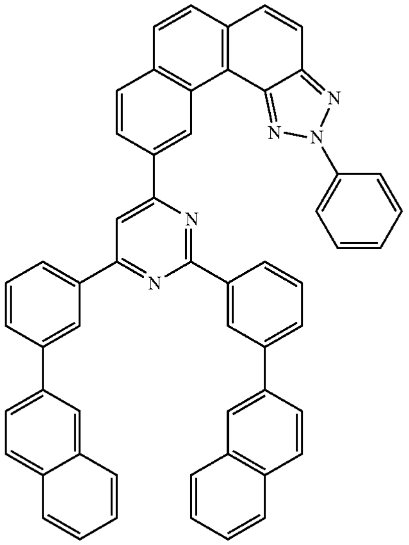
-continued
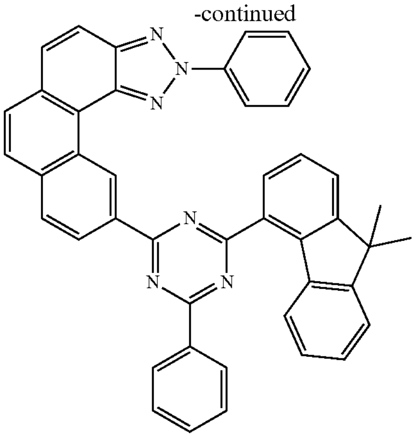
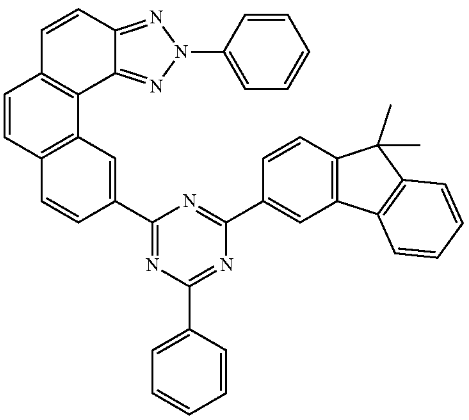
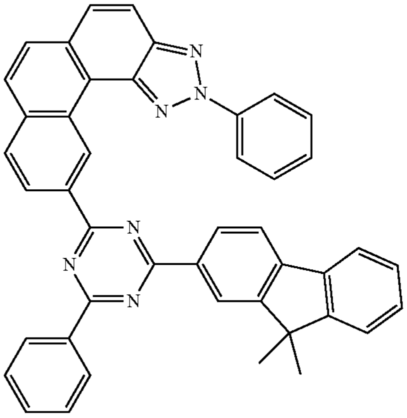

-continued
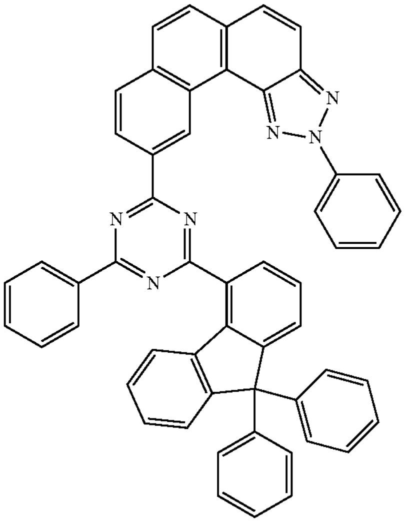
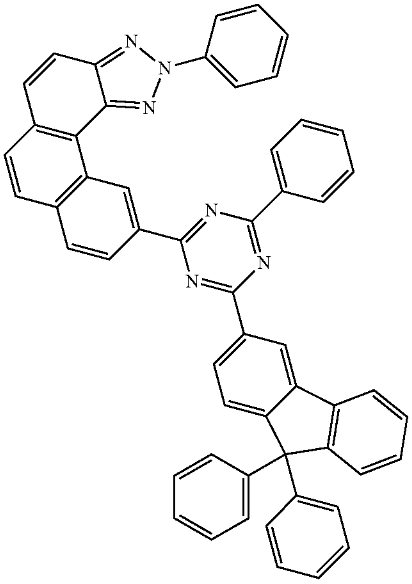
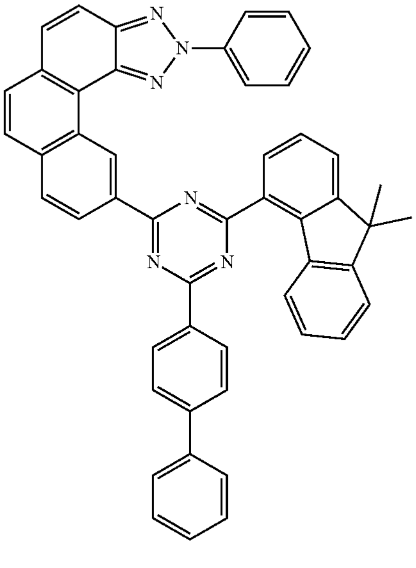
-continued
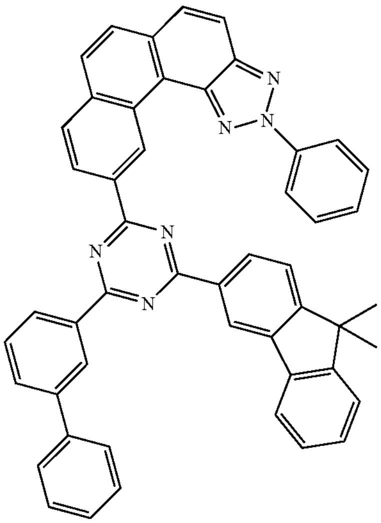
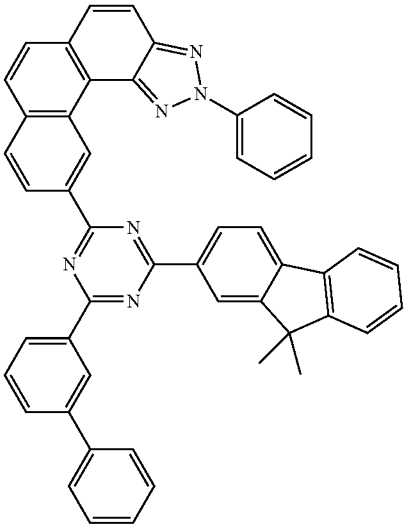
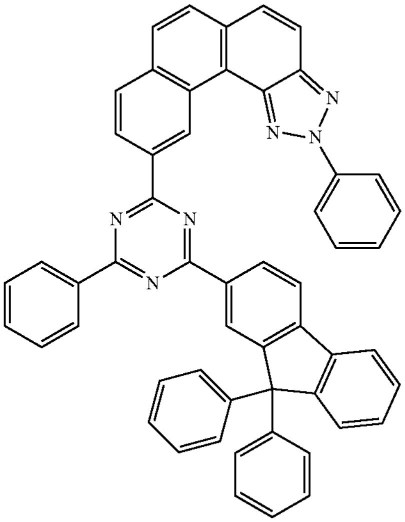

-continued
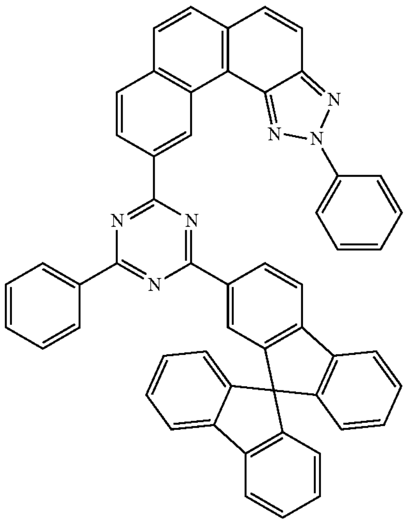
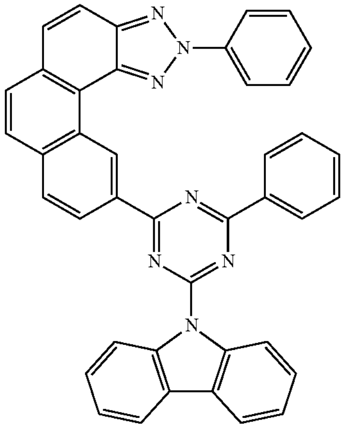
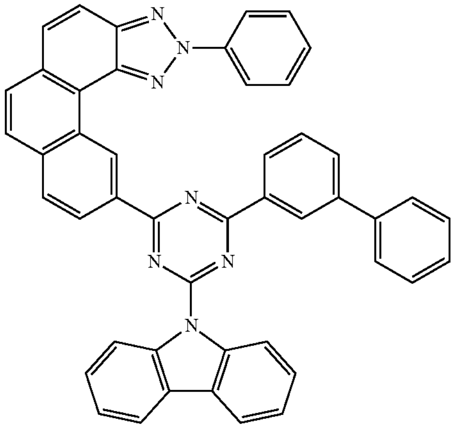
-continued
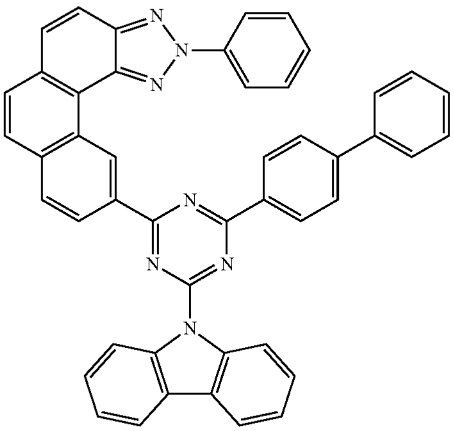
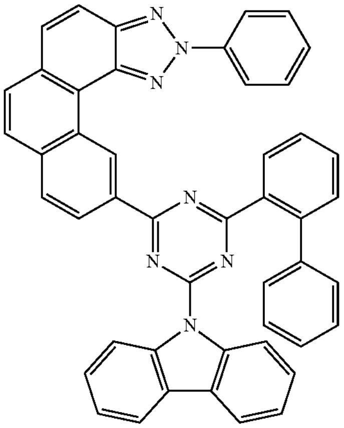
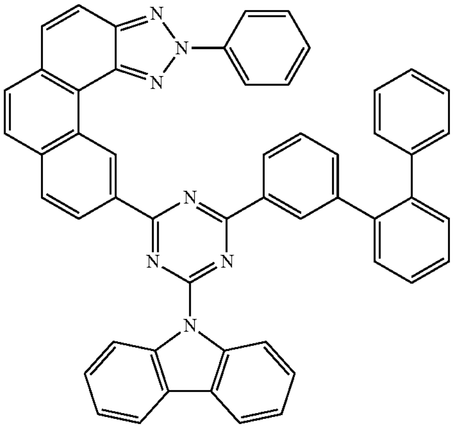

-continued
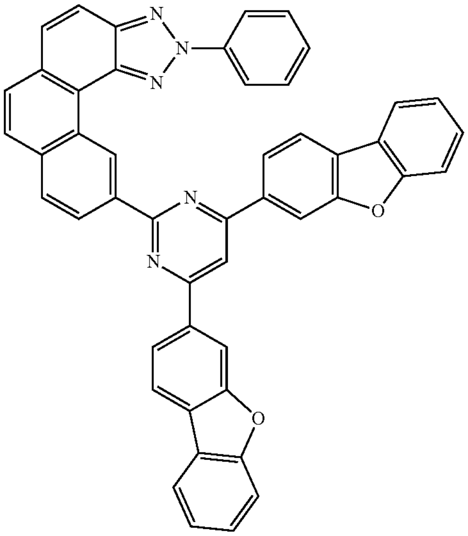
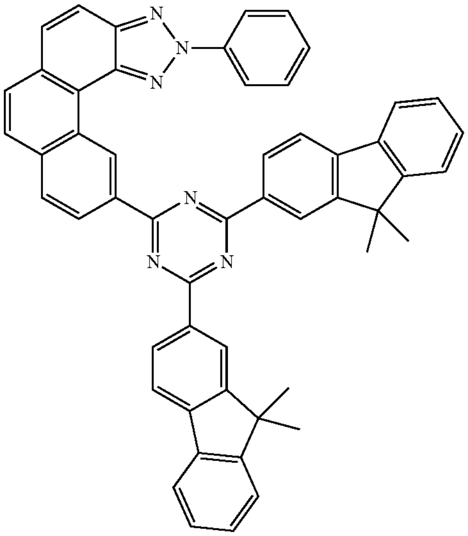
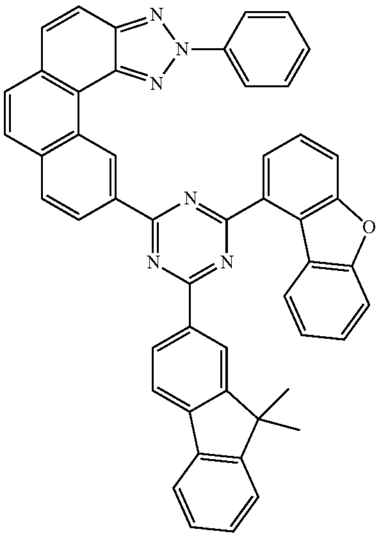
-continued
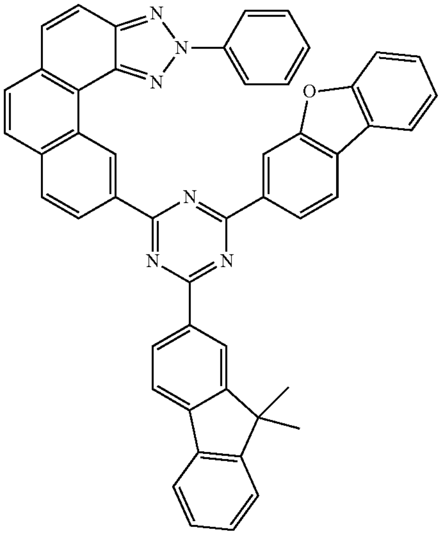
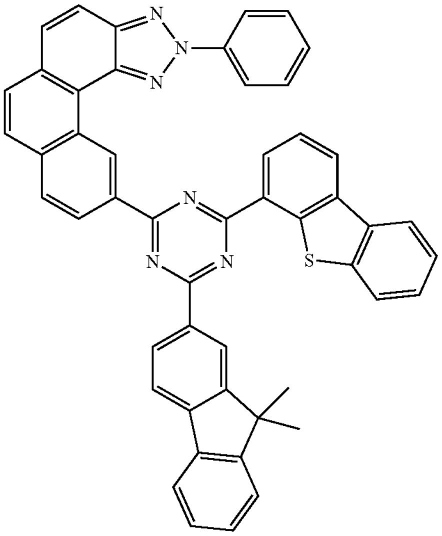
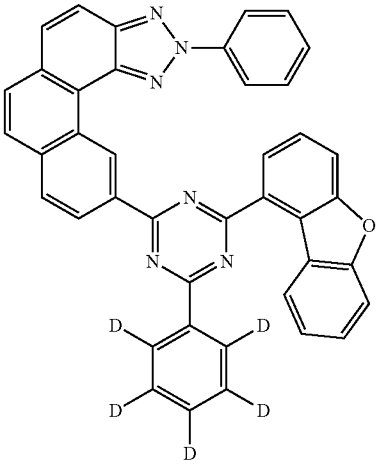

-continued
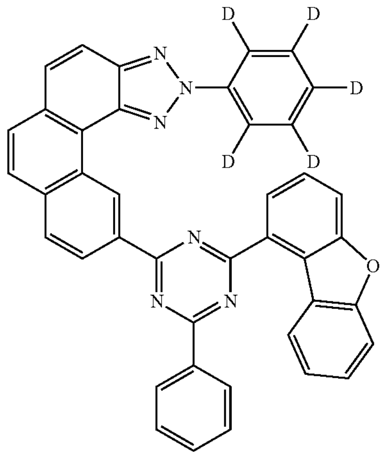
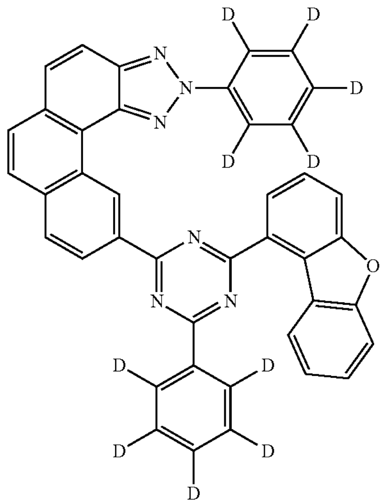
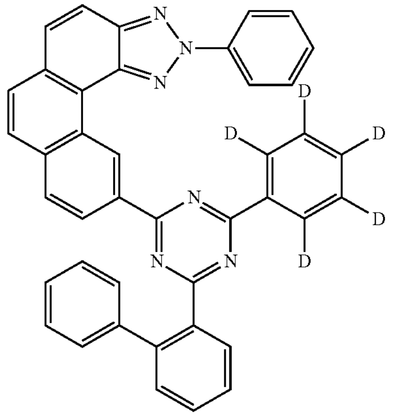
-continued
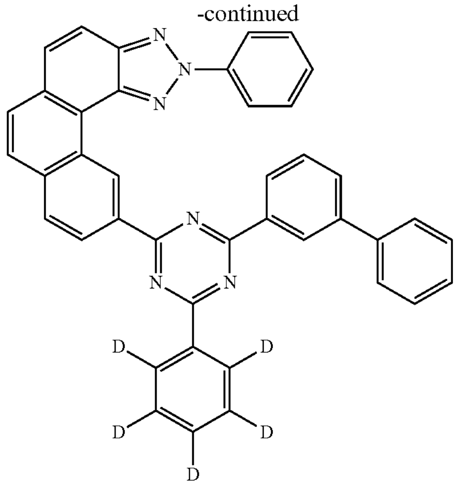
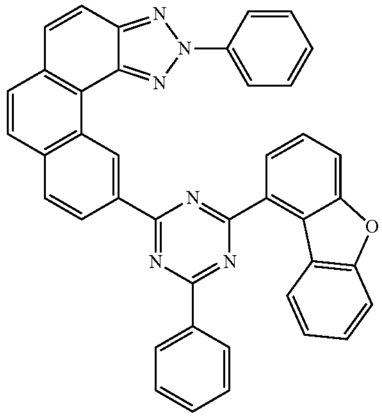
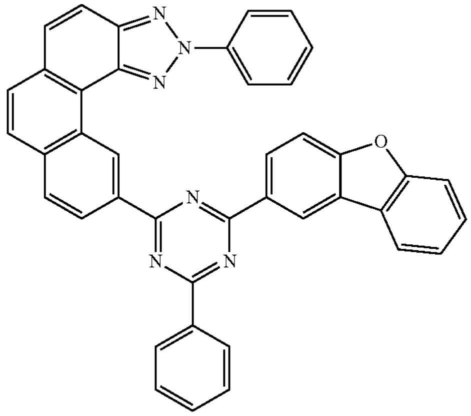
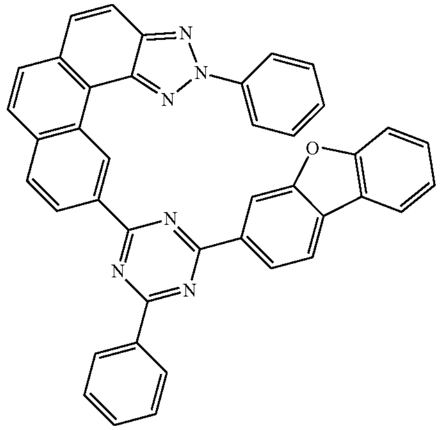

-continued
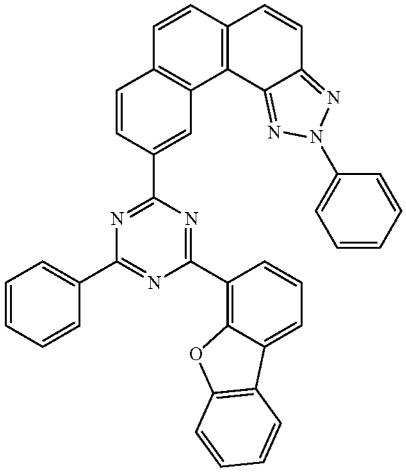
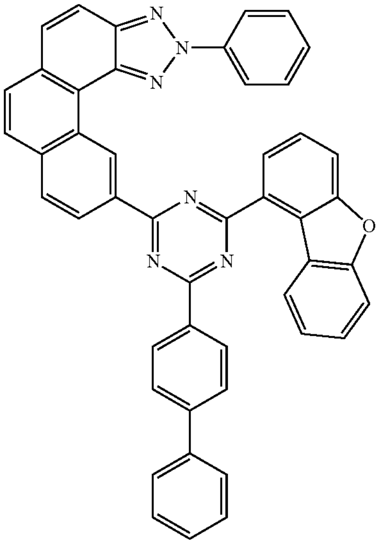
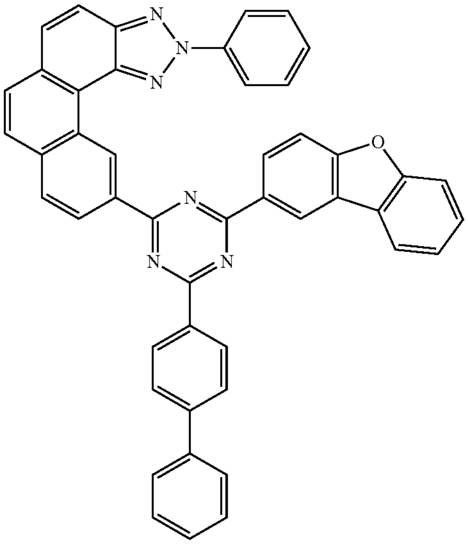
-continued
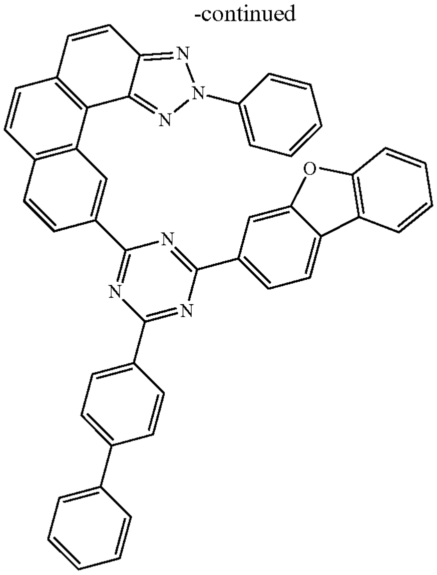
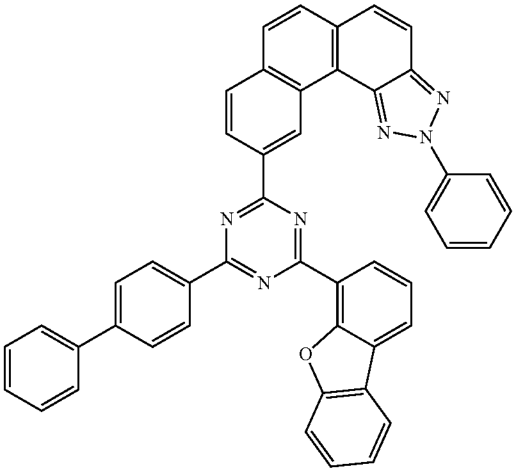
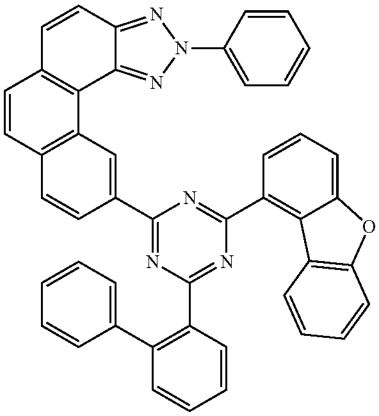

-continued
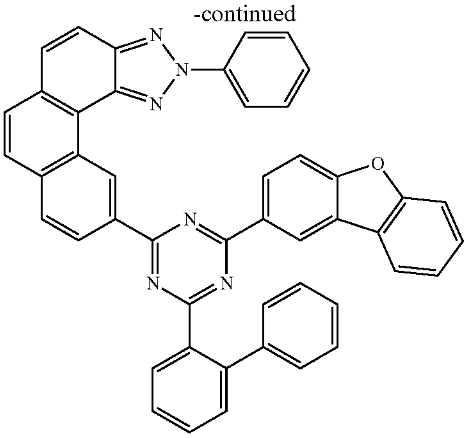
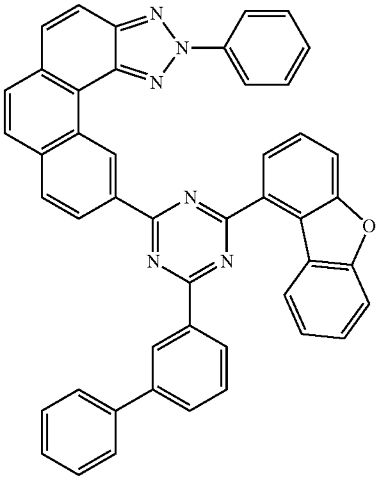
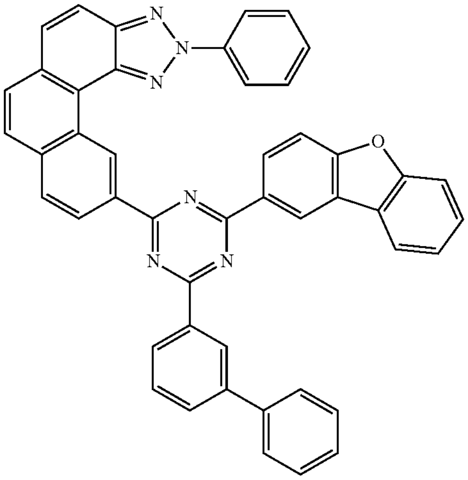
-continued
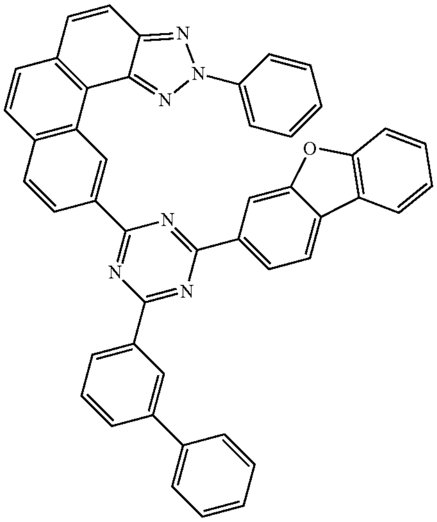
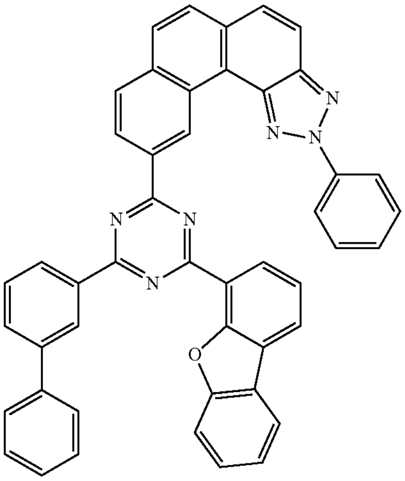
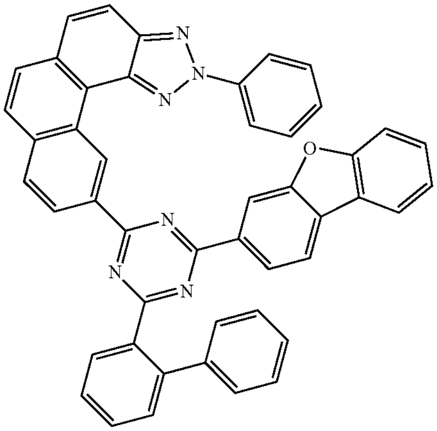

-continued
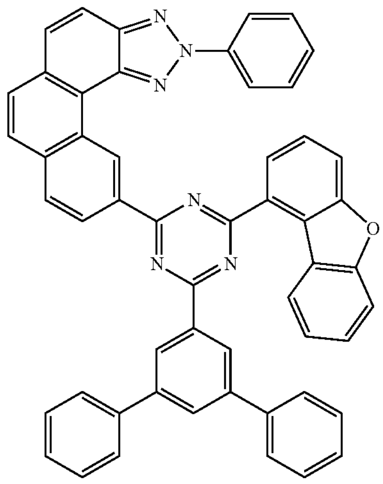
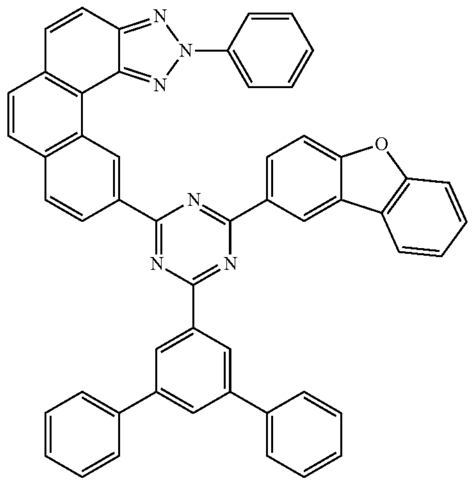
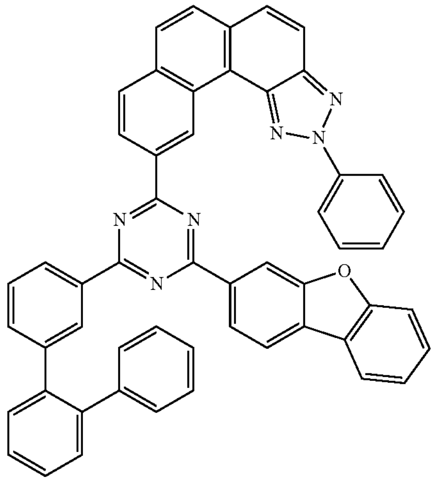
-continued
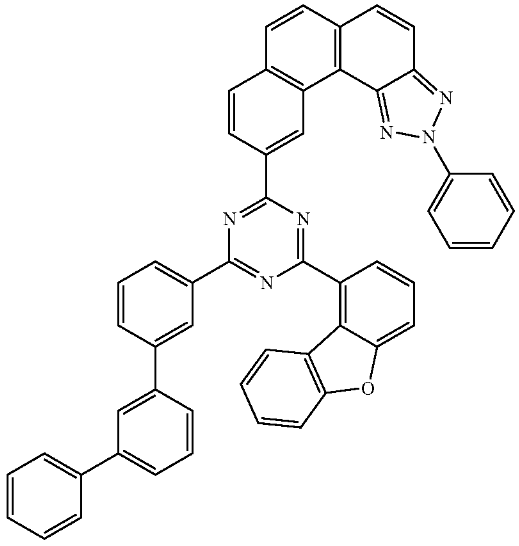
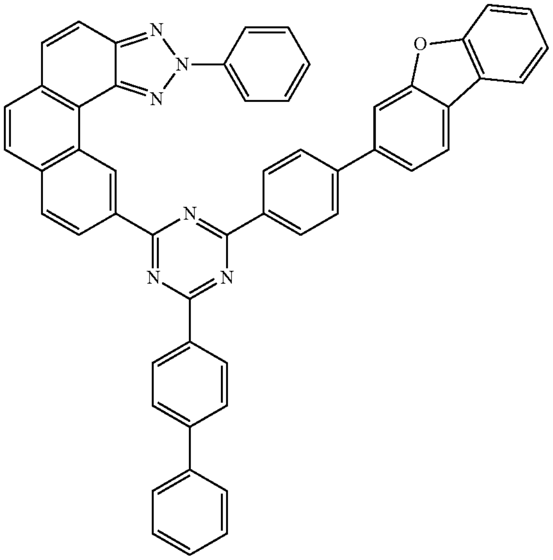
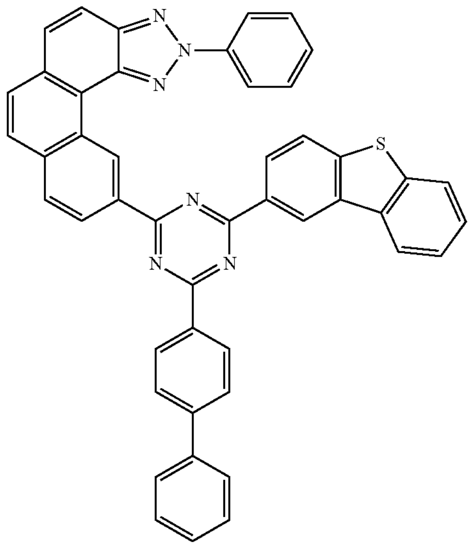

-continued
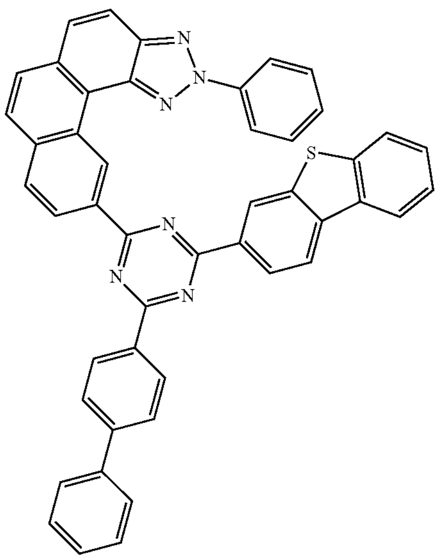
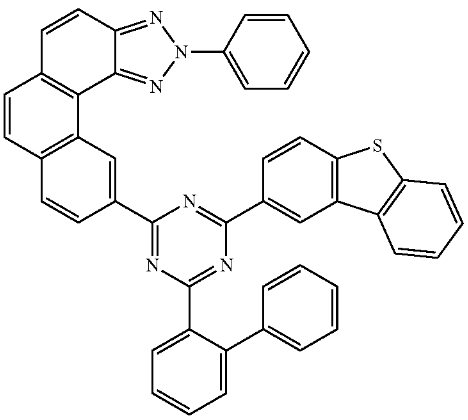
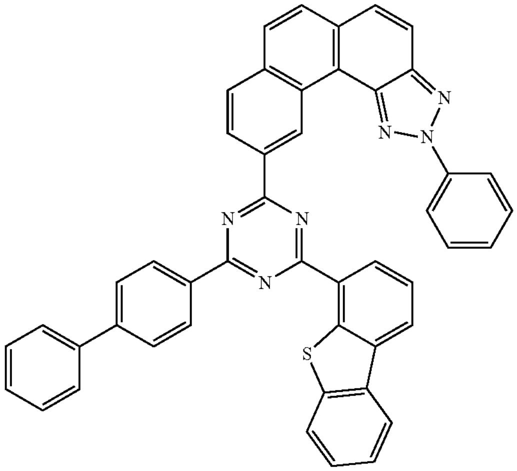
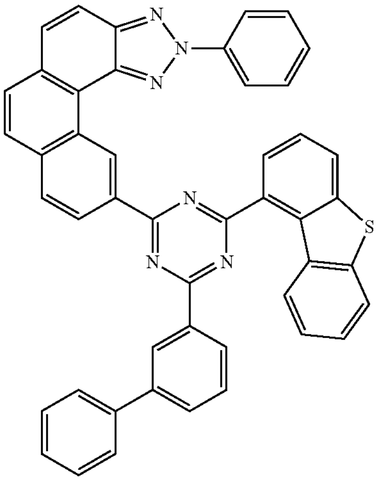
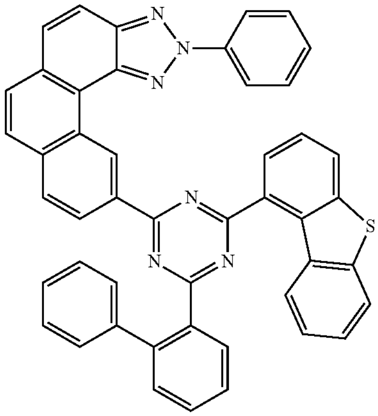
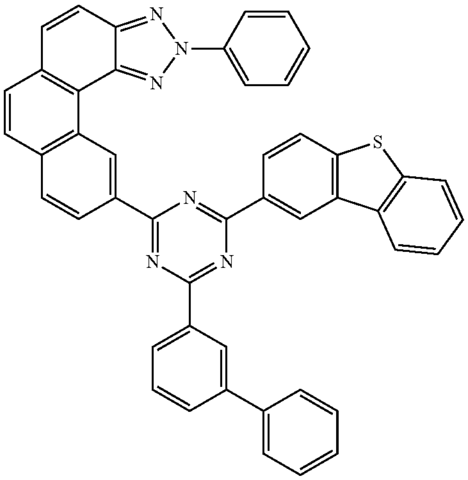

-continued
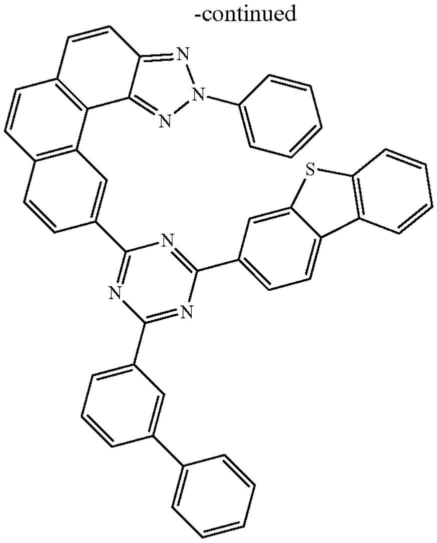
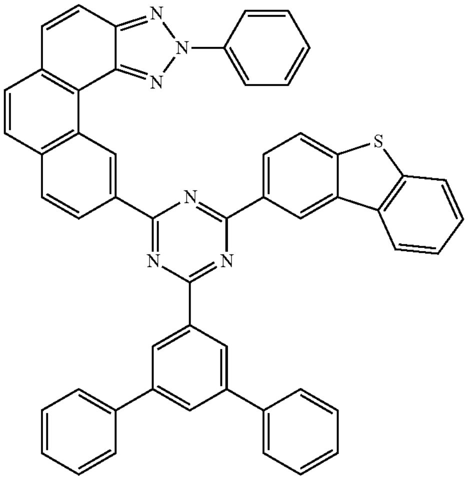
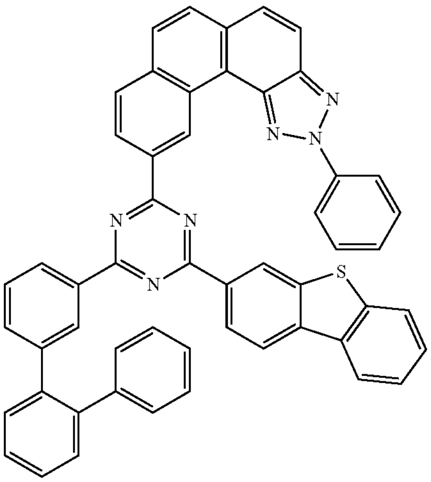
-continued
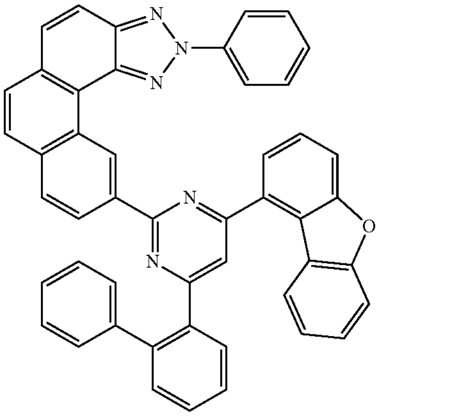
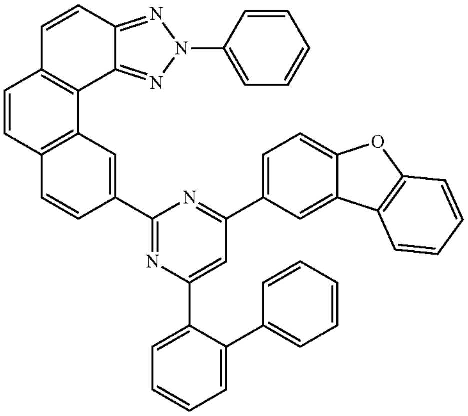
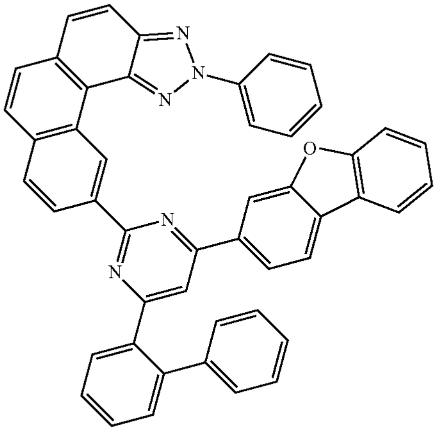

-continued
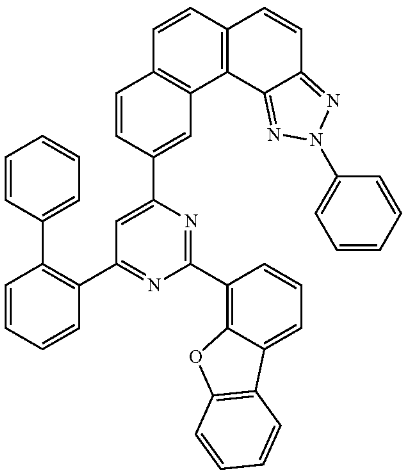
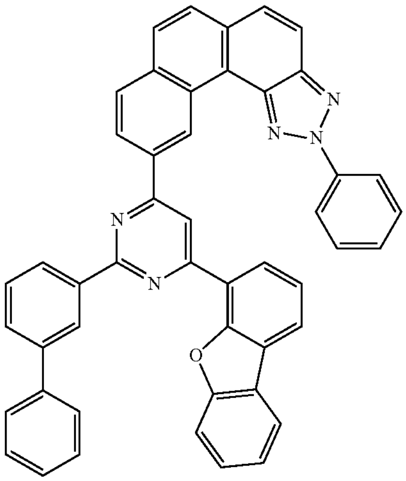
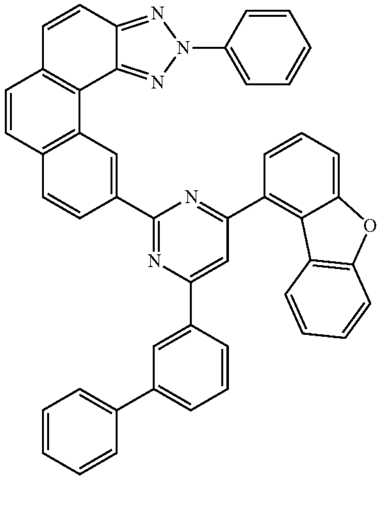
-continued
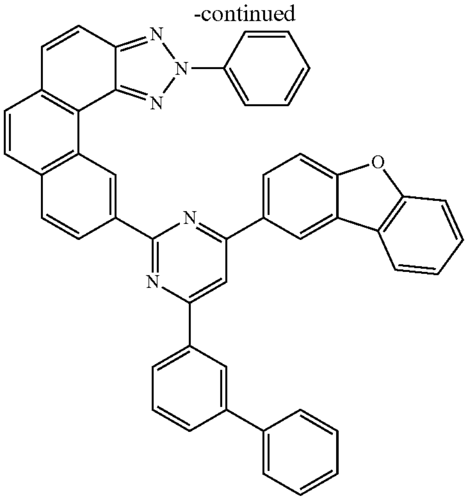
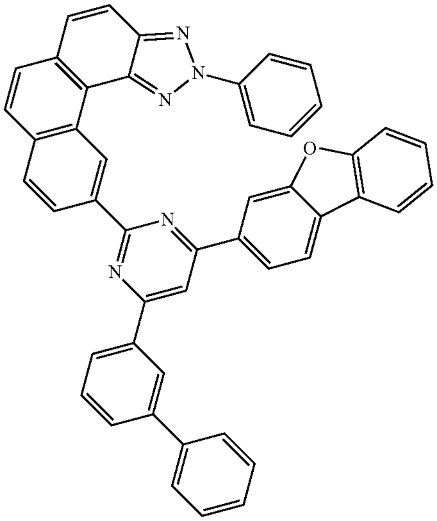
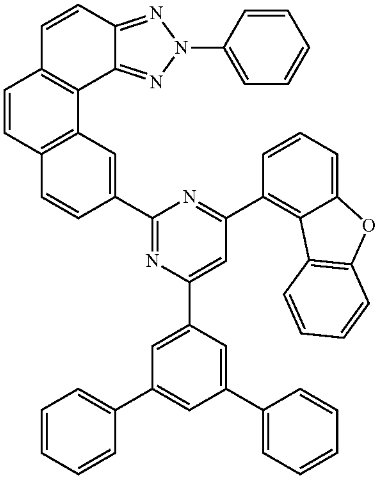

-continued
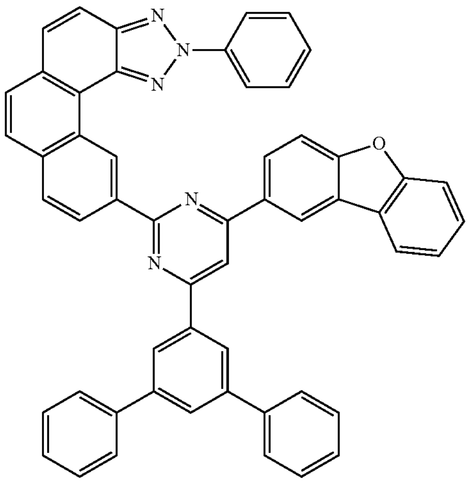
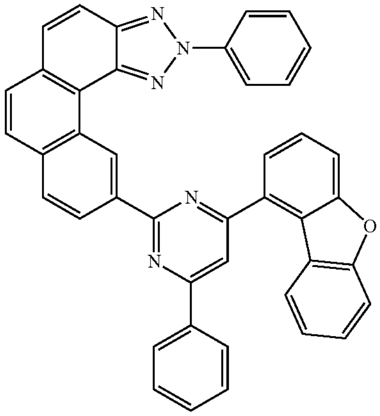
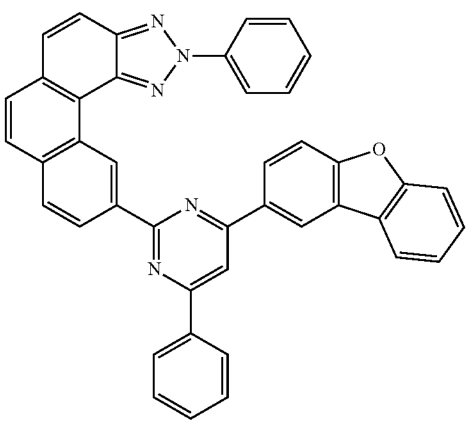
-continued
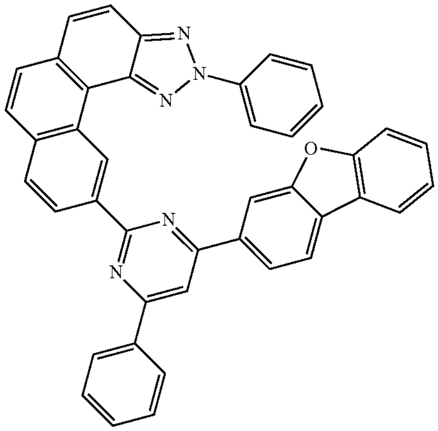
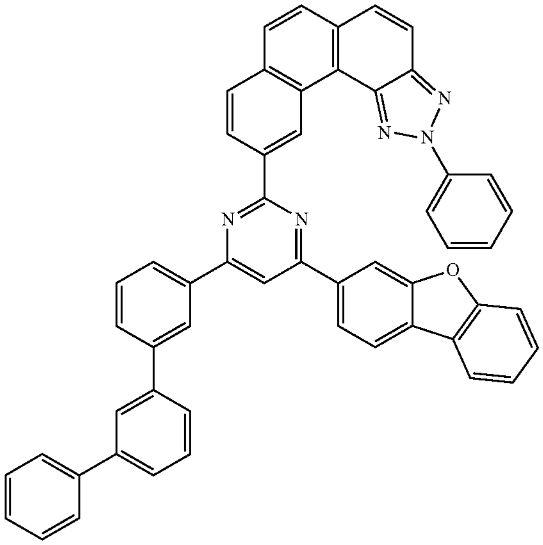
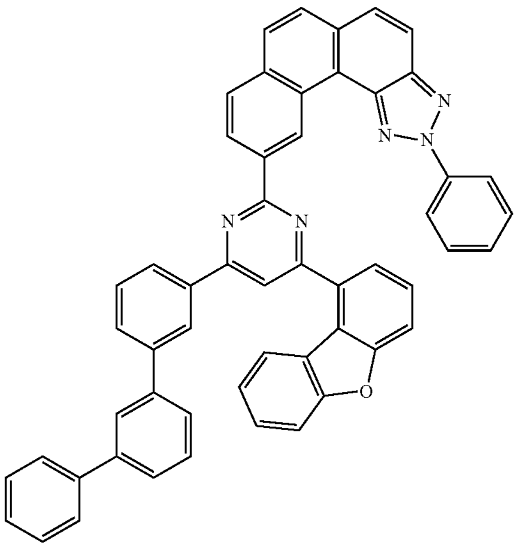

-continued
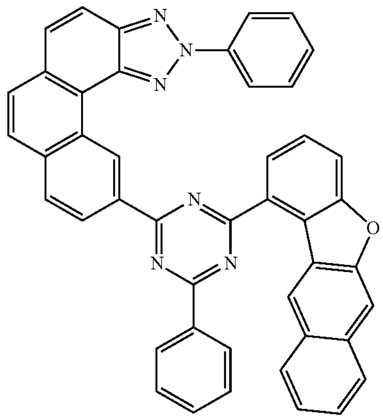
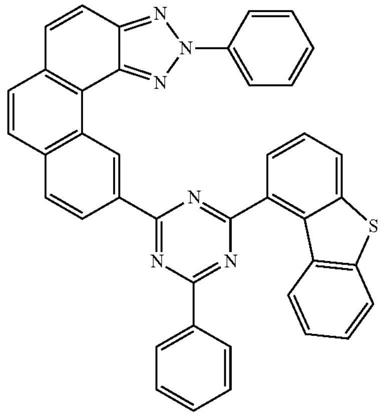
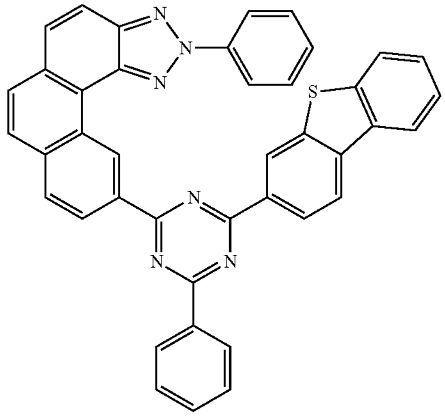
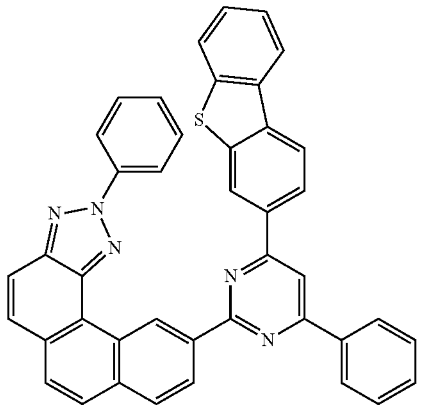
-continued
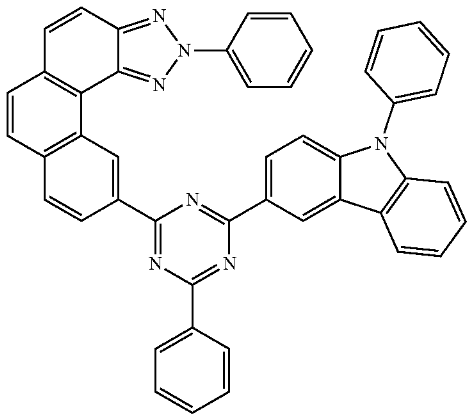
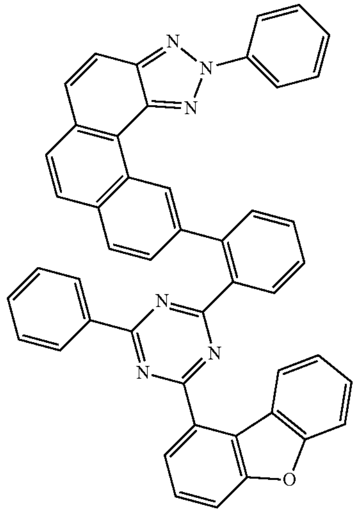
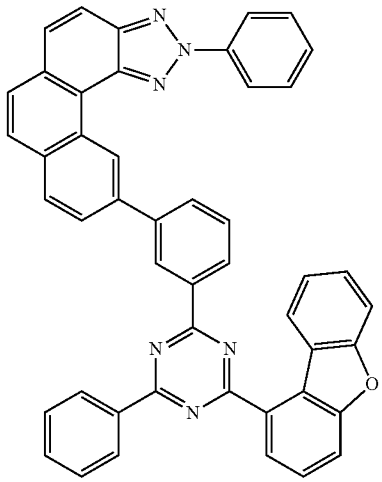

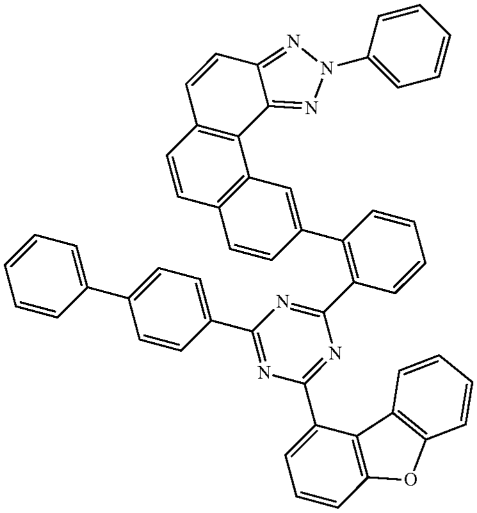
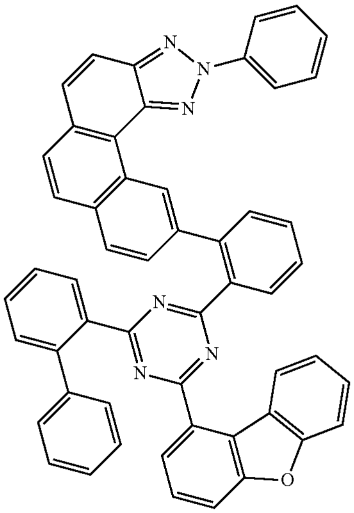
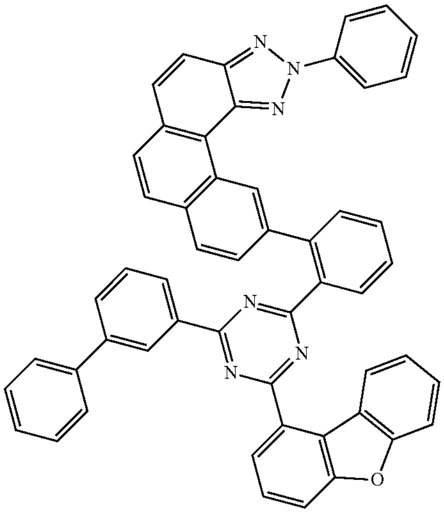
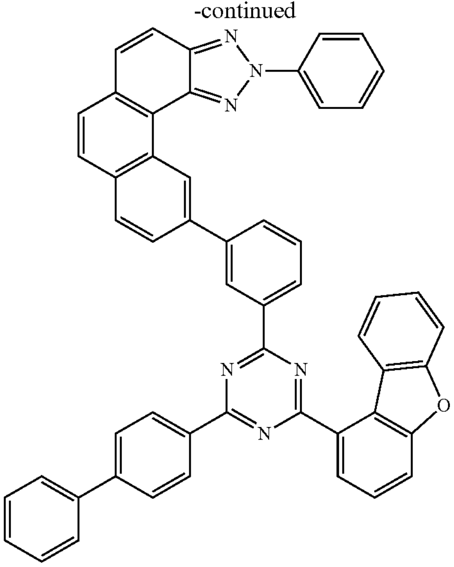
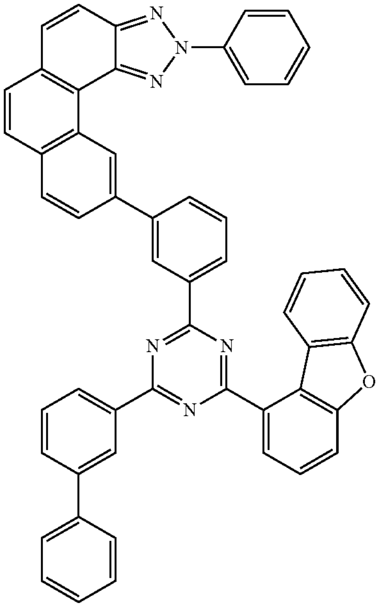

-continued
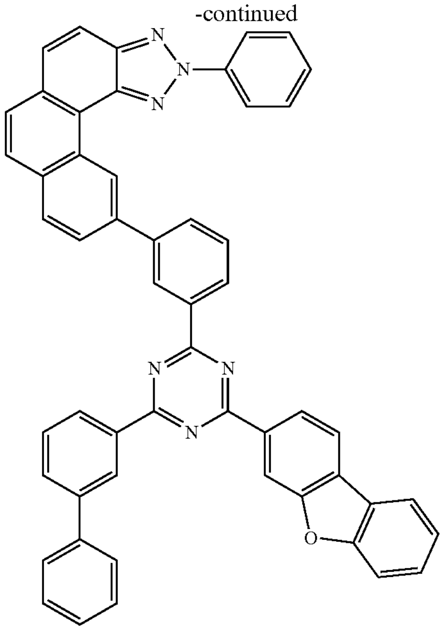
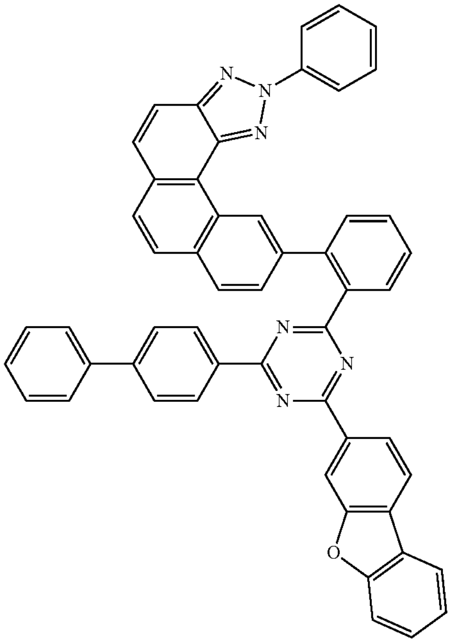
-continued
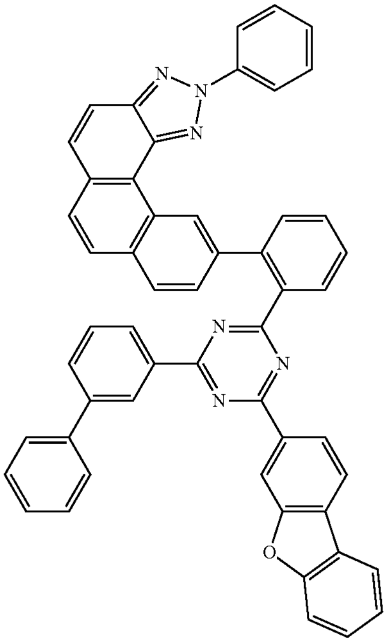
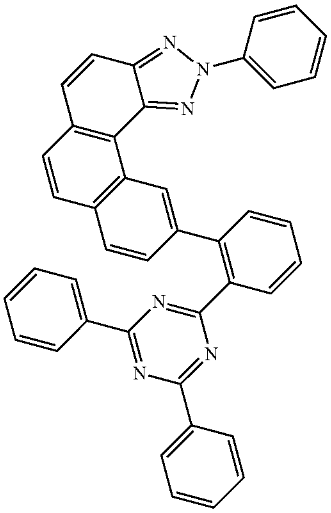
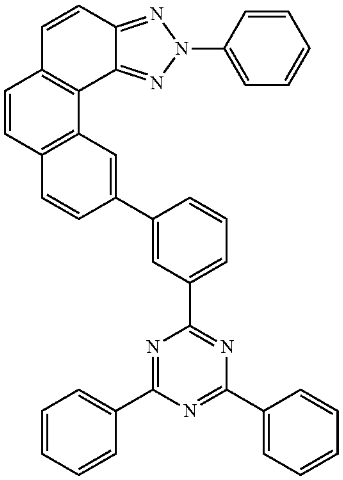

-continued
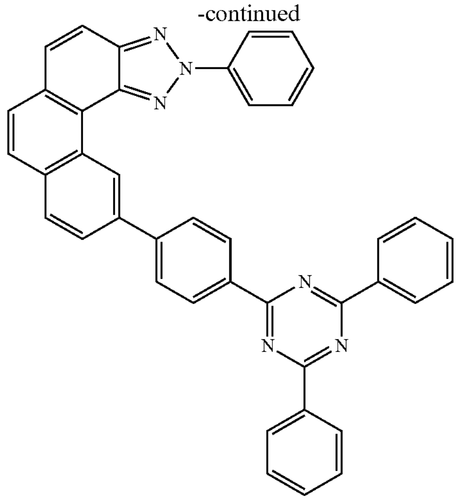
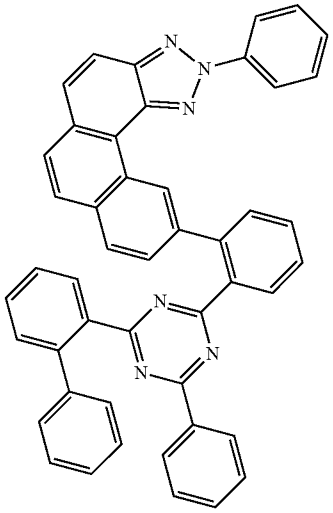
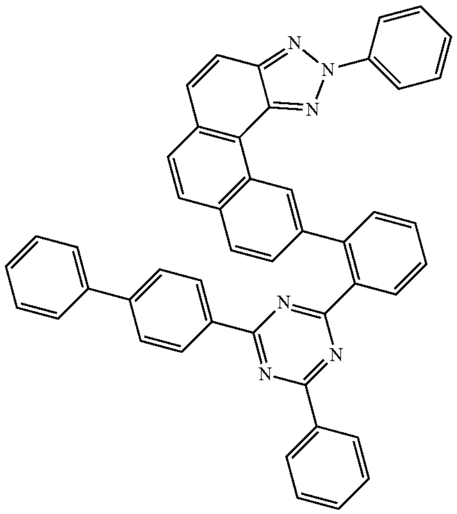 [SMILES: c1ccc(-c2ccc(-c3nc(-c4ccccc4)nc(-c4ccccc4-c4ccc5ccc6ccc7nn(-c8ccccc8)nc7c6c5c4)n3)cc2)cc1]
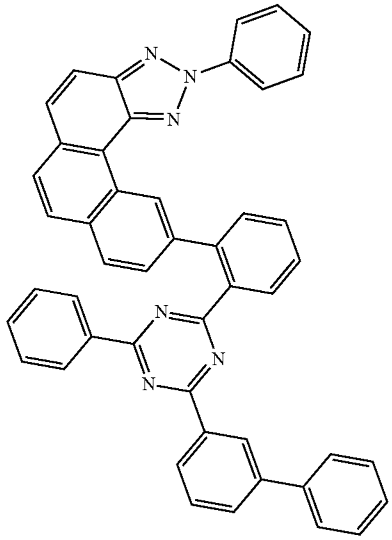
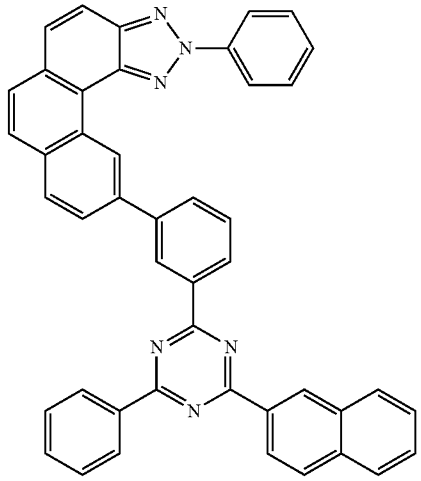
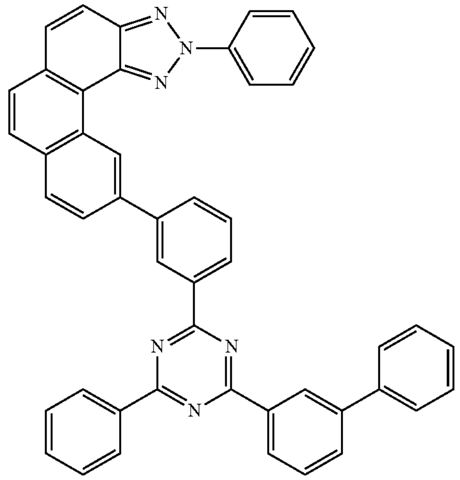

-continued
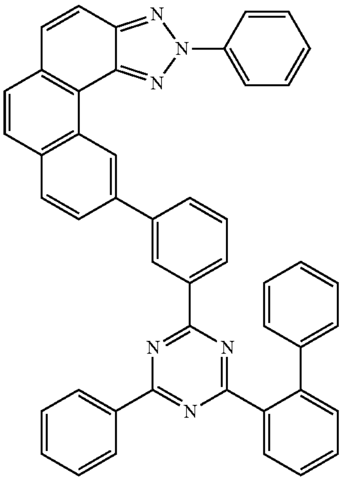
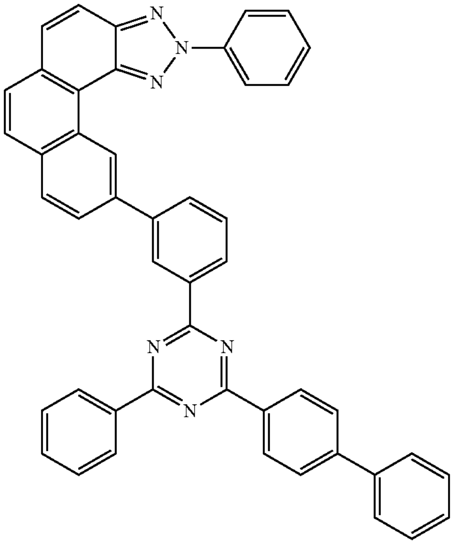
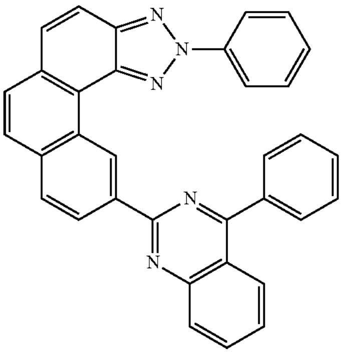
-continued
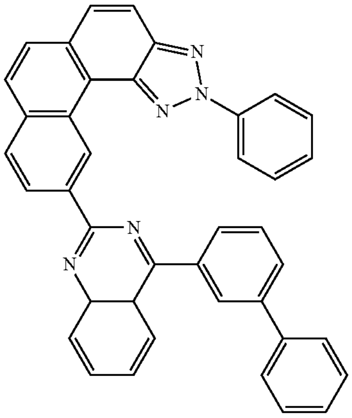
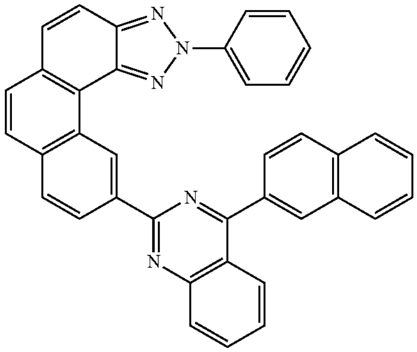
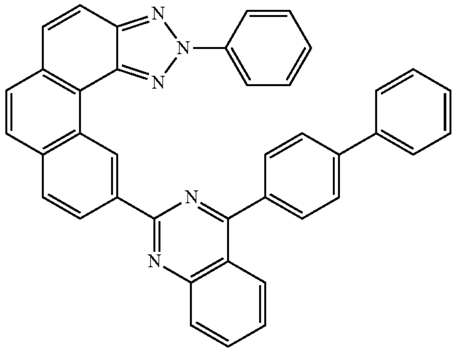
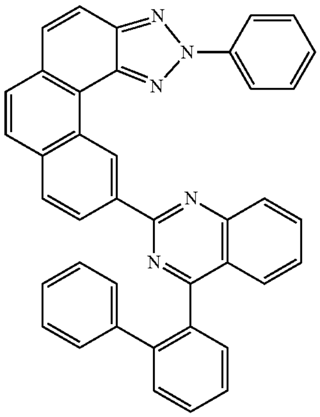

-continued
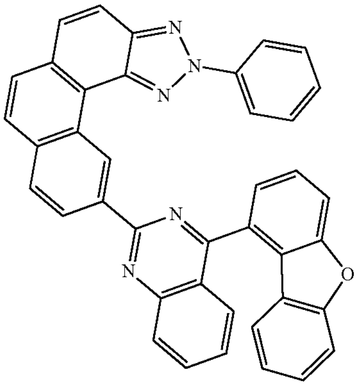
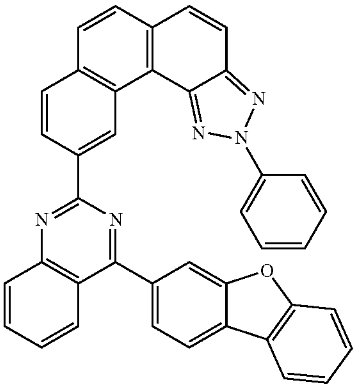
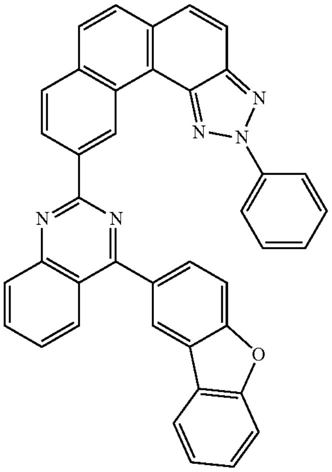
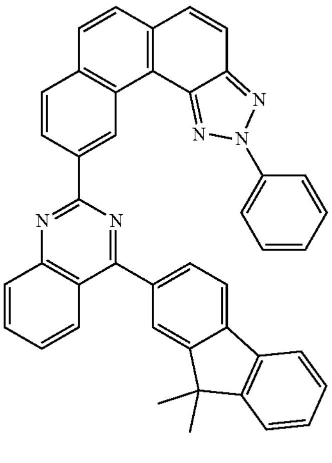
-continued
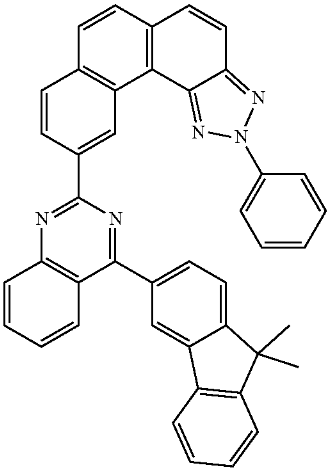
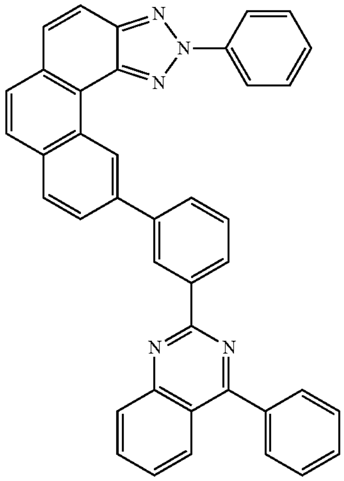
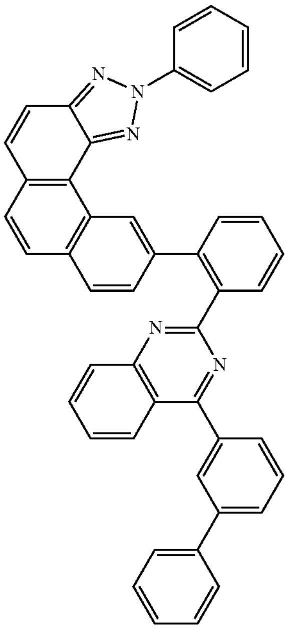

-continued
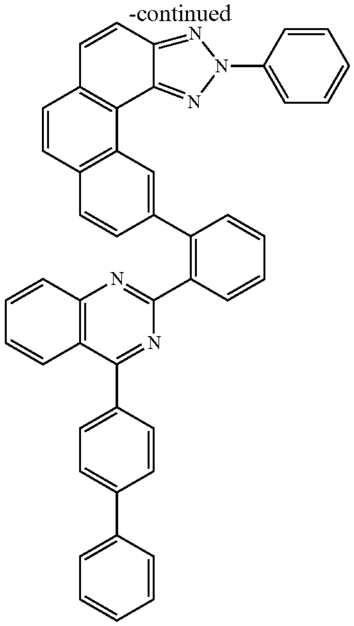
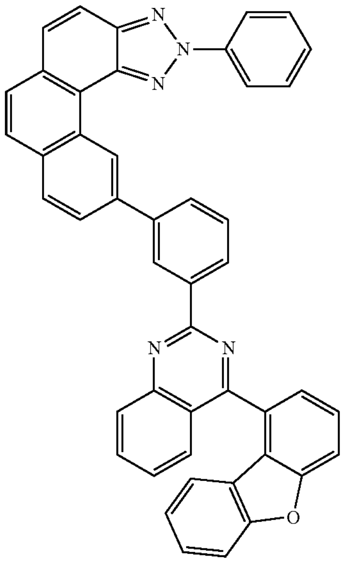
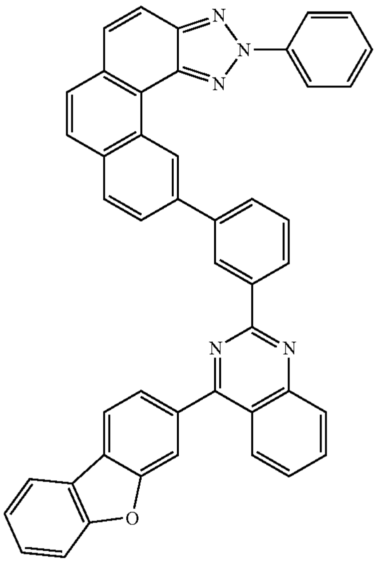
-continued
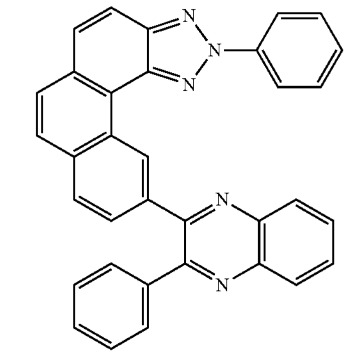
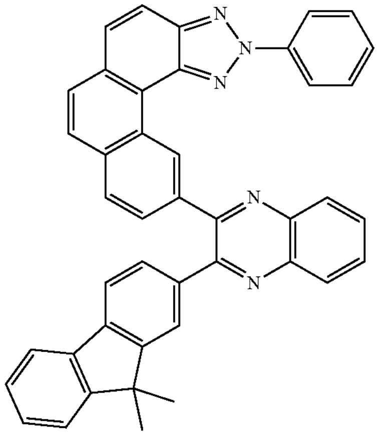
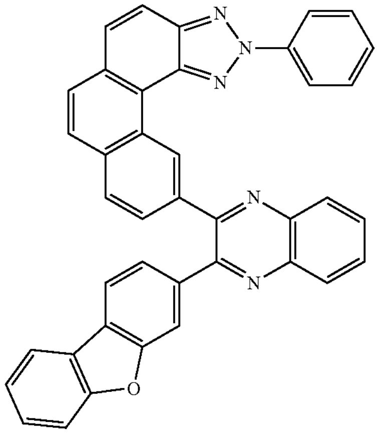
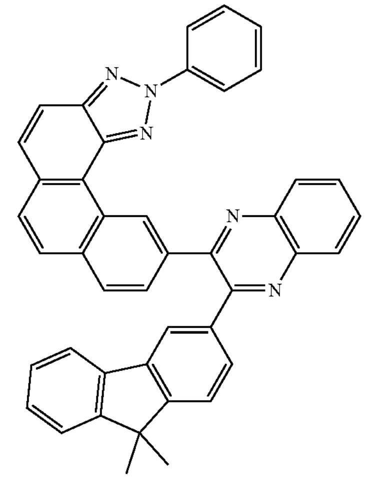

-continued
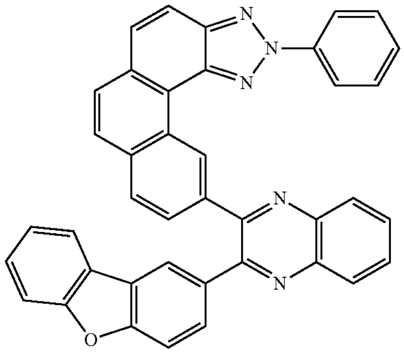
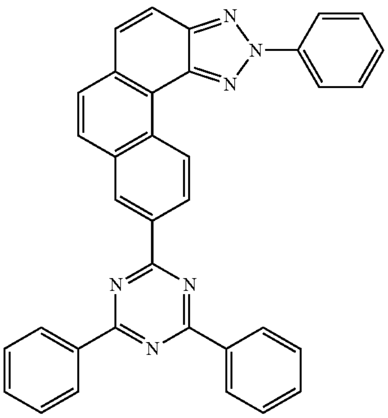
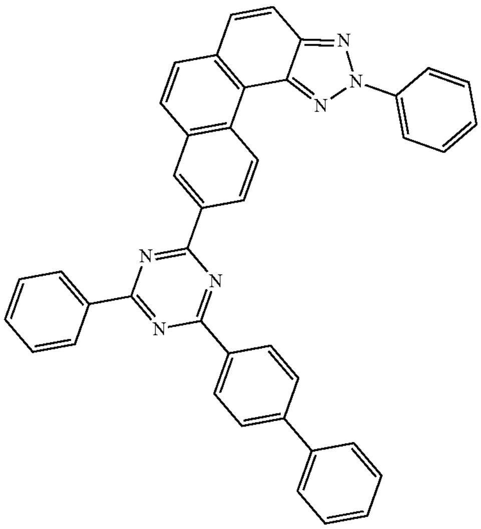
-continued
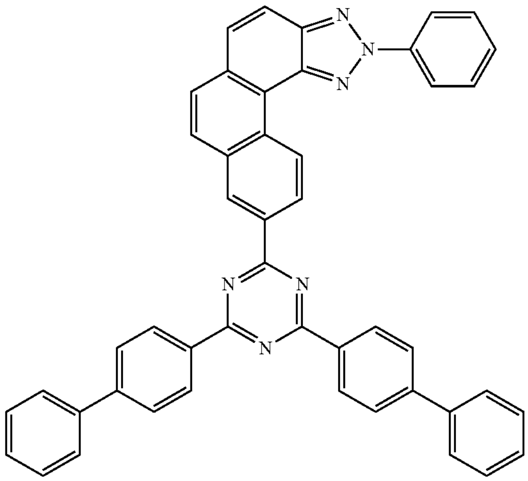
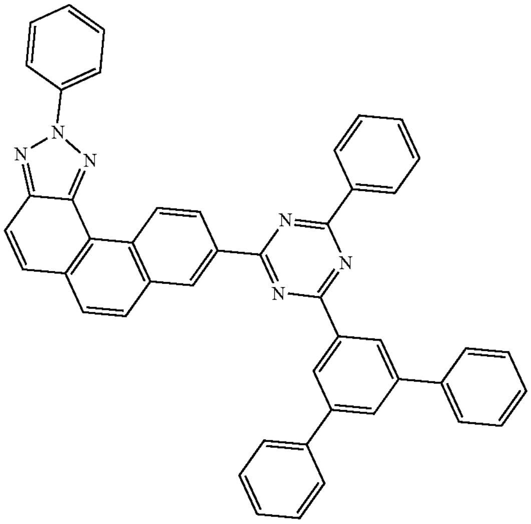
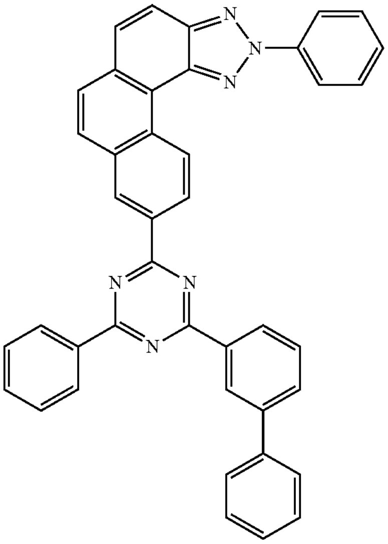

-continued
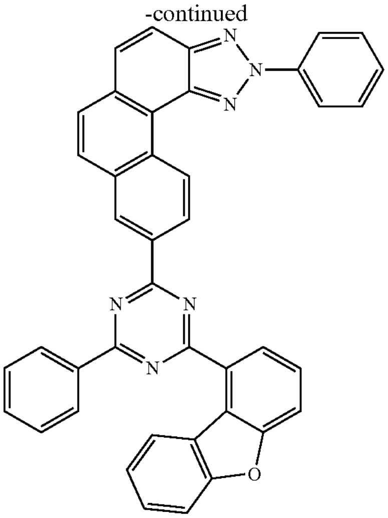
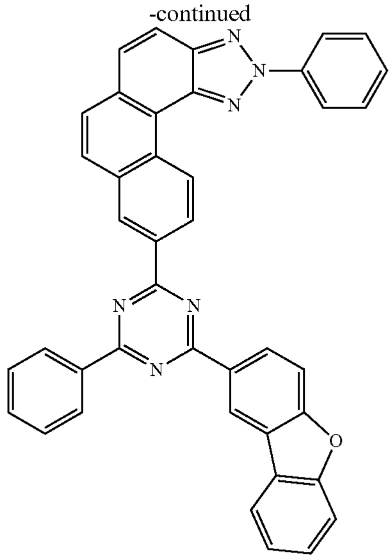
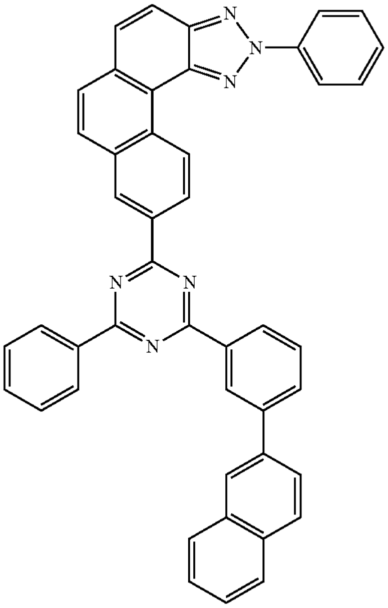
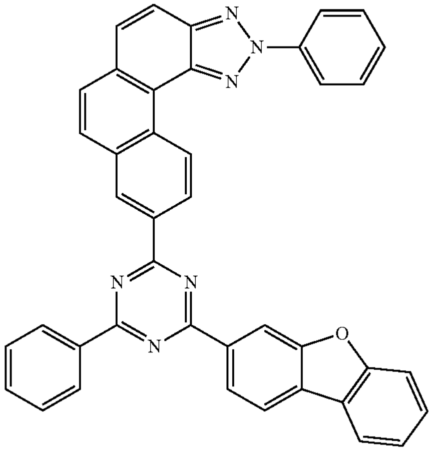
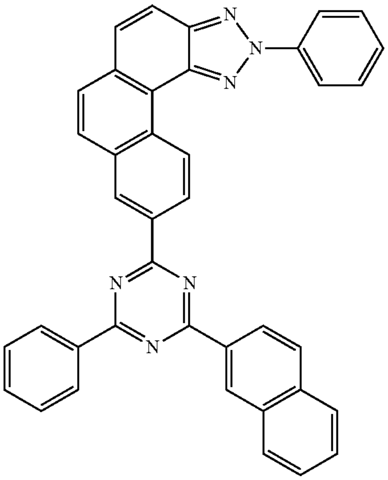
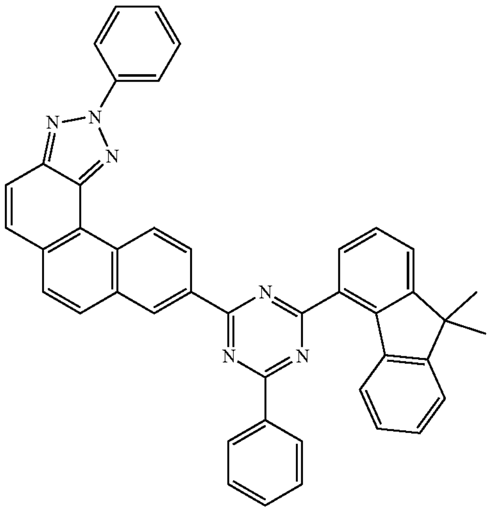

-continued
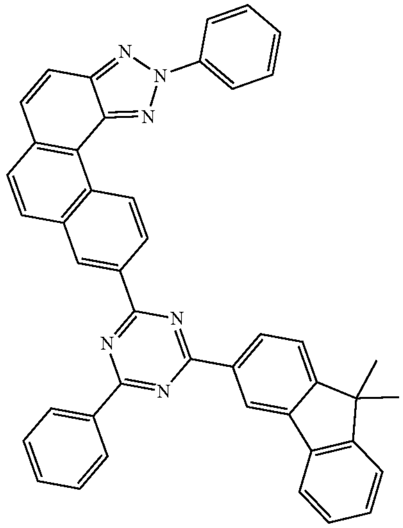
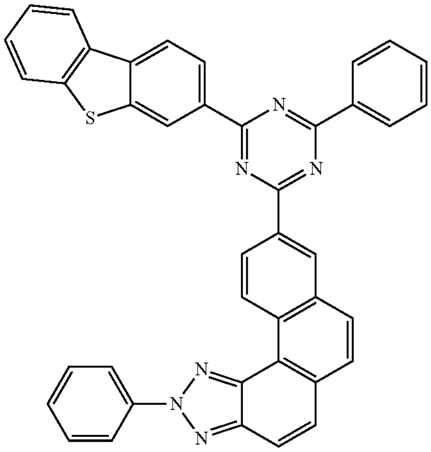
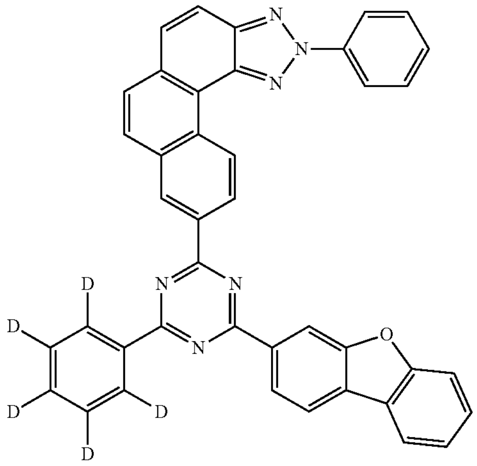
-continued
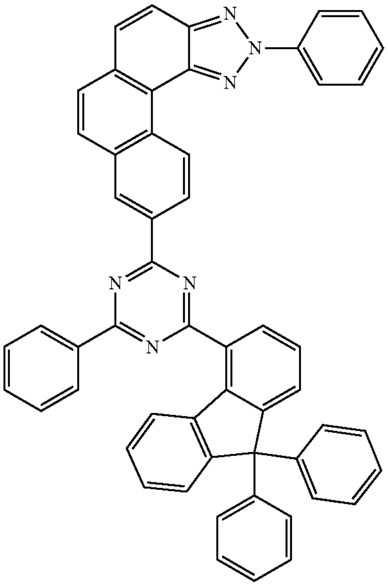
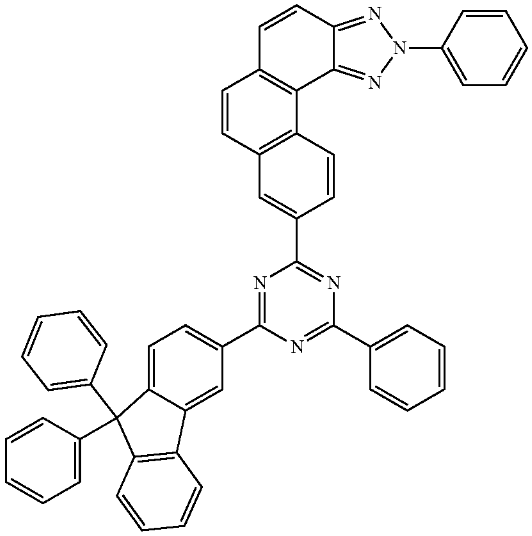
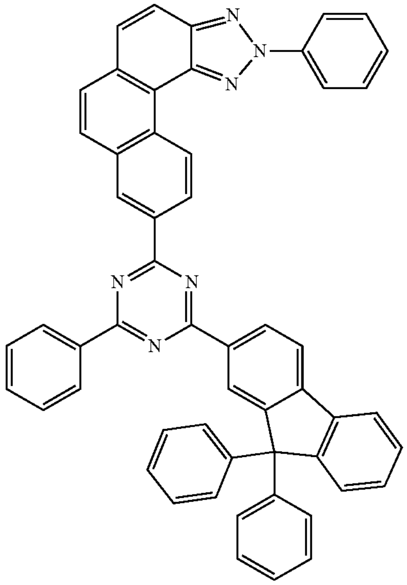

-continued
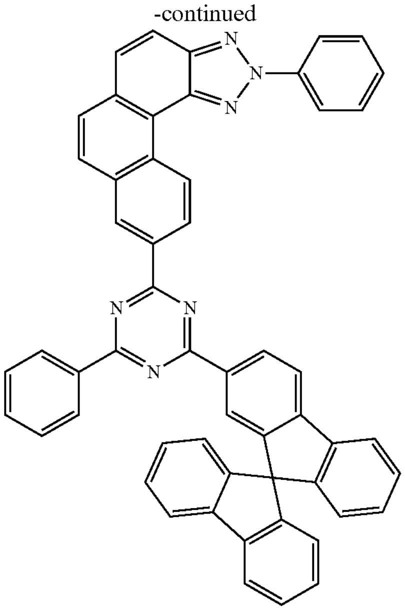
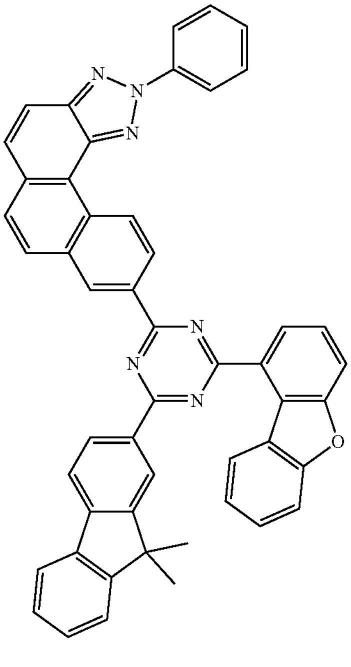 [SMILES: CC1(C)c2ccccc2-c2ccc(-c3nc(-c4ccc5c(ccc6ccc7nn(-c8ccccc8)nc7c65)c4)nc(-c4cccc5oc6ccccc6c45)n3)cc21]
-continued
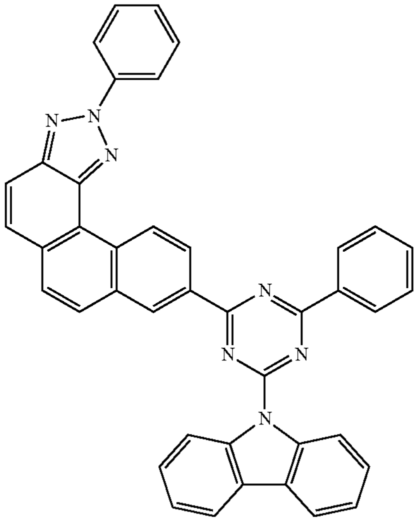
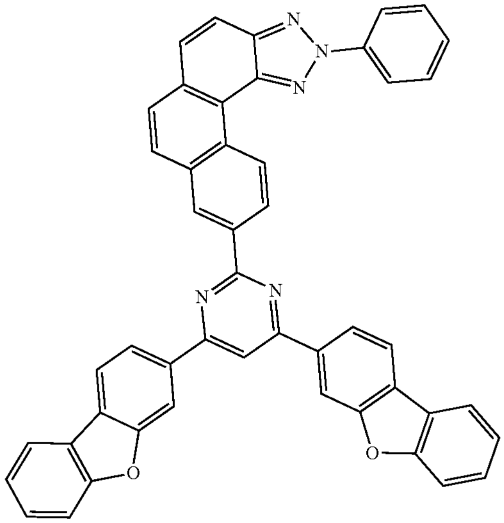
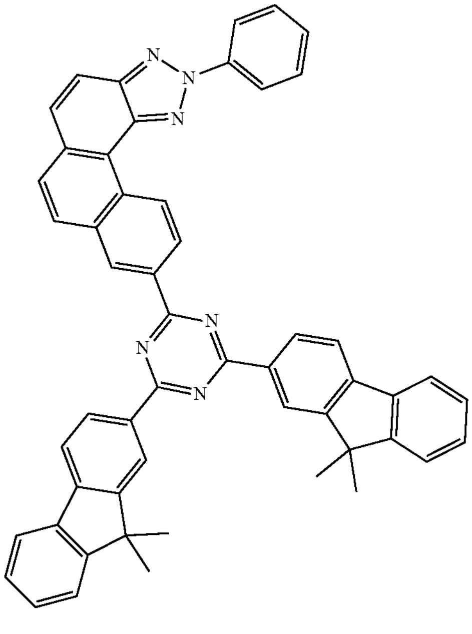

-continued
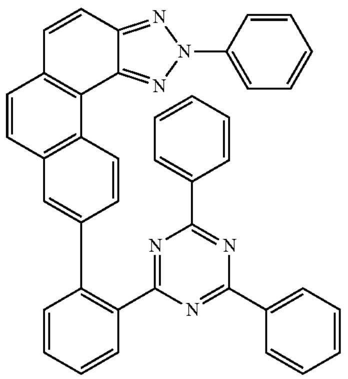
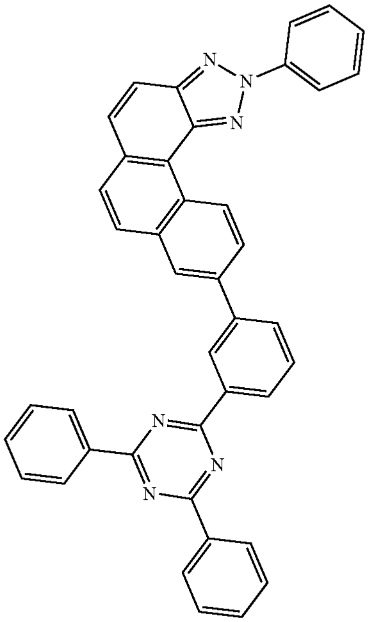
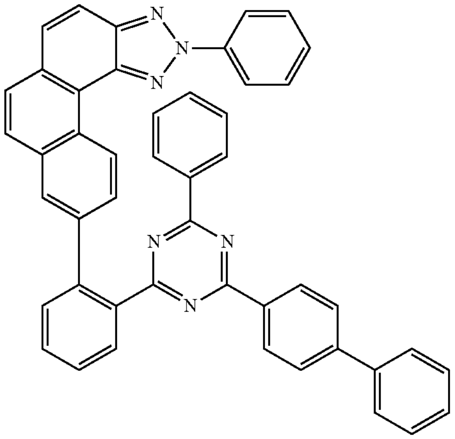
-continued
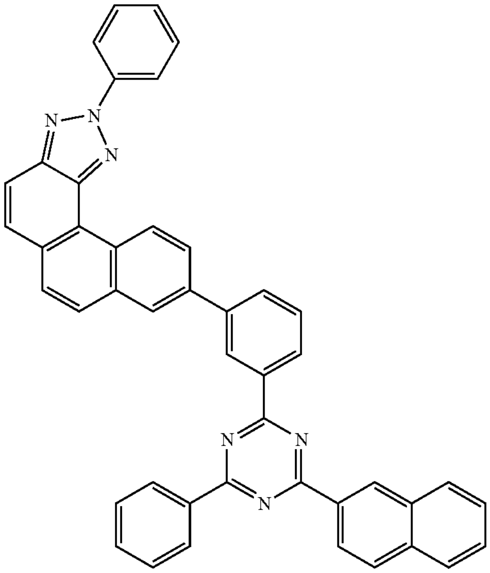
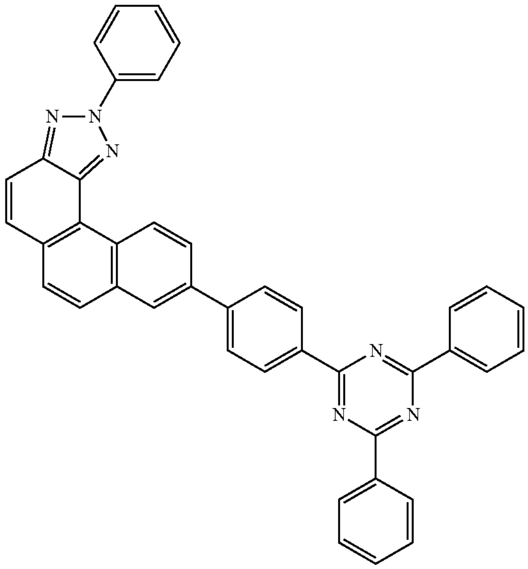

-continued
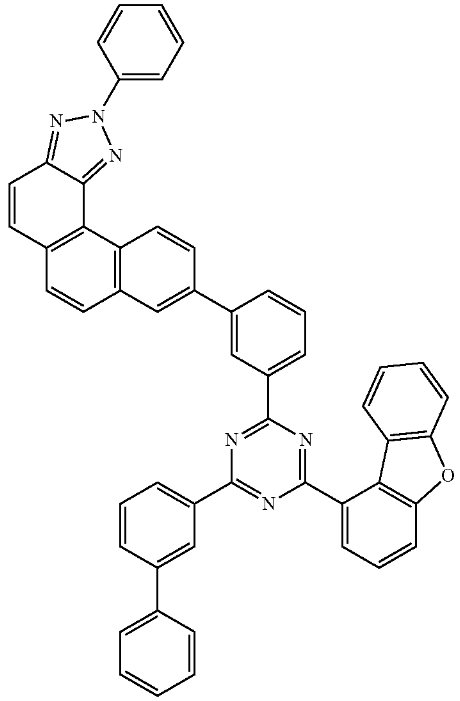
-continued
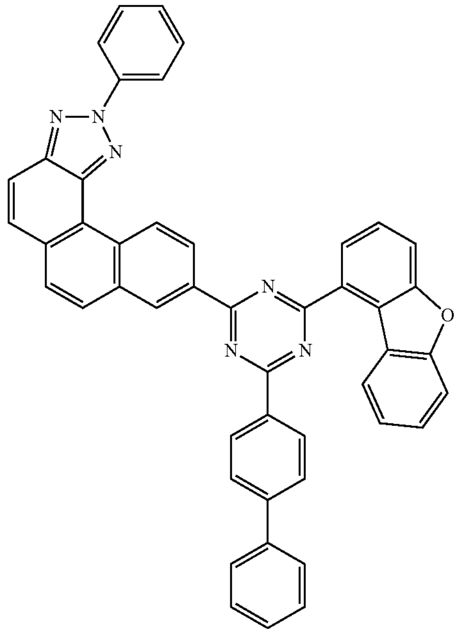
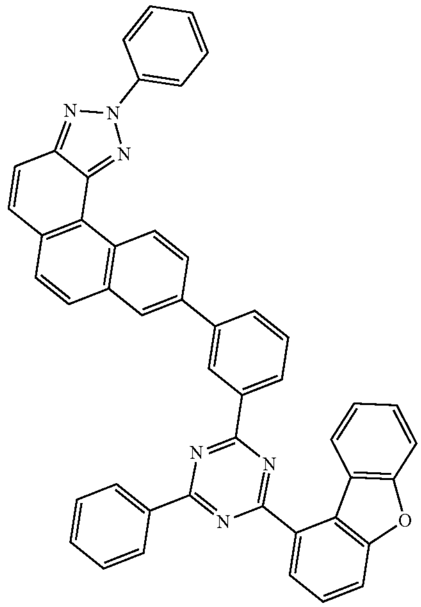
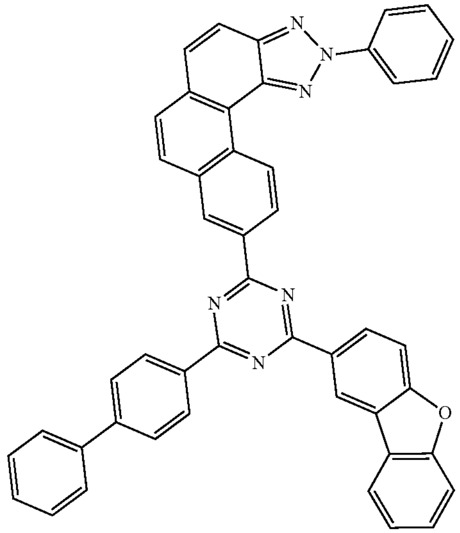

-continued
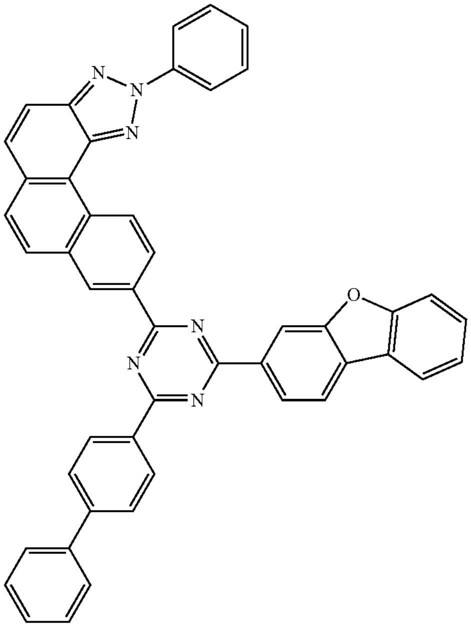
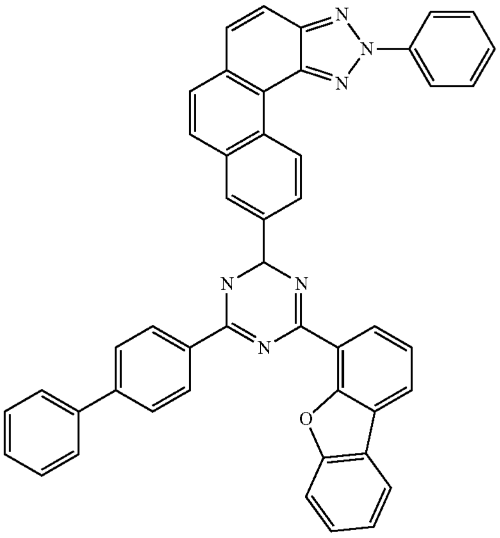
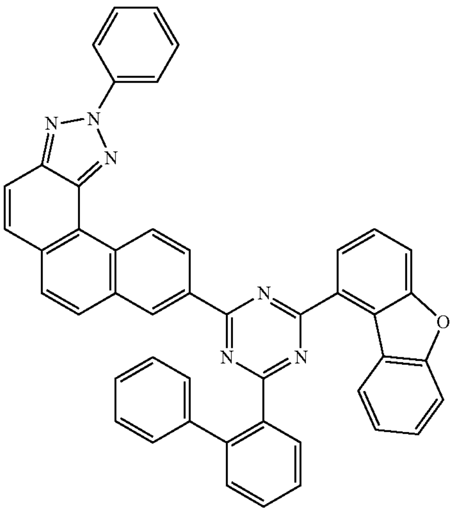
-continued
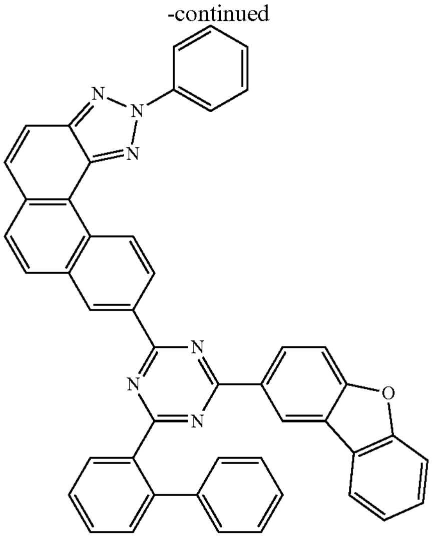
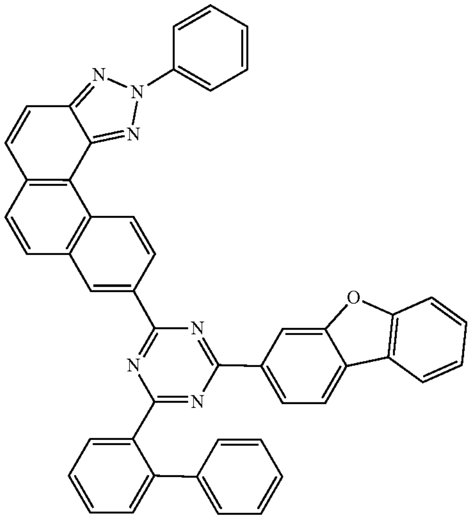
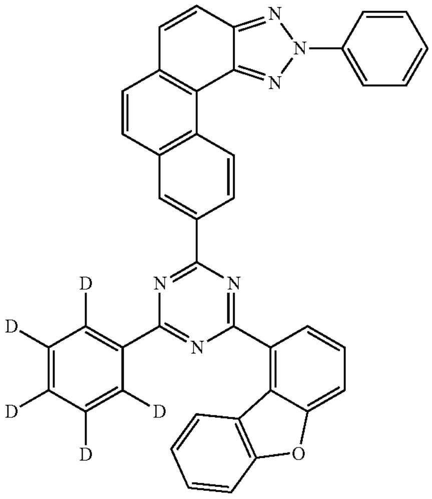

-continued
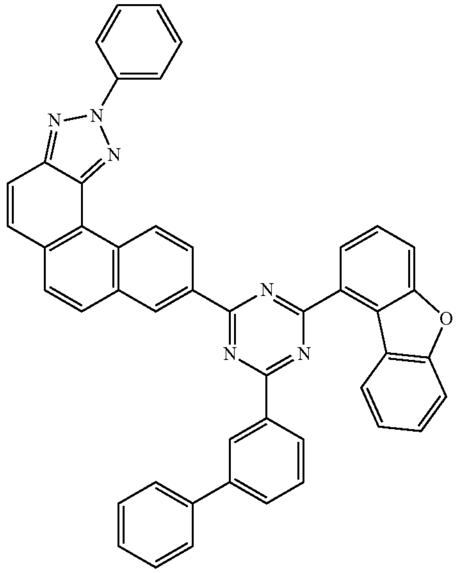
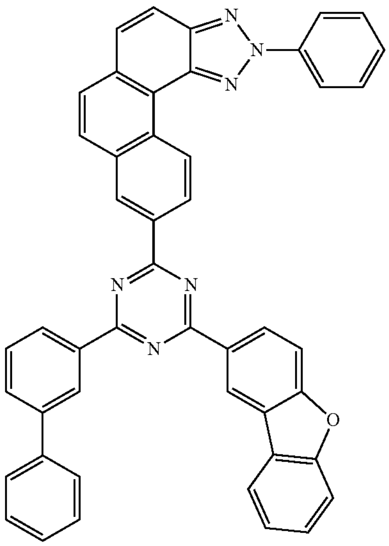
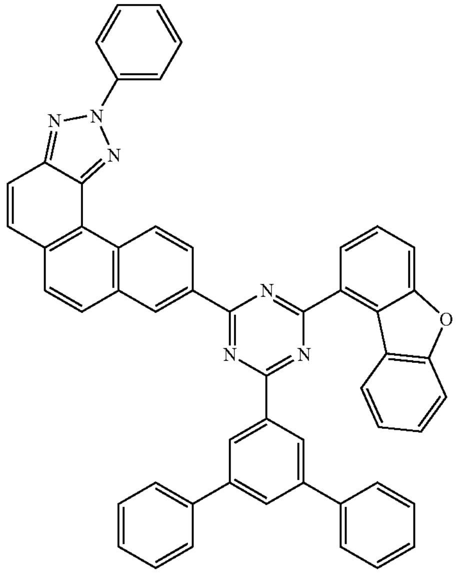
-continued
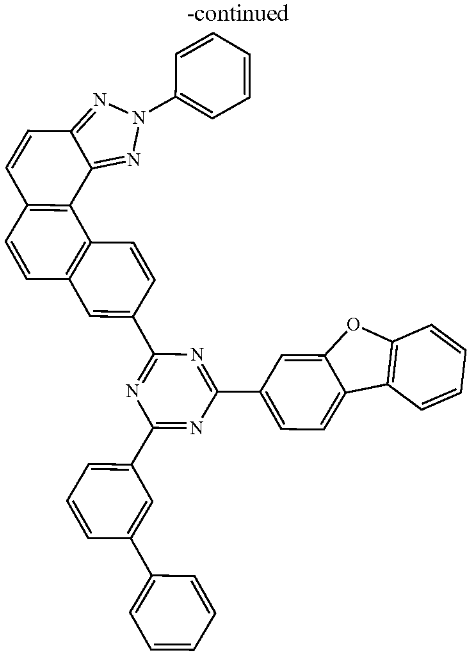
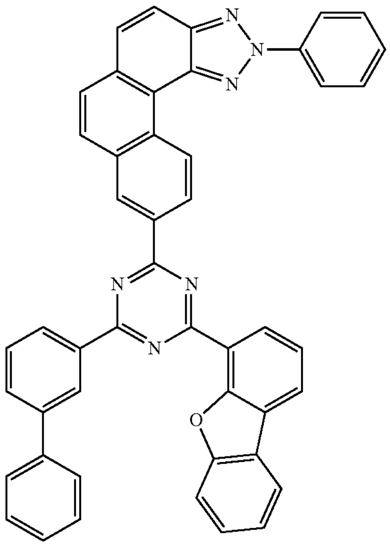

-continued
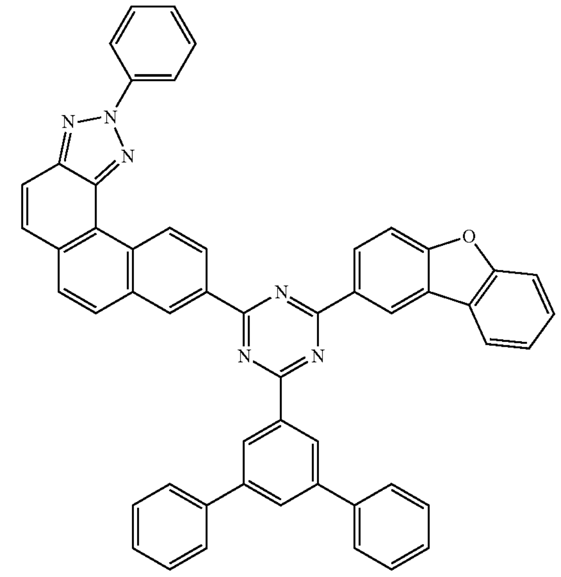
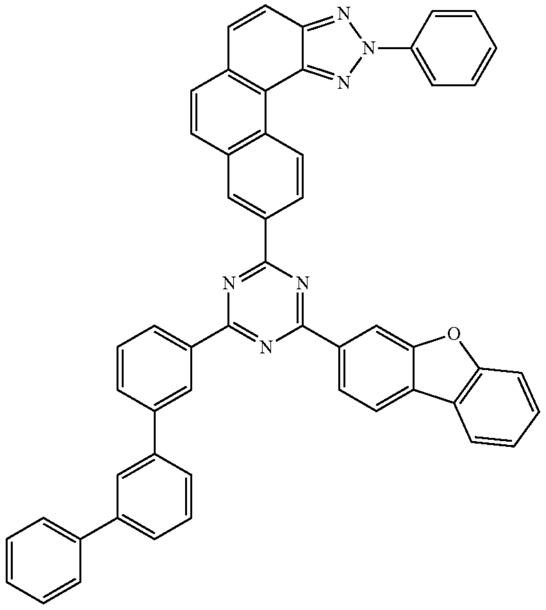
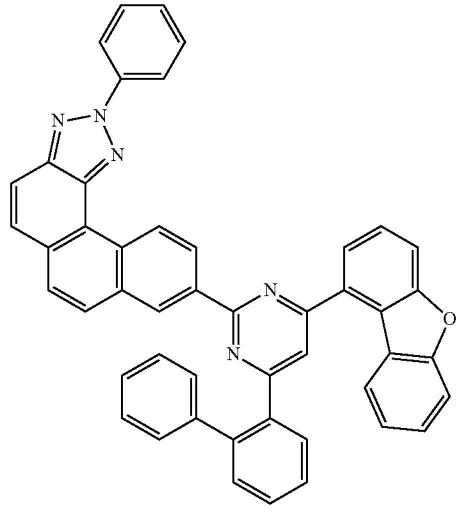
-continued
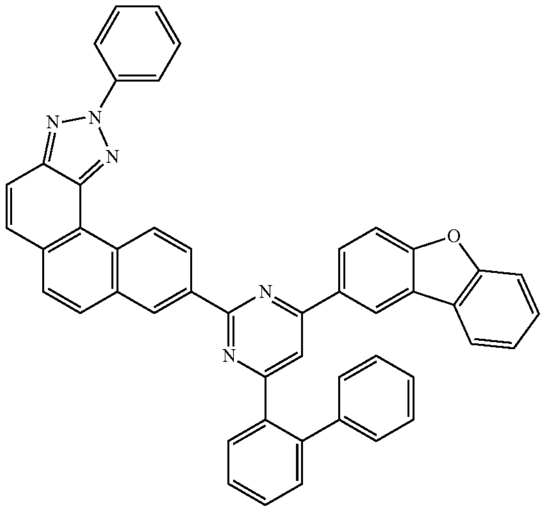
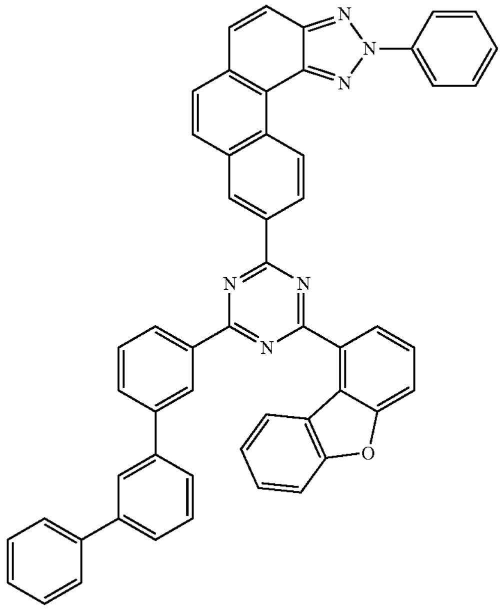
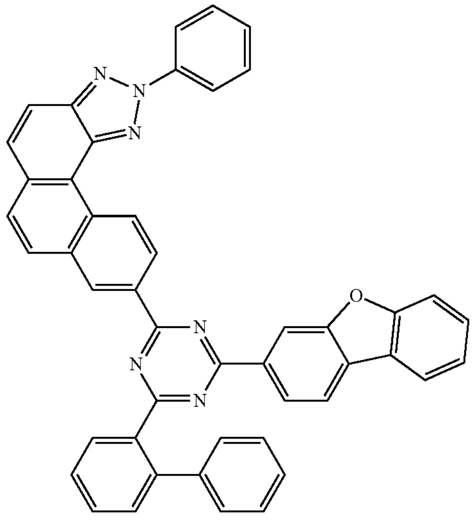

-continued
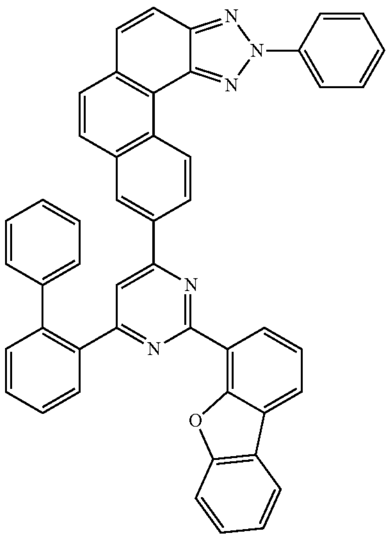
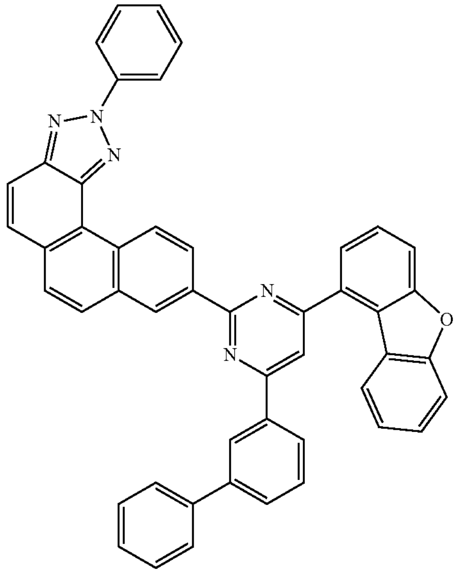
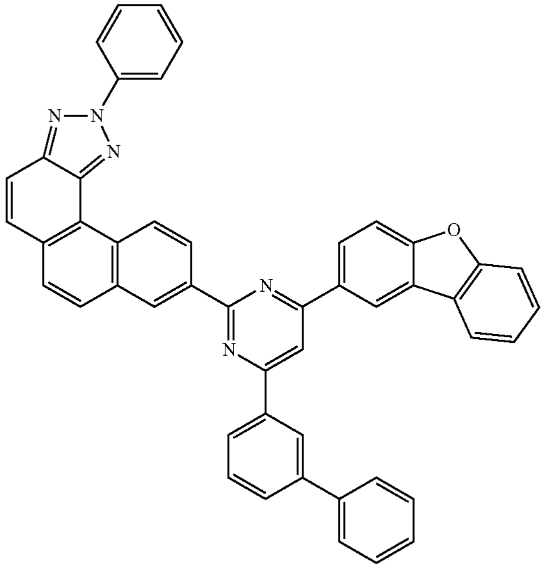
-continued
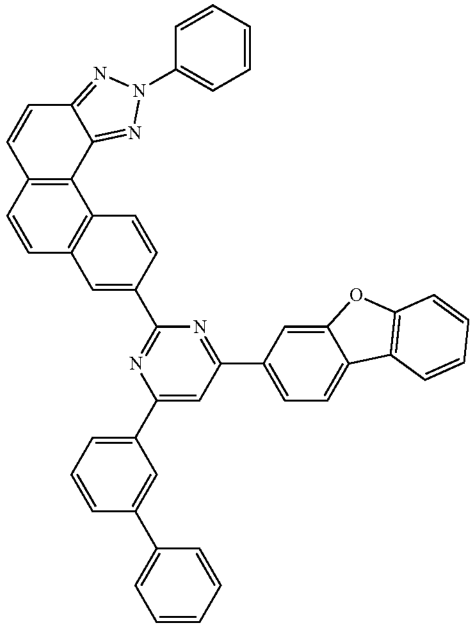
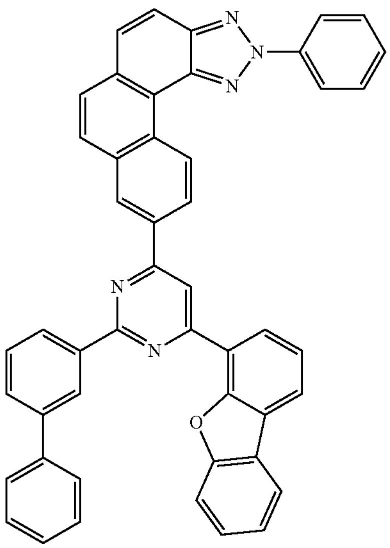

-continued
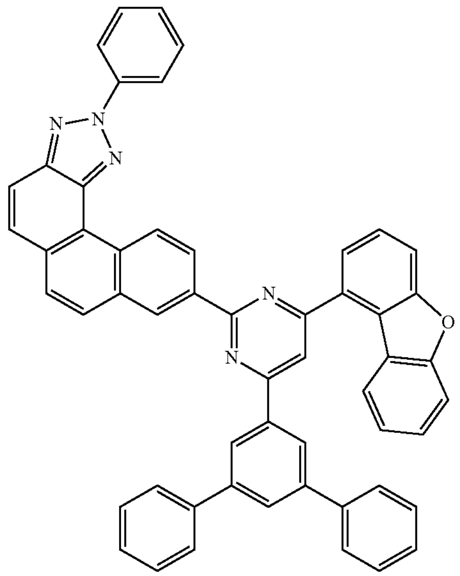
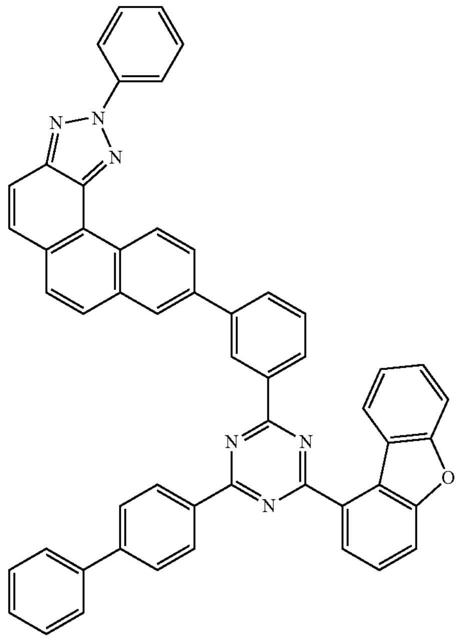
-continued
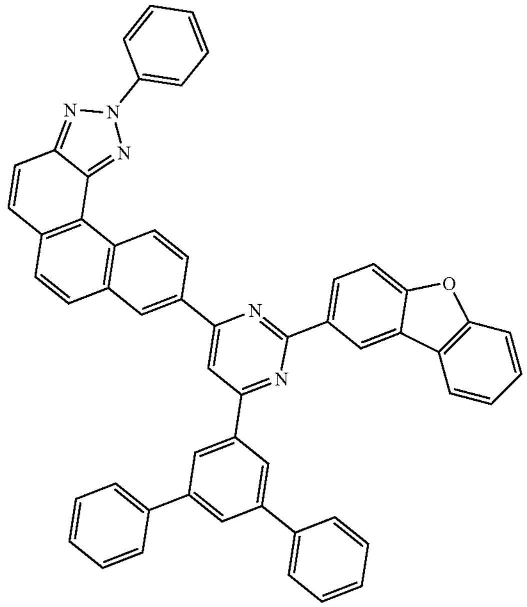
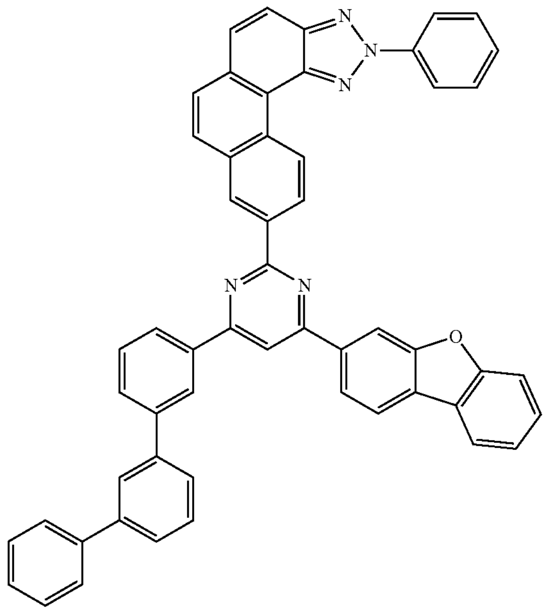

-continued
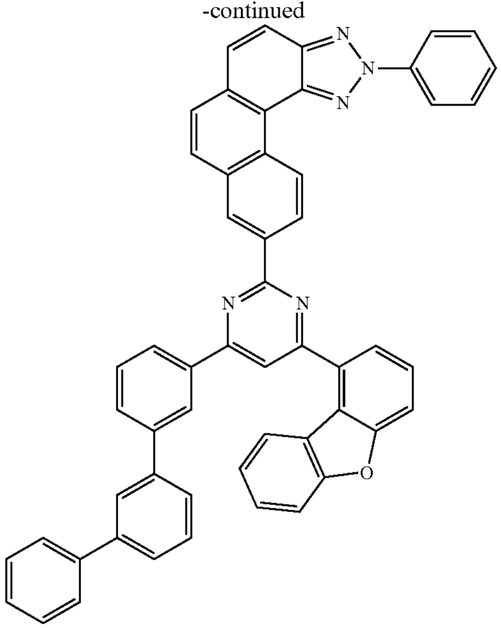
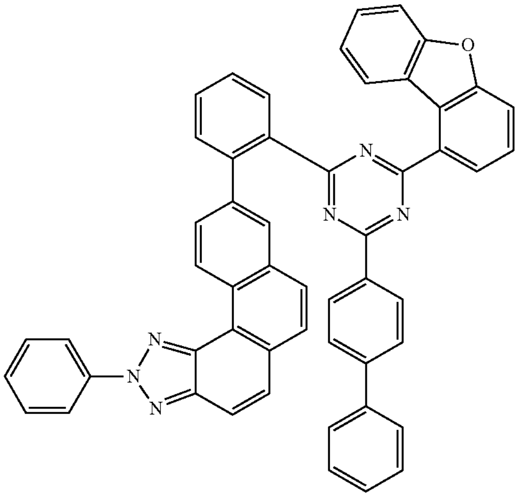
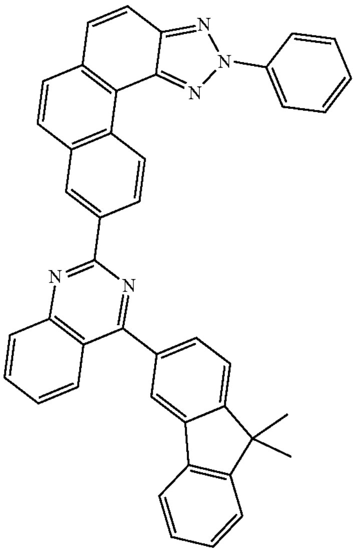
-continued
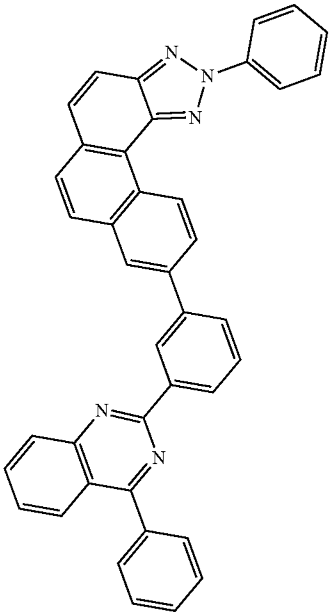
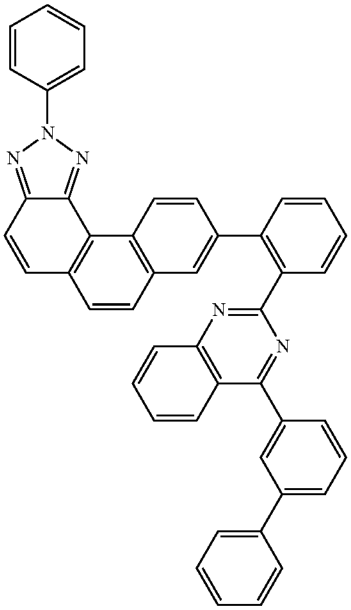

-continued
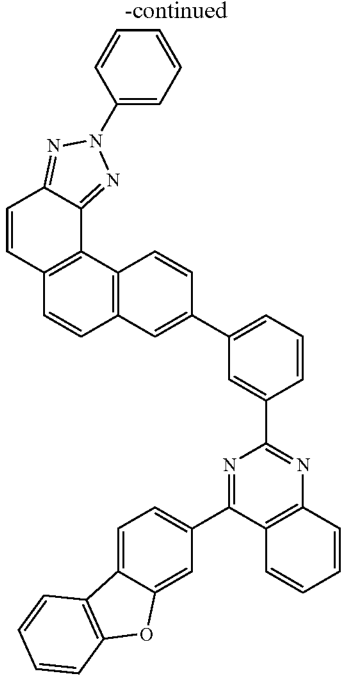
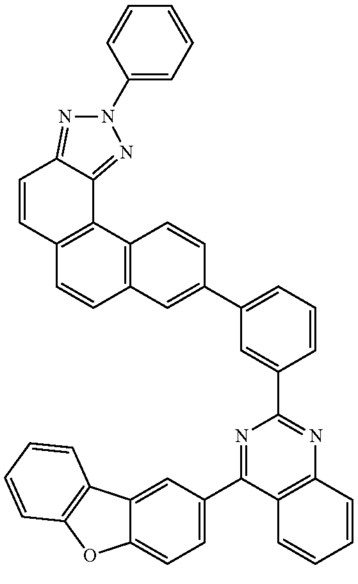
-continued
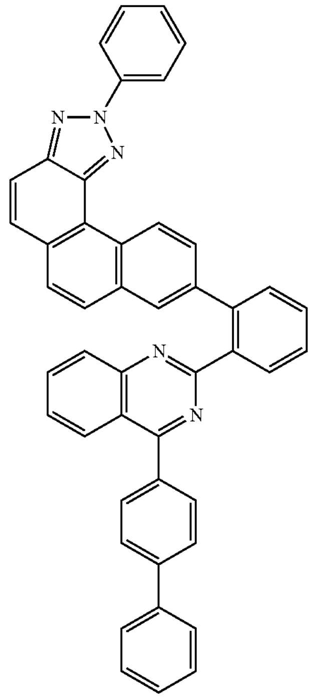
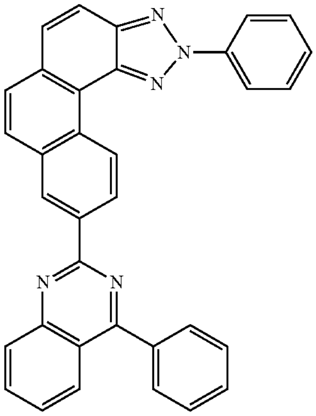
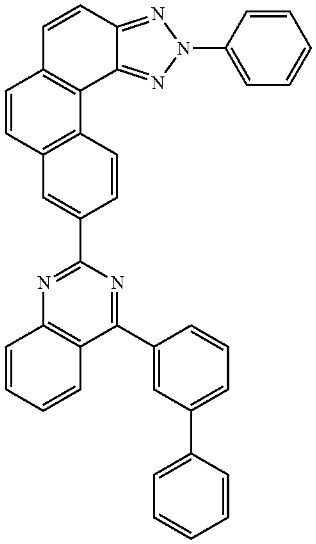

-continued
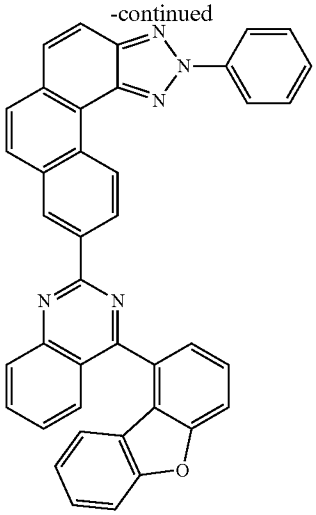
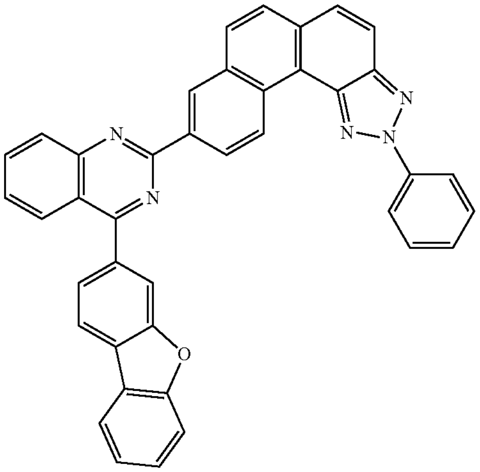
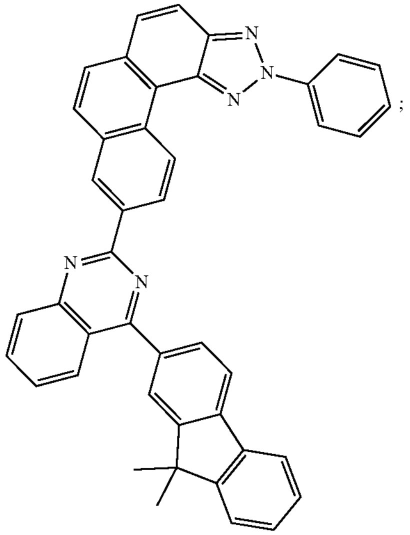
wherein D represents deuterium.
4. The organic material composition according to claim 1, wherein the compound having a structure represented by Formula 2 is a compound having any of the structures represented as below:
2-21
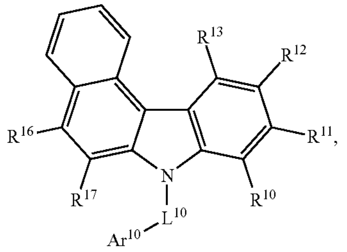
2-22
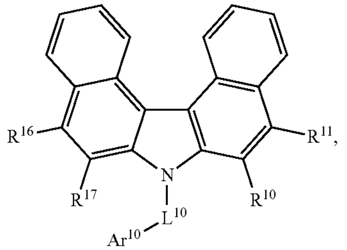
2-23
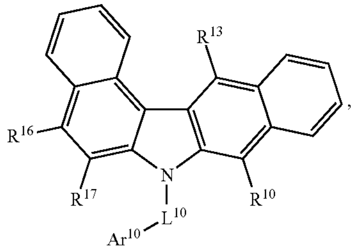
2-24
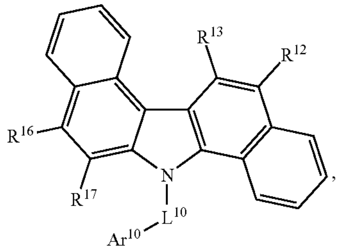
2-25
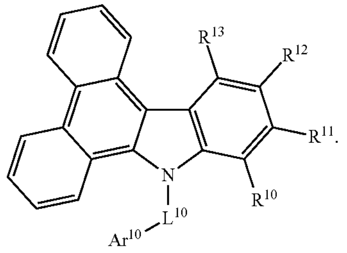
5. The organic material composition according to claim 1, wherein in Formula 2, any adjacent two of $R^{10}$ to $R^{17}$ are fused with
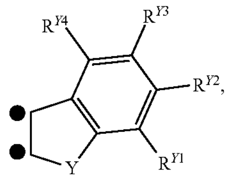

wherein the bonds at the positions marked with black dots are fusion bonds;

Y is selected from O, S, $CR^{Y5}R^{Y6}$ and $NR^{Y}$, in which RY is $—L^{Y7}R^{Y7}$;

$R^{Y1}$, $R^{Y2}$, $R^{Y3}$ and $R^{Y4}$ are each independently selected from hydrogen, deuterium, halogen, a cyano group, a substituted or unsubstituted C1-C30 alkyl group, a C1-C30 alkyl group in which one or more methylene groups are independently substituted by —O— and/or —S— in a manner that O atom and/or S atom are not adjacent to each other, a substituted or unsubstituted C7-C30 arylalkyl group, a substituted or unsubstituted C6-C30 aryl group, a substituted or unsubstituted C3-C30 heteroaryl group, a substituted or unsubstituted C4-C30 heteroarylalkyl group, a substituted or unsubstituted C3-C30 cycloalkyl group, a substituted or unsubstituted C3-C30 heterocycloalkyl group, a substituted or unsubstituted C3-C30 cycloalkenyl group, a substituted or unsubstituted C1-C30 alkoxy group, and a substituted or unsubstituted C6-C30 aryloxy group; $R^{Y1}$, $R^{Y2}$, $R^{Y3}$ and $R^{Y4}$ are present individually without forming a ring, or any adjacent two of $R^{Y1}$, $R^{Y2}$, $R^{Y3}$ and $R^{Y4}$ joined to form a benzene ring or a naphthalene ring;

$R^{Y5}$, $R^{Y6}$ are each independently selected from a substituted or unsubstituted C1-C30 alkyl group, and a substituted or unsubstituted C6-C30 aryl group;

$R^{Y7}$ is selected from a substituted or unsubstituted C1-C30 alkyl group, a substituted or unsubstituted C7-C30 arylalkyl group, a substituted or unsubstituted C6-C30 aryl group, a substituted or unsubstituted C3-C30 heteroaryl group, a substituted or unsubstituted C4-C30 heteroarylalkyl group, a substituted or unsubstituted C3-C30 cycloalkyl group, a substituted or unsubstituted C3-C30 heterocycloalkyl group, and a substituted or unsubstituted C6-C30 aryloxy group;

$L^{Y7}$ is selected from a bond, a substituted or unsubstituted C6-C30 arylene group, and a substituted or unsubstituted C3-C30 heteroarylene group.

6. The organic material composition according to claim 5, wherein the compound having a structure represented by Formula 2 is selected from the compounds shown as below:

2-31

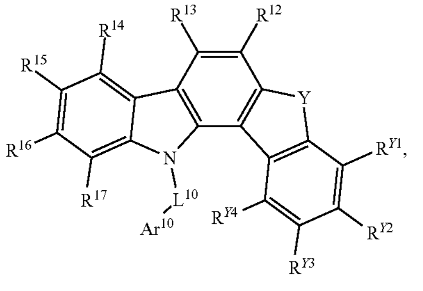

2-32

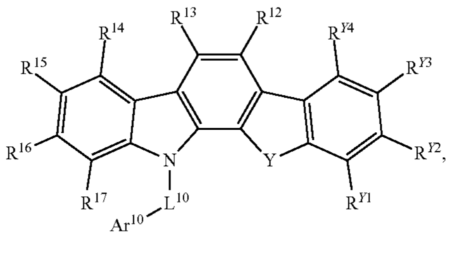

-continued 2-33

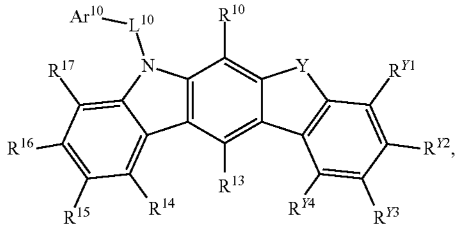

2-34

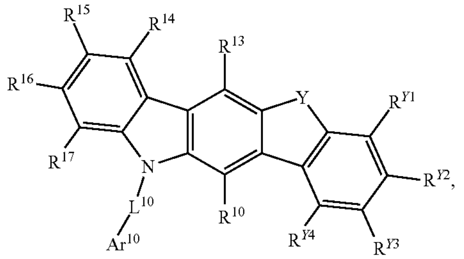

2-35

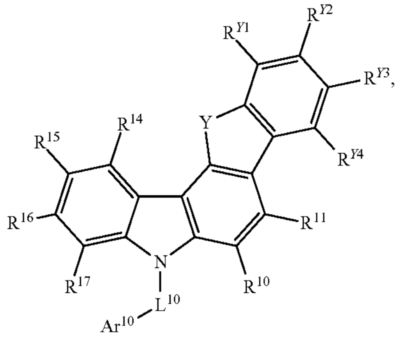

2-36

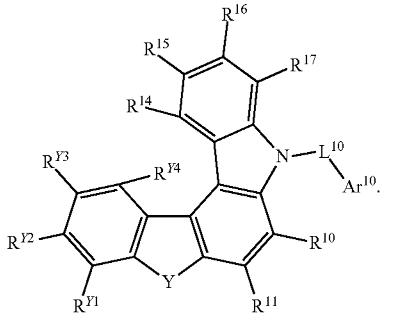

Y is selected from O, S, $CR^{Y5}R^{Y6}$ and $N^{RY}$, in which $R^{Y}$ is $—L^{Y7}R^{Y7}$;

$Ar^{10}$ and $R^{Y7}$ are each independently selected from a phenyl group, a biphenylyl group, a terphenylyl group, a triphenylenylene group, a naphthyl group, a phenylnaphthyl group, a naphthylphenyl group, an anthryl group, a phenanthryl group, a benzophenanthryl group, a pyridyl group, a dibenzofuryl group, a dibenzothiophenyl group, a carbazolyl group, a phenylcarbazolyl group, a pyridylcarbazolyl group, a naphthylcarbazolyl group, a biphenylylcarbazolyl group, a dibenzofurylphenyl group, a dibenzothiophenylphenyl group, a dimethylfluorenyl group, a diphenylfluorenyl group, a spiro-bifluorenyl group, a benzonaphthofuryl group, a benzonaphthothiophenyl group, a benzocarbazolyl group and a dibenzocarbazolyl group, each of which is substituted or unsubstituted;

$R^{10}$ to $R^{17}$ and $R^{Y1}$ to $R^{Y4}$ are each independently selected from hydrogen, deuterium, a phenyl group, a biphenylyl group, a terphenylyl group, a naphthyl group, a phenylnaphthyl group, a naphthylphenyl group, an anthryl group, a phenanthryl group, a benzophenanthryl group, a pyridyl group, a dibenzofuryl group, a dibenzothiophenyl group, a dibenzofurylphenyl group, a dibenzothiophenylphenyl group, a dimethylfluorenyl group, a diphenylfluorenyl group, a spirobifluorenyl group, a benzonaphthofuryl group, and a benzonaphthothiophenyl group; $R^{10}$ to $R^{17}$ and $R^{Y1}$ to $R^{Y4}$ are present individually without forming a ring, or any adjacent two of $R^{10}$ to $R^{17}$ and $R^{Y1}$ to $R^{Y4}$ joined to form a benzene ring or a naphthalene ring;

$R^{Y5}$ and $R^{Y6}$ are each independently selected from a methyl group and a phenyl group; or, $R^{Y5}$ and $R^{Y6}$ joined to form a fluorene ring group;

$L^{10}$ and $L^{Y7}$ are each independently selected from a bond, a phenylene group, a biphenylene group, and a naphthylene group.

7. The organic material composition according to claim 1, wherein the compound having a structure represented by Formula 2 is selected from the compounds shown as below:

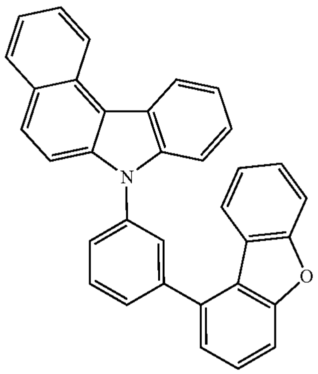

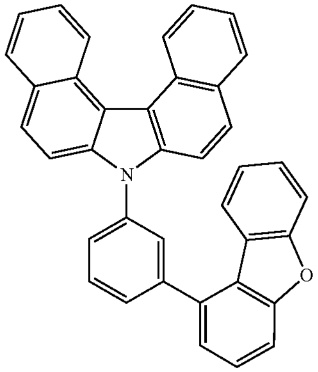

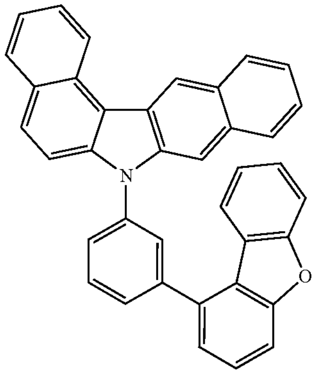

-continued

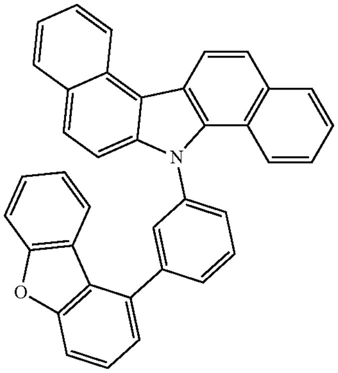

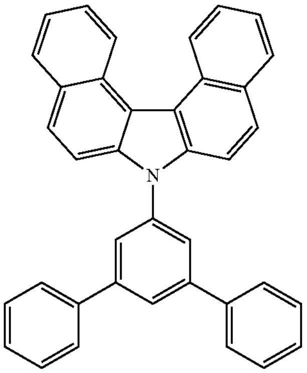

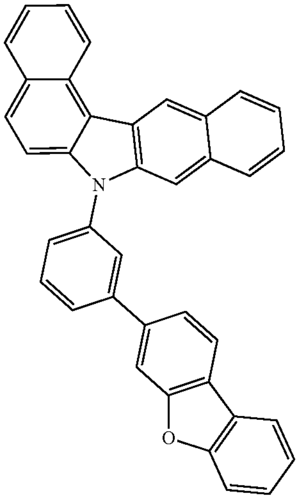

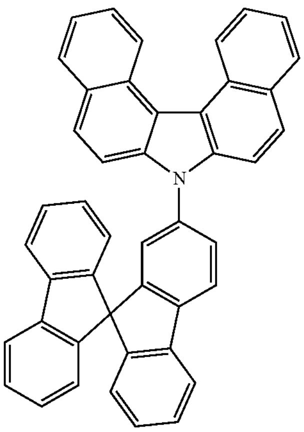

-continued
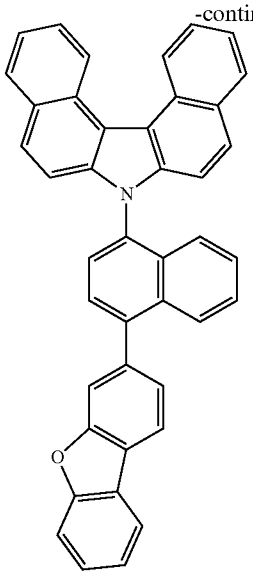
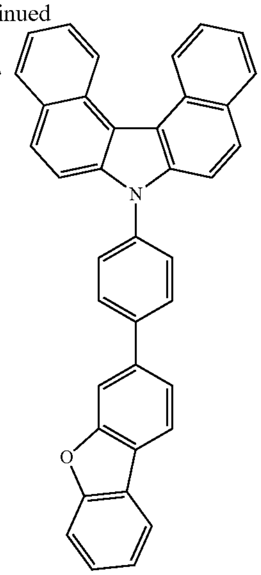
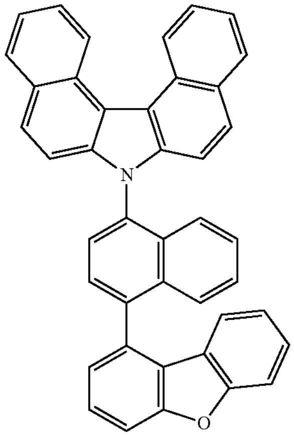
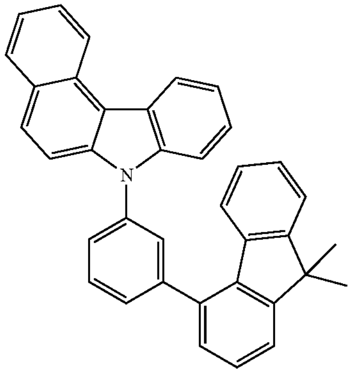
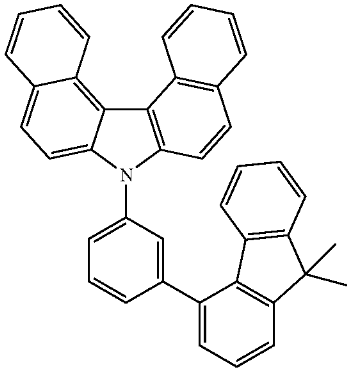
-continued
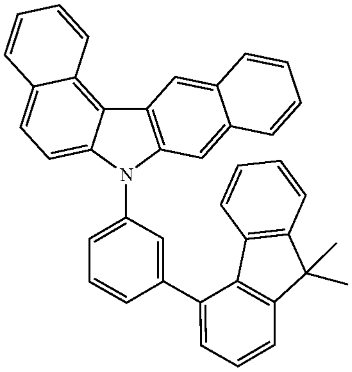
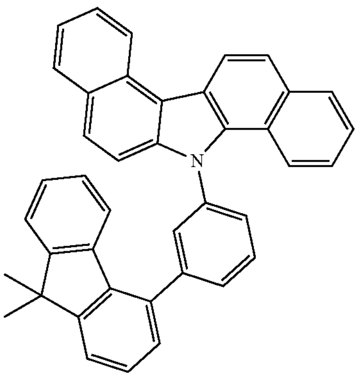
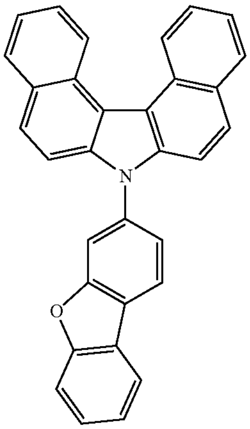

-continued
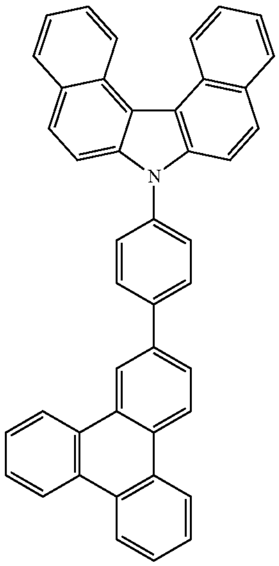
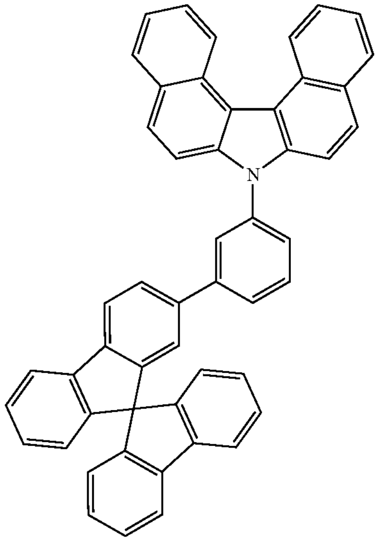
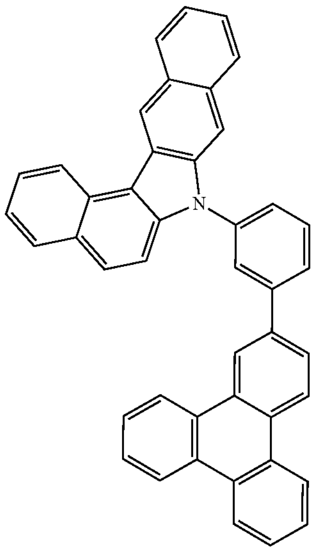
-continued
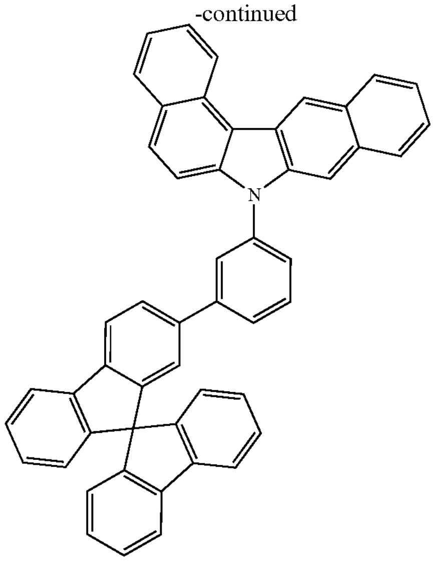
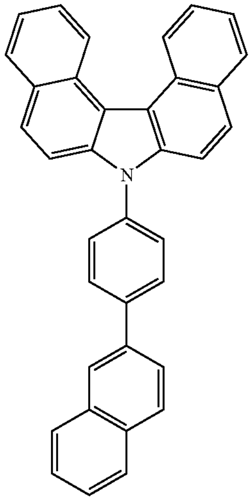
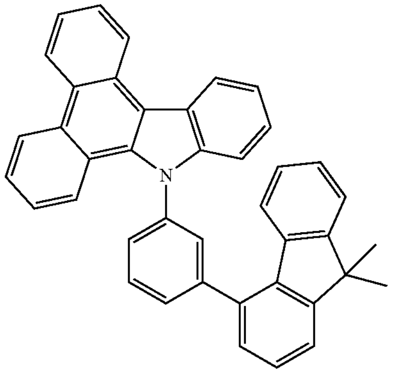
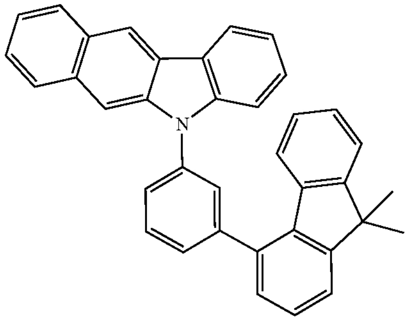

-continued
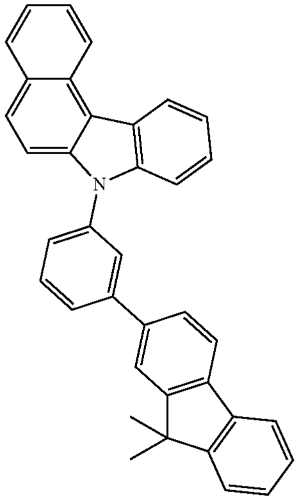
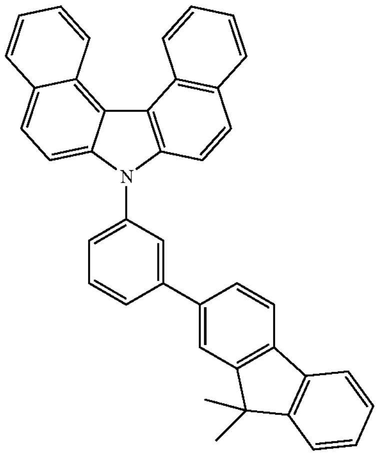
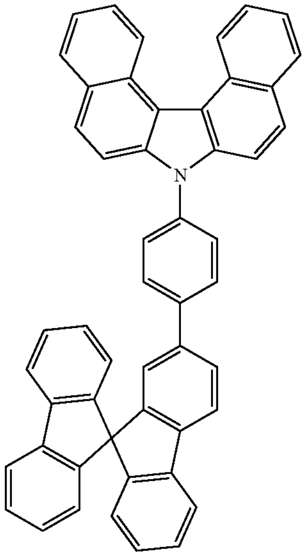
-continued
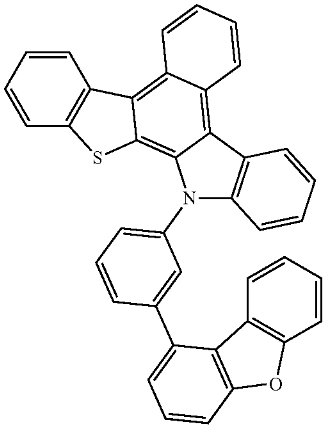
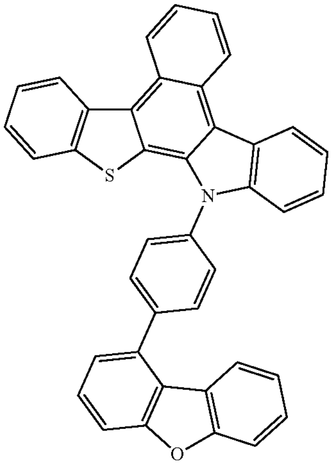
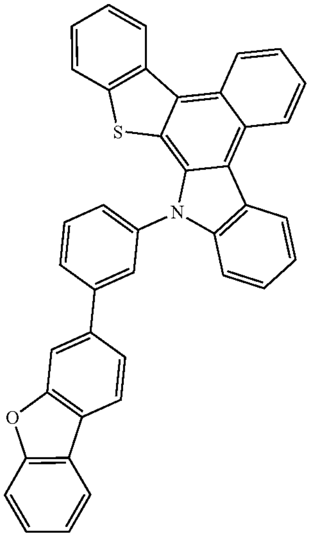

-continued
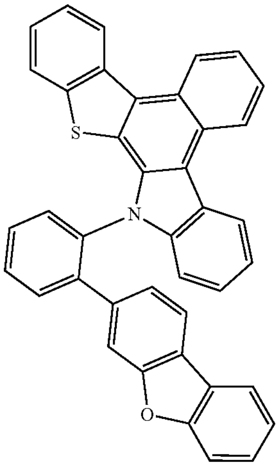
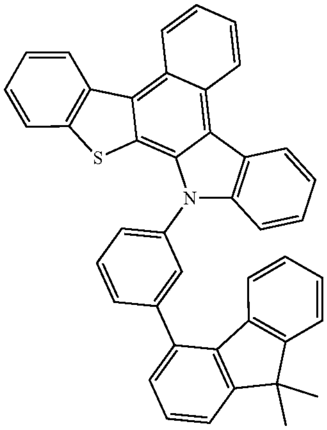
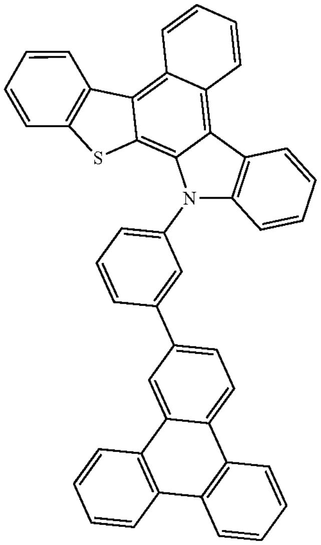
-continued
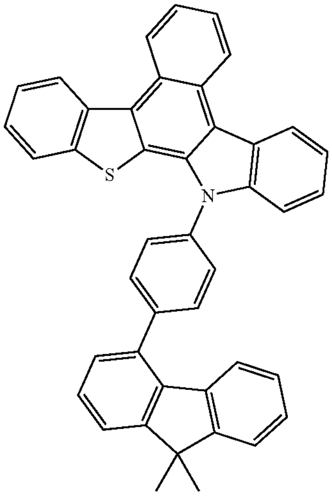
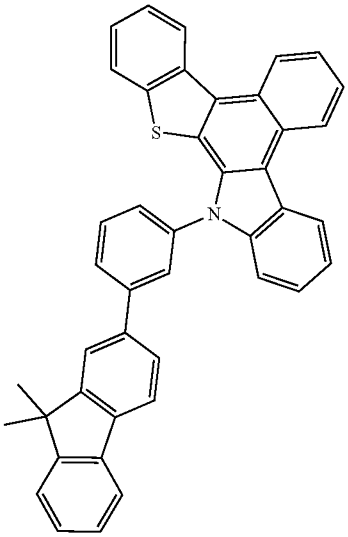
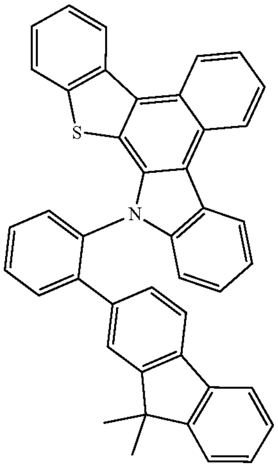

-continued
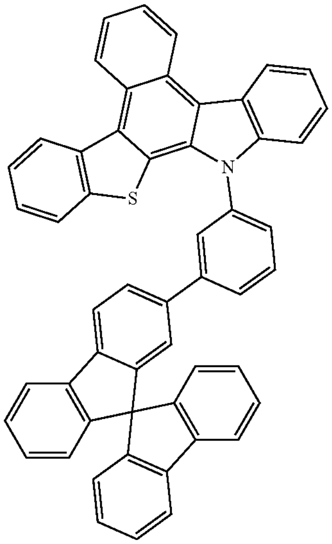
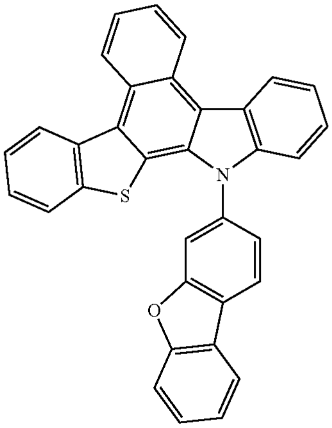
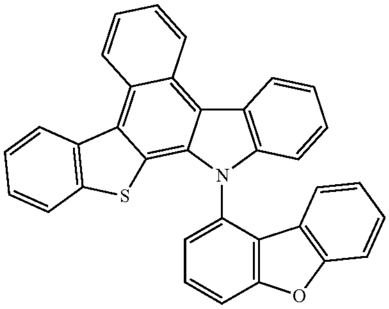
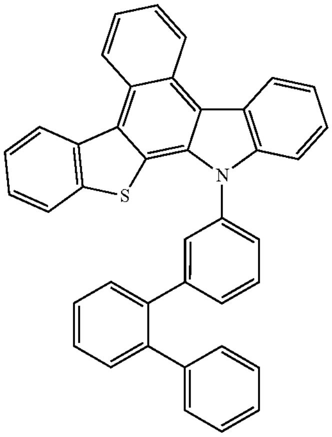
-continued
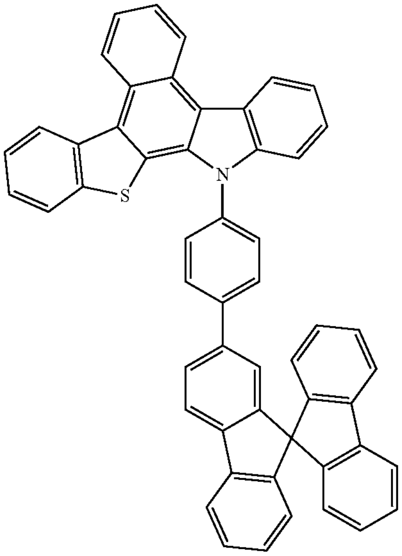
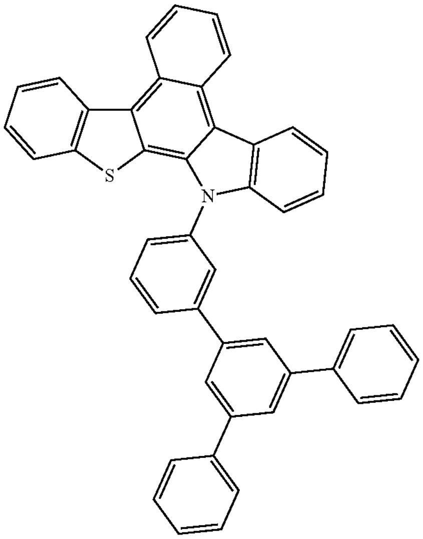
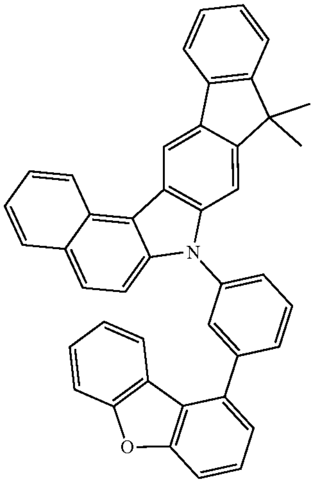

-continued
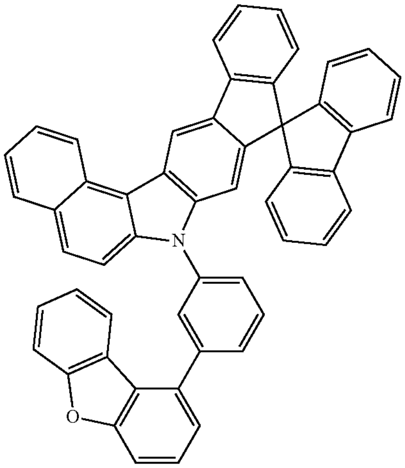
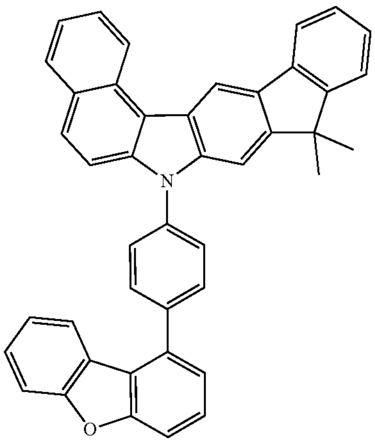
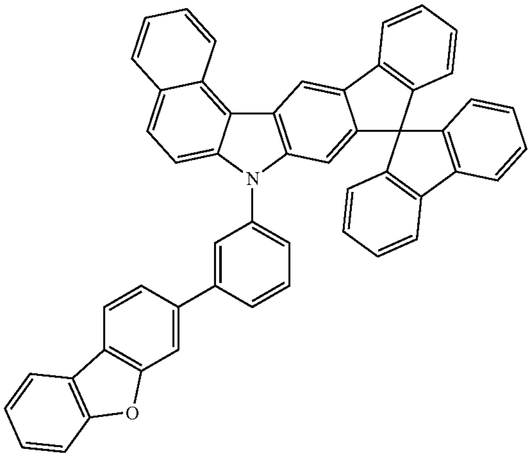
-continued
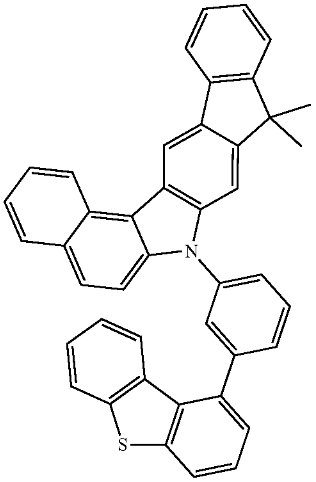
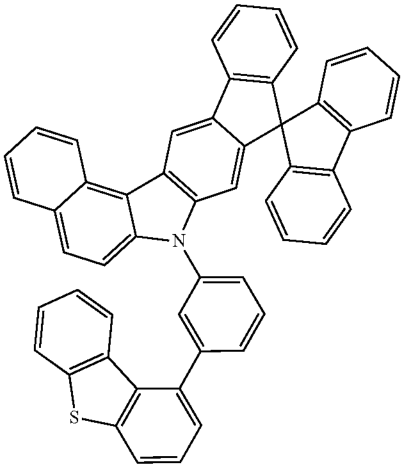
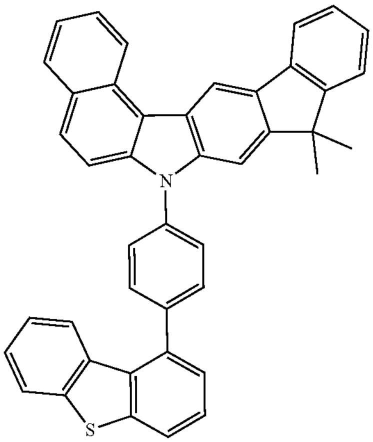

-continued
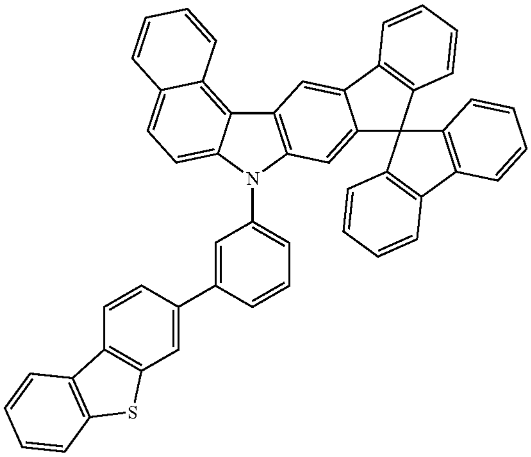
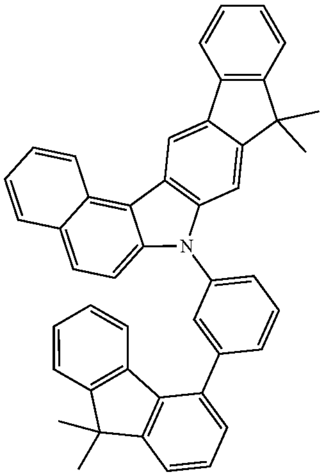
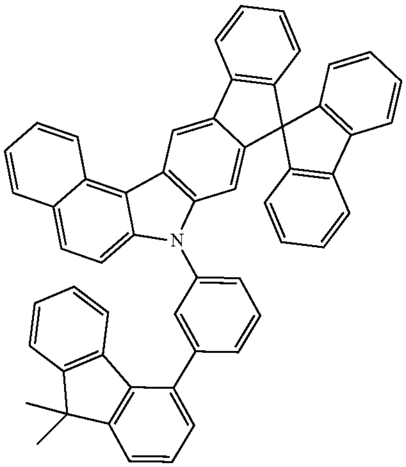
-continued
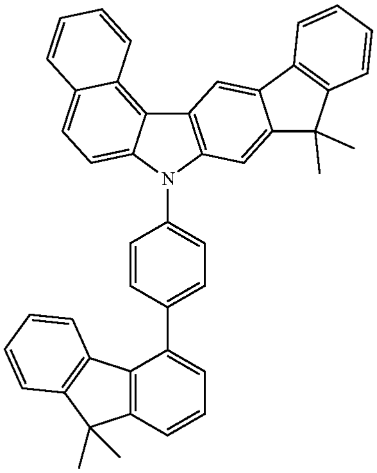
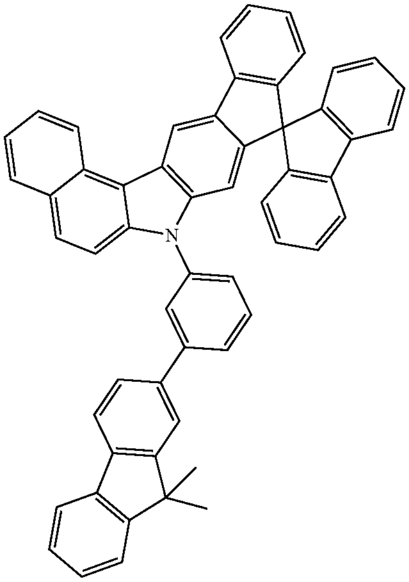
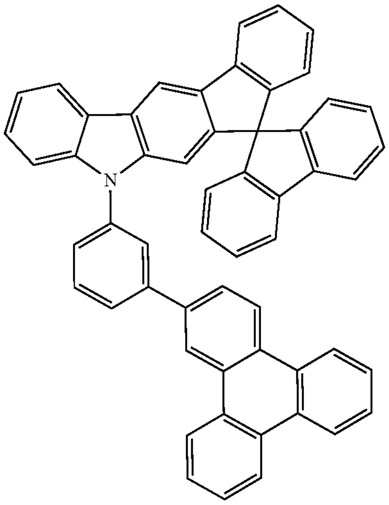

-continued
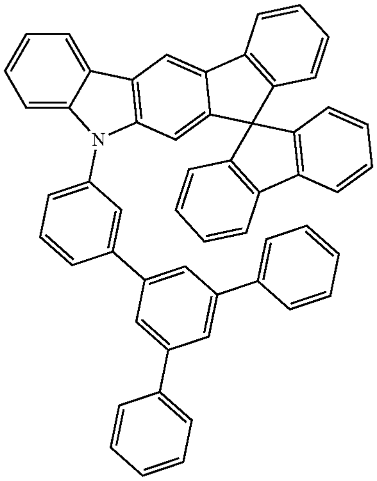
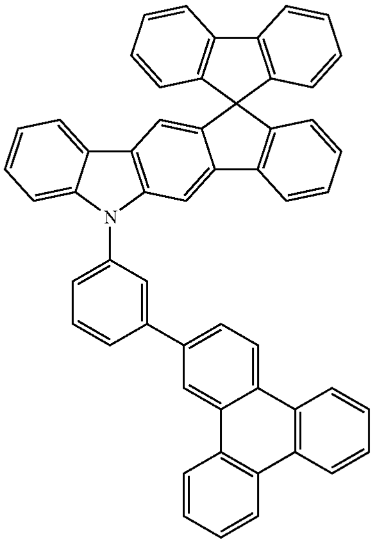
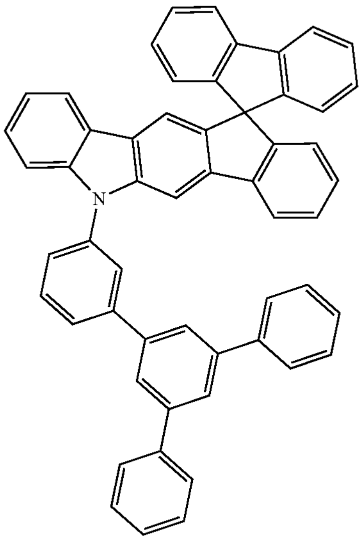
-continued
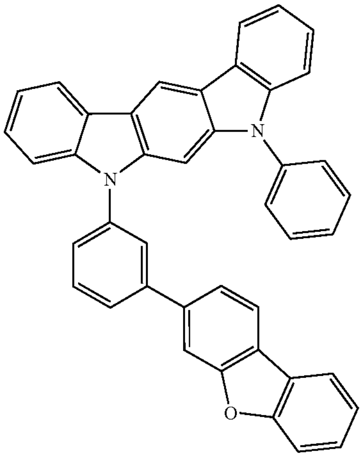
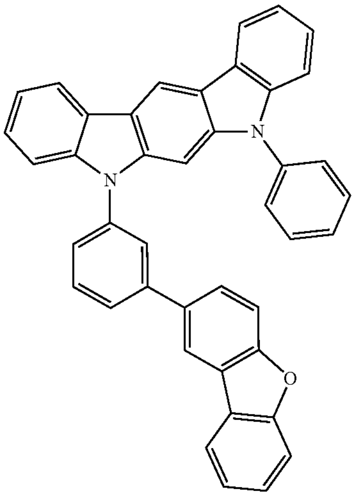
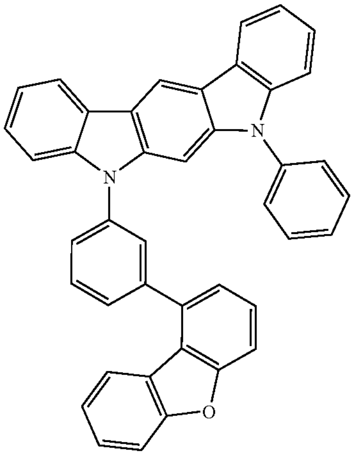

-continued
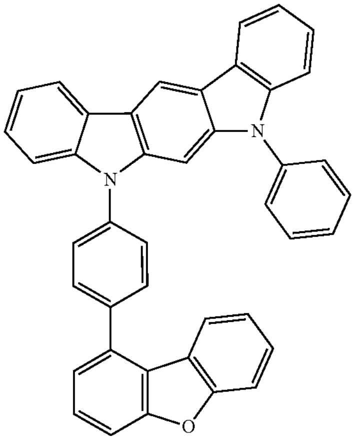
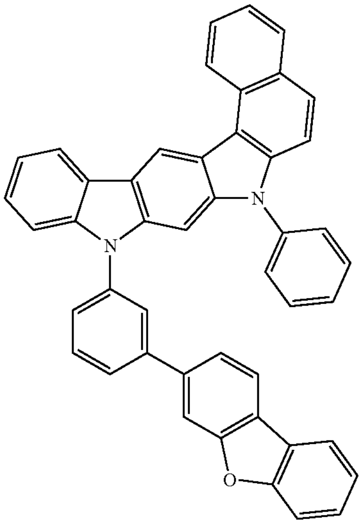
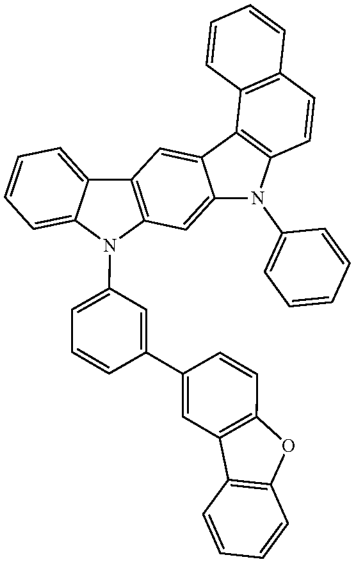
-continued
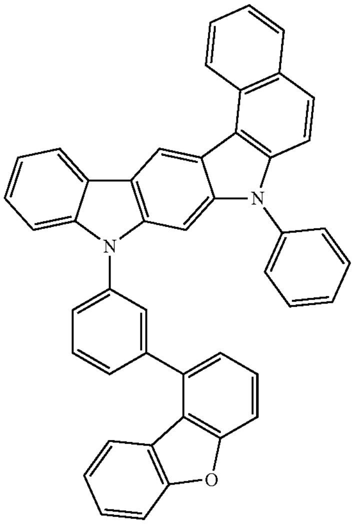
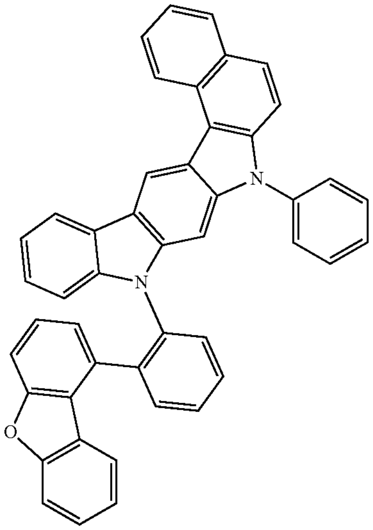
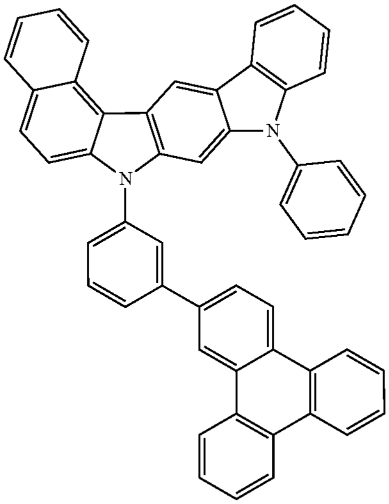

-continued
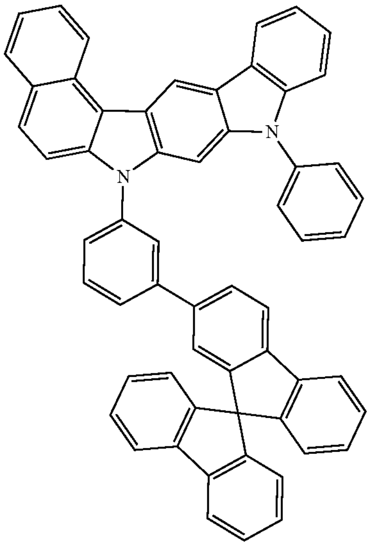
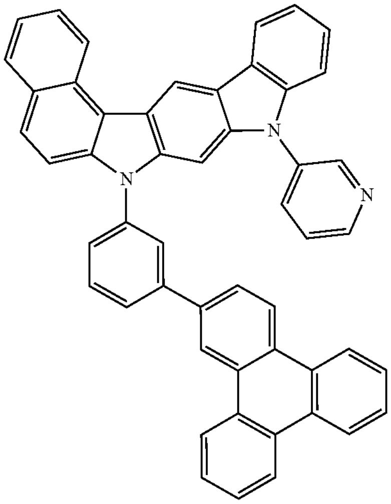
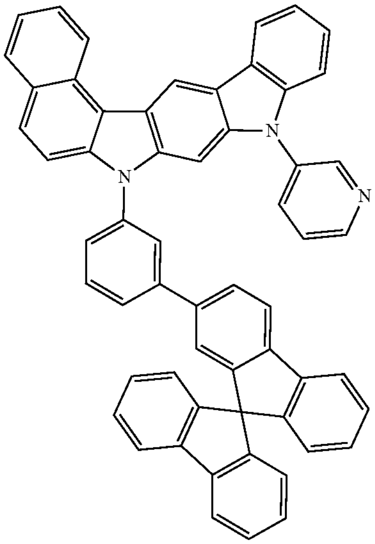
-continued
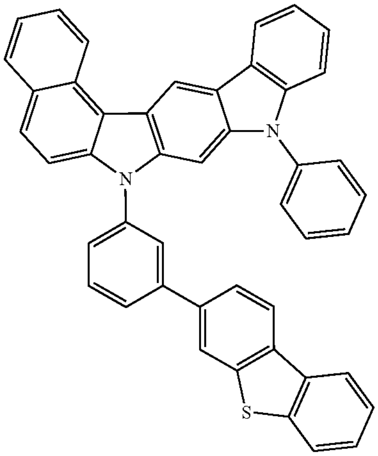
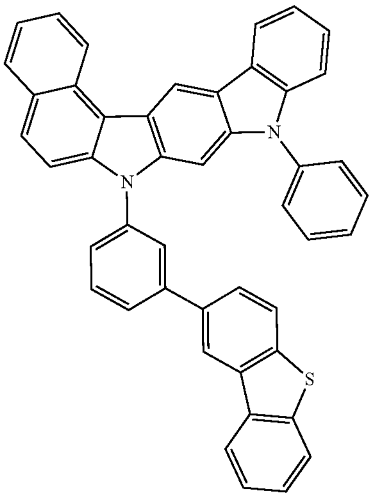
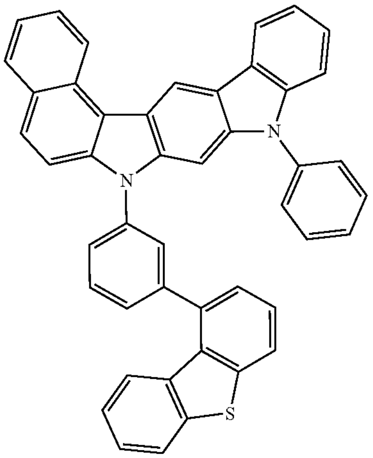

-continued
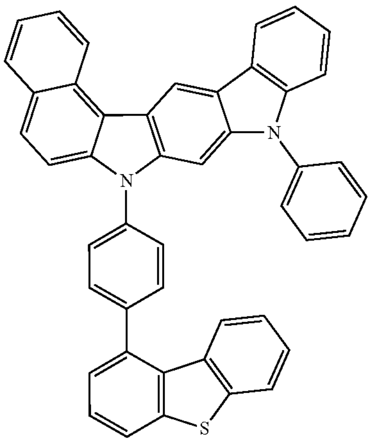
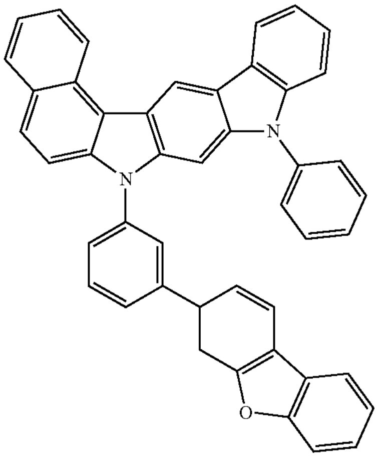
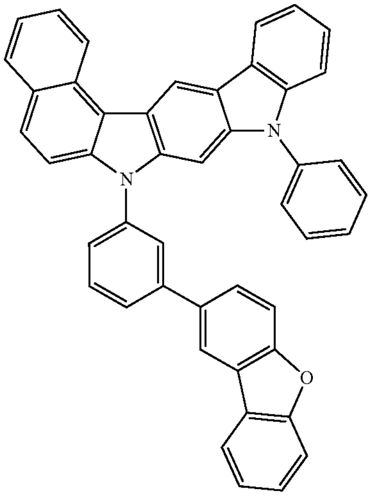
-continued
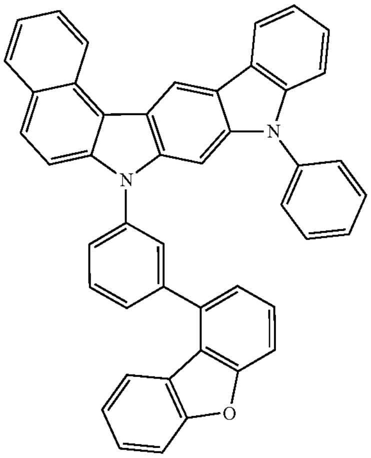
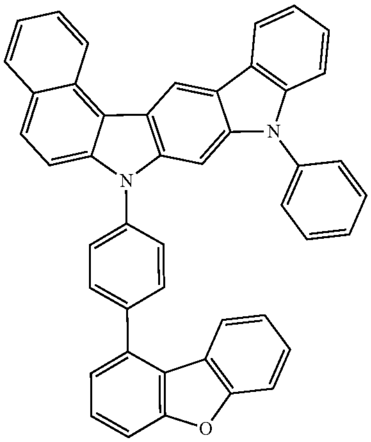
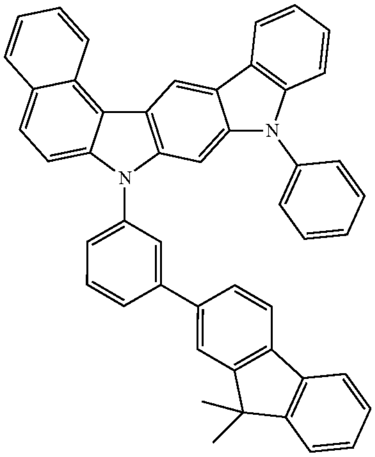

-continued
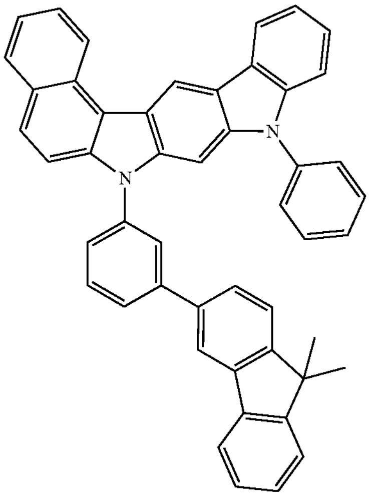
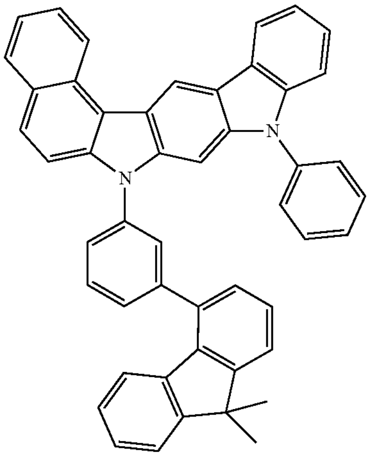
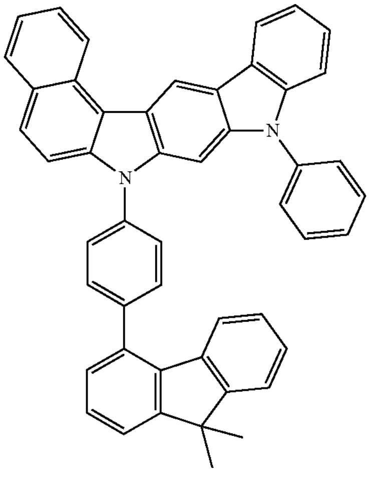
-continued
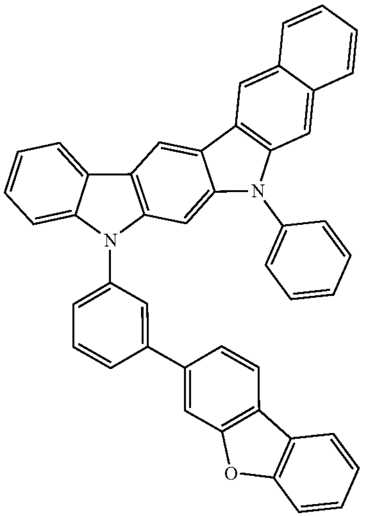
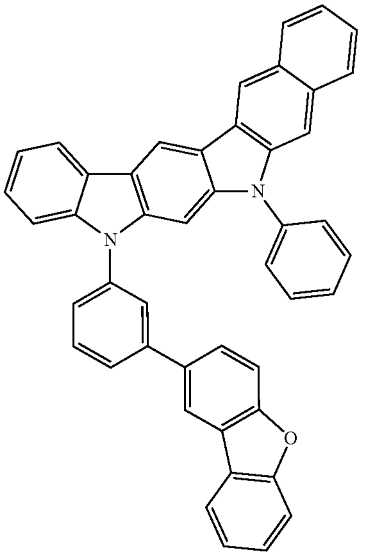
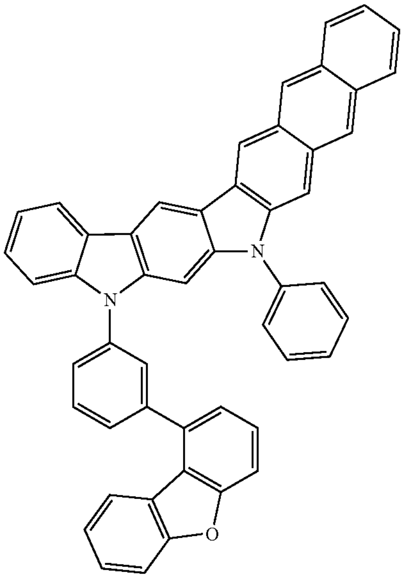

-continued
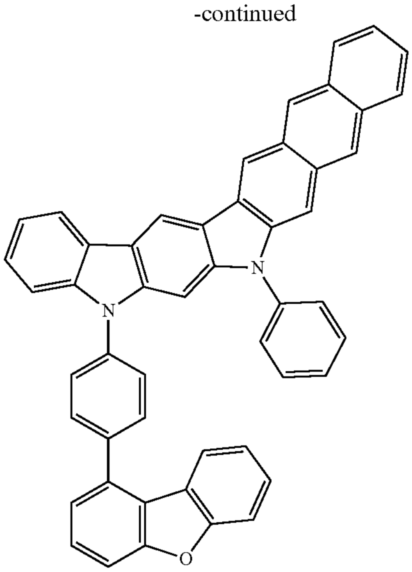
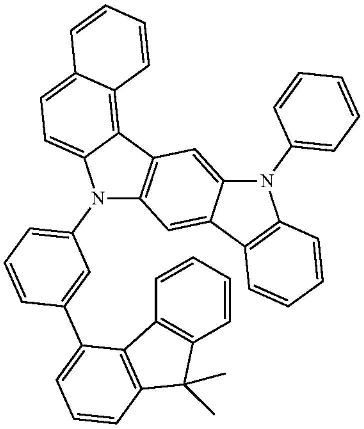
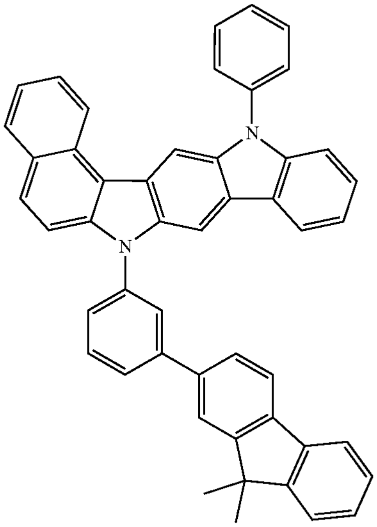
-continued
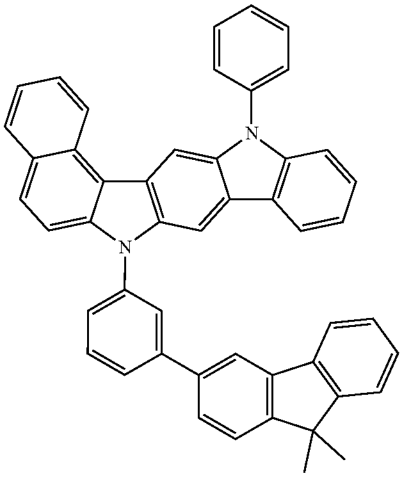
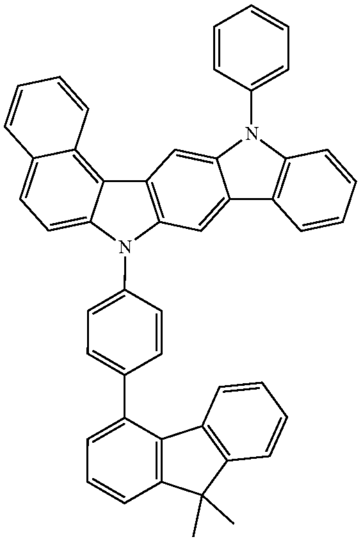
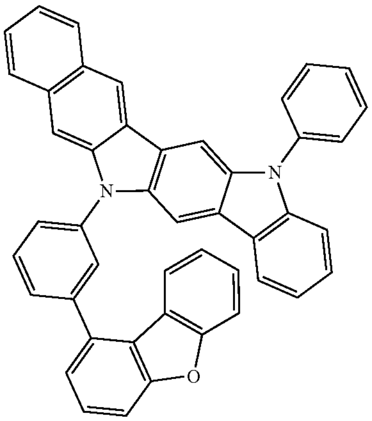

-continued
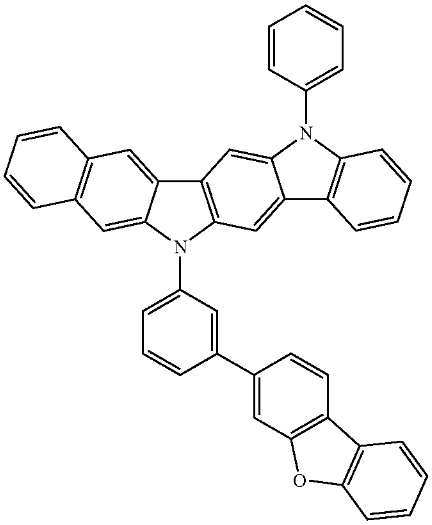
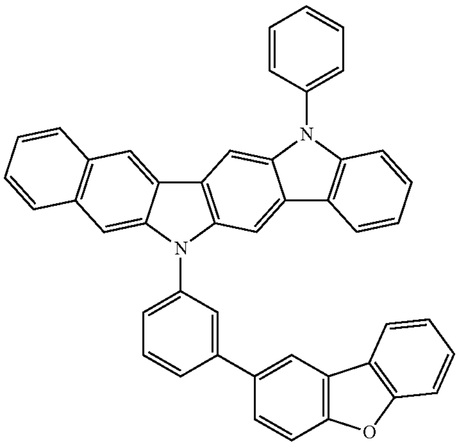
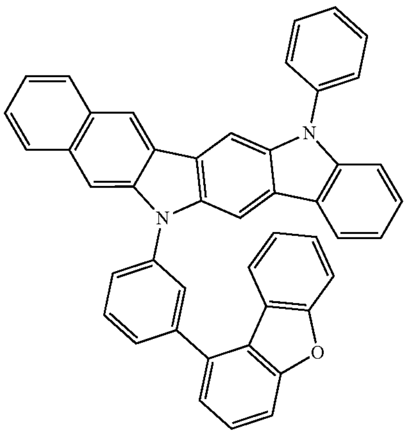
-continued
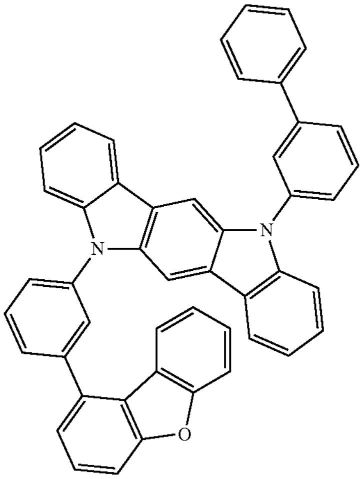
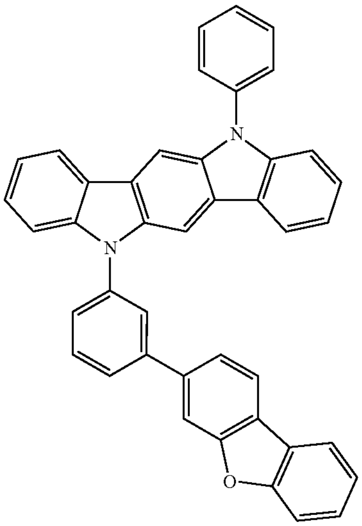
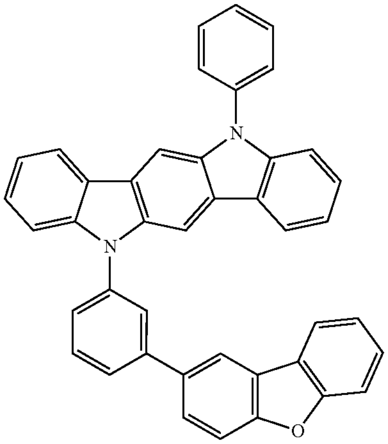

-continued
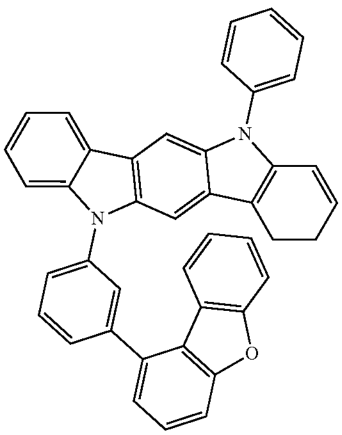
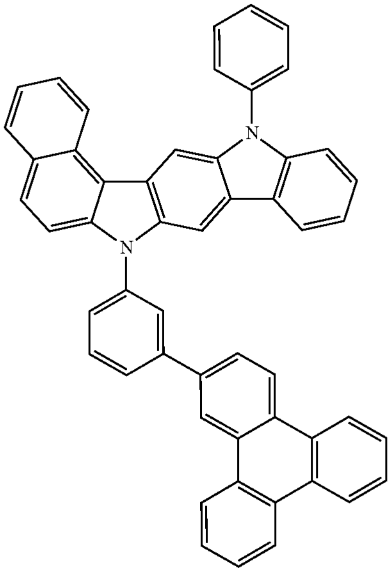
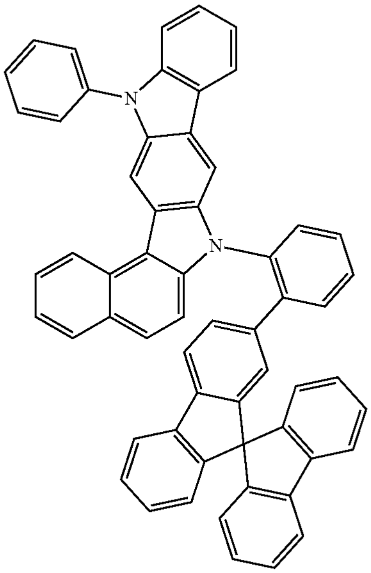
-continued
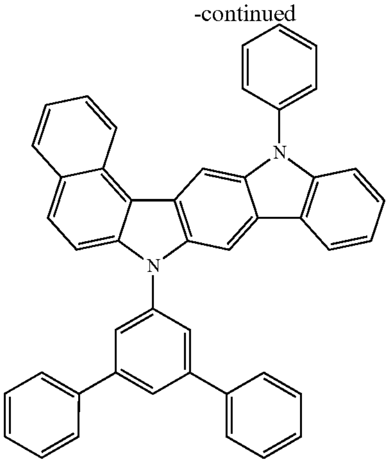
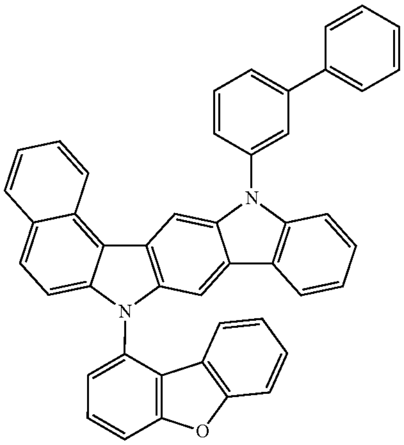
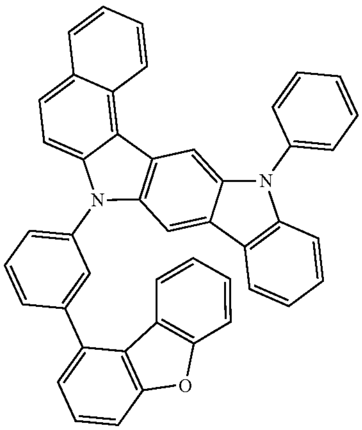

-continued
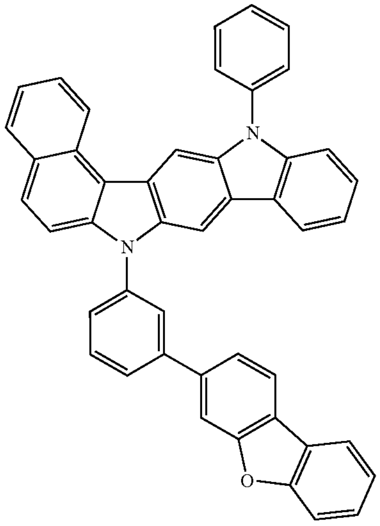
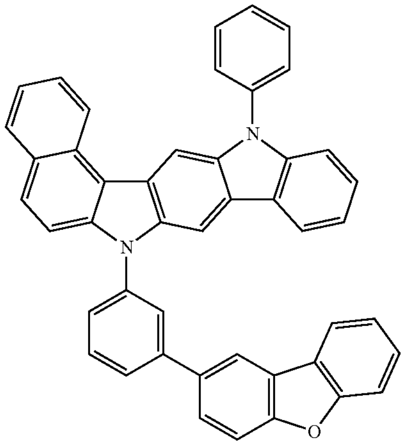
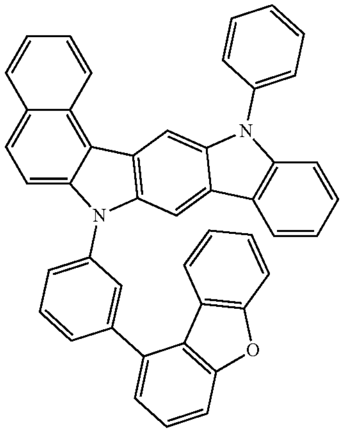
-continued
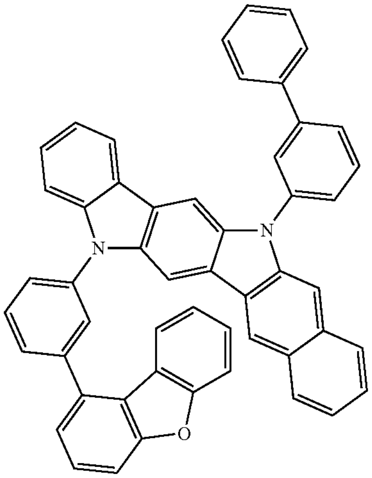
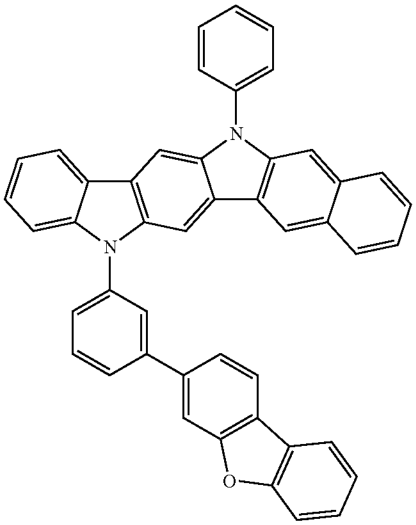
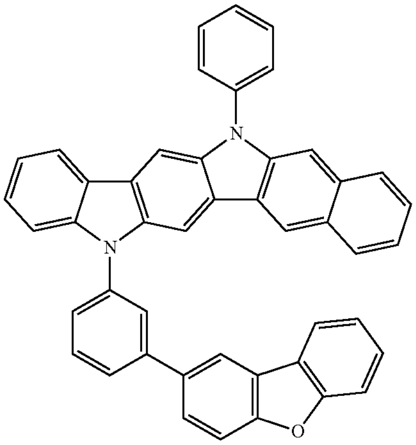

-continued
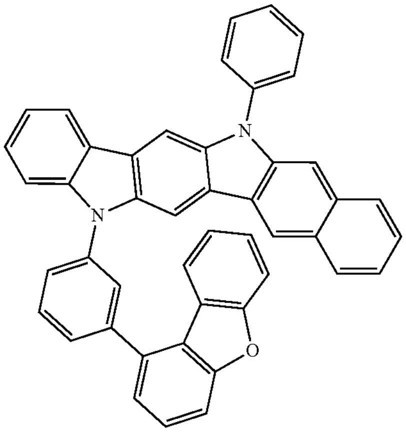
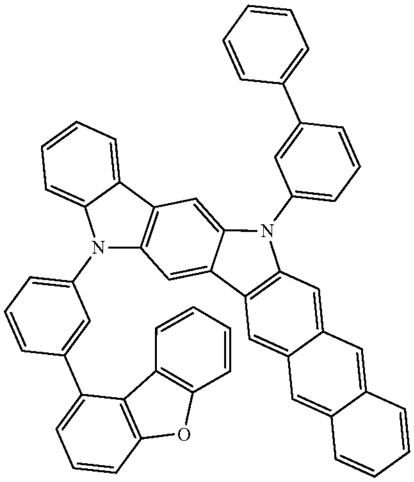
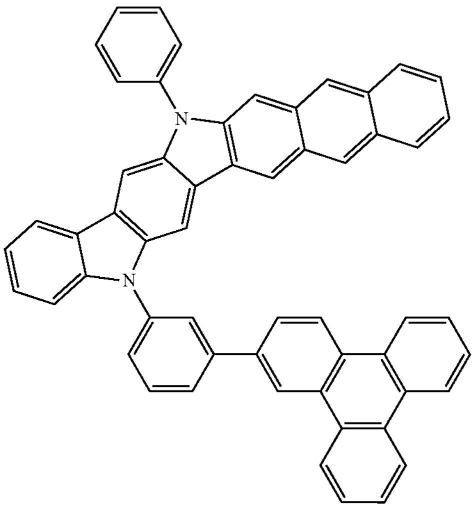
-continued
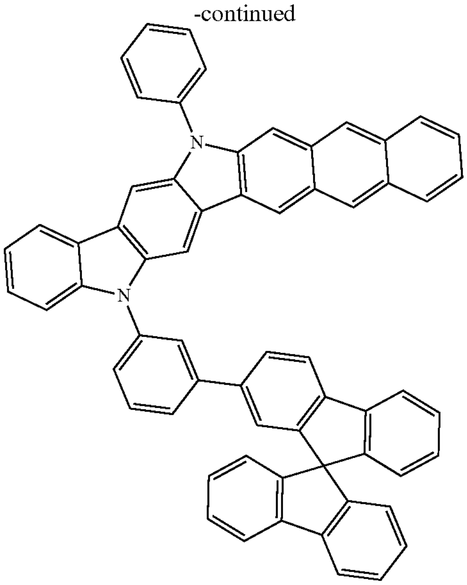
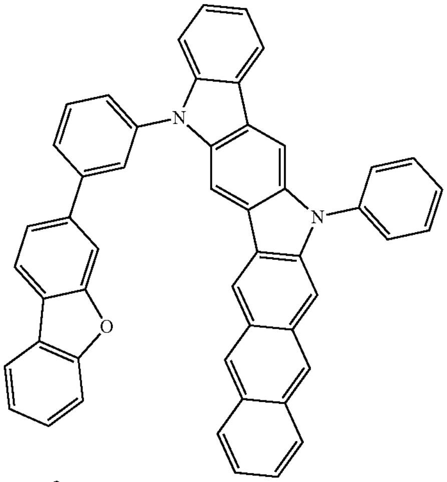
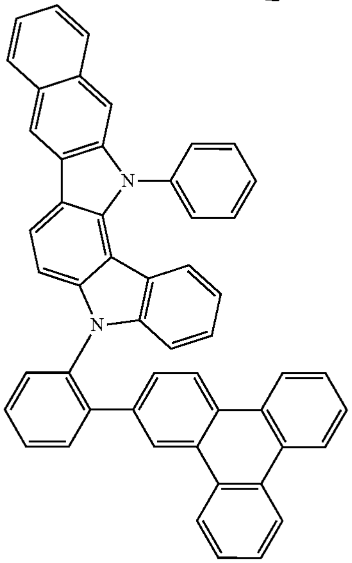

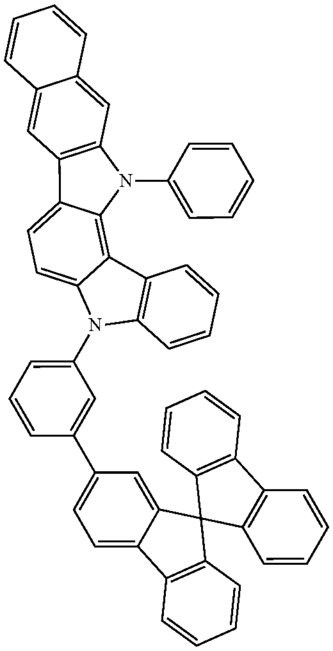
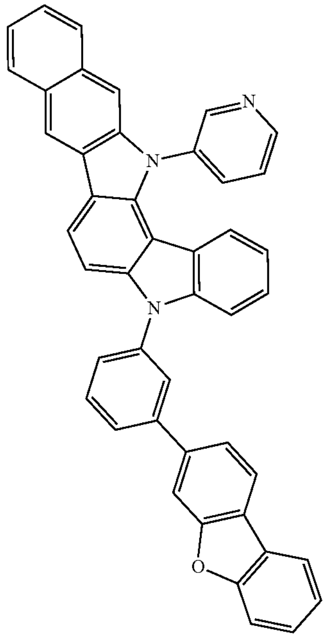
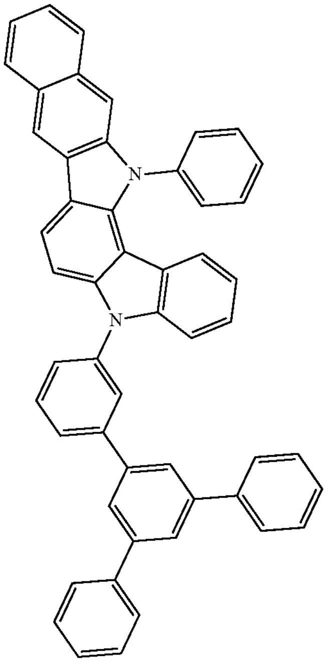
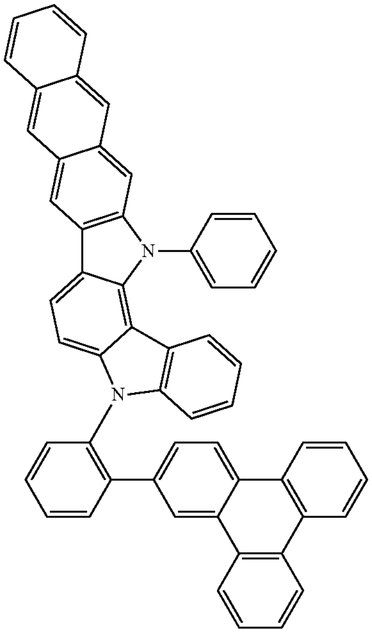

-continued
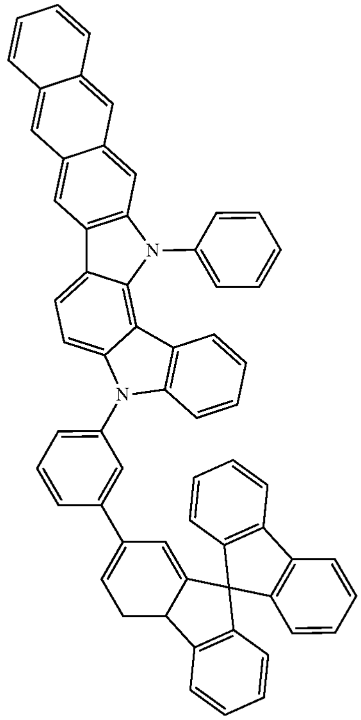
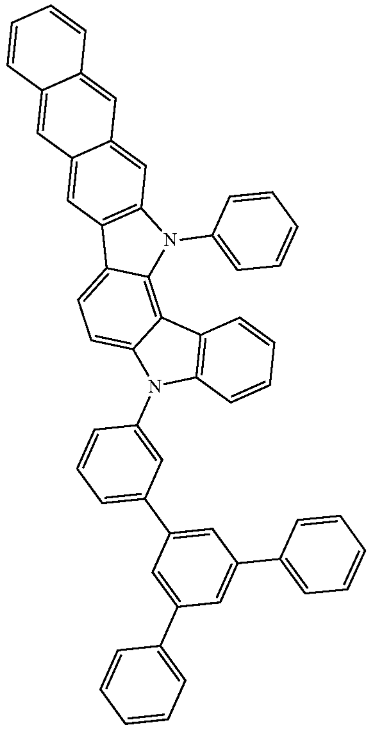
-continued
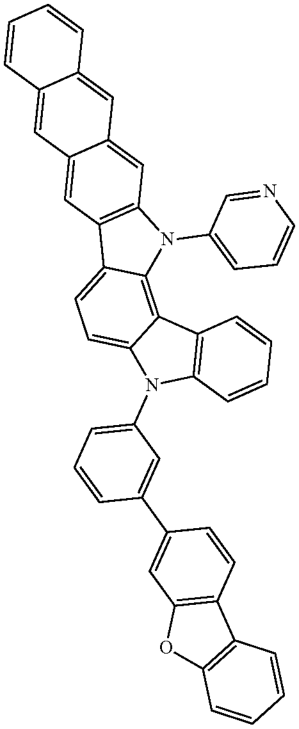
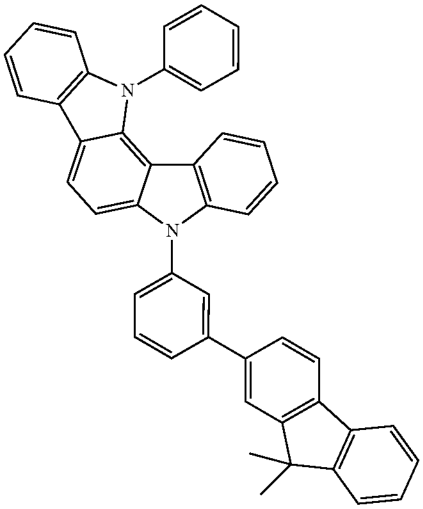
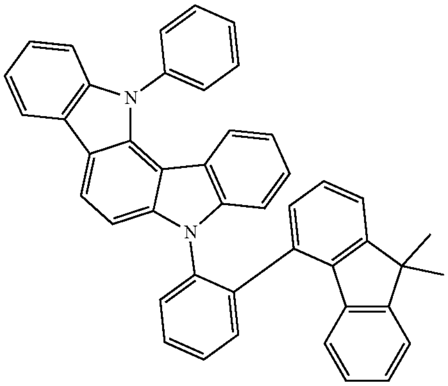

-continued
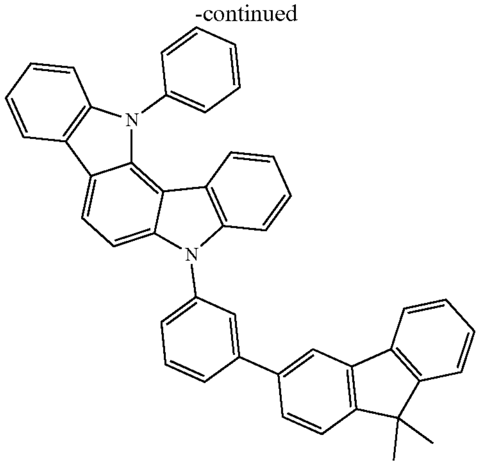
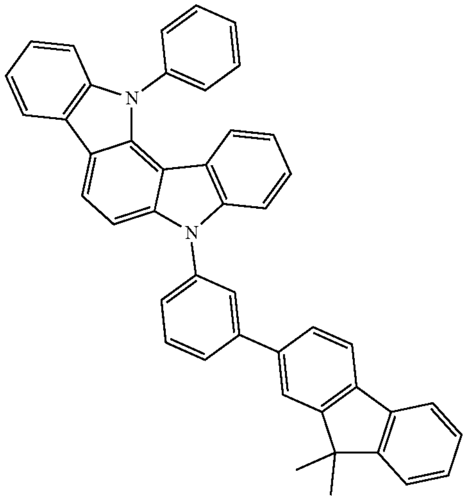
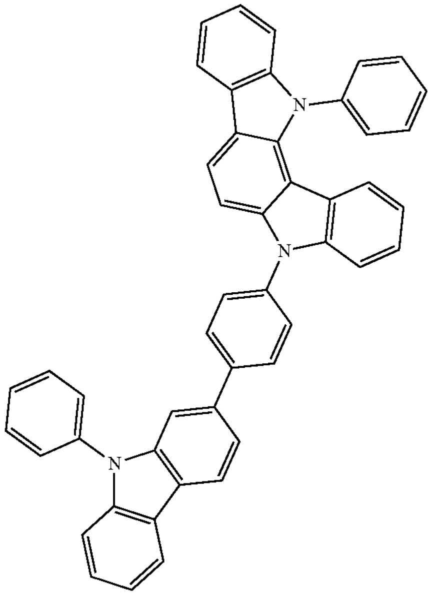
-continued
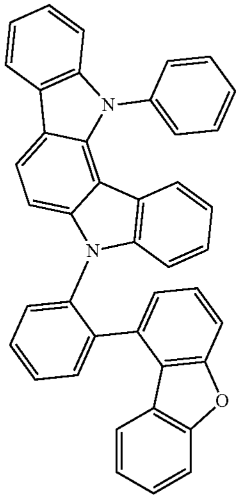
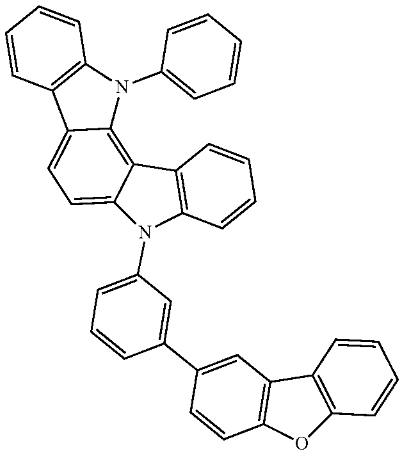
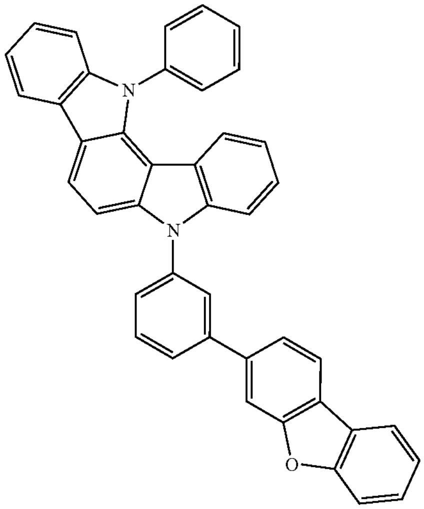

-continued
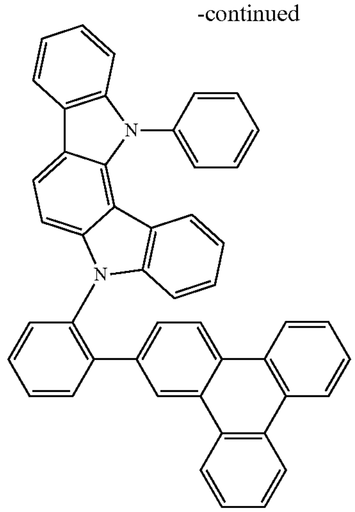
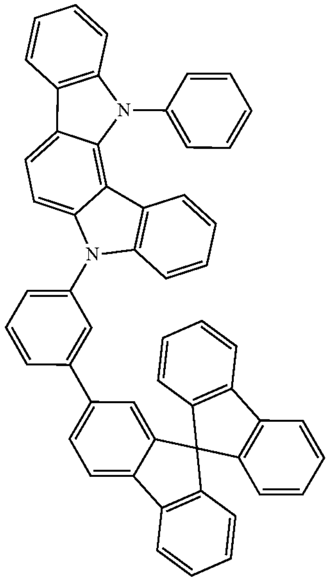
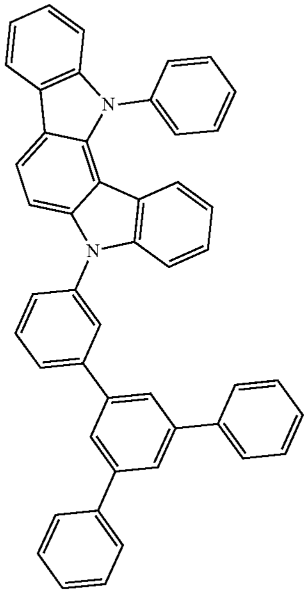
-continued
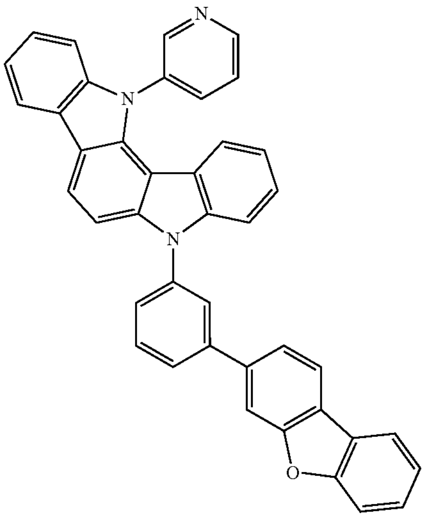
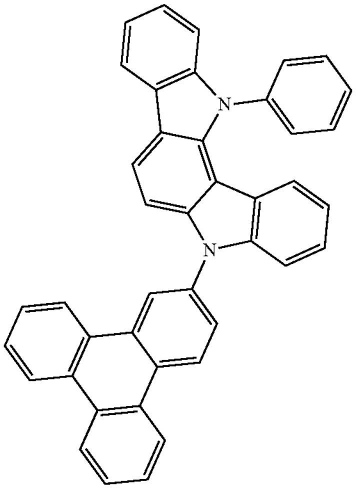
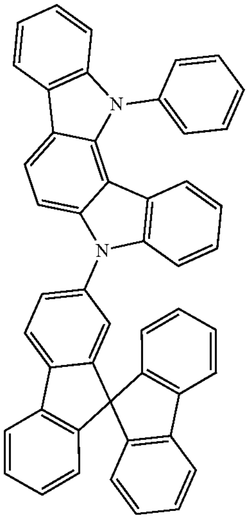

-continued
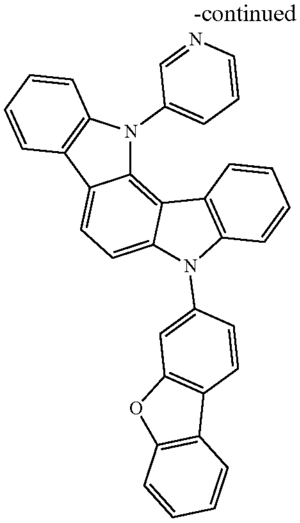
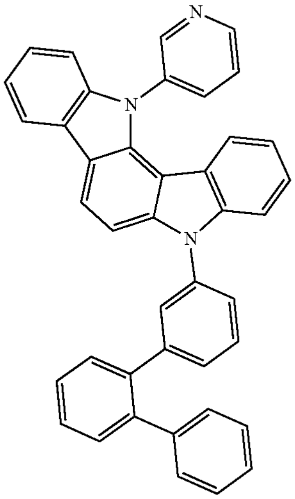
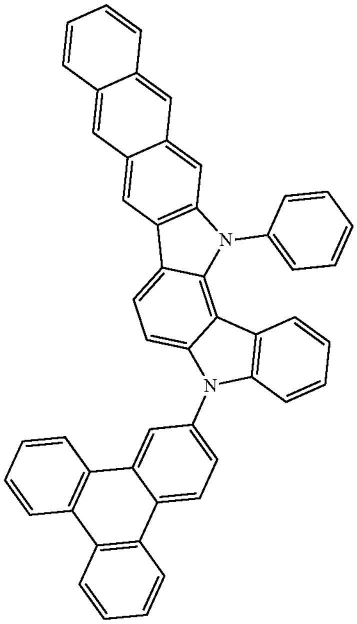
-continued
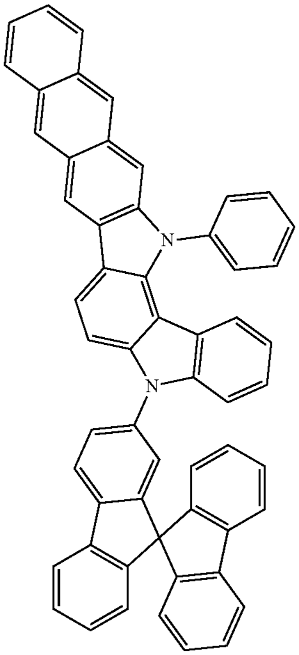
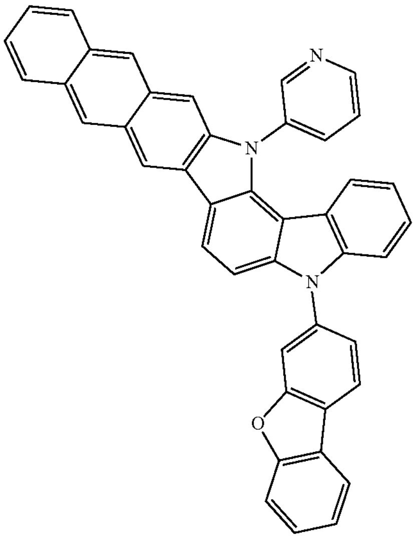

-continued

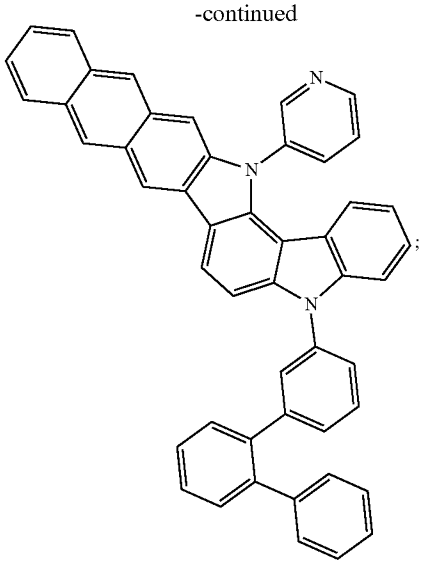

;

and the compound having a structure represented by Formula 1 and the compound having a structure represented by Formula 2 have a weight ratio of 1:9 to 9:1.

8. The organic material composition according to claim 7, wherein the compound having a structure represented by Formula 1 and the compound having a structure represented by Formula 2 have a weight ratio of 4:6 to 6:4.

9. An organic electroluminescence material, wherein the organic electroluminescence material comprises the organic material composition as according to claim 1.

10. A method for preparing an optical element comprising an emitting layer, the method comprising:

co-depositing a light-emitting host material and a guest material to form the emitting layer; wherein the light-emitting host material comprises the organic material composition according to claim 1, and the guest material comprises a phosphorescence dopant.

11. An organic electroluminescence element, wherein the organic electroluminescence element comprises an anode, a cathode and an organic layer disposed between the anode and the cathode; and the organic layer comprises the organic material composition according to claim 1.

12. An electronic device, wherein the electronic device comprises the organic electroluminescence element according to claim 11.

* * * * *